(12) United States Patent
Gaspar et al.

(10) Patent No.: US 11,795,481 B2
(45) Date of Patent: *Oct. 24, 2023

(54) PROCESSES FOR PRODUCING A FERMENTATION PRODUCT

(71) Applicant: Novozymes A/S, Bagsvaerd (DK)

(72) Inventors: Armindo Ribeiro Gaspar, Rolesville, NC (US); Victor Gabriel Guadalupe Medina, Araucaria Parana (BR); Xin Li, Raleigh, NC (US); Kelly Cristina Leite Mulder, Araucaria Parana (BR); Angela Shows, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,797

(22) Filed: Apr. 5, 2022

(65) Prior Publication Data

US 2022/0267811 A1 Aug. 25, 2022

Related U.S. Application Data

(62) Division of application No. 16/757,459, filed as application No. PCT/US2018/056659 on Oct. 19, 2018, now Pat. No. 11,326,187.

(60) Provisional application No. 62/575,852, filed on Oct. 23, 2017.

(51) Int. Cl.
| | |
|---|---|
| *C12P 7/06* | (2006.01) |
| *C12N 9/02* | (2006.01) |
| *C12P 1/02* | (2006.01) |
| *C12P 19/14* | (2006.01) |

(52) U.S. Cl.
CPC ............ *C12P 7/06* (2013.01); *C12N 9/0083* (2013.01); *C12P 1/02* (2013.01); *C12P 19/14* (2013.01); *C12Y 114/99* (2013.01); *C12Y 302/01001* (2013.01)

(58) Field of Classification Search
None
See application file for complete search history.

(56) References Cited

U.S. PATENT DOCUMENTS

| 11,326,187 B2* | 5/2022 | Gaspar | C12P 1/02 |
| 2009/0233340 A1 | 9/2009 | Dailey | |
| 2011/0143410 A1* | 6/2011 | Soong | C12P 7/06 |
| | | | 435/171 |
| 2017/0145443 A1 | 5/2017 | Shihadeh | |
| 2017/0369917 A1 | 12/2017 | Noordam | |

FOREIGN PATENT DOCUMENTS

| CN | 107002107 A | 8/2017 |
| WO | 2016/045569 A1 | 3/2016 |
| WO | 2018/096019 A1 | 5/2018 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AZJ19467.04—Aug. 2011 (Year: 2011).*
Thomas et al, 2001, J Appl Microbiol 90, 819-828.
Chica et al, 2005, Curr Op Biotechnol 16, 378-384.
Singh et al, 2017, Curr Protein and Peptide Science 18, 1-11.
WO 2011-080267 A2—Accession No. AZJ19467.
Muller et al., Biotechnol. Bioeng., 2016, 1-8, 9999.

* cited by examiner

*Primary Examiner* — Christian L Fronda
(74) *Attorney, Agent, or Firm* — David Fazzolare

(57) ABSTRACT

The present invention relates to a process for reducing and/or preventing an increase in lactic acid levels in a fermentation product production process, such as especially ethanol production, wherein a lytic polysaccharide monooxygenase (LPMO) or an enzyme composition comprising an LPMO is added before or during saccharification and/or fermentation, or before or during propagation, to reduce and/or prevent an increase in lactic acid levels.

20 Claims, 3 Drawing Sheets

Specification includes a Sequence Listing.

PROCESSES FOR PRODUCING A FERMENTATION PRODUCT

CROSS-REFERENCE TO RELATED APPLICATIONS

This application is a divisional application of U.S. patent application Ser. No. 16/757,459, filed on Apr. 20, 2020 which is a 35 U.S.C. 371 national application of international application no. PCT/US2018/056656 filed Oct. 19, 2018, which claims priority of U.S. provisional application No. 62/575,852 filed Oct. 23, 2017, the contents of which are fully incorporated herein by reference.

REFERENCE TO A SEQUENCE LISTING

This application contains a Sequence Listing in computer-readable form created on Oct. 19, 2018 as an ASCII text file, 432 kb in size, and named SQListing.txt, which is incorporated herein by reference.

FIELD OF THE INVENTION

The present invention relates to a process for reducing and/or preventing an increase in lactic acid devels (e.g., due to bacterial contamination) in a fermentation product production process, such as especially ethanol production, wherein a lytic polysaccharide monooxygenase is added before or during saccharification and/or fermentation to reduce and/or prevent an increase in lactic acid levels during fermentationn.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separates the desired fermentation product, e.g. ethanol, from other liquids and/or solids. The remaining fraction is referred to as "whole stillage". Whole stillage typically contains about 10 to 20% solids. The whole stillage is separated into a solid and a liquid fraction, e.g., by centrifugation. The separated solid fraction is referred to as "wet cake" (or "wet grains") and the separated liquid fraction is referred to as "thin stillage". Wet cake and thin stillage contain about 35 and 7% solids, respectively. Wet cake, with optional additional dewatering, is used as a component in animal feed or is dried to provide "Distillers Dried Grains" (DDG) used as a component in animal feed. Thin stillage is typically evaporated to provide evaporator condensate and syrup or may alternatively be recycled to the slurry tank as "backset". Evaporator condensate may either be forwarded to a methanator before being discharged and/or may be recycled to the slurry tank as "cook water". The syrup may be blended into DDG or added to the wet cake before or during the drying process, which can comprise one or more dryers in sequence, to produce DDGS (Distillers Dried Grain with Solubles). Syrup typically contains about 25 to 35% solids. Oil can also be extracted from the thin stillage and/or syrup as a by-product for use in biodiesel production, as a feed or food additive or product, or other biorenewable products.

Contaminating bacteria and their metabolic end-products, such as lactic acid and/or acetic acid, lead to reduced fermentation yields which lead to considerable economic loss to the producer (see Thomas et al., 2001, J. Applied Microbiology, 90: 819-828). The contaminating bacteria compete with the fermenting organism (e.g., yeast) for sugars in the fermentation medium. The lactic acid and/or acetic acid produced by the unwanted bacteria also negatively impact yeast growth. Therefore, it is desirable to decrease the levels of lactic acid and/or unwanted bacteria that compete with fermenting organisms for sugar.

SUMMARY OF THE INVENTION

The present invention provides a solution to the problem of unwanted bacteria competing for sugar in the fermentation medium and the lactic acid they produce, by providing proving a biological solution to reduce and/or eliminate the lactic acid (e.g., due tobacterial cells) for instance, by adding at least one lytic polysaccharide monoxyenase (LPMO) polypeptide or an enzyme composition comprising a LPMO before or during saccharification and/or fermentation.

In an aspect, the present invention relates to a process for reducing and/or preventing an increase in lactic acid levels in a biofuel fermentation system, the process comprising introducing a lytic polysaccharide monooxygenase (LPMO) polypeptide or an enzyme composition comprising a LPMO polypeptide to a biofuel fermentation system, wherein the fermentation system comprises one or more fermentation vessels, pipes and/or components. In an embodiment, the LPMO polypeptide or enzyme composition comprising the LPMO polypeptide is added at a concentration sufficient to reduce and/or prevent an increase in lactic acid levels in the biofuel fermentation system.

In an embodiment, at least one of the fermentation vessels is a fermentation tank and the LPMO polypeptide or the enzyme composition comprising the LPMO polypeptide is introduced into the propagation or fermentation tank. In an embodiment, at least one of the fermentation vessels is a yeast propagation tank and the LPMO polypeptide or the enzyme composition comprising the LPMO polypeptide is introduced into the yeast propagation tank. In an embodiment, the biofuel is ethanol.

In an aspect the present invention relates to a process for producing a fermentation product from a starch-containing material, the process comprising: a) liquefying a starch-containing material in the presence of an alpha-amylase to form a liquefied mash; b) saccharifying the liquefied mash using a carbohydrate source generating enzyme to produce a fermentable sugar; c) fermenting the sugar using a fermenting organism under conditions suitable to produce the fermentation product, wherein at least one LPMO polypeptide or enzyme composition comprising an LPMO polypeptide is added before or during saccharifying step b) and/or fermenting step c).

In an embodiment, steps b) and c) are carried out simultaneously. In an embodiment, a slurry of the starch containing material is heated to above the gelatinization temperature.

In an embodiment, the at least one LPMO polypeptide or enzyme composition comprising the LPMO polypeptide is added after liquefaction. In an embodiment, the at least one LPMO polypeptide or the enzyme composition comprising the LPMO polypeptide is added before or during saccharification. In an embodiment, the at least one LPMO polypeptide or the enzyme composition comprising the LPMO polypeptide is added before or during fermentation. In an embodiment, the fermenting organism is yeast and the at least one LPMO polypeptide or the enzyme composition comprising the LPMO polypeptide is added before or during yeast propagation. In an embodiment, the LPMO polypeptide or the enzyme composition comprising the LPMO polypeptide is introduced just after liquefaction and before the fermentation tank or propagation tank. In an embodiment, the LPMO polypeptide or the enzyme composition comprising the LPMO polypeptide is introduced at any point of the mash cooling system. In an embodiment, the LPMO polypeptide or the enzyme composition comprising the LPMO polypeptide is added to a heat exchanger. In an embodiment, the LPMO polypeptide or the enzyme composition comprising the LPMO polypeptide is added to a mixing tank.

In an embodiment, the fermentation product is an alcohol, preferably ethanol.

In an embodiment, the bacterial cells are gram-positive bacteria or gram-negative bacteria cells. In an embodiment, the bacterial cells are *Lactobacillus* cells, or cells that produce lactic acid.

In an aspect, the present invention relates to the use of an LPMO polypeptide or enzyme composition comprising an LPMO polypeptide for reducing the levels of lactic acid during fermentation in an ethanol production process.

In an aspect, the present invention relates to the use of an LPMO polypeptide or enzyme composition comprising an LPMO polypeptide for reducing the levels of lactic acid during yeast propagation.

In an embodiment, the LPMO is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

In an embodiment, the LPMO polypeptide is a AA9 polypeptide selected from the group consisting of: i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

In an embodiment, the LPMO polypeptide is a AA13 polypeptide selected from the group consisting of: i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; vi) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; vii) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; viii) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ix) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; x) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xi) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xii) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xiii) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xiv) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xv) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xvi) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xvii) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xviii) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xix) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xx) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xxi) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xxii) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

DESCRIPTION OF THE INVENTION

Figure 1:
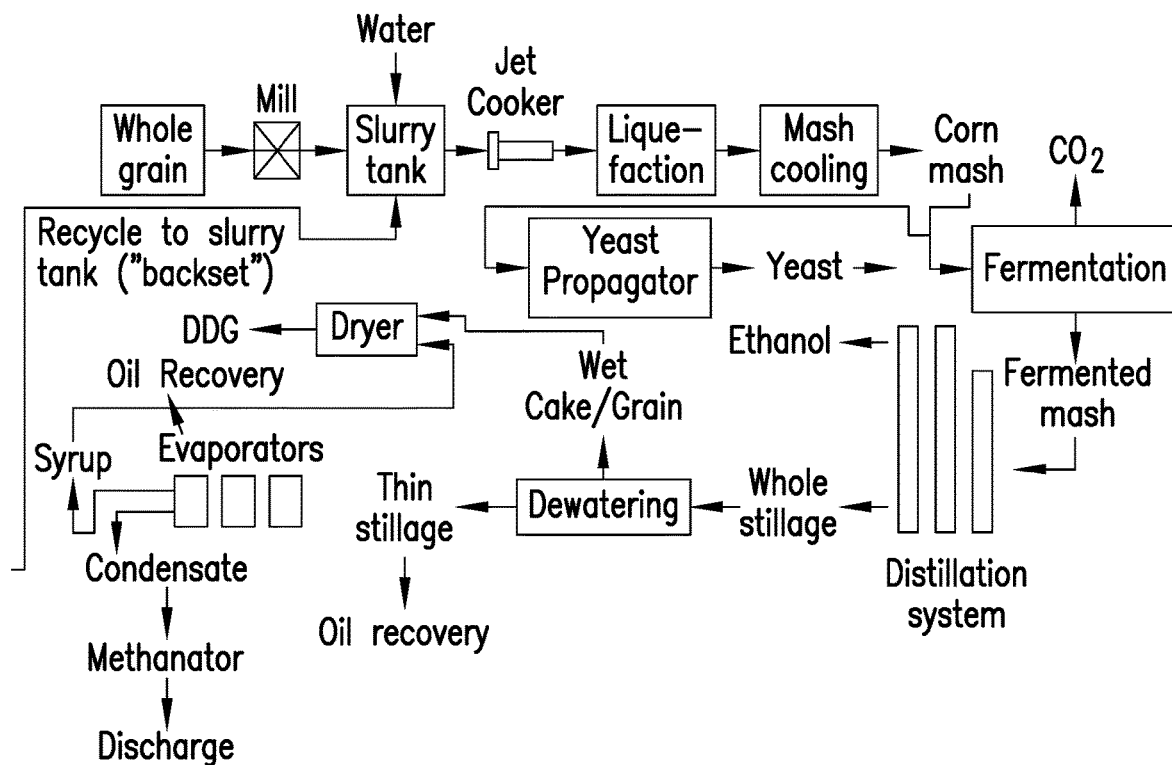
FIG. 1 shows an exemplary dry-grind ethanol production process.

The present invention relates to reducing and/or eliminating bacterial contamination, for instance, in biofuel fermentation systems. The present invention also relates to processes for producing a fermentation product from a starch-containing material using a fermenting organism, wherein at least one lytic polysaccharide monoxyenases (LPMO) is added before and/or during fermentation.

The inventors have surprisingly found that lytic polysaccharide monoxyenases (LPMOs), such as Auxiliary Activity 9 (AA9), are capable of reducing indicator levels of contamination (mainly by lactic acid bacteria) during ethanol fermentation, leading to lower lactic acid titers. Similar results were also demonstrated using certain Auxiliary Activity 13 (AA13) polypeptides. The addition of a LPMO during propagation or fermentation of a contaminated mash also results in increased ethanol yields compared to fermentation of a contaminated mash in the absence of a LPMO. Unexpectedly, LPMOs according to the present disclosure perform equal to or better than antibiotics, such as penicillin, at reducing levels of lactic acid during fermentation.

I. Reducing and/or Eliminating Bacterial Contamination in a Biofuel Fermentation System Accordingly, in an aspect the invention relates to a process for reducing and/or eliminating bacterial contamination in a biofuel fermentation system, the process comprising introducing a lytic polysaccharide monooxygenase (LPMO) polypeptide or an enzyme composition comprising a lytic polysaccharide monooxygenase (LPMO) polypeptide to a biofuel fermentation system. The LPMO polypeptide can be added at a concentration sufficient to inhibit growth of contaminating bacterial cells in the biofuel fermentation system.

The present disclosure contemplates reducing and/or eliminating bacterial contamination due to the presence of variety of types contaminating bacterial cells present in biofuel fermentation systems. In an embodiment, the bacterial cells are gram-positive bacteria or gram-negative bacteria cells. In an embodiment, the contaminating bacterial cells are, but are not limited to, lactic acid and/or acetic acid producing bacteria of the genus *Lactobacillus*, which are known to contaminate fermentation systems. Examples of *Lactobacillus* species that have been found to contaminate fermentation systems include strains of *Lactobacillus collinoides, Lactobacillus brevis, Lactobacillus fermentum, Lactobacillus paracasei, Lactobacillus plantarum,* and/or *Lactobacillus rhamnosus*, and mixtures thereof.

As used herein, the phrase "reducing and/or eliminating bacterial contamination" encompasses the reduction of existing populations of bacterial cells present in the fermentation system, as well as inhibition of bacterial growth. For instance, the LPMO polypeptide or the enzyme composition comprising at least one LPMO polypeptide can reduce the number of bacterial cells present in a fermentation system or inhibit bacterial growth by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100%.

Systems and methods for biofuel fermentation are well known in the art. The fermentation system may include one or more fermentation vessels, pipes, and/or components, which are configured to perform a fermentation product production process, such as the exemplary dry-grind ethanol production process shown in FIG. 1. Those skilled in the art will appreciate that the LPMO polypeptide or enzyme composition comprising the LPMO polypeptide may be introduced into, or prior to, the propagation or fermentation system at a variety of different locations. In an embodiment, at least one of the fermentation vessels in the fermentation system is a fermentation tank and the enzyme composition is introduced into the fermentation tank. In an embodiment, the LPMO polypeptide or enzyme composition comprising the LPMO polypeptide is introduced to the fermentation tank before fermentation begins. In an embodiment, at least one of the fermentation vessels is a yeast propagation tank and the LPMO polypeptide or enzyme composition comprising the LPMO polypeptide is introduced into the yeast propagation tank. In an embodiment, the LPMO polypeptide or enzyme composition comprising the LPMO polypeptide is introduced just after liquefaction and before the fermentation tank or propagation tank. In an embodiment, the LPMO polypeptide or enzyme composition comprising the LPMO polypeptide is introduced at any point of the mash cooling system. In an embodiment, the LPMO polypeptide or enzyme composition comprising the LPMO polypeptide is added to a heat exchanger. In an embodiment, the LPMO polypeptide or enzyme composition comprising the LPMO polypeptide is added to a mixing tank. In an embodiment, the biofuel is an alcohol. In an embodiment, the alcohol is ethanol. In an embodiment, the alcohol is methanol. In an embodiment, the alcohol is butanol.

It is to be understood that any LPMO polypeptide, for instance the LPMO polypeptides described in Section III below, can be used in a composition or process described in this section.

II. Reducing and/or Preventing an Increase in Lactic Acid

In an aspect the invention relates to a process for reducing and/or preventing an increase, in lactic acid in a biofuel fermentation system, the process comprising introducing a LPMO polypeptide or an enzyme composition comprising a lytic polysaccharide monooxygenase (LPMO) polypeptide to a biofuel fermentation system. The LPMO polypeptide or enzyme composition comprising the LPMO polypeptide can be added at a concentration sufficient to reduce and/or prevent an increase in lactic acid in the biofuel fermentation system.

As used herein, the phrase "reducing and/or preventing an increase in lactic acid" encompasses the reduction of existing lactic acid molecules, as well as the addition or build-up of lactic acid molecules in the fermentation system. For instance, an LPMO polypeptide or enzyme composition comprising at least one LPMO can reduce the level of lactic acid in a fermentation system by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100%. In an embodiment, an LPMO polypeptide or enzyme composition comprising at least one LPMO can prevent the increase in the level of lactic acid in a fermentation system by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100% or more.

Systems and methods for biofuel fermentation are well known in the art. The fermentation system may include one or more fermentation vessels, pipes, and/or components, which are configured to perform a fermentation product production process, such as the exemplary dry-grind ethanol production process shown in FIG. 1. Those skilled in the art will appreciate that the LPMO polypeptide or enzyme composition comprising thea LPMO polypeptide may be introduced into the fermentation system at a variety of different locations. In an embodiment, at least one of the fermentation vessels in the fermentation system is a fermentation tank and the LPMO polypeptide or enzyme composition comprising the LPMO polypeptide is introduced into the fermentation tank. In an embodiment, the LPMO polypeptide or enzyme composition comprising the LPMO polypeptide is introduced to the fermentation tank before fermentation begins. In an embodiment, at least one of the fermentation vessels is a yeast propagation tank and the LPMO polypeptide or enzyme composition comprising the LPMO polypeptide is introduced into the yeast propagation tank. In an embodiment, the LPMO polypeptide or enzyme composition comprising the LPMO polypeptide is introduced just after liquefaction and before the fermentation tank or propagation tank In an embodiment, the LPMO polypeptide or enzyme composition comprising the LPMO polypeptide is introduced at any point of the mash cooling system.

In an embodiment, the biofuel is an alcohol. In an embodiment, the alcohol is ethanol. In an embodiment, the alcohol is methanol. In an embodiment, the alcohol is butanol.

It is to be understood that any LPMO polypeptide, for instance the LPMO polypeptides described in Section III below, can be used in a composition or process described in this section.

III. Lytic Polysaccharide Monooxygenases

The present disclosure contemplates processes and compositions comprising any lytic polysaccharide monoxygenases (LPMO) polypeptide that reduces or prevents an increase in lactic acid levels during fermentation and/or reduces the impact of contaminating bacterial cells in a fermentation medium. The term "lytic polysaccharide monooxygenase" or "LPMO" is used synonymously herein with "lytic polyscahharide monooxygenase polypeptide" and "LPMO polypeptide", which refer to an enzyme that oxidizes sp(3) carbons in polysaccharides such as chitin, cellulose, and starch in the presence of an external electron donor and is believed to utilize copper at the active site to activate molecular oxygen. Exemplary LPMOs belong to Auxiliary Activity families AA9, AA10, AA11, and AA13, as defined in the database of carbohydrate active enzymes (http://www.cazy.org/). In an embodiment, the LPMO is selected from the group consisting of Auxiliary Activity 9 (AA9), Auxiliary Activity 10 (AA10), Auxiliary Activity 11 (AA11), Auxiliary Activity 13 (AA13), and combinations thereof.

In an embodiment, the LPMO polypeptide is a AA9 polypeptide. The term "Auxiliary Activity 9 polypeptide" or "AA9 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061). AA9 polypeptides were formerly classified into the glycoside hydrolase Family 61 (GH61) according to Henrissat, 1991, Biochem. J. 280: 309-316, and Henrissat and Bairoch, 1996, Biochem. J. 316: 695-696.

Any AA9 polypeptide can be used as a component of the enzyme composition or used in the processes of the present invention, e.g., bacterial, fungal, archaea, etc.

Examples of AA9 lytic polysaccharide monooxygenases useful in the processes of the present invention include, but are not limited to, AA9 lytic polysaccharide monooxygenases from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/

085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (WO 2011/041397 and WO 2012/000892), *Thermoascus* crustaceous (WO 2011/041504), *Aspergillus aculeatus* (WO 2012/030799), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), *Chaetomium thermophilum* (WO 2012/101206), *Talaromyces thermophilus* (WO 2012/129697 and WO 2012/130950), *Acrophialophora fusispora* (WO 2013/043910), and *Corynascus sepedonium* (WO 2013/043910).

In an embodiment, the AA9 polypeptide is from the genus *Thermoascus*, such as *Thermoascus aurantiacus* or *Thermoascus crustaceus*, for example: the *Thermoascus aurantiacus* AA9 polypeptide of SEQ ID NO: 1, SEQ ID NO: 13, SEQ ID NO: 20, or SEQ ID NO: 22, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Thermoascus crustaceus* AA9 polypeptide of SEQ ID NO: 2, SEQ ID NO: 35, SEQ ID NO: 36, or SEQ ID NO: 37, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Penicillium*, such as *Penicillium emersonii*, for example: the *Penicillium emersonii* AA9 polypeptide of SEQ ID NO: 3 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium pinophilum* AA9 polypeptide of SEQ ID NO: 21, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp. AA9 polypeptide of SEQ ID NO: 23, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Penicillium thomii* AA9 polypeptide of SEQ ID NO: 49, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Thielavia*, such as *Thielavia terrestris*, for example, the *Thielavia terrestris* AA9 polypeptide of SEQ ID NO: 4, SEQ ID NO: 7, SEQ ID NO: 8, SEQ ID NO: 9, SEQ ID NO: 10, SEQ ID NO: 11, SEQ ID NO: 12, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Aspergillus*, such as *Aspergillus fumigatus*, for example: the *Aspergillus fumigatus* AA9 polypeptide of SEQ ID NO: 5 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Aspergillus aculeatus* AA9 polypeptide of SEQ ID NO: 38, SEQ ID NO: 39, SEQ ID NO: 40, SEQ ID NO: 41, SEQ ID NO: 42, SEQ ID NO: 43, or SEQ ID NO: 44, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is the *Penicillium emersonii* AA9 polypeptide of SEQ ID NO: 6 expressed in a *Trichoderma reesei* background, or a variant of SEQ ID NO: 6 having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Trichoderma*, such as *Trichoderma reesei*, for example: the *Trichoderma reesei* AA9 polypeptide of SEQ ID NO: 14 or SEQ ID NO: 84, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Myceliophthora*, such as *Myceliophthora thermophila*, for example: the *Myceliophthora thermophila* AA9 polypeptide of SEQ ID: 15, SEQ ID: 16, SEQ ID: 17, SEQ ID: 18, SEQ ID: 19, SEQ ID: 88, SEQ ID: 93, or SEQ ID: 94, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Aurantiporus*, such as *Aurantiporus alborubescens*, for example, the *Aurantiporus alborubescens* AA9 polypeptide of SEQ ID: 45, or SEQ ID: 46, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Trichophaea*, such as *Trichophaea saccata*, for example, the *Trichophaea saccata* AA9 polypeptide of SEQ ID: 47, or SEQ ID: 48, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Talaromyces*, such as *Talaromyces stipitatus*, for example: the *Talaromyces stipitatus* AA9 polypeptide of SEQ ID: 50, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Talaromyces leycettanus* AA9 polypeptide of SEQ ID NO: 82, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Talaromyces emersonii* AA9 polypeptide of SEQ ID NO: 89, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Talaromyces thermophiles* AA9 polypeptide of SEQ ID NO: 90 or SEQ ID NO: 91, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Thermomyces*, such as *Thermomyces lanuginosus*, for example, the *Thermomyces lanuginosus* AA9 polypeptide of SEQ ID: 52, or SEQ ID: 53, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Humicola*, such as *Humicola insolens*, for example, the *Humicola insolens* AA9 polypeptide of SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO:73, SEQ ID NO: 74, SEQ ID NO: 75, SEQ ID NO: 76, SEQ ID NO:77, SEQ ID NO: 78, SEQ ID NO: 79, or SEQ ID NO: 80, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Malbranchea*, such as *Malbranchea cinnamomea*, for example, the *Malbranchea cinnamomea* AA9 polypeptide of SEQ ID: 81, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Chaetomium*, such as *Chaetomium thermophilum*, for example, the *Chaetomium thermophilum* AA9 polypeptide of SEQ ID: 83, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Acrophialophora*, such as *Acrophialophora fusispora*, for example, the *Acrophialophora fusispora* AA9 polypeptide of SEQ ID: 85, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Corynascus*, such as *Corynascus sepedonium*, for example, the *Corynascus sepedonium* AA9 polypeptide of SEQ ID: 86, or SEQ ID: 87, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is a AA9 variant comprising a substitution at one or more positions corresponding to positions 23, 61, 62, 63, 64, 103, 104, 105, 106, 108, 109, 156, 185, 186, and 194 of the full-length polypeptide of SEQ ID NO: 4 herein, wherein the variant reduces and/or eliminates contaminating bacterial cells in a fermentation medium.

In an embodiment, the AA9 variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94.

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 250 of SEQ ID NO: 4 based on the SignalP program that predicts amino acids 1 to 21 of SEQ ID NO: 4 are a signal peptide. In another aspect, the mature polypeptide is amino acids 20 to 326 of SEQ ID NO: 7 based on the SignalP 3.0 program (Bendtsen et al, 2004, J. Mol. Biol. 340: 783-795) that predicts amino acids 1 to 19 of SEQ ID NO: 7 are a signal peptide. In another aspect, the mature polypeptide is amino acids 18 to 239 of SEQ ID NO: 8 based on the SignalP program that predicts amino acids 1 to 17 of SEQ ID NO: 8 are a signal peptide. In another aspect, the mature polypeptide is amino acids 20 to 258 of SEQ ID NO: 9 based on the SignalP program that predicts amino acids 1 to 19 of SEQ ID NO: 9 are a signal peptide. In another aspect, the mature polypeptide is amino acids 19 to 226 of SEQ ID NO: 10 based on the SignalP program that predicts amino acids 1 to 18 of SEQ ID NO: 10 are a signal peptide. In another aspect, the mature polypeptide is amino acids 20 to 304 of SEQ ID NO: 11 based on the SignalP program that predicts amino acids 1 to 19 of SEQ ID NO: 11 are a signal peptide. In another aspect, the mature polypeptide is amino acids 16 to 317 of SEQ ID NO: 12 based on the SignalP program that predicts amino acids 1 to 15 of SEQ ID NO: 12 are a signal peptide. In another aspect, the mature polypeptide is amino acids 22 to 249 of SEQ ID NO: 13 based on the SignalP program that predicts amino acids 1 to 21 of SEQ ID NO: 13 are a signal peptide. In another aspect, the mature polypeptide is amino acids 20 to 249 of SEQ ID NO: 14 based on the SignalP program that predicts amino acids 1 to 19 of SEQ ID NO: 14 are a signal peptide. In another aspect, the mature polypeptide is amino acids 18 to 232 of SEQ ID NO: 15 based on the SignalP program that predicts amino acids 1 to 17 of SEQ ID NO: 15 are a signal peptide. In another aspect, the mature polypeptide is amino acids 16 to 235 of SEQ ID NO: 16 based on the SignalP program that predicts amino acids 1 to 15 of SEQ ID NO: 16 are a signal peptide. In another aspect, the mature polypeptide is amino acids 19 to 323 of SEQ ID NO: 17 based on the SignalP program that predicts amino acids 1 to 18 of SEQ ID NO: 17 are a signal peptide. In another aspect, the mature polypeptide is amino acids 16 to 310 of SEQ ID NO: 18 based on the SignalP program that predicts amino acids 1 to 15 of SEQ ID NO: 18 are a signal peptide. In another aspect, the mature polypeptide is amino acids 20 to 246 of SEQ ID NO: 19 based on the SignalP program that predicts amino acids 1 to 19 of SEQ ID NO: 19 are a signal peptide. In another aspect, the mature polypeptide is amino acids 22 to 354 of SEQ ID NO: 20 based on the SignalP program that predicts amino acids 1 to 21 of SEQ ID NO: 20 are a signal peptide. In another aspect, the mature polypeptide is amino acids 22 to 322 of SEQ ID NO: 21 based on the SignalP program that predicts amino acids 1 to 21 of SEQ ID NO: 21 are a signal peptide. In another aspect, the mature polypeptide is amino acids 24 to 444 of SEQ ID NO: 22 based on the SignalP program that predicts amino acids 1 to 23 of SEQ ID NO: 22 are a signal peptide. In another aspect, the mature polypeptide is amino acids 26 to 253 of SEQ ID NO: 23 based on the SignalP program that predicts amino acids 1 to 25 of SEQ ID NO: 23 are a signal peptide. In another aspect, the mature polypeptide is amino acids 18 to 246 of SEQ ID NO: 24 based on the SignalP program that predicts amino acids 1 to 17 of SEQ ID NO: 24 are a signal peptide. In another aspect, the mature polypeptide is amino acids 20 to 334 of SEQ ID NO: 25 based on the SignalP program that predicts amino acids 1 to 19 of SEQ ID NO: 25 are a signal peptide. In another aspect, the mature polypeptide is amino acids 18 to 227 of SEQ ID NO: 26 based on the SignalP program that predicts amino acids 1 to 17 of SEQ ID NO: 26 are a signal peptide. In another aspect, the mature polypeptide is amino acids 20 to 223 of SEQ ID NO: 27 based on the SignalP program that predicts amino acids 1 to 19 of SEQ ID NO: 27 are a signal peptide. In another aspect, the mature polypeptide is amino acids 22 to 368 of SEQ ID NO: 28 based on the SignalP program that predicts amino acids 1 to 21 of SEQ ID NO: 28 are a signal peptide. In another aspect, the mature polypeptide is amino acids 25 to 330 of SEQ ID NO: 29 based on the SignalP program that predicts amino acids 1 to 24 of SEQ ID NO: 29 are a signal peptide. In another aspect, the mature polypeptide is amino acids 17 to 236 of SEQ ID NO: 30 based on the SignalP program that predicts amino acids 1 to 16 of SEQ ID NO: 30 are a signal peptide. In another aspect, the mature polypeptide is amino acids 19 to 250 of SEQ ID NO: 31 based on the SignalP program that predicts amino acids 1 to 18 of SEQ ID NO: 31 are a signal peptide. In another aspect, the mature polypeptide is amino acids 23 to 478 of SEQ ID NO: 32 based on the SignalP program that predicts amino acids 1 to 22 of SEQ ID NO: 32 are a signal peptide. In another aspect, the mature polypeptide is amino acids 17 to 230 of SEQ ID NO: 33 based on the SignalP program that predicts amino acids 1 to 16 of SEQ ID NO: 33 are a signal peptide. In another aspect, the mature polypeptide is amino acids 20 to 257 of SEQ ID NO: 34 based on the SignalP program that predicts amino acids 1 to 19 of SEQ ID NO: 34 are a signal peptide. In another aspect, the mature polypeptide is amino acids 23 to 251 of SEQ ID NO: 35 based on the SignalP program that predicts amino acids 1 to 22 of SEQ ID NO: 35 are a signal peptide. In another aspect, the mature polypeptide is amino acids 19 to 349 of SEQ ID NO: 36 based on the SignalP program that predicts amino acids 1 to 18 of SEQ ID NO: 36 are a signal peptide. In another aspect, the mature polypeptide is amino acids 24 to 436 of SEQ ID NO: 37 based on the SignalP program that predicts amino acids 1 to 23 of SEQ ID NO: 37 are a signal peptide. In another aspect, the mature polypeptide is amino acids 21 to 344 of SEQ ID NO: 38 based on the SignalP program that predicts amino acids 1 to 23 of SEQ ID NO: 38 are a signal peptide. In another aspect, the mature polypeptide is amino acids 26 to 400 of SEQ ID NO: 39 based on the SignalP program that predicts amino acids 1 to 25 of SEQ ID NO: 39 are a signal peptide. In another aspect, the mature polypeptide is amino acids 21 to 389 of SEQ ID NO: 40 based on the SignalP program that predicts amino acids 1 to 20 of SEQ ID NO: 40 are a signal peptide. In another aspect, the mature polypeptide is amino acids 22 to 406 of SEQ ID NO: 41 based on the SignalP program that predicts amino acids 1 to 21 of SEQ ID NO: 41 are a signal peptide. In another aspect, the mature polypeptide is amino acids 20 to 427 of SEQ ID NO: 42 based on the SignalP program that predicts amino acids 1 to 19 of SEQ ID NO: 42 are a signal peptide. In another aspect, the mature polypeptide is amino acids 18 to 267 of SEQ ID NO: 43 based on the SignalP program that predicts amino acids 1 to 17 of SEQ ID NO: 43 are a signal peptide. In another aspect, the mature polypeptide is amino acids 21 to 273 of SEQ ID NO: 44 based on the SignalP program that predicts amino acids 1 to 20 of SEQ ID NO: 44 are a signal peptide. In another aspect, the mature polypeptide is amino acids 21 to 322 of SEQ ID NO: 45 based on the SignalP program that predicts amino acids 1 to 20 of SEQ ID NO: 45 are a signal peptide. In another aspect, the mature polypeptide is amino acids 18 to 234 of SEQ ID NO: 46 based on the SignalP program that predicts amino acids 1 to 17 of SEQ ID NO: 46 are a signal peptide. In another aspect, the mature polypeptide is amino acids 24 to 233 of SEQ ID NO: 47 based on the SignalP program that predicts amino acids 1 to 23 of SEQ ID NO: 47 are a signal peptide. In another aspect, the mature polypeptide is amino acids 17 to 237 of SEQ ID NO: 48 based on the SignalP program that predicts amino acids 1 to 16 of SEQ ID NO: 48 are a signal peptide. In another aspect, the mature polypeptide is amino acids 20 to 484 of SEQ ID NO: 49 based on the SignalP program that predicts amino acids 1 to 19 of SEQ ID NO: 49 are a signal peptide. In another aspect, the mature polypeptide is amino acids 22 to 320 of SEQ ID NO: 50 based on the SignalP program that predicts amino acids 1 to 21 of SEQ ID NO: 50 are a signal peptide. In another aspect, the mature polypeptide is amino acids 23 to 272 of SEQ ID NO: 51 based on the SignalP program that predicts amino acids 1 to 22 of SEQ ID NO: 51 are a signal peptide. In another aspect, the mature polypeptide is amino acids 22 to 327 of SEQ ID NO: 52 based on the SignalP program that predicts amino acids 1 to 21 of SEQ ID NO: 52 are a signal peptide. In another aspect, the mature polypeptide is amino acids 23 to 274 of SEQ ID NO: 53 based on the SignalP program that predicts amino acids 1 to 22 of SEQ ID NO: 53 are a signal peptide. In another aspect, the mature polypeptide is amino acids 18 to 227 of SEQ ID NO: 54 based on the SignalP program that predicts amino acids 1 to 17 of SEQ ID NO: 54 are a signal peptide. In another aspect, the mature polypeptide is amino acids 17 to 257 of SEQ ID NO: 55 based on the SignalP program that predicts amino acids 1 to 16 of SEQ ID NO: 55 are a signal peptide. In another aspect, the mature polypeptide is amino acids 20 to 246 of SEQ ID NO: 56 based on the SignalP program that predicts amino acids 1 to 19 of SEQ ID NO: 56 are a signal peptide. In another aspect, the mature polypeptide is amino acids 28 to 265 of SEQ ID NO: 57 based on the SignalP program that predicts amino acids 1 to 27 of SEQ ID NO: 57 are a signal peptide. In another aspect, the mature polypeptide is amino acids 16 to 310 of SEQ ID NO: 58 based on the SignalP program that predicts amino acids 1 to 15 of SEQ ID NO: 58 are a signal peptide. In another aspect, the mature polypeptide is amino acids 21 to 354 of SEQ ID NO: 59 based on the SignalP program that predicts amino acids 1 to 20 of SEQ ID NO: 59 are a signal peptide. In another aspect, the mature polypeptide is amino acids 22 to 267 of SEQ ID NO: 60 based on the SignalP program that predicts amino acids 1 to 21 of SEQ ID NO: 60 are a signal peptide. In another aspect, the mature polypeptide is amino acids 16 to 237 of SEQ ID NO: 61 based on the SignalP program that predicts amino acids 1 to 15 of SEQ ID NO: 61 are a signal peptide. In another aspect, the mature polypeptide is amino acids 20 to 234 of SEQ ID NO: 62 based on the SignalP program that predicts amino acids 1 to 19 of SEQ ID NO: 62 are a signal peptide. In another aspect, the mature polypeptide is amino acids 18 to 226 of SEQ ID NO: 63 based on the SignalP program that predicts amino acids 1 to 17 of SEQ ID NO: 63 are a signal peptide. In another aspect, the mature polypeptide is amino acids 17 to 231 of SEQ ID NO: 64 based on the SignalP program that predicts amino acids 1 to 16 of SEQ ID NO: 64 are a signal peptide. In another aspect, the mature polypeptide is amino acids 22 to 248 of SEQ ID NO: 65 based on the SignalP program that predicts amino acids 1 to 21 of SEQ ID NO: 65 are a signal peptide. In another aspect, the mature polypeptide is amino acids 18 to 233 of SEQ ID NO: 66 based on the SignalP program that predicts amino acids 1 to 17 of SEQ ID NO: 66 are a signal peptide. In another aspect, the mature polypeptide is amino acids 21 to 243 of SEQ ID NO: 67 based on the SignalP program that predicts amino acids 1 to 20 of SEQ ID NO: 67 are a signal peptide. In another aspect, the mature polypeptide is amino acids 21 to 363 of SEQ ID NO: 68 based on the SignalP program that predicts amino acids 1 to 20 of SEQ ID NO: 68 are a signal peptide. In another aspect, the mature polypeptide is amino acids 20 to 296 of SEQ ID NO: 69 based on the SignalP program that predicts amino acids 1 to 19 of SEQ ID NO: 69 are a signal peptide. In another aspect, the mature polypeptide is amino acids 16 to 318 of SEQ ID NO: 70 based on the SignalP program that predicts amino acids 1 to 15 of SEQ ID NO: 70 are a signal peptide. In another aspect, the mature polypeptide is amino acids 19 to 259 of SEQ ID NO: 71 based on the SignalP program that predicts amino acids 1 to 18 of SEQ ID NO: 71 are a signal peptide. In another aspect, the mature polypeptide is amino acids 20 to 325 of SEQ ID NO: 72 based on the SignalP program that predicts amino acids 1 to 19 of SEQ ID NO: 72 are a signal peptide. In another aspect, the mature polypeptide is amino acids 19 to 298 of SEQ ID NO: 74 based on the SignalP program that predicts amino acids 1 to 18 of SEQ ID NO: 74 are a signal peptide. In another aspect, the mature polypeptide is amino acids 20 to 298 of SEQ ID NO: 74 based on the SignalP program that predicts amino acids 1 to 19 of SEQ ID NO: 74 are a signal peptide. In another aspect, the mature polypeptide is amino acids 22 to 344 of SEQ ID NO: 75 based on the SignalP program that predicts amino acids 1 to 21 of SEQ ID NO: 75 are a signal peptide. In another aspect, the mature polypeptide is amino acids 20 to 330 of SEQ ID NO: 76 based on the SignalP program that predicts amino acids 1 to 19 of SEQ ID NO: 76 are a signal peptide. In another aspect, the mature polypeptide is amino acids 19 to 216 of SEQ ID NO: 77 based on the SignalP program that predicts amino acids 1 to 18 of SEQ ID NO: 77 are a signal peptide. In another aspect, the mature polypeptide is amino acids 18 to 490 of SEQ ID NO: 78 based on the SignalP program that predicts amino acids 1 to 17 of SEQ ID NO: 78 are a signal peptide. In another aspect, the mature polypeptide is amino acids 21 to 306 of SEQ ID NO: 79 based on the SignalP program that predicts amino acids 1 to 20 of SEQ ID NO: 79 are a signal peptide. In another aspect, the mature polypeptide is amino acids 22 to 339 of SEQ ID NO: 80 based on the SignalP program that predicts amino acids 1 to 21 of SEQ ID NO: 80 are a signal peptide. In another aspect, the mature polypeptide is amino acids 23 to 334 of SEQ ID NO: 81 based on the SignalP program that predicts amino acids 1 to 22 of SEQ ID NO:

81 are a signal peptide. In another aspect, the mature polypeptide is amino acids 24 to 366 of SEQ ID NO: 82 based on the SignalP program that predicts amino acids 1 to 23 of SEQ ID NO: 82 are a signal peptide. In another aspect, the mature polypeptide is amino acids 21 to 364 of SEQ ID NO: 83 based on the SignalP program that predicts amino acids 1 to 20 of SEQ ID NO: 83 are a signal peptide. In another aspect, the mature polypeptide is amino acids 22 to 344 of SEQ ID NO: 84 based on the SignalP program that predicts amino acids 1 to 21 of SEQ ID NO: 84 are a signal peptide. In another aspect, the mature polypeptide is amino acids 20 to 252 of SEQ ID NO: 85 based on the SignalP program that predicts amino acids 1 to 19 of SEQ ID NO: 85 are a signal peptide. In another aspect, the mature polypeptide is amino acids 20 to 344 of SEQ ID NO: 86 based on the SignalP program that predicts amino acids 1 to 19 of SEQ ID NO: 86 are a signal peptide. In another aspect, the mature polypeptide is amino acids 22 to 347 of SEQ ID NO: 87 based on the SignalP program that predicts amino acids 1 to 21 of SEQ ID NO: 87 are a signal peptide. In another aspect, the mature polypeptide is amino acids 20 to 342 of SEQ ID NO: 88 based on the SignalP program that predicts amino acids 1 to 19 of SEQ ID NO: 88 are a signal peptide. In another aspect, the mature polypeptide is amino acids 27 to 254 of SEQ ID NO: 89 based on the SignalP program that predicts amino acids 1 to 26 of SEQ ID NO: 89 are a signal peptide. In another aspect, the mature polypeptide is amino acids 23 to 272 of SEQ ID NO: 90 based on the SignalP program that predicts amino acids 1 to 22 of SEQ ID NO: 90 are a signal peptide. In another aspect, the mature polypeptide is amino acids 23 to 272 of SEQ ID NO: 91 based on the SignalP program that predicts amino acids 1 to 22 of SEQ ID NO: 91 are a signal peptide. In another aspect, the mature polypeptide is amino acids 19 to 381 of SEQ ID NO: 128 based on the SignalP program that predicts amino acids 1 to 18 of SEQ ID NO: 128 are a signal peptide. In another aspect, the mature polypeptide is amino acids amino acids 22 to 386 of SEQ ID NO: 130 based on the SignalP program that predicts amino acids 1 to 21 of SEQ ID NO: 130 are a signal peptide. In another aspect, the mature polypeptide is amino acids 20 to 387 of SEQ ID NO: 131 based on the SignalP program that predicts amino acids 1 to 19 of SEQ ID NO: 131 are a signal peptide. In another aspect, the mature polypeptide is amino acids 19 to 253 of SEQ ID NO: 132 based on the SignalP program that predicts amino acids 1 to 18 of SEQ ID NO: 132 are a signal peptide. In another aspect, the mature polypeptide is amino acids 19 to 377 of SEQ ID NO: 133 based on the SignalP program that predicts amino acids 1 to 18 of SEQ ID NO: 133 are a signal peptide. In another aspect, the mature polypeptide is amino acids 18 to 388 of SEQ ID NO: 134 based on the SignalP program that predicts amino acids 1 to 17 of SEQ ID NO: 134 are a signal peptide. In another aspect, the mature polypeptide is amino acids 19 to 391 of SEQ ID NO: 135 based on the SignalP program that predicts amino acids 1 to 18 of SEQ ID NO: 135 are a signal peptide. In another aspect, the mature polypeptide is amino acids 19 to 387 of SEQ ID NO: 136 based on the SignalP program that predicts amino acids 1 to 18 of SEQ ID NO: 136 are a signal peptide. In another aspect, the mature polypeptide is amino acids 19 to 390 of SEQ ID NO: 139 based on the SignalP program that predicts amino acids 1 to 18 of SEQ ID NO: 139 are a signal peptide. In another aspect, the mature polypeptide is amino acids 19 to 386 of SEQ ID NO: 141 based on the SignalP program that predicts amino acids 1 to 18 of SEQ ID NO: 141 are a signal peptide. In another aspect, the mature polypeptide is amino acids 19 to 394 of SEQ ID NO: 144 based on the SignalP program that predicts amino acids 1 to 18 of SEQ ID NO: 144 are a signal peptide. In another aspect, the mature polypeptide is amino acids 19 to 391 of SEQ ID NO: 145 based on the SignalP program that predicts amino acids 1 to 18 of SEQ ID NO: 145 are a signal peptide. In another aspect, the mature polypeptide is amino acids 16 to 393 of SEQ ID NO: 148 based on the SignalP program that predicts amino acids 1 to 15 of SEQ ID NO: 148 are a signal peptide. In another aspect, the mature polypeptide is amino acids 18 to 382 of SEQ ID NO: 149 based on the SignalP program that predicts amino acids 1 to 17 of SEQ ID NO: 149 are a signal peptide. In another aspect, the mature polypeptide is amino acids 18 to 379 of SEQ ID NO: 150 based on the SignalP program that predicts amino acids 1 to 17 of SEQ ID NO: 150 are a signal peptide. In another aspect, the mature polypeptide is amino acids 19 to 383 of SEQ ID NO: 151 based on the SignalP program that predicts amino acids 1 to 18 of SEQ ID NO: 151 are a signal peptide. It is known in the art that a host cell may produce a mixture of two of more different mature polypeptides (i.e., with a different C-terminal and/or N-terminal amino acid) expressed by the same polynucleotide.

In an embodiment, the AA9 polypeptide is the mature AA9 polypeptide of any one of SEQ ID NOs: 1-91, or a variant of any of SEQ ID NOs: 1-91 having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the LPMO polypeptide is a AA10 polypeptide. The term "Auxiliary Activity 10 polypeptide" or "AA10 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061). The AA10 may comprise a CBM33 domain comprising a carbohydrate-binding module (CBM), which is defined as a contiguous amino acid sequence within a carbohydrate binding protein with a discreet fold having carbohydrate-binding activity. For example, chitinases are known which contain one or more chitin binding modules in addition to catalytic regions. ChiA of *Serratia marcescens* contains a fibronectin type III-type CBM, ChiB of *Serratia marcescens* contains a family 5 CBM and ChiC of *Serratia marcescens* contains a family 12 and a fibronectin type III-like CBM. See Bourne and Henrissat, 2001, Curr. Opin. Struct. Biol. 11: 593 for domain nomenclature. Likewise, many cellulases contain CBMs that bind to cellulose. Proteins binding to chitin and containing CBMs that stimulate such binding may for example be structural or signaling molecules or they can be enzymes and the overall function of the protein may be determined by domains that are present in addition to the carbohydrate binding module.

Any AA10 polypeptide can be used as a component of the enzyme composition or used in the processes of the present invention, e.g., bacterial, fungal, archaea, etc. AA10 polypeptides of use herein may be identified according to the CAZY classification system (cazy.org/CAZY/fam/acc_CBM.html), which is based on sequence similarities (Davies and Henrissat, 2002, Biochem Soc T 30: 291-297 and Bourne and Henrissat, 2001, supra). Proteins in this family are known to bind to chitin, but binding to other polysaccharides, including cellulose, has also been observed (Moser et al., 2008, *Biotechnol. Bioeng.* 100(6):1066-77). For some of these proteins it has been shown that they act synergistically with chitinases and cellulases in the degradation of chitin and cellulose, respectively (Vaaje-Kolstad et al., 2005, *J. Biol. Chem.* 280(31): 28492-7; Vaaje-Kolstad et al., 2009, *FEBS J.* 276(8):2402-15).

AA10 polypeptides contain a family 33 carbohydrate binding module (CBM33). In several cases, the CBM33 module makes up the whole protein, i.e., the protein consists of or consists essentially of a single family 33 CBM, which is in nature synthesized and secreted as such. However some family 33 CBMs may be fused to one or more additional non-catalytic carbohydrate binding modules (e.g., CBM family 2, CBM family 3 and CBM family 5 modules). These proteins are bi- or multi-domain proteins. There is also one known example of a family 33 carbohydrate binding module that is present as an individual module within a much larger catalytic protein. This is the beta-1,4-mannanase protein of *Caldibacillus cellulovorans* (Sunna et al., 2000, Appl. Environ. Micro. 66(2): 664-670).

The family 33 CBMs are usually approximately 150-250 amino acids, e.g., 160-240, 170-230, 180-220, 190-210 amino acids in size and have a molecular weight of approximately 20 kDa, preferably 19-21 kDa, 18-21 kDa, 19-22 kDa or 18-20 kDa in size, though CBM33 domains as large as 300-400 amino acids with a molecular weight of approximately 30-40 kDa may also be used. The size of a protein can readily be determined by standard methods that are known in the art.

Preferably, the AA10 polypeptide consists of a single family 33 CBM, or consists essentially of a family 33 CBM. If said AA10 polypeptide "consists essentially of" a family 33 CBM, it is meant that additional amino acids may be present in the protein, in addition to those that make up the family 33 CBM. Preferably there are 1-3, 1-5, 1-10, 10-20, 20-30, 30-40, 40-50, 50-60, 60-70, 70-80, 80-90 or 90-100 or more additional amino acids present. These additional amino acids are in general present C terminal to the family 33 CBM.

Alternatively, the AA10 polypeptide can comprise a family 33 CBM. Additional modules or domains may thus be present in the protein. Examples of such modules are CBM family 2, CBM family 3 and CBM family 5 modules. If additional domains or modules are present, they are in general found C-terminal to the family 33 CBM.

Thus in a preferred aspect, the AA10 polypeptide can contain, consist or consist essentially of a naturally occurring family 33 CBM (or CBM33 family protein) such as CBP21 (or to a homologue thereof from another species) or a biologically active fragment thereof. It can alternatively contain, consist or consist essentially of a variant of a naturally occurring family 33 CBM (or CBM33 family protein) or a biologically active fragment thereof.

AA10 polypeptides which comprise or consist of a family 33 CBM module or the full family 33 CBM protein (which comprises the family 33 CBM module) or its fragments or variants are referred to herein, collectively, as CBM33 proteins or CBM33 family members or proteins. Naturally occurring CBM33 proteins that can be used in the invention include microbial (e.g., bacterial), eukaryotic (e.g., Dictyostelium) or viral CBM33 proteins. Bacterial CBM33 proteins are, however, preferred.

Examples of known CBM33 proteins which may be used in the compositions and methods of the invention and relevant database accession numbers (which are hereby incorporated by reference) are set out in Table 1 of WO 2012/019151 (incorporated herein by reference in its entirety).

Bacterial CBM33 proteins can be from any appropriate source but are preferably from a genus selected from the group consisting of *Bacillus, Chromobacterium, Enterococcus, Francisella, Hahella, Lactobacillus, Lactococcus, Legionella, Listeria, Oceanobacillus, Photobacterium, Photothabdus, Proteus, Pseudoalteromonas, Pseudomonas, Rickettsia, Saccharophagus, Salinvibrio, Serratia, Shewanella, Sodalis, Streptomyces, Thermobifida, Vibrio* and *Yersini* and optionally *Cellulomonas* and *Cellvibrio*.

In an embodiment, the CBM33 protein is a CBP21 as described in U.S. Patent Application No. 2007/0218046 which is incorporated herein by reference. For example the CBP21 of *Serratia* marescens (SEQ ID NO: 4 in WO2012/019151) may be used. Alternatively, the EfCBM33 of *Enterococcus faecalis* (SEQ ID NO: 5 in WO2012/019151), E7 of *Thermobifida fusca* (SEQ ID NO: 6 in WO2012/019151), CelS2 of *Streptomyces coelicolor*A3(2) (SEQ ID NO: 7 in WO2012/019151), Cfla_0175 of *Cellulomonas flavigena* DSM 20109) (SEQ ID NO: 8 in WO2012/019151), Cfla_0172 of *Cellulomonas flavigena* DSM 20109) (SEQ ID NO: 9), Cfla_0316 of *Cellulomonas flavigena* DSM 20109) (SEQ ID NO: 10 in WO2012/019151), Cfla_0490 of *Cellulomonas flavigena* DSM 20109) (SEQ ID NO: 11 in WO2012/019151), CJA_2191 (Cbp33A) of *Cellvibrio japonicus* Ueda107 (SEQ ID NO: 12 in WO2012/019151), CJA_3139 (Cbp33/10B) of *Cellvibrio japonicus* Ueda107 (SEQ ID NO: 13 in WO2012/019151) and SC01734 of *Streptomyces coelicolar* A3(2)) (SEQ ID NO: 14 in WO2012/019151), may be used. ChbA of *B. amyloliquefaciens* (Chu et al., 2001, Microbiology 147 (Pt 7):1793-803) CHB1, 2 and 3 of *Streptomyces* (Svergun et al., 2000, Biochemistry 39(35):10677-83, Zeltins et al., 1997, *Eur. J. Biochem.* 246(2):557-64, Zeltins et al., 1995, *Anal. Biochem.* 231(2):287-94, Schnellmann et al., 1994, Mol. Microbiol. 13(5):807-19; Kolbe et al., 1998, *Microbiology* 144 (Pt 5):1291-7; Saito et al., 2001, *Appl. Environ. Microbiol.* 67(3):1268-73) and CBP1 of *Alteramonas* (Tsujibo et al., 2002, *Appl. Environ. Microbiol.* 68:263-270) are also preferred CBM33 proteins for use in the invention. All of these references are incorporated herein by reference.

The AA10 polypeptides can thus be or correspond to or comprise a naturally occurring CBM33 family protein (such as CBP21, EfCBM33, ChbA, CHB1, 2 and 3 and CBP1 or E7, CelS2, Cfla_0175, Cfla_0172, Cfla_0316, Cfla_0490, CJA_2191 (Cbp33A), CJA_3139 (Cbp33/10B) and SC01734) that it is found in nature or a biologically active fragment thereof. In the alternative the AA10 polypeptide may be a non-native variant.

In an embodiment, the AA10 polypeptide is from the genus *Streptomyces*, such as *Streptomyces coelicolor*, or another *Streptomyces* sp., for example: the *Streptomyces coelicolor* AA10 polypeptide of SEQ ID NO: 114, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Streptomyces* sp. AA10 polypeptide of SEQ ID NO: 115, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA10 polypeptide is the polypeptide of SEQ ID NO: 116, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In an embodiment, the AA10 polypeptide is the polypeptide of SEQ ID NO: 116, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but not 100%, sequence identity thereto.

In an embodiment, the AA10 polypeptide is the polypeptide of SEQ ID NO: 117, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In an embodiment, the AA10 polypeptide is the polypeptide of SEQ ID NO: 117, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but not 100%, sequence identity thereto.

In an embodiment, the LPMO polypeptide is a AA11 polypeptide. The term "Auxiliary Activity 11 polypeptide" or "AA11 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061).

Any AA11 polypeptide can be used as a component of the enzyme composition or used in the processes of the present invention, e.g., bacterial, fungal, archaea, etc. In an embodiment, the AA11 polypeptide is of fungal origin. Exemplary AA11 polypeptides suitable for use in the compositions and processes herein are from the genera *Aspergillus*, such as, *A. niger, A. nidulans, A. terreus, A. clavatus, A. oryzae* or *A. flavus, Neurospora*, such as *N. crassa* or *N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces*, and *Myceliophthora*.

In an embodiment, the AA11 polypeptide is from the genus *Acremonium*, such as *Acremonium alcalophilum*, for example the *Acremonium alcalophilum* AA10 polypeptide of SEQ ID NO: 118, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto. In an embodiment, the AA11 polypeptide is the *Acremonium alcalophilum* AA10 polypeptide of SEQ ID NO: 118.

In an embodiment, the LPMO polypeptide is a AA13 polypeptide. The term "Auxiliary Activity 13 polypeptide" or "AA13 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061).

Any AA13 polypeptide can be used as a component of the enzyme composition or used in the processes of the present invention, e.g., bacterial, fungal, archaea, etc. In an embodiment, the AA13 polypeptide is of fungal origin. Exemplary AA13 polypeptides suitable for use in the compositions and processes herein are from the genera *Aspergillus*, such as, *A. niger, A. nidulans, A. terreus, A. clavatus, A. oryzae* or *A. flavus, Neurospora*, such as *N. crassa* or *N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces*, and *Myceliophthora*.

In an embodiment, the AA13 polypeptide is from the genus *Aspergillus*, such as *Aspergillus terreus, Aspergillus lentulus, Aspergillus fischerianus, Aspergillus nidulans, Aspergillus insuetus*, etc., for example: the *Aspergillus terreus* AA13 polypeptide of SEQ ID NO: 119, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus lentulus* AA13 polypeptide of SEQ ID NO: 120 or SEQ ID NO: 121, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus fischerianus* AA13 polypeptide of SEQ ID NO: 122, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus nidulans* AA13 polypeptide of SEQ ID NO: 123, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Aspergillus insuetus* AA13 polypeptide of SEQ ID NO: 130, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 22 to 386 of SEQ ID NO: 130 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Penicillium*, such as *Penicillium polonicum*, *Penicillium oxalicum*, *Penicillium arizonense*, etc., for example: the *Penicillium polonicum* AA13 polypeptide of SEQ ID NO: 124 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium oxalicum* AA13 polypeptide of SEQ ID NO: 125, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium arizonense* AA13 polypeptide of SEQ ID NO: 126, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium antarcticum* AA13 polypeptide of SEQ ID NO: 135, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium concentricum* AA13 polypeptide of SEQ ID NO: 136, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium hoeksii* AA13 polypeptide of SEQ ID NO: 137, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium paxiffi* AA13 polypeptide of SEQ ID NO: 138, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium roseopurpureum* AA13 polypeptide of SEQ ID NO: 139, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium samsonianum* AA13 polypeptide of SEQ ID NO: 140, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium sclerotiorum* AA13 polypeptide of SEQ ID NO: 141, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-52627 AA13 polypeptide of SEQ ID NO: 142, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-54569 AA13 polypeptide of SEQ ID NO: 143, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-72443 AA13 polypeptide of SEQ ID NO: 144, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium steckii* AA13 polypeptide of SEQ ID NO: 145, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium viticola* AA13 polypeptide of SEQ ID NO: 146, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Penicillium*

*vulpinum* AA13 polypeptide of SEQ ID NO: 147, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 391 of SEQ ID NO: 135, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 387 of SEQ ID NO: 136, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 390 of SEQ ID NO: 139, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 386 of SEQ ID NO: 141, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 394 of SEQ ID NO: 144, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 391 of SEQ ID NO: 145, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Mycothermus*, such as *Mycothermus thermophilus*, for example, the *Mycothermus thermophilus* AA13 polypeptide of SEQ ID NO: 127, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Acremonium*, such as *Acremonium* sp. XZ1982, for example, the *Acremonium* sp. XZ1982AA13 AA13 polypeptide of SEQ ID NO: 128, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto. In an embodiment, the AA13 polypeptide is amino acids 19 to 381 of SEQ ID NO: 128, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Acrostalagmus*, such as *Acrostalagmus luteoalbus*, for example, the *Acrostalagmus luteoalbus* AA13 polypeptide of SEQ ID NO: 129, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Cladosporium*, such as *Cladosporium gossypiicola*, for example, the *Cladosporium gossypiicola* AA13 polypeptide of SEQ ID NO: 131, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 20 to 387 of SEQ ID NO: 131, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Fusarium*, such as *Fusarium* sp-75363, for example, the *Fusarium* sp-75363 AA13 polypeptide of SEQ ID NO: 132, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 253 of SEQ ID NO: 132, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Myrothecium*, such as *Myrothecium* sp., for example, the *Myrothecium* sp AA13 polypeptide of SEQ ID NO: 133, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 377 of SEQ ID NO: 133, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Paraphoma*, such as *Paraphoma* sp., for example, the *Paraphoma* sp. AA13 polypeptide of SEQ ID NO: 134, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 388 of SEQ ID NO: 134, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Pestalotiopsis*, such as *Pestalotiopsis* sp-71627, for example, the *Pestalotiopsis* sp-71627 AA13 polypeptide of SEQ ID NO: 148, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 16 to 393 of SEQ ID NO: 148, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Setophaeosphaeria*, such as *Setophaeosphaeria* sp. NN051506, for example, the *Setophaeosphaeria* sp. NN051506AA13 AA13 polypeptide of SEQ ID NO: 149, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 382 of SEQ ID NO: 149, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Talaromyces*, such as *Talaromyces sayulitensis*, for example, the *Talaromyces sayulitensis* AA13 polypeptide of SEQ ID NO: 150, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 379 of SEQ ID NO: 150, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Trichocladium*, such as *Trichocladium asperum*, for example, the *Trichocladium asperum* AA13 polypeptide of SEQ ID NO: 151, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 383 of SEQ ID NO: 151, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

IV. Enzyme Compositions

The present invention also relates to compositions comprising at least one lytic polysaccharide monooxygenase (LPMO) polypeptide of the present invention. Preferably, the compositions are enriched in the at least one LPMO polypeptide of the invention. The term "enriched" indicates that the activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the composition comprises at least one, at least two, at least three, or at least four LPMO polypeptides of the invention.

The compositions may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, glucan 1,4-a-glucosidase, glucan 1,4-alpha-maltohydrolase, glucan 1,4-a-glucosidase, glucan 1,4-alpha-maltohydrolase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

IV. Processes for Producing Fermentation Products

The invention also relates to processes for producing a fermentation product from starch-containing material using a fermenting organism, wherein a lytic polysaccharide monooxygenase (LPMO) or an enzyme composition comprising at least one lytic polysaccharide monooxygenase (LPMO) is added before and/or during saccharification and/or fermentation.

Processes for Producing Fermentation Products from Un-Gelatinized Starch-Containing Material In an aspect, the invention relates to processes for producing fermentation products from starch-containing material without gelatinization (i.e., without cooking) of the starch-containing material (often referred to as a "raw starch hydrolysis" process), wherein at least one lytic polysaccharide monooxygenase is added. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a variant protease of the invention. Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;

wherein step (i) and/or (ii) is carried out using at least a glucoamylase and at least one LPMO polypeptide of the invention or an enzyme composition comprising at least one LPMO polypeptide of the invention. In an embodiment, said at least one LPMO polypeptide or enzyme composition comprising an LPMO polypeptide is added at a concentration sufficient to inhibit growth of contaminating bacterial cells. In an embodiment, said at least one LPMO or enzyme composition comprising at least one LPMO polypeptide is added at a concentration sufficient to reduce the levels of lactic acid during saccharification, fermentation, and/or simultaneous saccharification or fermentation (SSF).

In an embodiment, the at least one LPMO polypeptide or enzyme composition comprising at least one LPMO polypeptide is added during saccharifying step (i). In an embodiment, the at least one LPMO polypeptide or enzyme composition comprising at least one LPMO polypeptide is added during fermenting step (ii).

In one embodiment, an alpha amylase, in particular a fungal alpha-amylase, is also added in step (i). Steps (i) and (ii) may be performed simultaneously. In an embodiment, the at least one LPMO is added during simultaneous saccharification and fermentation (SSF). In an embodiment, the process further includes propagating a fermenting organism under conditions suitable to be further used in fermentation. In an embodiment, the fermenting organism is yeast and the at least one LPMO enzyme composition comprising at least one LPMO polypeptide is added during yeast propagation. In an embodiment, said at least one LPMO or enzyme composition comprising at least one LPMO polypeptide is added at a concentration sufficient to reduce the levels of lactic acid during propagation.

Processes for Producing Fermentation Products from Gelatinized Starch-Containing Material In an aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase to form a liquefied mash;

(b) saccharifying the liquefied mash using a carbohydrate-source generating enzyme to produce a fermentable sugar; and (c) fermenting the sugar using a fermenting organism under conditions suitable to produce the fermentation product;

wherein at least one LPMO enzyme composition comprising at least one LPMO polypeptide is added before or during saccharifying step (b) and/or fermenting step (c). In an embodiment, said at least one LPMO or enzyme composition comprising at least one LPMO polypeptide is added at a concentration sufficient to inhibit growth of contaminating bacterial cells. In an embodiment, said at least one LPMO or enzyme composition comprising at least one LPMO polypeptide is added at a concentration sufficient to reduce the levels of lactic acid during saccharification, fermentation, and/or simultaneous saccharification or fermentation (SSF).

In an embodiment, the at least one LPMO enzyme composition comprising at least one LPMO polypeptide is added before or during saccharifying step (b). In an embodiment, the at least one LPMO enzyme composition comprising at least one LPMO polypeptide is added before or during fermenting step (c). In one embodiment, an alpha amylase, in particular a fungal alpha-amylase, is also added in step (b). Steps (b) and (c) may be performed simultaneously. In an embodiment, the at least one LPMO enzyme composition comprising at least one LPMO polypeptide is added during simultaneous saccharification and fermentation (SSF). In an embodiment, the process further includes propagating a fermenting organism under conditions suitable to be further used in fermentation. In an embodiment, the fermenting organism is yeast and the at least one LPMO enzyme composition comprising at least one LPMO polypeptide is added before or during yeast propagation. In an embodiment, said at least one LPMO or enzyme composition comprising at least one LPMO polypeptide is added at a concentration sufficient to reduce the levels of lactic acid during propagation.

The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at a pH of 4-6, in particular at a pH of 4.5-5.5, and alpha-amylase variant, optionally together with a hemicellulase, an endoglucanase, a protease, a carbohydrate-source generating enzyme, such as a glucoamylase, a phospholipase, a phytase, and/or pullulanase, are added to initiate liquefaction (thinning). The liquefaction process is usually carried out at a pH of 4-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., in particular 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an embodiment the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis,* or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Recovery of Fermentation Products

Subsequent to fermentation or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art. Typically, the fermentation product, e.g., ethanol, with a purity of up to, e.g., about 96 vol. percent ethanol is obtained.

Thus, in one embodiment, the method of the invention further comprises distillation to obtain the fermentation product, e.g., ethanol. The fermentation and the distillation may be carried out simultaneously and/or separately/sequentially; optionally followed by one or more process steps for further refinement of the fermentation product.

Following the completion of the distillation process, the material remaining is considered the whole stillage. As used herein, the term "whole stillage" includes the material that remains at the end of the distillation process after recovery of the fermentation product, e.g., ethanol. The fermentation product can optionally be recovered by any method known in the art.

Separating (Dewatering) Whole Stillage into Thin Stillage and Wet Cake

In one embodiment, the whole stillage is separated or partitioned into a solid and liquid phase by one or more methods for separating the thin stillage from the wet cake. Separating whole stillage into thin stillage and wet cake in order to remove a significant portion of the liquid/water, may be done using any suitable separation technique, including centrifugation, pressing and filtration. In a preferred embodiment, the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment, the separation is carried out using other conventional separation equipment such as a plate/frame filter presses, belt filter presses, screw presses, gravity thickeners and deckers, or similar equipment.

Processing of Thin Stillage

Thin stillage is the term used for the supernatant of the centrifugation of the whole stillage. Typically, the thin stillage contains 4-6 percent dry solids (DS) (mainly proteins, soluble fiber, fine fibers, and cell wall components) and has a temperature of about 60-90 degrees centigrade. The thin stillage stream may be condensed by evaporation to provide two process streams including: (i) an evaporator condensate stream comprising condensed water removed from the thin stillage during evaporation, and (ii) a syrup stream, comprising a more concentrated stream of the non-volatile dissolved and non-dissolved solids, such as non-fermentable sugars and oil, remaining present from the thin stillage as the result of removing the evaporated water. Optionally, oil can be removed from the thin stillage or can be removed as an intermediate step to the evaporation process, which is typically carried out using a series of several evaporation stages. Syrup and/or de-oiled syrup may be introduced into a dryer together with the wet grains (from the whole stillage separation step) to provide a product referred to as distillers dried grain with solubles, which also can be used as animal feed.

In an embodiment, syrup and/or de-oiled syrup is sprayed into one or more dryers to combine the syrup and/or de-oiled syrup with the whole stillage to produce distillers dried grain with solubles.

Between 5-90 vol-%, such as between 10-80%, such as between 15-70%, such as between 20-60% of thin stillage (e.g., optionally hydrolyzed) may be recycled (as backset) to step (a). The recycled thin stillage (i.e., backset) may constitute from about 1-70 vol.-%, preferably 15-60% vol.-%, especially from about 30 to 50 vol.-% of the slurry formed in step (a).

In an embodiment, the process further comprises recycling at least a portion of the thin stillage stream treated with a LPMO of the invention to the slurry, optionally after oil has been extracted from the thin stillage stream.

Drying of Wet Cake and Producing Distillers Dried Grains and Distillers Dried Grains with Solubles After the wet cake, containing about 25-40 wt-%, preferably 30-38 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for animals, such as livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS). Partially dried intermediate products, such as are sometimes referred to as modified wet distillers grains, may be produced by partially drying wet cake, optionally with the addition of syrup before, during or after the drying process.

Alpha-Amylase Present and/or Added During Liquefaction

According to the invention an alpha-amylase is present and/or added in liquefaction optionally together with a hemicellulase, an endoglucanase, a protease, a carbohydrate-source generating enzyme, such as a glucoamylase, a phospholipase, a phytase, and/or pullulanase.

The alpha-amylase added during liquefaction step i) may be any alpha-amylase. Preferred are bacterial alpha-amylases, such as especially *Bacillus* alpha-amylases, such as *Bacillus stearothermophilus* alpha-amylases, which are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus, Bacillus* sp. TS-23, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 95 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 and the *Bacillus* sp. TS-23 alpha-amylase disclosed as SEQ ID NO: 1 in WO 2009/061380 (all sequences are hereby incorporated by reference).

In an embodiment the bacterial alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467 and SEQ ID NO: 1 in WO 2009/061380.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 95 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases, or variant thereof, may be naturally truncated during recombinant production. For instance, the mature *Bacillus stearothermophilus* alpha-amylase may be truncated at the C-terminal so it is around 491 amino acids long (compared to SEQ ID NO: 3 in WO 99/19467 or SEQ ID NO: 95 herein), such as from 480-495 amino acids long.

The *Bacillus* alpha-amylase may also be a variant and/or hybrid. Examples of such a variant can be found in any of WO 96/23873, WO 96/23874, WO 97/41213, WO 99/19467, WO 00/60059, WO 02/10355 and WO2009/061380 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 95 herein or the deletion of amino acids R179 and G180 using SEQ ID NO: 3 in WO 99/19467 or SEQ ID NO: 95 herein. Even more preferred are *Bacillus* alpha-amylases, especially *Bacillus stearothermophilus* (BSG) alpha-amylases, which have at one or two amino acid deletions corresponding to positions R179, G180, I181 and G182, preferably which have a double deletion corresponding to R179 and G180, or preferably a deletion of positions 181 and 182 (denoted I181*+G182*), and optionally further comprises a N193F substitution (denoted I181*+G182*+N193F) compared to the wild-type BSG alpha-amylase amino acid sequence set forth in SEQ ID NO: 3 disclosed in WO 99/19467 or SEQ ID NO: 95 herein. The bacterial alpha-amylase may also have a substitution in a position corresponding to S239 in the *Bacillus licheniformis* alpha-amylase shown in SEQ ID NO: 4 in WO 99/19467, or a S242 variant in the *Bacillus stearothermophilus* alpha-amylase of SEQ ID NO: 3 in WO 99/19467 or SEQ ID NO: 95 herein.

In an embodiment the variant is a S242A, E or Q variant, preferably a S242Q or A variant, of the *Bacillus stearothermophilus* alpha-amylase (using SEQ ID NO: 95 herein for numbering).

In an embodiment the variant is a position E188 variant, preferably E188P variant of the *Bacillus stearothermophilus* alpha-amylase (using SEQ ID NO: 95 herein for numbering).

Other contemplated variant are *Bacillus* sp. TS-23 variant disclosed in WO2009/061380, especially variants defined in claim 1 of WO2009/061380 (hereby incorporated by reference).

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al., 2002, The Journal of Biological Chemistry 277(29): 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase is used in combination with a hemicellulase, preferably xylanase, having a Melting Point (DSC) above 80° C. Optionally an endoglucanase having a Melting Point (DSC) above 70° C., such as above 75° C., in particular above 80° C. may be included. The thermostable alpha-amylase, such as a bacterial an alpha-amylase, is preferably derived from *Bacillus stearothermophilus* or *Bacillus* sp. TS-23. In an embodiment the alpha-amylase has a T½ (min) at pH 4.5, 85° C., 0.12 mM CaCl$_2$ of at least 10.

In an embodiment the alpha-amylase has a T½ (min) at pH 4.5, 85° C., 0.12 mM CaCl$_2$, of at least 15.

In an embodiment the alpha-amylase has a T½ (min) at pH 4.5, 85° C., 0.12 mM CaCl$_2$, of at least 20.

In an embodiment the alpha-amylase has a T½ (min) at pH 4.5, 85° C., 0.12 mM CaCl$_2$, of at least 25.

In an embodiment the alpha-amylase has a T½ (min) at pH 4.5, 85° C., 0.12 mM CaCl$_2$, of at least 30.

In an embodiment the alpha-amylase has a T½ (min) at pH 4.5, 85° C., 0.12 mM CaCl$_2$, of at least 40.

In an embodiment the alpha-amylase has a T½ (min) at pH 4.5, 85° C., 0.12 mM CaCl$_2$, of at least 50.

In an embodiment the alpha-amylase has a T½ (min) at pH 4.5, 85° C., 0.12 mM CaCl$_2$, of at least 60.

In an embodiment the alpha-amylase has a T½ (min) at pH 4.5, 85° C., 0.12 mM CaCl$_2$, between 10-70.

In an embodiment the alpha-amylase has a T½ (min) at pH 4.5, 85° C., 0.12 mM CaCl$_2$, between 15-70.

In an embodiment the alpha-amylase has a T½ (min) at pH 4.5, 85° C., 0.12 mM CaCl$_2$, between 20-70.

In an embodiment the alpha-amylase has a T½ (min) at pH 4.5, 85° C., 0.12 mM CaCl$_2$, between 25-70.

In an embodiment the alpha-amylase has a T½ (min) at pH 4.5, 85° C., 0.12 mM CaCl$_2$, between 30-70.

In an embodiment the alpha-amylase has a T½ (min) at pH 4.5, 85° C., 0.12 mM CaCl$_2$, between 40-70.

In an embodiment the alpha-amylase has a T½ (min) at pH 4.5, 85° C., 0.12 mM CaCl$_2$, between 50-70.

In an embodiment the alpha-amylase has a T½ (min) at pH 4.5, 85° C., 0.12 mM CaCl$_2$, between 60-70.

In an embodiment the alpha-amylase is a bacterial alpha-amylase, preferably derived from the genus *Bacillus*, especially a strain of *Bacillus stearothermophilus*, in particular the *Bacillus stearothermophilus* as disclosed in WO 99/19467 as SEQ ID NO: 3 or SEQ ID NO: 95 herein with one or two amino acids deleted at positions R179, G180, I181 and/or G182, in particular with R179 and G180 deleted, or with I181 and G182 deleted, with mutations in below list of mutations. In preferred embodiments the *Bacillus stearothermophilus* alpha-amylases have double deletion I181+G182, and optional substitution N193F, optionally further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.

In an embodiment the alpha-amylase is selected from the group of *Bacillus stearomthermphilus* alpha-amylase variants:

I181*+G182*;
I181*+G182*+N193F;
preferably
I181*+G182*+E129V+K177L+R179E;
I181*+G182*+N193F+E129V+K177L+R179E;
181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 95 herein for numbering).

In an embodiment the bacterial alpha-amylase, such as *Bacillus* alpha-amylase, such as as *Bacillus stearomthermphilus* alpha-amylase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 95 herein.

In an embodiment the bacterial alpha-amylase variant, such as *Bacillus* alpha-amylase variant, such as *Bacillus stearomthermphilus* alpha-amylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 95 herein.

It should be understood that when referring to *Bacillus stearothermophilus* alpha-amylase and variants thereof they are normally produced naturally in truncated form. In particular, the truncation may be so that the *Bacillus stearothermophilus* alpha-amylase shown in SEQ ID NO: 3 in WO 99/19467 or SEQ ID NO: 95 herein, or variants thereof, are truncated in the C-terminal and are typically around 491 amino acids long, such as from 480-495 amino acids long.

Thermostable Hemicellulase Present and/or Added During Liquefaction

According to the invention an optional hemicellulase, preferably xylanase, having a Melting Point (DSC) above 80° C. is present and/or added to liquefaction step i) in combination with an alpha-amylase, such as a bacterial alpha-amylase (described above).

The thermostability of a hemicellulase, preferably xylanase may be determined as described in the "Materials & Methods"-section under "Determination of T$_d$ by Differential Scanning calorimetry for Endoglucanases and Hemicellulases".

In an embodiment the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

In a preferred embodiment the hemicellulase, in particular xylanase, especially GH10 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 96 herein, preferably derived from a strain of the genus *Dictyoglomus*, such as a strain of *Dictyogllomus thermophilum*.

In a preferred embodiment the hemicellulase, in particular xylanase, especially GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 97 herein, preferably derived from a strain of the genus *Dictyoglomus*, such as a strain of *Dictyogllomus thermophilum*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 98 herein, preferably derived from a strain of the genus *Rasamsonia*, such as a strain of *Rasomsonia byssochlamydoides*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 99 herein, preferably derived from a strain of the genus *Talaromyces*, such as a strain of *Talaromyces leycettanus*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 100 herein, preferably derived from a strain of the genus *Aspergillus*, such as a strain of *Aspergillus fumigatus*.

Thermostable Endoglucanase Present and/or Added During Liquefaction

According to the invention an optional endoglucanase ("E") having a Melting Point (DSC) above 70° C., such as between 70° C. and 95° C. may be present and/or added in liquefaction step i) in combination with an alpha-amylase, such as a thermostable bacterial alpha-amylase and an optional hemicellulase, preferably xylanase, having a Melting Point (DSC) above 80° C.

The thermostability of an endoglucanase may be determined as described in the "Materials & Methods"-section of WO 2017/112540 (incorporated herein by reference in its entirety) under the heading "Determination of $T_d$ by Differential Scanning calorimetry for Endoglucanases and Hemicellulases".

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention or comprised in a composition of the invention is a Glycoside Hydrolase Family 5 endoglucnase or GH5 endoglucanase (see the CAZy database on the "www.cazy.org" webpage.

In an embodiment the GH5 endoglucanase is from family EG II, such as the *Talaromyces leycettanus* endoglucanase shown in SEQ ID NO: 101 herein; *Penicillium capsulatum* endoglucanase shown in SEQ ID NO: 102 herein, and *Trichophaea saccata* endoglucanase shown in SEQ ID NO: 103 herein.

In an embodiment the endoglucanase is a family GH45 endoglucanase. In an embodiment the GH45 endoglucanase is from family EG V, such as the *Sordaria fimicola* shown in SEQ ID NO: 104 herein or the *Thielavia terrestris* endoglucanase shown in SEQ ID NO: 105 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 101 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 102 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 103 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 104 herein, preferably derived from a strain of the genus *Sordaria*, such as a strain of *Sordaria fimicola*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 105 herein, preferably derived from a strain of the genus *Thielavia*, such as a strain of *Thielavia terrestris*.

In an embodiment the endoglucanase is added in liquefaction step i) at a dose from 1-10,000 μg EP (Enzymes Protein)/g DS, such as 10-1,000 μg EP/g DS.

Carbohydrate-Source Generating Enzyme Present and/or Added During Liquefaction

According to the invention an optional carbohydrate-source generating enzyme, in particular a glucoamylase, preferably a thermostable glucoamylase, may be present and/or added in liquefaction together with an alpha-amylase and optional hemicellulase, preferably xylanase, having a Melting Point (DSC) above 80° C., and an optional endoglucanase having a Melting Point (DSC) above 70° C., and an optional a pullulanase and/or optional phytase.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 106 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 106 herein.

In an embodiment the carbohydrate-source generating enzyme, in particular thermostable glucoamylase, is the *Penicillium oxalicum* glucoamylase shown in SEQ ID NO: 106 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 106 herein, having a K79V substitution (referred to as "PE001") (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

Contemplated *Penicillium oxalicum* glucoamylase variants are disclosed in WO 2013/053801 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 106 herein for numbering), corresponding to the PE001 variant, and further comprises at least one of the following substitutions or combination of substitutions:

T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504*; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+

P4S+P11F+D26N+K34Y+T65A+Q327F; P2N+P4S+ P11F+T65A+Q327F+I375A+E501V+Y504T; P2N+ P4S+P11F+T65A+K218A+K221D+Q327F+E501V+ Y504T; P2N+P4S+P11F+T65A+S103N+Q327F+ E501V+Y504T; P2N+P4S+T10D+T65A+Q327F+ E501V+Y504T; P2N+P4S+F12Y+T65A+Q327F+ E501V+Y504T; K5A+P11F+T65A+Q327F+E501V+ Y504T; P2N+P4S+T10E+E18N+T65A+Q327F+ E501V+Y504T; P2N+T10E+E18N+T65A+Q327F+ E501V+Y504T; P2N+P4S+P11F+T65A+Q327F+ E501V+Y504T+T568N; P2N+P4S+P11F+T65A+ Q327F+E501V+Y504T+K524T+G526A; P2N+P4S+ P11F+K34Y+T65A+Q327F+D445N+V447S+ E501V+Y504T; P2N+P4S+P11F+R31S+K33V+ T65A+Q327F+D445N+V447S+E501V+Y504T; P2N+ P4S+P11F+D26N+K34Y+T65A+Q327F+E501V+ Y504T; P2N+P4S+P11F+T65A+F80*+Q327F+ E501V+Y504T; P2N+P4S+P11F+T65A+K112S+ Q327F+E501V+Y504T; P2N+P4S+P11F+T65A+ Q327F+E501V+Y504T+T516P+K524T+G526A; P2N+P4S+P11F+T65A+Q327F+E501V+N502T+ Y504*; P2N+P4S+P11F+T65A+Q327F+E501V+ Y504T; P2N+P4S+P11F+T65A+S103N+Q327F+ E501V+Y504T; K5A+P11F+T65A+Q327F+E501V+ Y504T; P2N+P4S+P11F+T65A+Q327F+E501V+ Y504T+T516P+K524T+G526A; P2N+P4S+P11F+ T65A+V79A+Q327F+E501V+Y504T; P2N+P4S+ P11F+T65A+V79G+Q327F+E501V+Y504T; P2N+ P4S+P11F+T65A+V79I+Q327F+E501V+Y504T; P2N+P4S+P11F+T65A+V79L+Q327F+E501V+ Y504T; P2N+P4S+P11F+T65A+V79S+Q327F+ E501V+Y504T; P2N+P4S+P11F+T65A+L72V+ Q327F+E501V+Y504T; S255N+Q327F+E501V+ Y504T; P2N+P4S+P11F+T65A+E74N+Q327F+ E501V+Y504T; P2N+P4S+P11F+T65A+G220N+ Q327F+E501V+Y504T; P2N+P4S+P11F+T65A+ Y245N+Q327F+E501V+Y504T; P2N+P4S+P11F+ T65A+Q253N+Q327F+E501V+Y504T; P2N+P4S+ P11F+T65A+D279N+Q327F+E501V+Y504T; P2N+ P4S+P11F+T65A+Q327F+S359N+E501V+Y504T; P2N+P4S+P11F+T65A+Q327F+D370N+E501V+ Y504T; P2N+P4S+P11F+T65A+Q327F+V460S+ E501V+Y504T; P2N+P4S+P11F+T65A+Q327F+ V460T+P468T+E501V+Y504T; P2N+P4S+P11F+ T65A+Q327F+T463N+E501V+Y504T; P2N+P4S+ P11F+T65A+Q327F+S465N+E501V+Y504T; or P2N+P4S+P11F+T65A+Q327F+T477N+E501V+ Y504T.

In a preferred embodiment the *Penicillium oxalicum* glucoamylase variant has a K79V substitution using SEQ ID NO: 106 herein for numbering (PE001 variant), and further comprises one of the following mutations:

P11F+T65A+Q327F;
P2N+P4S+P11F+T65A+Q327F;
P11F+D26C+K330+T65A+Q327F;
P2N+P4S+P11F+T65A+Q327W+E501V+Y504T;
P2N+P4S+P11F+T65A+Q327F+E501V+Y504T; or
P11F+T65A+Q327W+E501V+Y504T.

In an embodiment the glucoamylase variant, such as *Penicillium oxalicum* glucoamylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature polypeptide of SEQ ID NO: 106 herein.

The carbohydrate-source generating enzyme, in particular glycoamylase, may be added in amounts from 0.1-100 micrograms EP/g DS, such as 0.5-50 micrograms EP/g DS, such as 1-25 micrograms EP/g DS, such as 2-12 micrograms EP/g DS.

Pullulanase Present and/or Added During Liquefaction

Optionally a pullulanase may be present and/or added during liquefaction step i) together with an alpha-amylase and an optional hemicellulase, preferably xylanase, having a melting point (DSC) above 80° C. As mentioned above a protease, a carbohydrate-source generating enzyme, preferably a thermostable glucoamylase, may also optionally be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown WO 2011/087836 truncated at the X4 site right after the X47 domain. The pullulanase may also be a hybrid of the *Thermococcus litoralis* and *Thermococcus hydrothermalis* pullulanases or a *T. hydrothermalis/ T. litoralis* hybrid enzyme with truncation site X4 disclosed in WO 2011/087836 (which is hereby incorporated by reference).

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME 400L, PROMOZYME™ D2 (Novozymes A/S, Denmark), OPTIMAX L-300 (Genencor Int., USA), and AMANO 8 (Amano, Japan).

Phytase Present and/or Added During Liquefaction

Optionally a phytase may be present and/or added in liquefaction in combination with an alpha-amylase and hemicellulase, preferably xylanase, having a melting point (DSC) above 80° C.

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., be a 3-phytase (EC 3.1.3.8), a 6-phytase (EC 3.1.3.26) or a 5-phytase (no EC number). In an embodiment the phytase has a temperature optimum above 50° C., such as in the range from 50-90° C.

The phytase may be derived from plants or microorganisms, such as bacteria or fungi, e.g., yeast or filamentous fungi.

A plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from genus *Bacillus, Citrobacter, Hafnia, Pseudomonas, Buttiauxella* or *Escherichia*, specifically the species *Bacillus subtilis, Citrobacter braakii, Citrobacter freundii, Hafnia alvei, Buttiauxella gaviniae, Buttiauxella agrestis, Buttiauxella noackies* and *E. coli*. Suitable bacterial phytases are described in Paver and Jagannathan, 1982, Journal of Bacteriology 151:1102-1108; Cosgrove, 1970, Australian Journal of Biological Sciences 23:1207-1220; Greiner et al, Arch. Biochem. Biophys., 303, 107-113, 1993; WO 1997/33976; WO 1997/48812, WO 1998/06856, WO 1998/028408, WO 2004/085638, WO 2006/037327, WO 2006/038062, WO 2006/063588, WO 2008/092901, WO 2008/116878, and WO 2010/034835.

A yeast phytase may be derived from genus *Saccharomyces* or *Schwanniomyces*, specifically species *Saccharomyces cerevisiae* or *Schwanniomyces occidentalis*. The former enzyme has been described as a Suitable yeast phytases are described in Nayini et al, 1984, Lebensmittel Wissenschaft and Technologie 17:24-26; Wodzinski et al, Adv. Appl. Microbiol., 42, 263-303; AU-A-24840/95;

Phytases from filamentous fungi may be derived from the fungal phylum of Ascomycota (ascomycetes) or the phylum Basidiomycota, e.g., the genus *Aspergillus, Thermomyces* (also called *Humicola*), *Myceliophthora, Manascus, Penicillium, Peniophora, Agrocybe, Paxillus*, or *Trametes*, specifically the species *Aspergillus terreus, Aspergillus niger, Aspergillus niger* var. *awamori, Aspergillus ficuum, Aspergillus fumigatus, Aspergillus oryzae, T. lanuginosus* (also known as *H. lanuginosa*), *Myceliophthora thermophila, Peniophora lycii, Agrocybe pediades, Manascus anka, Paxillus involtus*, or *Trametes pubescens*. Suitable fungal phytases are described in Yamada et al., 1986, Agric. Biol. Chem. 322:1275-1282; Piddington et al., 1993, Gene 133: 55-62; EP 684,313; EP 0 420 358; EP 0 684 313; WO 1998/28408; WO 1998/28409; JP 7-67635; WO 1998/44125; WO 1997/38096; WO 1998/13480.

In a preferred embodiment the phytase is derived from *Buttiauxella*, such as *Buttiauxella gaviniae, Buttiauxella agrestis*, or *Buttiauxella noackies*, such as the ones disclosed as SEQ ID NO: 2, SEQ ID NO: 4 and SEQ ID NO: 6, respectively, in WO 2008/092901 (hereby incorporated by reference).

In a preferred embodiment the phytase is derived from *Citrobacter*, such as *Citrobacter braakii*, such as one disclosed in WO 2006/037328 (hereby incorporated by reference).

Modified phytases or phytase variants are obtainable by methods known in the art, in particular by the methods disclosed in EP 897010; EP 897985; WO 99/49022; WO 99/48330, WO 2003/066847, WO 2007/112739, WO 2009/129489, and WO 2010/034835.

Commercially available phytase containing products include BIO-FEED PHYTASE™, PHYTASE NOVO™ CT or L (all from Novozymes), LIQMAX (DuPont) or RONOZYME™ NP, RONOZYME® HiPhos, RONOZYME® P5000 (CT), NATUPHOS™ NG 5000 (from DSM).

According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, Glucoamylase According to the invention the glucoamylase present and/or added in saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), or from a strain of the genus *Gloephyllum*, in particular a strain of *Gloephyllum* as described in WO 2011/068803 (SEQ ID NO: 2, 4, 6, 8, 10, 12, 14 or 16) or a strain of the genus *Nigrofomes*, in particular a strain of *Nigrofomes* sp. disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SANT™ SUPER, SANT™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME™ ACHIEVE and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Danisco US).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Cellulase or Cellulolytic Enzyme Composition Present and/or Added During Saccharification and/or Fermentation or SSF The cellulolytic composition used in a process of the invention may be derived from any microorganism. As used herein, "derived from any microorganism" means that the cellulolytic composition comprises one or more enzymes that were expressed in the microorganism. For instance, a cellulolytic composition derived from a strain of *Trichoderma reesei* means that the cellulolytic composition comprises one or more enzymes that were expressed in *Trichoderma reesei*.

In an embodiment, the cellulolytic composition is derived from a strain of *Aspergillus*, such as a strain of *Aspergillus aurantiacus*, *Aspergillus niger* or *Aspergillus oryzae*.

In an embodiment, the cellulolytic composition is derived from a strain of *Chrysosporium*, such as a strain of *Chrysosporium lucknowense*.

In an embodiment, the cellulolytic composition is derived from a strain of *Humicola*, such as a strain of *Humicola insolens*.

In an embodiment, the cellulolytic composition is derived from a strain of *Penicilium*, such as a strain of *Penicilium emersonii* or *Penicilium oxalicum*.

In an embodiment, the cellulolytic composition is derived from a strain of *Talaromyces*, such as a strain of *Talaromyces aurantiacus* or *Talaromyces* emersonii.

In an embodiment, the cellulolytic composition is derived from a strain of *Trichoderma*, such as a strain of *Trichoderma reesei*.

In a preferred embodiment, the cellulolytic composition is derived from a strain of *Trichoderma reesei*.

The cellulolytic composition may comprise one or more of the following polypeptides, including enzymes: GH61 polypeptide having cellulolytic enhancing activity, beta-glucosidase, CBHI and CBHII, or a mixture of two, three, or four thereof.

In a preferred embodiment, the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. The hemicellulase may come from the cellulolytic composition producing organism or from other sources, e.g., the hemicellulase may be foreign to the cellulolytic composition producing organism, such as, e.g., *Trichoderma reesei*.

In a preferred embodiment the hemicellulase content in the cellulolytic composition constitutes less than 10 wt. % such as less than 5 wt. % of the cellulolytic composition.

In an embodiment the cellulolytic composition comprises a beta-glucosidase.

In an embodiment the cellulolytic composition comprises a GH61 polypeptide having cellulolytic enhancing activity and a beta-glucosidase.

In another embodiment the cellulolytic composition comprises a beta-glucosidase and a CBH.

In another embodiment the cellulolytic composition comprises a GH61 polypeptide having cellulolytic enhancing activity, a beta-glucosidase, and a CBHI.

In another embodiment the cellulolytic composition comprises a beta-glucosidase and a CBHI.

In another embodiment the cellulolytic composition comprises a GH61 polypeptide having cellulolytic enhancing activity, a beta-glucosidase, a CBHI, and a CBHII.

In another embodiment the cellulolytic composition comprises a beta-glucosidase, a CBHI, and a CBHII.

The cellulolytic composition may further comprise one or more enzymes selected from the group consisting of a cellulase, a GH61 polypeptide having cellulolytic enhancing activity, an esterase, an expansin, a laccase, a ligninolytic enzyme, a pectinase, a peroxidase, a protease, and a swollenin.

In an embodiment the cellulase is one or more enzymes selected from the group consisting of an endoglucanase, a cellobiohydrolase, and a beta-glucosidase.

In an embodiment the endoglucanase is an endoglucanase I.

In an embodiment the endoglucanase is an endoglucanase II.

Beta-Glucosidase

The cellulolytic composition used according to the invention may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 107 herein or an *Aspergillus fumigatus* beta-glucosidase variant, such as one disclosed in WO 2012/044915 or co-pending PCT application PCT/US11/054185 (or U.S. provisional application No. 61/388,997), such as one with the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment betaglucosidase is an *Aspergillus fumigatus* beta-glucosidase or homolog thereof selected from the group consisting of:
(i) a beta-glucosidase comprising the mature polypeptide of SEQ ID NO: 107;
(ii) a beta-glucosidase comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 107 herein;
(iii) a beta-glucosidase encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 5 in WO 2013/148993; and
(iv) a beta-glucosidase encoded by a polynucleotide that hybridizes under at least high stringency conditions, e.g., very high stringency conditions, with the mature polypeptide coding sequence of SEQ ID NO: 5 in WO 2013/148993 or the full-length complement thereof.

In an embodiment the beta-glucosidase is a variant comprises a substitution at one or more (several) positions corresponding to positions 100, 283, 456, and 512 of the mature polypeptide of SEQ ID NO: 107 herein, wherein the variant has beta-glucosidase activity.

In an embodiment the parent beta-glucosidase of the variant is (a) a polypeptide comprising the mature polypeptide of SEQ ID NO: 107 herein; (b) a polypeptide having at least 80% sequence identity to the mature polypeptide of SEQ ID NO: 107 herein; (c) a polypeptide encoded by a polynucleotide that hybridizes under high or very high stringency conditions with (i) the mature polypeptide coding sequence of SEQ ID NO: 5 in WO 2013/148993, (ii) the cDNA sequence contained in the mature polypeptide coding sequence of SEQ ID NO: 5 in WO 2013/148993, or (iii) the full-length complementary strand of (i) or (ii); (d) a polypeptide encoded by a polynucleotide having at least 80% identity to the mature polypeptide coding sequence of SEQ ID NO: 5 in WO 2013/148993 or the cDNA sequence thereof; or (e) a fragment of the mature polypeptide of SEQ ID NO: 107 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 107 herein.

In an embodiment the beta-glucosidase is from a strain of *Aspergillus*, such as a strain of *Aspergillus fumigatus*, such as *Aspergillus fumigatus* beta-glucosidase (SEQ ID NO: 107 herein), which comprises one or more substitutions selected from the group consisting of L89M,
G91L, F100D, I140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

In an embodiment the number of substitutions is between 1 and 4, such as 1, 2, 3, or 4 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 107 herein.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70.

GH61 Polypeptide Having Cellulolytic Enhancing Activity

The cellulolytic composition used according to the invention may in one embodiment comprise one or more GH61 polypeptide having cellulolytic enhancing activity. In one embodiment the enzyme composition comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397 or SEQ ID NO: 108 herein.

In an embodiment the *Penicillium* sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 108 herein;
(ii) a GH61 polypeptide having cellulolytic enhancing activity comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 108 herein;
(iii) a GH61 polypeptide having cellulolytic enhancing activity encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 7 in WO 2013/148993; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 in WO 2013/148993 or the full-length complement thereof.

Cellobiohydrolase I

The cellulolytic composition used according to the invention may in one embodiment may comprise one or more CBH I (cellobiohydrolase I). In one embodiment the cellulolytic composition comprises a cellobiohydrolase I (CBHI), such as one derived from a strain of the genus *Aspergillus*, such as a strain of *Aspergillus fumigatus*, such as the Cel7A CBHI disclosed in SEQ ID NO: 6 in WO 2011/057140 or SEQ ID NO: 109 herein, or a strain of the genus *Trichoderma*, such as a strain of *Trichoderma reesei*.

In an embodiment the *Aspergillus fumigatus* cellobiohydrolase I or homolog thereof is selected from the group consisting of:

(i) a cellobiohydrolase I comprising the mature polypeptide of SEQ ID NO: 109 herein;

(ii) a cellobiohydrolase I comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 109 herein;

(iii) a cellobiohydrolase I encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 1 in WO 2013/148993; and (iv) a cellobiohydrolase I encoded by a polynucleotide that hybridizes under at least high stringency conditions, e.g., very high stringency conditions, with the mature polypeptide coding sequence of SEQ ID NO: 1 in WO 2013/148993 or the full-length complement thereof.

Cellobiohydrolase II

The cellulolytic composition used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 110 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:

(i) a cellobiohydrolase II comprising the mature polypeptide of SEQ ID NO: 110 herein;

(ii) a cellobiohydrolase II comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 110 herein;

(iii) a cellobiohydrolase II encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 3 in WO 2013/148993; and (iv) a cellobiohydrolase II encoded by a polynucleotide that hybridizes under at least high stringency conditions, e.g., very high stringency conditions, with the mature polypeptide coding sequence of SEQ ID NO: 3 in WO 2013/148993 or the full-length complement thereof.

Cellulolytic Compositions

As mentioned above the cellulolytic composition may comprise a number of difference polypeptides, such as enzymes.

In an embodiment the cellulolytic composition comprises a *Trichoderma reesei* cellulolytic composition, further comprising *Thermoascus aurantiacus* GH61A polypeptide having cellulolytic enhancing activity (WO 2005/074656) and *Aspergillus oryzae* beta-glucosidase fusion protein (WO 2008/057637).

In another embodiment the cellulolytic composition comprises a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

In another embodiment the cellulolytic composition comprises a *Trichoderma reesei* cellulolytic composition, further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) or a variant thereof with the following substitutions: F100D, S283G, N456E, F512Y.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In a preferred embodiment the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

In an embodiment cellulolytic enzyme composition is dosed (i.e. during saccharification in step ii) and/or fermentation in step iii) or SSF) from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Protease Present and/or Added During Liquefaction

In an embodiment of the invention an optional protease, such as a thermostable protease, may be present and/or added in liquefaction together with an alpha-amylase, such as a thermostable alpha-amylase, and a hemicellulase, preferably xylanase, having a melting point (DSC) above 80° C., and optionally an endoglucanase, a carbohydrate-source generating enzyme, in particular a glucoamylase, optionally a pullulanase and/or optionally a phytase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section of WO 2017/112540 (incorporated herein by reference), of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the JTP196 variant (Example 2 from WO 2017/112540) or Protease Pfu (SEQ ID NO: 111 herein) determined by the AZCL-casein assay described in the "Materials & Methods"-section in WO 2017/112540.

There are no limitations on the origin of the thermostable protease used in a process or composition of the invention as long as it fulfills the thermostability properties defined below.

In one embodiment the protease is of fungal origin.

In a preferred embodiment the thermostable protease is a variant of a metallo protease as defined above. In an embodiment the thermostable protease used in a process or composition of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 112 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;

S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the mature metallo protease disclosed as the mature part of SEQ ID NO: 2 disclosed in WO 2003/048353 or the mature part of SEQ ID NO: 1 in WO 2010/008841 or SEQ ID NO: 112 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 112 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 111 herein.

In an embodiment the thermostable protease is one disclosed in SEQ ID NO: 111 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 111 herein. The *Pyrococcus furiosus* protease can be purchased from Takara Bio, Japan.

The *Pyrococcus furiosus* protease is a thermostable protease according to the invention. The commercial product *Pyrococcus furiosus* protease (Pfu S) was found (see Example 5 of) to have a thermostability of 110% (80° C./70° C.) and 103% (90° C./70° C.) at pH 4.5 determined as described in Example 2 of WO 2017/112540.

In one embodiment a thermostable protease has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2 of WO 2017/112540.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2 of WO 2017/112540.

In an embodiment the protease may have a thermostability for above 90, such as above 100 at 85° C. as determined using the Zein-BCA assay as disclosed in Example 3 of WO 2017/112540.

In an embodiment the protease has a thermostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay described in the "Materials & Methods"-section of WO 2017/112540.

V. Further Aspects of the Invention

In a further aspect of the invention it relates to the use of an LPMO polypeptide or enzyme composition comprising at least one LPMO polypeptide for reducing and/or eliminating bacterial contamination in a biofuel fermentation system.

In a further aspect of the invention it relates to the use of an LPMO polypeptide or enzyme composition comprising at least one LPMO polypeptide for reducing and/or eliminating bacterial contamination during yeast propagation.

In a further aspect of the invention it relates to the use of an LPMO polypeptide or enzyme composition comprising at least one LPMO polypeptide for reducing and/or eliminating bacterial contamination in a fermentation medium.

In a further aspect of the invention it relates to the use of an LPMO polypeptide enzyme composition comprising at least one LPMO polypeptide for reducing the levels of lactic acid in a biofuel fermentation system.

In a further aspect of the invention it relates to the use of an LPMO polypeptide or enzyme composition comprising at least one LPMO polypeptide for reducing the levels of lactic acid in a fermentation medium.

In a further aspect of the invention it relates to the use of an LPMO polypeptide or enzyme composition comprising at least one LPMO polypeptide for reducing the levels of lactic acid during yeast propagation.

Those skilled in the art will appreciate that the aspects and embodiments described in this section are applicable to any LPMO, for instance the LPMO's described section III herein.

In an embodiment, the LPMO polypeptide is selected from the group consisting of Auxiliary Activity 9 (AA9), Auxiliary Activity 10 (AA10), Auxiliary Activity 11 (AA11), Auxiliary Activity 13 (AA13), and combinations thereof.

The LPMO polypeptide may be a fungal, bacterial, or archeae LPMO polypeptide. In an embodiment, the LPMO polypeptide is a fungal AA9 polypeptide. In an embodiment, the LPMO polypeptide is a bacterial AA9 polypeptide. In an embodiment, the LPMO is an archeae AA9 polypeptide.

In an embodiment, the LPMO polypeptide is an AA9 selected from the group consisting of:
  i) the Ta AA9 shown in SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ii) the Pe AA9 shown in SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iii) the Tt AA9 shown in SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iv) the Af AA9 shown in SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  v) the Tc AA9 shown in SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and
  iv) the VL AA9 shown in SEQ ID NO: 6 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

In an embodiment, the LPMO polypeptide is a fungal AA10 polypeptide. In an embodiment, the LPMO polypeptide is a bacterial AA10 polypeptide. In an embodiment, the LPMO is an archeae AA10 polypeptide.

In an embodiment, the LPMO polypeptide is a fungal AA11 polypeptide. In an embodiment, the LPMO polypeptide is a bacterial AA11 polypeptide. In an embodiment, the LPMO is an archeae AA11 polypeptide.

In an embodiment, the LPMO polypeptide is a fungal AA13 polypeptide. In an embodiment, the LPMO polypeptide is a bacterial AA13 polypeptide. In an embodiment, the LPMO is an archeae AA13 polypeptide.

In an embodiment, the LPMO polypeptide is a AA13 polypeptide selected from the group consisting of: i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

The invention is further summarized in the following paragraphs:

1. A process for reducing and/or preventing an increase in lactic acid levels in a biofuel fermentation system, the process comprising introducing a LPMO polypeptide or an enzyme composition comprising a lytic polysaccharide monooxygenase (LPMO) polypeptide to a biofuel fermentation system, wherein the fermentation system comprises one or more fermentation vessels, pipes and/or components, and wherein the LPMO polypeptide or enzyme composition comprising the LPMO polypeptide is added at a concentration sufficient to reduce and/or prevent an increase in lactic acid levels in the biofuel fermentation system.

2. A process for reducing and/or eliminating bacterial contamination in a biofuel fermentation system, the process comprising introducing a LPMO polypeptide or an enzyme composition comprising a lytic polysaccharide monooxygenase (LPMO) to a biofuel fermentation system, wherein the fermentation system comprises one or more fermentation vessels, pipes and/or components, and wherein the LPMO polypeptide or enzyme composition comprising the LPMO polypeptide is added at a concentration sufficient to inhibit growth of contaminating bacterial cells in the biofuel fermentation system.

3. The process of paragraph 2, wherein the bacterial cells are gram-positive bacteria or gram-negative bacteria cells.

4. The process of any one of paragraphs 1 to 3, wherein the bacterial cells are *Lactobacillus* cells.

5. The process of any of paragraphs 1 to 4, wherein at least one of the fermentation vessels is a fermentation tank and the LPMO polypeptide or the enzyme composition is introduced into the fermentation tank.

6. The process of any of paragraphs 1 to 5, wherein at least one of the fermentation vessels is a fermentation tank and the LPMO polypeptide or the enzyme composition is introduced into the fermentation tank.

7. The process of any of paragraphs 1 to 6, wherein at least one of the fermentation vessels is a yeast propagation tank and the LPMO polypeptide or the enzyme composition is introduced into the yeast propagation tank.

8. The process of any one of paragraphs 1 to 7, wherein the biofuel is ethanol.

9. The process of any of paragraphs 1 to 8, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

10. The process of any of paragraphs 1 to 9, wherein the LPMO polypeptide is a AA9 polypeptide selected from the group consisting of:

i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

11. The process of any of paragraphs 1 to 10, wherein the LPMO polypeptide is a AA13 polypeptide selected from the group consisting of:
  i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  v) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  vi) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  vii) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  viii) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ix) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  x) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xi) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xii) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xiii) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xiv) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xv) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xvi) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xvii) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xviii) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xix) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xx) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxi) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxii) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

12. A process for producing a fermentation product from a starch-containing material, the process comprising:
a) liquefying a starch-containing material in the presence of an alpha-amylase to form a liquefied mash;
b) saccharifying the liquefied mash using a carbohydrate source generating enzyme to produce a fermentable sugar;
c) fermenting the sugar using a fermenting organism under conditions suitable to produce the fermentation product, wherein at least one LPMO polypeptide or an enzyme composition comprising an LPMO polypeptide is added before or during saccharifying step b) and/or fermenting step c).

13. The process of paragraph 12, wherein steps b) and c) are carried out simultaneously.

14. The process of paragraph 12 or 13, wherein a slurry of the starch containing material is heated to above the gelatinization temperature.

15. The process of any one of paragraphs 12 to 14, wherein the at least one LPMO polypeptide or enzyme composition is added during liquefaction.

16. The process of any one of paragraphs 12 to 15, wherein the at least one LPMO polypeptide or enzyme composition is added before or during saccharification.

17. The process of any one of paragraphs 12 to 16, wherein the at least one LPMO polypeptide or enzyme composition is added before or during fermentation.

18. The process of any one of paragraphs 12 to 17, wherein the fermenting organism is yeast and the at least one LPMO polypeptide or enzyme composition is added before or during yeast propagation.

19. The process of any one of paragraphs 12 to 18, wherein the fermentation product is an alcohol, preferably ethanol.

20. The process of any one of paragraphs 12 to 19, wherein the bacterial cells are gram-positive bacteria or gram-negative bacteria cells.

21. The process of any one of paragraphs 12 to 20, wherein the bacterial cells are *Lactobacillus* cells.

22. The process of any of any one of paragraphs 12 to 21, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

23. The process of any one of paragraphs 12 to 22, wherein the LPMO polypeptide is a AA9 polypeptide selected from the group consisting of:
i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

24. The process of any of paragraphs 12 to 23, wherein the LPMO polypeptide is a AA13 polypeptide selected from the group consisting of:
i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vi) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vii) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

viii) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ix) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

x) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xi) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xii) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiii) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiv) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xv) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvi) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvii) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xviii) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xix) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xx) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxi) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxii) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

25. Use of an LPMO polypeptide or enzyme composition comprising an LPMO polypeptide for reducing and/or eliminating bacterial contamination in a biofuel fermentation system.

26. Use of an LPMO polypeptide or enzyme composition comprising an LPMO polypeptide for reducing and/or eliminating bacterial contamination during yeast propagation.

27. Use of an LPMO polypeptide or enzyme composition comprising an LPMO polypeptide for reducing the levels of lactic acid during fermentation in an ethanol production process.

28. Use of an LPMO polypeptide or enzyme composition comprising an LPMO polypeptide for reducing the levels of lactic acid during yeast propagation.

29. Use according to any one of paragraphs 25 to 28, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

30. Use according to any one of paragraphs 25 to 29, wherein the LPMO polypeptide is an AA9 polypeptide selected from the group consisting of:

i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

31. Use according to any one of paragraphs 25 to 30, wherein the LPMO polypeptide is a AA13 polypeptide selected from the group consisting of:

i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vi) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vii) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

viii) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ix) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

x) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xi) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xii) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiii) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiv) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xv) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvi) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvii) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xviii) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xix) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xx) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxi) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxii) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Materials & Methods

Ta AA9: AA9 polypeptide from *Thermoascus aurantiacus* having the amino acid sequence of SEQ ID NO: 1.

Pe AA9: AA9 polypeptide from *Penicillium emersonii* having the amino acid sequence of SEQ ID NO: 2.

Tt AA9: AA9 polypeptide from *Thielavia terrestris* having the amino acid sequence of SEQ ID NO: 3.

Af AA9: AA9 polypeptide from *Aspergillus fumigatus* having the amino acid sequence of SEQ ID NO: 4.

Tc AA9: AA9 polypeptide from *Thermoascus crustaceus* having the amino acid sequence of SEQ ID NO: 5.

VL-AA9: AA9 polypeptide from *Penicillium emersonii* expressed in *Trichoderma reesei* background having the amino acid sequence of SEQ ID NO: 6.

At-AA13: AA13 polypeptide from *Aspergillus terreus* having the amino acid sequence of SEQ ID NO: SEQ ID NO: 119.

Al-AA13: AA13 polypeptide from *Aspergillus lentulus* having the amino acid sequence of SEQ ID NO: SEQ ID NO: 120.

An-AA13: AA13 polypeptide from *Aspergillus nidulans* having the amino acid sequence of SEQ ID NO: 123.

Pp-AA13: AA13 polypeptide from *Penicillium polonicum* having the amino acid sequence of SEQ ID NO: 124.

Po-AA13: AA13 polypeptide from *Penicillium oxalicum* having the amino acid sequence of SEQ ID NO: 125.

Mt-AA13: AA13 polypeptide from *Mycothermus thermophiles* having the amino acid sequence of SEQ ID NO: 127.

Alpha-Amylase 369 (AA369): *Bacillus stearothermophilus* alpha-amylase with the mutations: I181*+G182*+N193F+V59A+Q89R+E129V+K177L+R179E+Q254S+M284V (SEQ ID NO: 95 herein) truncated to 491 amino acids.

Glucoamylase SA (GSA): Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and starch binding domain (SBD) disclosed in SEQ ID NO: 113 herein having the following substitutions G128D+D143N (activity ratio in AGU:AGU:FAU-F is about 20:5:1).

Protease Pfu: Protease derived from *Pyrococcus furiosus* shown in SEQ ID NO: 111 herein.

EXAMPLES

Example 1—Evaluation of LPMO as Microbial Control Bio-Solution in Biofuels Fermentation This example demonstrates that LPMO's can be used to reduce the levels of bacterial contamination during ethanol fermentation as evidenced by the reduction of levels of a metabolic product of the bacteria present in infected corn mash. In particular, this example demonstrates that LPMO's, such as AA9 polypeptides, can reduce the impact of bacterial contamination in corn mash during ethanol fermentation, as evidenced by a reduction in the levels of lactic acid formation in the fermenting mash.

Clean corn mash: Corn mash was prepared in our laboratories under typical liquefaction conditions using a blend of AA369 and Protease Pfu. Infection was found to be undetectable via plating in selective media. Substrate is frozen and thawed before use.

Infected corn mash: Commercial industrial relevant corn mash with an unknown degree of infection (identified by lactic acid formation and initial cell counts around $10^5$ cells/mL) was incubated overnight and used as our source of contamination.

Control: Clean corn mash plus 1% infected corn mash was used at 36% dry solids and mixed with urea, to a final concentration of 400 ppm, and commercial glucoamylase GSA, at 0.6 AGU per g dry solids in fermentation. The mix was incubated for 60 minutes at 32° C. Thereafter, yeast was added aiming a pitch of 0.5 g/L in fermentation. Six replicates of fermentations were run for 3 days.

Control with commercial antibiotic: Clean corn mash plus 1% infected corn mash was used at 36% dry solids and mixed with urea, to a final concentration of 400 ppm, commercial glucoamylase GSA, at 0.6 AGU per g dry solids in fermentation, and penicillin at 2, 6 or 12 ppm per dry solids. The mix was incubated for 60 minutes at 32° C. Thereafter, yeast was added aiming a pitch of 0.5 g/L in fermentation. Fermentations were run in triplicate for 3 days.

Clean corn mash plus 1% infected corn mash was used at 36% dry solids and mixed with urea, to a final concentration of 400 ppm, commercial glucoamylase GSA, at 0.6 AGU per g dry solids in fermentation, and the AA9 polypeptides listed in the Materials & Methods section above, at 5, 25 or 125 ppm of protein per dry solids. The mix was incubated for 60 minutes at 32° C. Thereafter, yeast was added aiming a pitch of 0.5 g/L in fermentation. Fermentations were run in triplicate for 3 days.

Figure 2:
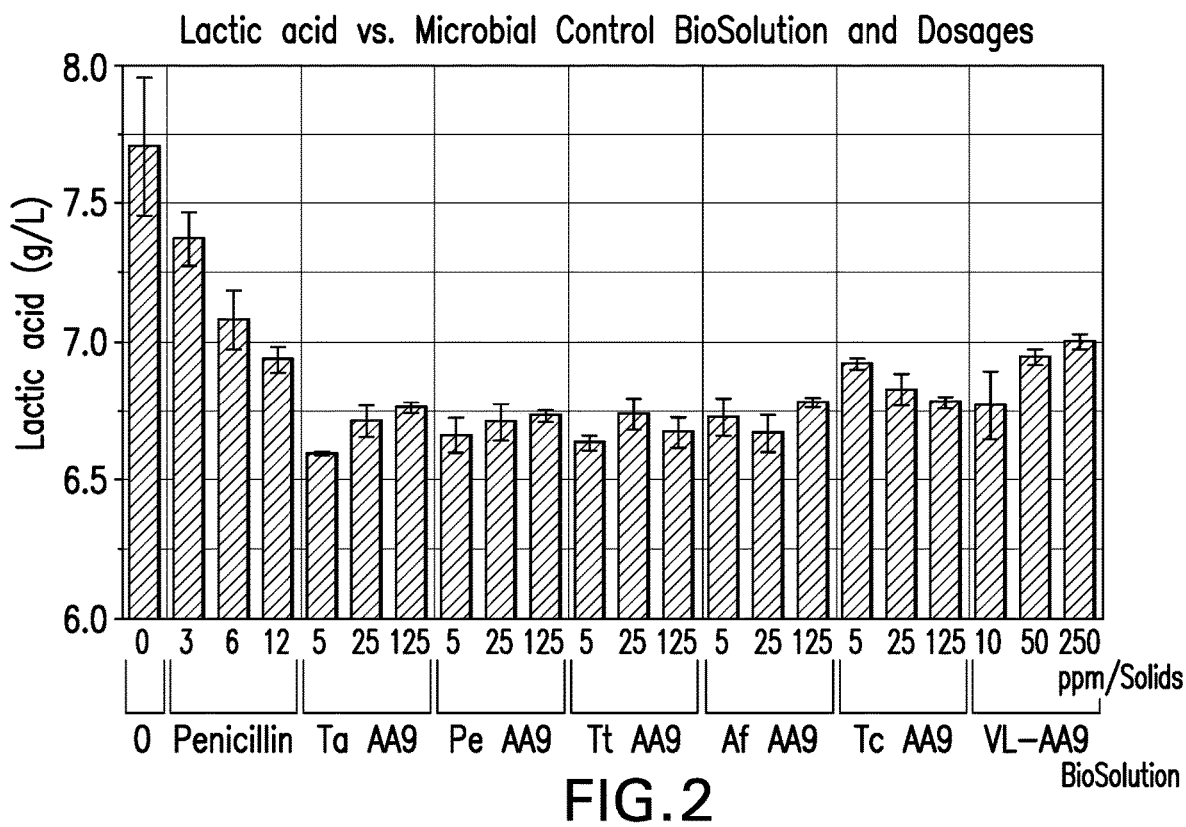
FIG. 2 shows lactic acid concentrations after fermentation of corn mash in the presence of various AA9 polypeptides compared to control (0, 0).
Figure 3:
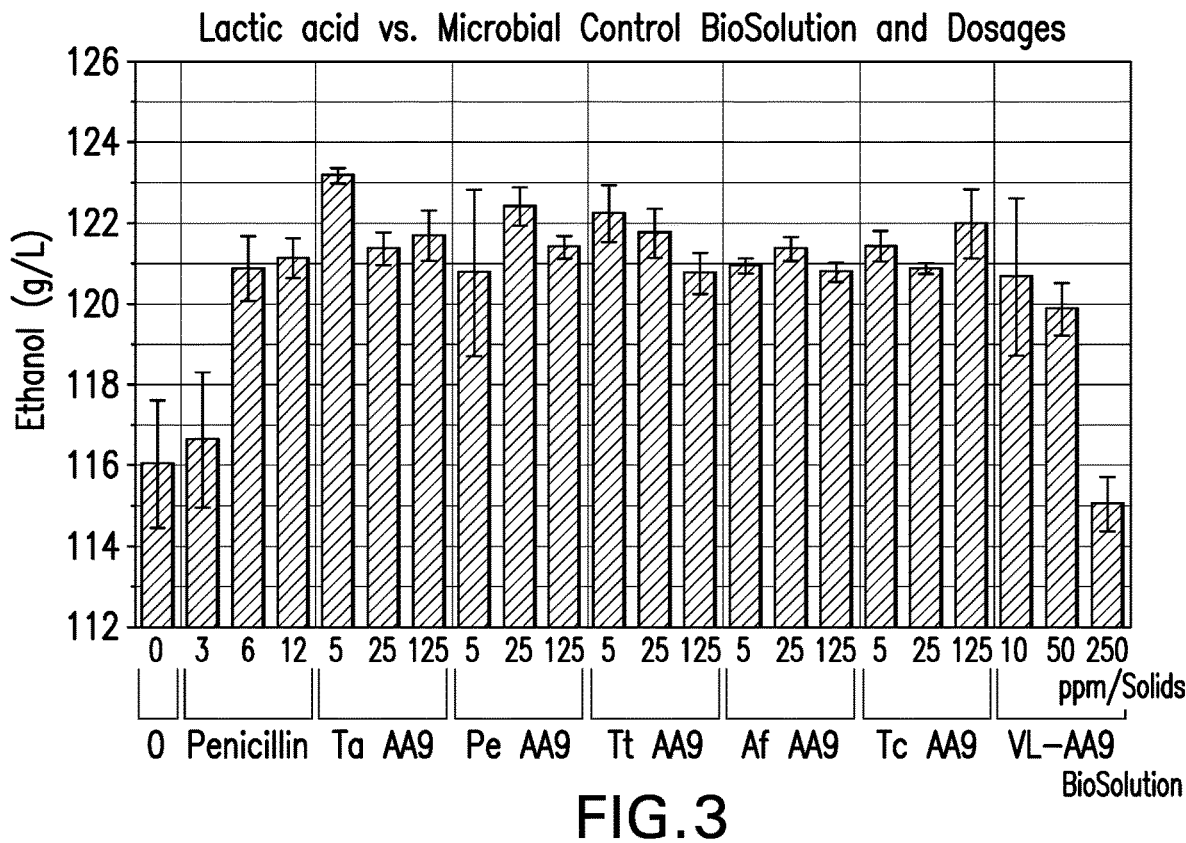
FIG. 3 shows ethanol concentrations after fermentation of corn mash in the presence of various AA9 polypeptides compared to control (0, 0).

FIG. 2 shows lactic acid concentrations after fermentation of corn mash in the presence of various AA9 polypeptides and control (Control, Control with commercial antibiotic). As shown in FIG. 2, each of the AA9 polypeptides tested reduced the lactic acid formation to a greater extent than in the control (no antibiotic used) and comparable to the positive control in which the largest dosage of penicillin was used. These data demonstrate that LPMO's, such as AA9 polypeptides, are effective at reducing the levels of lactic acid formation in an infected mash during ethanol fermentation. FIG. 3 shows ethanol concentrations after fermentation of corn mash in the presence of various AA9 polypeptides and control (Control, Control with commercial antibiotic). As shown in FIG. 3, the AA9 polypeptides tested improved the ethanol formation to a greater extent than in the control (no antibiotic used) and comparable to the positive control in which the largest dosage of penicillin was used. These data demonstrate that LPMO's, such as AA9 polypeptides, are effective at improving the levels of ethanol formation in an infected mash during ethanol fermentation The LPMO's of the present disclosure can be used during ethanol fermentation to reduce the impact of baseline bacterial contamination as well as infection events caused by lactic acid and acetic acid producing bacteria, aligned with improvements in ethanol production, in biofuel fermentation systems.

Example 2—Evaluation of LPMO as Microbial Control Bio-Solution in Biofuels Fermentation This example demonstrates that LPMO's can be used to reduce the impact of bacterial contamination during ethanol fermentation as evidenced by the reduction of levels of a metabolic product of the bacteria present in infected corn mash. In particular, this example demonstrates that LPMO's, such as AA13 polypeptides, can reduce lactic acid produced from unwanted bacterial cells present from during ethanol fermentation.

Clean liquefied corn mash: Clean corn mash was prepared in our laboratories under typical liquefaction conditions using a blend of AA369 and Protease Pfu. Infection rate was found to be undetectable via plating in selective media. Substrate is stored frozen and thawed before use.

Infected liquefied corn mash: Clean corn mash was inoculated with a mixed bacterial population previously isolated from an infected commercial corn mash. The infected mash was incubated with the inoculant for up to 24 hours at approximately 32° C. Final infection rate was found to be greater than $10^8$ colony forming units (CFUs) per plating on MRS selective media. Substrate is frozen in 20% glycerol solution and then thawed before use.

1% Infected liquefied mash: Per every 100 g of "clean" mash, 1 g of infected mash is added and mixed thoroughly.

Fermentation Procedures

Low Dry Solids fermentation. 1% Infected Mash was diluted to 20% dry solids. 200 ppm target urea was added as an exogenous nitrogen source for yeast. Commercial glucoamylase GSA, was used at a dose of 0.6 AGU/g-dry solids. Yeast was pitched at a rate of 0.25 g/L. Experimental enzymes were dosed between 2 ppm and 100 ppm. Dosage were against dry solids.

Positive control: Penicillin was used at 25 ppm.

Negative control: No treatment was added.

Yeast, enzymes, and any additional tap water was added at approximately the same time to start fermentation. Fermentations were incubated in a 32° C. static water bath for up to 24 hours. All treatments were performed in triplicate.

HPLC Analysis

Fermentations were sampled at various time points to examine soluble carbohydrates and organic acids. Samples were first centrifuged at approximately 3 krpm for up to 5 minutes. The supernatant was then filtered through a 0.2 μm filter. The filtrate was diluted up 5× (to be within the linear range of internal standards) with 5 mmolL$^{-1}$ sulfuric acid mobile phase and using an H-column for separation of the analytes. Refractive index was used has detection mode. Analytes were quantified against internal standards. Analytes of interest were: maltotriose, maltose, glucose, fructose, arabinose, lactic acid, glycerol, acetic acid, and ethanol.

Data Analysis

Data was analyzed using SAS JMP statistical software.

Results

Figure 4:
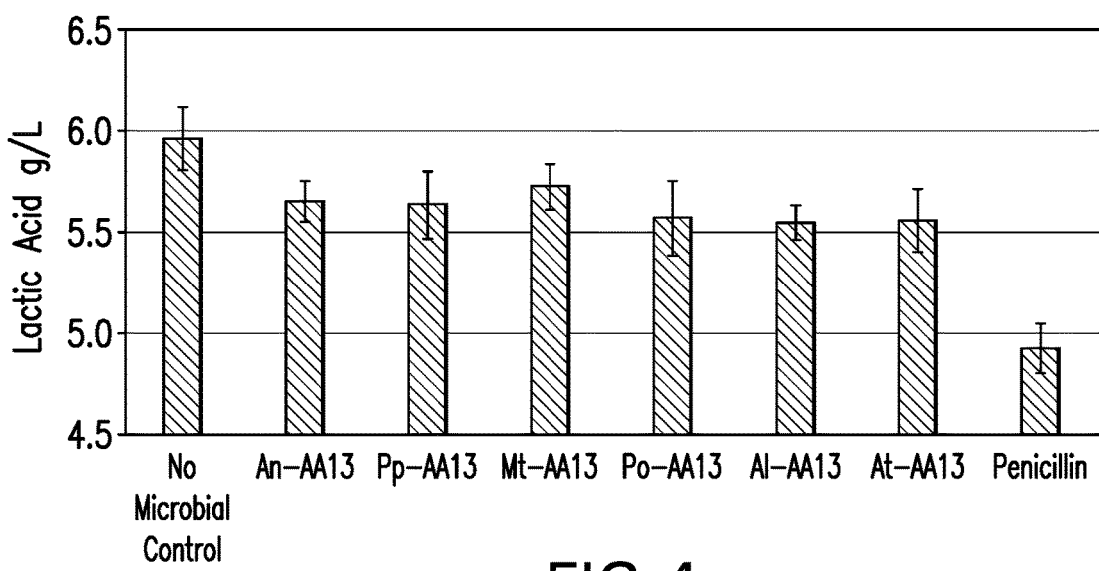
FIG. 4 shows lactic acid concentrations after fermentation of corn mash in the presence of various AA13 polypeptides compared to controls.

At the start of fermentation, treatments have measured lactic acid titers of lower than 0.3 g/L. FIG. 4 shows lactic acid concentrations after 24 hours of Low Dry Solids fermentations of corn mash in the presence of various AA13 polypeptides and controls. As shown in FIG. 4, each of the AA13 polypeptides tested reduced the lactic acid formation more than the negative control. These data suggest that LPMOs, such as AA13 polypeptides, can reduce the levels of lactic formation in an infected mash during ethanol fermentation, like the AA9 polypeptides in Example 1 above.

Figure 5:
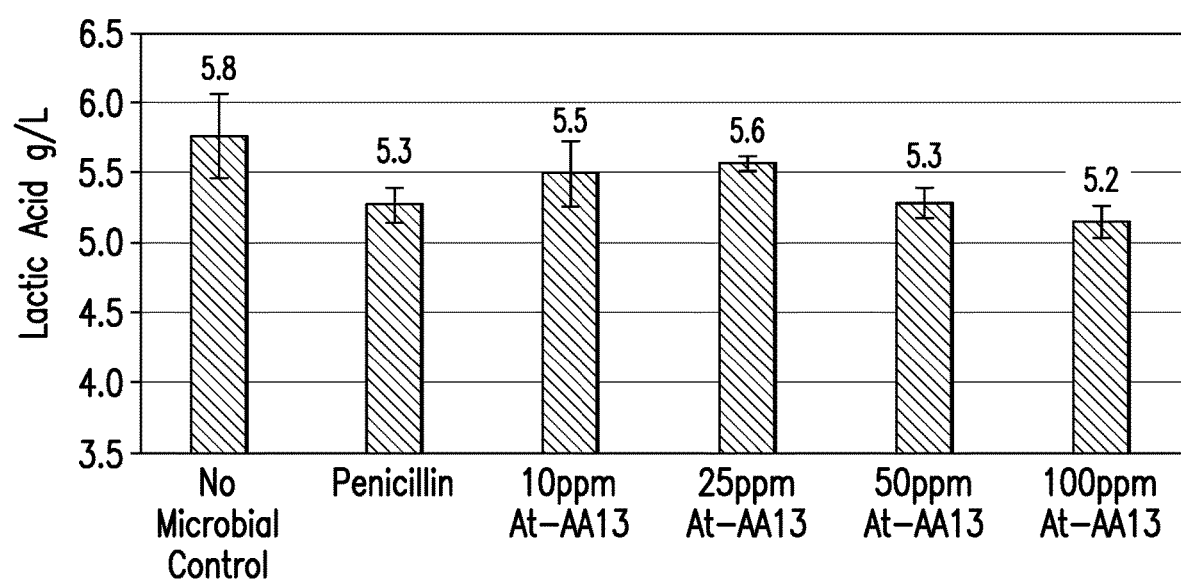
FIG. 5 shows lactic acid concentrations after fermentation of corn mash in the presence of increasing doses of an At-AA13 polypeptide compared to controls.

At-AA13 was selected for additional screening for dose response, and it continued to show reduced lactic acid titers compared to the control after 20 hrs of Low Dry Solids fermentation of corn mash under the above described conditions. These results are shown in FIG. 5.

Example 3—Evaluation of LPMO as Lactic Acid Control Bio-Solution in Biofuels Fermentation This example demonstrates that LPMO's can be used to reduce the levels of lactic acid during ethanol fermentation challenged by infection. In particular, this example demonstrates that LPMO's, such as AA13 polypeptides, can reduce the levels of lactic acid during ethanol fermentation when challenged by infection.

A control mash was prepared in-house with an industry relevant blend of AA369 and Protease Pfu using a Lab-O-Mat incubator for 2 hours at 85° C. and 36% DS to simulate typical industry conditions. The mash was then frozen prior to use in SSF. An infected mash was prepared by infecting the control mash with a multi-strain LAB culture grown in MRS. The bacteria in control mash was incubated overnight, and then frozen with 20% glycerol. For this experiment, 1% weight/weight of the infected mash was mixed into the control mash. This mimics an infection event at a large-scale ethanol facility. For SSF, all mash was prepared with 1000 ppm of urea to aid with yeast fermentation. All treatments were dosed with a baseline commercial glucoamylase GSA, while AA13 candidates were dosed at either 10 ug/g-DS or 50 ug/g-DS. SSF was performed at 5 g scale with 10 uL/g rehydrated Ethanol Red yeast at 32° C. for up to 24 hours at 20% DS. At the end of fermentation, samples were deactivated with 50 uL of 40% sulfuric acid and then centrifuged. The supernatant was filtered through a 0.2 μm filter and then measured for soluble carbohydrates and organic acids using an ion-exchange H-column on HPLC.

In this study, several candidates showed decreased lactic acid in addition to increased ethanol compared to the no treatment control at both the high and low dose, as presented in the table below. Candidates of interest are highlighted in bold.

Results:

| Treatment_Dose | Dose in ppm or ug/g-% DS | % delta Lactic Acid | % delta Ethanol | average Lactic Acid g/L | average Ethanol g/L |
|---|---|---|---|---|---|
| No Treatment | 0 | 0.0% | 0.0% | 3.3 | 77.6 |
| Penicillin | 25 | −62.4% | 3.1% | 1.2 | 80.1 |
| Aspergillus terreus | 10 | 1.3% | −0.7% | 3.4 | 77.1 |
| Penicillium viticola | 10 | 2.2% | −1.3% | 3.4 | 76.6 |
| Fusarium sp-75363 | 10 | −3.5% | 0.6% | 3.2 | 78.1 |
| Aspergillus insuetus | 10 | 1.7% | −1.2% | 3.4 | 76.7 |
| Penicillium samsonianum | 10 | 2.2% | −0.6% | 3.4 | 77.1 |
| Penicillium sp-52627 | 10 | 3.9% | 0.0% | 3.4 | 77.6 |
| Pestalotiopsis sp-71627 | 10 | 0.0% | 0.5% | 3.3 | 78.0 |
| Myrothecium sp. | 10 | −0.8% | 0.4% | 3.3 | 77.9 |
| Paraphoma sp. | 10 | 1.4% | 1.2% | 3.4 | 78.5 |
| Penicillium vulpinum | 10 | −2.9% | 1.7% | 3.2 | 79.0 |
| Talaromyces sayulitensis | 10 | 1.5% | 1.3% | 3.4 | 78.7 |
| Penicillium steckii | 10 | 4.5% | −1.4% | 3.5 | 76.6 |
| Penicillium antarcticum | 10 | 2.2% | −1.6% | 3.4 | 76.4 |
| Penicillium paxilli | 10 | −4.9% | 0.2% | 3.2 | 77.8 |
| Acremonium sp. XZ1982 | 10 | −9.5% | 1.3% | 3.0 | 78.7 |
| Penicillium sp-72443 | 10 | −12.5% | 2.2% | 2.9 | 79.3 |
| Acrostalagmus luteoalbus | 10 | −10.9% | 1.7% | 3.0 | 78.9 |
| Cladosporium gossypiicola | 10 | −1.8% | −0.2% | 3.3 | 77.5 |
| Setophaeosphaeria sp. NN051506 | 10 | −0.2% | −0.5% | 3.3 | 77.2 |
| Trichocladium asperum | 10 | −1.5% | 0.5% | 3.3 | 78.0 |
| Penicillium roseopurpureum | 10 | −1.3% | 0.5% | 3.3 | 78.0 |
| Penicillium sclerotiorum | 10 | 6.9% | −1.6% | 3.5 | 76.4 |
| Penicillium sp-54569 | 10 | 3.0% | −1.8% | 3.4 | 76.2 |
| Penicillium hoeksii | 10 | −2.8% | 0.6% | 3.2 | 78.1 |
| Penicillium concentricum | 10 | −0.6% | 0.6% | 3.3 | 78.1 |
| No Treatment | 0 | 0.0% | 0.0% | 3.3 | 77.6 |
| Penicillin | 25 | −62.4% | 3.1% | 1.2 | 80.1 |
| Aspergillus terreus | 50 | 1.3% | 0.4% | 3.4 | 78.0 |
| Penicillium viticola | 50 | 2.8% | 0.2% | 3.4 | 77.8 |
| Fusarium sp-75363 | 50 | −1.6% | 1.2% | 3.3 | 78.5 |
| Aspergillus insuetus | 50 | 2.1% | −0.6% | 3.4 | 77.2 |
| Penicillium samsonianum | 50 | 2.0% | −0.4% | 3.4 | 77.4 |
| Penicillium sp-52627 | 50 | 0.8% | 0.1% | 3.3 | 77.7 |
| Pestalotiopsis sp-71627 | 50 | 2.9% | 0.4% | 3.4 | 78.0 |
| Myrothecium sp. | 50 | −0.9% | 0.7% | 3.3 | 78.2 |
| Paraphoma sp. | 50 | 6.9% | 0.2% | 3.5 | 77.8 |
| Penicillium vulpinum | 50 | 4.6% | 0.9% | 3.5 | 78.3 |
| Talaromyces sayulitensis | 50 | 1.4% | 1.2% | 3.4 | 78.5 |
| Penicillium steckii | 50 | −1.0% | −0.4% | 3.3 | 77.3 |
| Penicillium antarcticum | 50 | 3.0% | −1.8% | 3.4 | 76.2 |
| Penicillium paxilli | 50 | −5.7% | 0.5% | 3.1 | 78.1 |
| Acremonium sp. XZ1982 | 50 | −4.1% | 0.4% | 3.2 | 78.0 |
| Penicillium sp-72443 | 50 | −10.3% | 2.3% | 3.0 | 79.5 |
| Acrostalagmus luteoalbus | 50 | −13.2% | 3.0% | 2.9 | 80.0 |
| Cladosporium gossypiicola | 50 | −4.6% | 1.1% | 3.2 | 78.5 |
| Setophaeosphaeria sp. NN051506 | 50 | −1.7% | −0.1% | 3.3 | 77.5 |
| Trichocladium asperum | 50 | −0.4% | 0.3% | 3.3 | 77.8 |
| Penicillium roseopurpureum | 50 | −1.8% | 0.6% | 3.3 | 78.1 |
| Penicillium sclerotiorum | 50 | −0.9% | 0.6% | 3.3 | 78.1 |
| Penicillium sp-54569 | 50 | −0.6% | −0.3% | 3.3 | 77.4 |
| Penicillium hoeksii | 50 | −4.8% | 1.9% | 3.2 | 79.1 |
| Penicillium concentricum | 50 | −3.2% | 0.7% | 3.2 | 78.2 |

The invention claimed is:

1. A process for producing ethanol from corn, the process comprising:
   a) saccharifying a starch-containing material at a temperature below the initial gelatinization temperature using an alpha-amylase and a glucoamylase, wherein the starch-containing material comprises corn;
   b) fermenting using a fermenting organism,
   wherein at least one lytic polysaccharide monooxygenase (LPMO) polypeptide or enzyme composition comprising at least one LPMO polypeptide is added before or during saccharifying step a) and/or fermenting step b),
   wherein steps a) and b) are carried out simultaneously; and
   wherein the fermenting organism is yeast and the at least one LPMO polypeptide or the at least one enzyme composition is added before or during yeast propagation.

2. The process of claim 1, wherein the LPMO polypeptide is selected from the group consisting of a Auxiliary Activity 9 (AA9) polypeptide, Auxiliary Activity 10 (AA10) polypeptide, a Auxiliary Activity 11 (AA11) polypeptide, a Auxiliary Activity 13 (AA13) polypeptide, and combinations thereof.

3. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 60% sequence identity thereto;
   ii) the *Penicillium emersonii* AA9 polypeptide of SEQ ID NO: 2 or a variant thereof having at least 60% sequence identity thereto;
   iii) the *Thielavia terrestris* AA9 polypeptide of SEQ ID NO: 3 or a variant thereof having at least 60% sequence identity thereto;
   iv) the *Aspergillus fumigatus* AA9 polypeptide of SEQ ID NO: 4 or a variant thereof having at least 60% sequence identity thereto;
   v) the *Thermoascus crustaceus* AA9 polypeptide of SEQ ID NO: 5 or a variant thereof having at least 60% sequence identity thereto; and
   vi) the *Penicillium emersonii* polypeptide of SEQ ID NO: 6 expressed in *Trichoderma reesei* background, or a variant thereof having at least 60% sequence identity thereto.

4. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 65% sequence identity thereto;
   ii) the *Penicillium emersonii* AA9 polypeptide of SEQ ID NO: 2 or a variant thereof having at least 65% sequence identity thereto;
   iii) the *Thielavia terrestris* AA9 polypeptide of SEQ ID NO: 3 or a variant thereof having at least 65% sequence identity thereto;
   iv) the *Aspergillus fumigatus* AA9 polypeptide of SEQ ID NO: 4 or a variant thereof having at least 65% sequence identity thereto;
   v) the *Thermoascus crustaceus* AA9 polypeptide of SEQ ID NO: 5 or a variant thereof having at least 65% sequence identity thereto; and
   vi) the *Penicillium emersonii* polypeptide of SEQ ID NO: 6 expressed in *Trichoderma reesei* background, or a variant thereof having at least 65% sequence identity thereto.

5. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 70% sequence identity thereto;
   ii) the *Penicillium emersonii* AA9 polypeptide of SEQ ID NO: 2 or a variant thereof having at least 70% sequence identity thereto;
   iii) the *Thielavia terrestris* AA9 polypeptide of SEQ ID NO: 3 or a variant thereof having at least 70% sequence identity thereto;
   iv) the *Aspergillus fumigatus* AA9 polypeptide of SEQ ID NO: 4 or a variant thereof having at least 70% sequence identity thereto;
   V) the *Thermoascus crustaceus* AA9 polypeptide of SEQ ID NO: 5 or a variant thereof having at least 70% sequence identity thereto; and
   vi) the *Penicillium emersonii* polypeptide of SEQ ID NO: 6 expressed in *Trichoderma reesei* background, or a variant thereof having at least 70% sequence identity thereto.

6. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 75% sequence identity thereto;
   ii) the *Penicillium emersonii* AA9 polypeptide of SEQ ID NO: 2 or a variant thereof having at least 75% sequence identity thereto;
   iii) the *Thielavia terrestris* AA9 polypeptide of SEQ ID NO: 3 or a variant thereof having at least 75% sequence identity thereto;
   iv) the *Aspergillus fumigatus* AA9 polypeptide of SEQ ID NO: 4 or a variant thereof having at least 75% sequence identity thereto;
   v) the *Thermoascus crustaceus* AA9 polypeptide of SEQ ID NO: 5 or a variant thereof having at least 75% sequence identity thereto; and
   vi) the *Penicillium emersonii* polypeptide of SEQ ID NO: 6 expressed in *Trichoderma reesei* background, or a variant thereof at least 75% sequence identity thereto.

7. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 80% sequence identity thereto;
   ii) the *Penicillium emersonii* AA9 polypeptide of SEQ ID NO: 2 or a variant thereof having at least 80% sequence identity thereto;
   iii) the *Thielavia terrestris* AA9 polypeptide of SEQ ID NO: 3 or a variant thereof having at least 80% sequence identity thereto;
   iv) the *Aspergillus fumigatus* AA9 polypeptide of SEQ ID NO: 4 or a variant thereof having at least 80% sequence identity thereto;
   v) v) the *Thermoascus crustaceus* AA9 polypeptide of SEQ ID NO: 5 or a variant thereof having at least 80% sequence identity thereto; and
   vi) the *Penicillium emersonii* polypeptide of SEQ ID NO: 6 expressed in *Trichoderma reesei* background, or a variant thereof having at least 80% sequence identity thereto.

8. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 85% sequence identity thereto;
   ii) the *Penicillium emersonii* AA9 polypeptide of SEQ ID NO: 2 or a variant thereof having at least 85% sequence identity thereto;
   iii) the *Thielavia terrestris* AA9 polypeptide of SEQ ID NO: 3 or a variant thereof having at least 85% sequence identity thereto;
   iv) the *Aspergillus fumigatus* AA9 polypeptide of SEQ ID NO: 4 or a variant thereof having at least 85% sequence identity thereto;
   v) the *Thermoascus crustaceus* AA9 polypeptide of SEQ ID NO: 5 or a variant thereof having at least 85% sequence identity thereto; and
   vi) the *Penicillium emersonii* polypeptide of SEQ ID NO: 6 expressed in *Trichoderma reesei* background, or a variant thereof having at least 85% sequence identity thereto.

9. The process of claim 1, wherein the LPMO polypeptide is a AA9 polypeptide selected from the group consisting of:
   i) the *Thermoascus aurantiacus* AA9 polypeptide of SEQ ID NO: 1 or a variant thereof having at least 90% sequence identity thereto;

ii) the *Penicillium emersonii* AA9 polypeptide of SEQ ID NO: 2 or a variant thereof at least 90% sequence identity thereto;

iii) the *Thielavia terrestris* AA9 polypeptide of SEQ ID NO: 3 or a variant thereof having at least 90% sequence identity thereto;

iv) the *Aspergillus fumigatus* AA9 polypeptide of SEQ ID NO: 4 or a variant thereof having at least 90% sequence identity thereto;

v) the *Thermoascus crustaceus* AA9 polypeptide of SEQ ID NO: 5 or a variant thereof having at least 90% sequence identity thereto; and vi) the *Penicillium emersonii* polypeptide of SEQ ID NO: 6 expressed in *Trichoderma reesei* background, or a variant thereof having at least 90% sequence identity thereto.

10. The process of claim 1, wherein the LPMO polypeptide is a AA9 polypeptide selected from the group consisting of:

i) the *Thermoascus aurantiacus* AA9 polypeptide of SEQ ID NO: 1 or a variant thereof having at least 95% sequence identity thereto;

ii) the *Penicillium emersonii* AA9 polypeptide of SEQ ID NO: 2 or a variant thereof having at least 95% sequence identity thereto;

iii) the *Thielavia terrestris* AA9 polypeptide of SEQ ID NO: 3 or a variant thereof having at least 95% sequence identity thereto;

iv) the *Aspergillus fumigatus* AA9 polypeptide of SEQ ID NO: 4 or a variant thereof having at least 95% sequence identity thereto;

v) the *Thermoascus crustaceus* AA9 polypeptide of SEQ ID NO: 5 or a variant thereof having at least 95% sequence identity thereto; and vi) the *Penicillium emersonii* polypeptide of SEQ ID NO: 6 expressed in *Trichoderma reesei* background, or a variant thereof having at least 95% sequence identity thereto.

11. The process of claim 1, wherein the LPMO polypeptide is a AA9 polypeptide selected from the group consisting of:

i) the *Thermoascus aurantiacus* AA9 polypeptide of SEQ ID NO: 1 or a variant thereof having at least 99% sequence identity thereto;

ii) the *Penicillium emersonii* AA9 polypeptide of SEQ ID NO: 2 or a variant thereof having at least 99% sequence identity thereto;

iii) the *Thielavia terrestris* AA9 polypeptide of SEQ ID NO: 3 or a variant thereof having at least 99% sequence identity thereto;

iv) the *Aspergillus fumigatus* AA9 polypeptide of SEQ ID NO: 4 or a variant thereof having at least 99% sequence identity thereto;

v) the *Thermoascus crustaceus* AA9 polypeptide of SEQ ID NO: 5 or a variant thereof having at least 99% sequence identity thereto; and vi) the *Penicillium emersonii* polypeptide of SEQ ID NO: 6 expressed in *Trichoderma reesei* background, or a variant thereof having at least 99% sequence identity thereto.

12. The process of claim 1, wherein the LPMO polypeptide is a AA13 polypeptide selected from the group consisting of:

i) the *Aspergillus terreus* AA13 polypeptide of SEQ ID NO: 119 or a variant thereof having at least 60% sequence identity thereto;

ii) the *Aspergillus lentulus* AA13 polypeptide of SEQ ID NO: 120 or a variant thereof having at least 60% sequence identity thereto;

iii) the *Aspergillus nidulans* polypeptide of SEQ ID NO: 123 or a variant thereof having at least 60% sequence identity thereto;

iv) the *Penicillium polonicum* polypeptide of SEQ ID NO: 124 or a variant thereof having at least 60% sequence identity thereto;

v) the *Penicillium oxalicum* polypeptide of SEQ ID NO: 125 or a variant thereof having at least 60% sequence identity thereto;

vi) the *Mycothermus thermophiles* polypeptide of SEQ ID NO: 127 or a variant thereof having at least 60% sequence identity thereto;

vii) the *Acremonium* sp. XZ1982 polypeptide of SEQ ID NO: 128 or a variant thereof having at least 60% sequence identity thereto;

viii) the *Aspergillus insuetus* polypeptide of SEQ ID NO: 130 or a variant thereof having at least 60% sequence identity thereto;

ix) the *Cladosporium gossypiicola* polypeptide of SEQ ID NO: 131 or a variant thereof having at least 60% sequence identity thereto;

x) the *Fusarium* sp-75363 polypeptide of SEQ ID NO: 132 or a variant thereof having at least 60% sequence identity thereto;

xi) the *Myrothecium* sp. polypeptide of SEQ ID NO: 133 or a variant thereof having at least 60% sequence identity thereto;

xii) the *Paraphoma* sp. polypeptide of SEQ ID NO: 134 or a variant thereof having at least 60% sequence identity thereto;

xiii) the *Penicillium antarcticum* polypeptide of SEQ ID NO: 135 or a variant thereof having at least 60% sequence identity thereto;

xiv) the *Penicillium concentricum* polypeptide of SEQ ID NO: 136 or a variant thereof having at least 60% sequence identity thereto;

XV) the *Penicillium roseopurpureum* polypeptide of SEQ ID NO: 139 or a variant thereof having at least 60% sequence identity thereto;

xvi) the *Penicillium sclerotiorum* polypeptide of SEQ ID NO: 141 or a variant thereof having at least 60% sequence identity thereto;

xvii) the *Penicillium* sp-52627 polypeptide of SEQ ID NO: 142 or a variant thereof having at least 60% sequence identity thereto;

xviii) the *Penicillium* sp-72443 polypeptide of SEQ ID NO: 144 or a variant thereof having at least 60% sequence identity thereto;

xix) the *Penicillium steckii* polypeptide of SEQ ID NO: 145 or a variant thereof having at least 60% sequence identity thereto;

xx) the *Penicillium vulpinum* polypeptide of SEQ ID NO: 147 or a variant thereof having at least 60% sequence identity thereto;

xxi) the *Pestalotiopsis* sp-71627 polypeptide of SEQ ID NO: 148 or a variant thereof having at least 60% sequence identity thereto;

xxii) the *Setophaeosphaeria* sp. NN051506 polypeptide of SEQ ID NO: 149 or a variant thereof having at least 60% sequence identity thereto;

xxiii) the *Talaromyces sayulitensis* polypeptide of SEQ ID NO: 150 or a variant thereof having at least 60% sequence identity thereto; and xxiv) the *Trichocladium asperum* polypeptide of SEQ ID NO: 151 or a variant thereof having at least 60% sequence identity thereto.

13. The process of claim 1, wherein the LPMO polypeptide is a AA13 polypeptide selected from the group consisting of:
  i) the *Aspergillus terreus* AA13 polypeptide of SEQ ID NO: 119 or a variant thereof having at least 65% sequence identity thereto;
  ii) the *Aspergillus lentulus* AA13 polypeptide of SEQ ID NO: 120 or a variant thereof having at least 65% sequence identity thereto;
  iii) the *Aspergillus nidulans* polypeptide of SEQ ID NO: 123 or a variant thereof having at least 65% sequence identity thereto;
  iv) the *Penicillium polonicum* polypeptide of SEQ ID NO: 124 or a variant thereof having at least 65% sequence identity thereto;
  v) the *Penicillium oxalicum* polypeptide of SEQ ID NO: 125 or a variant thereof having at least 65% sequence identity thereto;
  vi) the *Mycothermus thermophiles* polypeptide of SEQ ID NO: 127 or a variant thereof having at least 65% sequence identity thereto;
  vii) the *Acremonium* sp. XZ1982 polypeptide of SEQ ID NO: 128 or a variant thereof having at least 65% sequence identity thereto;
  viii) the *Aspergillus insuetus* polypeptide of SEQ ID NO: 130 or a variant thereof having at least 65% sequence identity thereto;
  ix) the *Cladosporium gossypiicola* polypeptide of SEQ ID NO: 131 or a variant thereof having at least 65% sequence identity thereto;
  x) the *Fusarium* sp-75363 polypeptide of SEQ ID NO: 132 or a variant thereof having at least 65% sequence identity thereto;
  xi) the *Myrothecium* sp. polypeptide of SEQ ID NO: 133 or a variant thereof having at least 65% sequence identity thereto;
  xii) the *Paraphoma* sp. polypeptide of SEQ ID NO: 134 or a variant thereof having at least 65% sequence identity thereto;
  xiii) the *Penicillium antarcticum* polypeptide of SEQ ID NO: 135 or a variant thereof having at least 65% sequence identity thereto;
  xiv) the *Penicillium concentricum* polypeptide of SEQ ID NO: 136 or a variant thereof having at least 65% sequence identity thereto;
  xv) the *Penicillium roseopurpureum* polypeptide of SEQ ID NO: 139 or a variant thereof having at least 65% sequence identity thereto;
  xvi) the *Penicillium sclerotiorum* polypeptide of SEQ ID NO: 141 or a variant thereof having at least 65% sequence identity thereto;
  xvii) the *Penicillium* sp-52627 polypeptide of SEQ ID NO: 142 or a variant thereof having at least 65% sequence identity thereto;
  xviii) the *Penicillium* sp-72443 polypeptide of SEQ ID NO: 144 or a variant thereof having at least 65% sequence identity thereto;
  xix) the *Penicillium steckii* polypeptide of SEQ ID NO: 145 or a variant thereof having at least 65% sequence identity thereto;
  xx) the *Penicillium vulpinum* polypeptide of SEQ ID NO: 147 or a variant thereof having at least 65% sequence identity thereto;
  xxi) the *Pestalotiopsis* sp-71627 polypeptide of SEQ ID NO: 148 or a variant thereof having at least 65% sequence identity thereto;
  xxii) the *Setophaeosphaeria* sp. NN051506 polypeptide of SEQ ID NO: 149 or a variant thereof having at least 65% sequence identity thereto;
  xxiii) the *Talaromyces sayulitensis* polypeptide of SEQ ID NO: 150 or a variant thereof having at least 65% sequence identity thereto; and
  xxiv) the *Trichocladium asperum* polypeptide of SEQ ID NO: 151 or a variant thereof having at least 65% sequence identity thereto.

14. The process of claim 1, wherein the LPMO polypeptide is a AA13 polypeptide selected from the group consisting of:
  i) the *Aspergillus terreus* AA13 polypeptide of SEQ ID NO: 119 or a variant thereof having at least 70% sequence identity thereto;
  ii) the *Aspergillus lentulus* AA13 polypeptide of SEQ ID NO: 120 or a variant thereof having at least 70% sequence identity thereto;
  iii) the *Aspergillus nidulans* polypeptide of SEQ ID NO: 123 or a variant thereof having at least 70% sequence identity thereto;
  iv) the *Penicillium polonicum* polypeptide of SEQ ID NO: 124 or a variant thereof having at least 70% sequence identity thereto;
  v) the *Penicillium oxalicum* polypeptide of SEQ ID NO: 125 or a variant thereof having at least 70% sequence identity thereto;
  vi) the *Mycothermus thermophiles* polypeptide of SEQ ID NO: 127 or a variant thereof having at least 70% sequence identity thereto;
  vii) the *Acremonium* sp. XZ1982 polypeptide of SEQ ID NO: 128 or a variant thereof having at least 70% sequence identity thereto;
  viii) the *Aspergillus insuetus* polypeptide of SEQ ID NO: 130 or a variant thereof having at least 70% sequence identity thereto;
  ix) the *Cladosporium gossypiicola* polypeptide of SEQ ID NO: 131 or a variant thereof having at least 70% sequence identity thereto;
  x) the *Fusarium* sp-75363 polypeptide of SEQ ID NO: 132 or a variant thereof having at least 70% sequence identity thereto;
  xi) the *Myrothecium* sp. polypeptide of SEQ ID NO: 133 or a variant thereof having at least 70% sequence identity thereto;
  xii) the *Paraphoma* sp. polypeptide of SEQ ID NO: 134 or a variant thereof having at least 70% sequence identity thereto;
  xiii) the *Penicillium antarcticum* polypeptide of SEQ ID NO: 135 or a variant thereof having at least 70% sequence identity thereto;
  xiv) the *Penicillium concentricum* polypeptide of SEQ ID NO: 136 or a variant thereof having at least 70% sequence identity thereto;
  Xv) the *Penicillium roseopurpureum* polypeptide of SEQ ID NO: 139 or a variant thereof having at least 70% sequence identity thereto;
  xvii) the *Penicillium sclerotiorum* polypeptide of SEQ ID NO: 141 or a variant thereof having at least 70% sequence identity thereto;
  xvii) the *Penicillium* sp-52627 polypeptide of SEQ ID NO: 142 or a variant thereof having at least 70% sequence identity thereto;

xviii) the *Penicillium* sp-72443 polypeptide of SEQ ID NO: 144 or a variant thereof having at least 70% sequence identity thereto;
xix) the *Penicillium steckii* polypeptide of SEQ ID NO: 145 or a variant thereof having at least 70% sequence identity thereto;
xx) the *Penicillium vulpinum* polypeptide of SEQ ID NO: 147 or a variant thereof having at least 70% sequence identity thereto;
xxi) the *Pestalotiopsis* sp-71627 polypeptide of SEQ ID NO: 148 or a variant thereof having at least 70% sequence identity thereto;
xxii) the *Setophaeosphaeria* sp. NN051506 polypeptide of SEQ ID NO: 149 or a variant thereof having at least 70% sequence identity thereto;
xxiii) the *Talaromyces sayulitensis* polypeptide of SEQ ID NO: 150 or a variant thereof having at least 70% sequence identity thereto; and
xxiv) the *Trichocladium asperum* polypeptide of SEQ ID NO: 151 or a variant thereof having at least 70% sequence identity thereto.

15. The process of claim 1, wherein the LPMO polypeptide is a AA13 polypeptide selected from the group consisting of:
i) the *Aspergillus terreus* AA13 polypeptide of SEQ ID NO: 119 or a variant thereof having at least 75% sequence identity thereto;
ii) the *Aspergillus lentulus* AA13 polypeptide of SEQ ID NO: 120 or a variant thereof having at least 75% sequence identity thereto;
iii) the *Aspergillus nidulans* polypeptide of SEQ ID NO: 123 or a variant thereof having at least 75% sequence identity thereto;
iv) the *Penicillium polonicum* polypeptide of SEQ ID NO: 124 or a variant thereof having at least 75% sequence identity thereto;
v) the *Penicillium oxalicum* polypeptide of SEQ ID NO: 125 or a variant thereof having at least 75% sequence identity thereto;
vi) the *Mycothermus thermophiles* polypeptide of SEQ ID NO: 127 or a variant thereof having at least 75% sequence identity thereto;
vii) the *Acremonium* sp. XZ1982 polypeptide of SEQ ID NO: 128 or a variant thereof having at least 75% sequence identity thereto;
viii) the *Aspergillus insuetus* polypeptide of SEQ ID NO: 130 or a variant thereof having at least 75% sequence identity thereto;
ix) the *Cladosporium gossypiicola* polypeptide of SEQ ID NO: 131 or a variant thereof having at least 75% sequence identity thereto;
x) the *Fusarium* sp-75363 polypeptide of SEQ ID NO: 132 or a variant thereof having at least 75% sequence identity thereto;
xi) the *Myrothecium* sp. polypeptide of SEQ ID NO: 133 or a variant thereof having at least 75% sequence identity thereto;
xii) the *Paraphoma* sp. polypeptide of SEQ ID NO: 134 or a variant thereof having at least 75% sequence identity thereto;
xiii) the *Penicillium antarcticum* polypeptide of SEQ ID NO: 135 or a variant thereof having at least 75% sequence identity thereto;
xiv) the *Penicillium concentricum* polypeptide of SEQ ID NO: 136 or a variant thereof having at least 75% sequence identity thereto;
xv) the *Penicillium roseopurpureum* polypeptide of SEQ ID NO: 139 or a variant thereof having at least 75% sequence identity thereto;
xvi) the *Penicillium sclerotiorum* polypeptide of SEQ ID NO: 141 or a variant thereof having at least 75% sequence identity thereto;
xvii) the *Penicillium* sp-52627 polypeptide of SEQ ID NO: 142 or a variant thereof having at least 75% sequence identity thereto;
xviii) the *Penicillium* sp-72443 polypeptide of SEQ ID NO: 144 or a variant thereof having at least 75% sequence identity thereto;
xix) the *Penicillium steckii* polypeptide of SEQ ID NO: 145 or a variant thereof having at least 75% sequence identity thereto;
xx) the *Penicillium vulpinum* polypeptide of SEQ ID NO: 147 or a variant thereof having at least 75% sequence identity thereto;
xxi) the *Pestalotiopsis* sp-71627 polypeptide of SEQ ID NO: 148 or a variant thereof having at least 75% sequence identity thereto;
xxii) the *Setophaeosphaeria* sp. NN051506 polypeptide of SEQ ID NO: 149 or a variant thereof having at least 75% sequence identity thereto;
xxiii) the *Talaromyces sayulitensis* polypeptide of SEQ ID NO: 150 or a variant thereof having at least 75% sequence identity thereto; and
xxiv) the *Trichocladium asperum* polypeptide of SEQ ID NO: 151 or a variant thereof having at least 75% sequence identity thereto.

16. The process of claim 1, wherein the LPMO polypeptide is a AA13 polypeptide selected from the group consisting of:
i) the *Aspergillus terreus* AA13 polypeptide of SEQ ID NO: 119 or a variant thereof having at least 80% sequence identity thereto;
ii) the *Aspergillus lentulus* AA13 polypeptide of SEQ ID NO: 120 or a variant thereof having at least 80% sequence identity thereto;
iii) the *Aspergillus nidulans* polypeptide of SEQ ID NO: 123 or a variant thereof having at least 80% sequence identity thereto;
iv) the *Penicillium polonicum* polypeptide of SEQ ID NO: 124 or a variant thereof having at least 80% sequence identity thereto;
v) the *Penicillium oxalicum* polypeptide of SEQ ID NO: 125 or a variant thereof having at least 80% sequence identity thereto;
vi) the *Mycothermus thermophiles* polypeptide of SEQ ID NO: 127 or a variant thereof having at least 80% sequence identity thereto;
vii) the *Acremonium* sp. XZ1982 polypeptide of SEQ ID NO: 128 or a variant thereof having at least 80% sequence identity thereto;
viii) the *Aspergillus insuetus* polypeptide of SEQ ID NO: 130 or a variant thereof having at least 80% sequence identity thereto;
ix) the *Cladosporium gossypiicola* polypeptide of SEQ ID NO: 131 or a variant thereof having at least 80% sequence identity thereto;
x) the *Fusarium* sp-75363 polypeptide of SEQ ID NO: 132 or a variant thereof having at least 80% sequence identity thereto;
xi) the *Myrothecium* sp. polypeptide of SEQ ID NO: 133 or a variant thereof having at least 80% sequence identity thereto;

xii) the *Paraphoma* sp. polypeptide of SEQ ID NO: 134 or a variant thereof having at least 80% sequence identity thereto;

xiii) the *Penicillium antarcticum* polypeptide of SEQ ID NO: 135 or a variant thereof having at least 80% sequence identity thereto;

xiv) the *Penicillium concentricum* polypeptide of SEQ ID NO: 136 or a variant thereof having at least 80% sequence identity thereto;

xv) the *Penicillium roseopurpureum* polypeptide of SEQ ID NO: 139 or a variant thereof having at least 80% sequence identity thereto;

xvi) the *Penicillium sclerotiorum* polypeptide of SEQ ID NO: 141 or a variant thereof having at least 80% sequence identity thereto;

xvii) the *Penicillium* sp-52627 polypeptide of SEQ ID NO: 142 or a variant thereof having at least 80% sequence identity thereto;

xviii) the *Penicillium* sp-72443 polypeptide of SEQ ID NO: 144 or a variant thereof having at least 80% sequence identity thereto;

xix) the *Penicillium steckii* polypeptide of SEQ ID NO: 145 or a variant thereof having at least 80% sequence identity thereto;

xx) the *Penicillium vulpinum* polypeptide of SEQ ID NO: 147 or a variant thereof having at least 80% sequence identity thereto;

xxi) the *Pestalotiopsis* sp-71627 polypeptide of SEQ ID NO: 148 or a variant thereof having at least 80% sequence identity thereto;

xxii) the *Setophaeosphaeria* sp. NN051506 polypeptide of SEQ ID NO: 149 or a variant thereof having at least 80% sequence identity thereto;

xxiii) the *Talaromyces sayulitensis* polypeptide of SEQ ID NO: 150 or a variant thereof having at least 80% sequence identity thereto; and xxiv) the *Trichocladium asperum* polypeptide of SEQ ID NO: 151 or a variant thereof having at least 80% sequence identity thereto.

17. The process of claim 1, wherein the LPMO polypeptide is a AA13 polypeptide selected from the group consisting of:

i) the *Aspergillus terreus* AA13 polypeptide of SEQ ID NO: 119 or a variant thereof having at least 85% sequence identity thereto;

ii) the *Aspergillus lentulus* AA13 polypeptide of SEQ ID NO: 120 or a variant thereof having at least 85% sequence identity thereto;

iii) the *Aspergillus nidulans* polypeptide of SEQ ID NO: 123 or a variant thereof having at least 85% sequence identity thereto;

iv) the *Penicillium polonicum* polypeptide of SEQ ID NO: 124 or a variant thereof having at least 85% sequence identity thereto;

v) the *Penicillium oxalicum* polypeptide of SEQ ID NO: 125 or a variant thereof having at least 85% sequence identity thereto;

vi) the *Mycothermus thermophiles* polypeptide of SEQ ID NO: 127 or a variant thereof having at least 85% sequence identity thereto;

vii) the *Acremonium* sp. XZ1982 polypeptide of SEQ ID NO: 128 or a variant thereof having at least 85% sequence identity thereto;

viii) the *Aspergillus insuetus* polypeptide of SEQ ID NO: 130 or a variant thereof having at least 85% sequence identity thereto;

ix) the *Cladosporium gossypiicola* polypeptide of SEQ ID NO: 131 or a variant thereof having at least 85% sequence identity thereto;

x) the *Fusarium* sp-75363 polypeptide of SEQ ID NO: 132 or a variant thereof having at least 85% sequence identity thereto;

xi) the *Myrothecium* sp. polypeptide of SEQ ID NO: 133 or a variant thereof having at least 85% sequence identity thereto;

xii) the *Paraphoma* sp. polypeptide of SEQ ID NO: 134 or a variant thereof having at least 85% sequence identity thereto;

xiii) the *Penicillium antarcticum* polypeptide of SEQ ID NO: 135 or a variant thereof having at least 85% sequence identity thereto;

xiv) the *Penicillium concentricum* polypeptide of SEQ ID NO: 136 or a variant thereof having at least 85% sequence identity thereto;

xv) the *Penicillium roseopurpureum* polypeptide of SEQ ID NO: 139 or a variant thereof having at least 85% sequence identity thereto;

xvi) the *Penicillium sclerotiorum* polypeptide of SEQ ID NO: 141 or a variant thereof having at least 85% sequence identity thereto;

xvii) the *Penicillium* sp-52627 polypeptide of SEQ ID NO: 142 or a variant thereof having at least 85% sequence identity thereto;

xviii) the *Penicillium* sp-72443 polypeptide of SEQ ID NO: 144 or a variant thereof having at least 85% sequence identity thereto;

xix) the *Penicillium steckii* polypeptide of SEQ ID NO: 145 or a variant thereof having at least 85% sequence identity thereto;

xx) the *Penicillium vulpinum* polypeptide of SEQ ID NO: 147 or a variant thereof having at least 85% sequence identity thereto;

xxi) the *Pestalotiopsis* sp-71627 polypeptide of SEQ ID NO: 148 or a variant thereof having at least 85% sequence identity thereto;

xxii) the *Setophaeosphaeria* sp. NN051506 polypeptide of SEQ ID NO: 149 or a variant thereof having at least 85% sequence identity thereto;

xxiii) the *Talaromyces sayulitensis* polypeptide of SEQ ID NO: 150 or a variant thereof having at least 85% sequence identity thereto; and xxiv) the *Trichocladium asperum* polypeptide of SEQ ID NO: 151 or a variant thereof having at least 85% sequence identity thereto.

18. The process of claim 1, wherein the LPMO polypeptide is a AA13 polypeptide selected from the group consisting of:

i) the *Aspergillus terreus* AA13 polypeptide of SEQ ID NO: 119 or a variant thereof having at least 90% sequence identity thereto;

ii) the *Aspergillus lentulus* AA13 polypeptide of SEQ ID NO: 120 or a variant thereof having at least 90% sequence identity thereto;

iii) the *Aspergillus nidulans* polypeptide of SEQ ID NO: 123 or a variant thereof having at least 90% sequence identity thereto;

iv) the *Penicillium polonicum* polypeptide of SEQ ID NO: 124 or a variant thereof having at least 90% sequence identity thereto;

v) the *Penicillium oxalicum* polypeptide of SEQ ID NO: 125 or a variant thereof having at least 90% sequence identity thereto;

vi) the *Mycothermus thermophiles* polypeptide of SEQ ID NO: 127 or a variant thereof having at least 90% sequence identity thereto;

vii) the *Acremonium* sp. XZ1982 polypeptide of SEQ ID NO: 128 or a variant thereof having at least 90% sequence identity thereto;

viii) the *Aspergillus insuetus* polypeptide of SEQ ID NO: 130 or a variant thereof having at least 90% sequence identity thereto;

ix) the *Cladosporium gossypiicola* polypeptide of SEQ ID NO: 131 or a variant thereof having at least 90% sequence identity thereto;

x) the *Fusarium* sp-75363 polypeptide of SEQ ID NO: 132 or a variant thereof having at least 90% sequence identity thereto;

xi) the *Myrothecium* sp. polypeptide of SEQ ID NO: 133 or a variant thereof having at least 90% sequence identity thereto;

xii) the *Paraphoma* sp. polypeptide of SEQ ID NO: 134 or a variant thereof having at least 90% sequence identity thereto;

xiii) the *Penicillium antarcticum* polypeptide of SEQ ID NO: 135 or a variant thereof having at least 90% sequence identity thereto;

xiv) the *Penicillium concentricum* polypeptide of SEQ ID NO: 136 or a variant thereof having at least 90% sequence identity thereto;

xv) the *Penicillium roseopurpureum* polypeptide of SEQ ID NO: 139 or a variant thereof having at least 90% sequence identity thereto;

xvi) the *Penicillium sclerotiorum* polypeptide of SEQ ID NO: 141 or a variant thereof having at least 90% sequence identity thereto;

xvii) the *Penicillium* sp-52627 polypeptide of SEQ ID NO: 142 or a variant thereof having at least 90% sequence identity thereto;

xviii) the *Penicillium* sp-72443 polypeptide of SEQ ID NO: 144 or a variant thereof having at least 90% sequence identity thereto;

xix) the *Penicillium steckii* polypeptide of SEQ ID NO: 145 or a variant thereof having at least 90% sequence identity thereto;

xx) the *Penicillium vulpinum* polypeptide of SEQ ID NO: 147 or a variant thereof having at least 90% sequence identity thereto;

xxi) the *Pestalotiopsis* sp-71627 polypeptide of SEQ ID NO: 148 or a variant thereof having at least 90% sequence identity thereto;

xxi) the *Setophaeosphaeria* sp. NN051506 polypeptide of SEQ ID NO: 149 or a variant thereof having at least 90% sequence identity thereto;

xxiii) the *Talaromyces sayulitensis* polypeptide of SEQ ID NO: 150 or a variant thereof having at least 90% sequence identity thereto; and xxiv) the *Trichocladium asperum* polypeptide of SEQ ID NO: 151 or a variant thereof having at least 90% sequence identity thereto.

19. The process of claim 1, wherein the LPMO polypeptide is a AA13 polypeptide selected from the group consisting of:

i) the *Aspergillus terreus* AA13 polypeptide of SEQ ID NO: 119 or a variant thereof having at least 95% sequence identity thereto;

ii) the *Aspergillus lentulus* AA13 polypeptide of SEQ ID NO: 120 or a variant thereof having at least 95% iii) the *Aspergillus nidulans* polypeptide of SEQ ID NO: 123 or a variant thereof having at least 95% sequence identity thereto;

iv) the *Penicillium polonicum* polypeptide of SEQ ID NO: 124 or a variant thereof having at least 95% sequence identity thereto;

v) the *Penicillium oxalicum* polypeptide of SEQ ID NO: 125 or a variant thereof having at least 95% sequence identity thereto;

vi) the *Mycothermus thermophiles* polypeptide of SEQ ID NO: 127 or a variant thereof having at least 95% sequence identity thereto;

vii) the *Acremonium* sp. XZ1982 polypeptide of SEQ ID NO: 128 or a variant thereof having at least 95% sequence identity thereto;

viii) the *Aspergillus insuetus* polypeptide of SEQ ID NO: 130 or a variant thereof having at least 95% sequence identity thereto;

ix) the *Cladosporium gossypiicola* polypeptide of SEQ ID NO: 131 or a variant thereof having at least 95% sequence identity thereto;

x) the *Fusarium* sp-75363 polypeptide of SEQ ID NO: 132 or a variant thereof having at least 95% sequence identity thereto;

xi) the *Myrothecium* sp. polypeptide of SEQ ID NO: 133 or a variant thereof having at least 95% sequence identity thereto;

xii) the *Paraphoma* sp. polypeptide of SEQ ID NO: 134 or a variant thereof having at least 95% sequence identity thereto;

xiii) the *Penicillium antarcticum* polypeptide of SEQ ID NO: 135 or a variant thereof having at least 95% sequence identity thereto;

xiv) the *Penicillium concentricum* polypeptide of SEQ ID NO: 136 or a variant thereof having at least 95% sequence identity thereto;

xv) the *Penicillium roseopurpureum* polypeptide of SEQ ID NO: 139 or a variant thereof having at least 95% sequence identity thereto;

xvi) the *Penicillium sclerotiorum* polypeptide of SEQ ID NO: 141 or a variant thereof having at least 95% sequence identity thereto;

xvii) the *Penicillium* sp-52627 polypeptide of SEQ ID NO: 142 or a variant thereof having at least 95% sequence identity thereto;

xviii) the *Penicillium* sp-72443 polypeptide of SEQ ID NO: 144 or a variant thereof having at least 95% sequence identity thereto;

xix) the *Penicillium steckii* polypeptide of SEQ ID NO: 145 or a variant thereof having at least 95% sequence identity thereto;

xx) the *Penicillium vulpinum* polypeptide of SEQ ID NO: 147 or a variant thereof having at least 95% sequence identity thereto;

xxi) the *Pestalotiopsis* sp-71627 polypeptide of SEQ ID NO: 148 or a variant thereof having at least 95% sequence identity thereto;

xxii) the *Setophaeosphaeria* sp. NN051506 polypeptide of SEQ ID NO: 149 or a variant thereof having at least 95% sequence identity thereto;

xxiii) the *Talaromyces sayulitensis* polypeptide of SEQ ID NO: 150 or a variant thereof having at least 95% sequence identity thereto; and xxiv) the *Trichocladium asperum* polypeptide of SEQ ID NO: 151 or a variant thereof having at least 95% sequence identity thereto.

20. The process of claim 1, wherein the LPMO polypeptide is a AA13 polypeptide selected from the group consisting of:
  i) the *Aspergillus terreus* AA13 polypeptide of SEQ ID NO: 119 or a variant thereof having at least 99% sequence identity thereto;
  ii) the *Aspergillus lentulus* AA13 polypeptide of SEQ ID NO: 120 or a variant thereof having at least 99% sequence identity thereto;
  iii) the *Aspergillus nidulans* polypeptide of SEQ ID NO: 123 or a variant thereof having at least 99% sequence identity thereto;
  iv) the *Penicillium polonicum* polypeptide of SEQ ID NO: 124 or a variant thereof having at least 99% sequence identity thereto;
  v) the *Penicillium oxalicum* polypeptide of SEQ ID NO: 125 or a variant thereof having at least 99% sequence identity thereto;
  vi) the *Mycothermus thermophiles* polypeptide of SEQ ID NO: 127 or a variant thereof having at least 99% sequence identity thereto;
  vii) the *Acremonium* sp. XZ1982 polypeptide of SEQ ID NO: 128 or a variant thereof having at least 99% sequence identity thereto;
  viii) the *Aspergillus insuetus* polypeptide of SEQ ID NO: 130 or a variant thereof having at least 99% sequence identity thereto;
  ix) the *Cladosporium gossypiicola* polypeptide of SEQ ID NO: 131 or a variant thereof having at least 99% sequence identity thereto;
  x) the *Fusarium* sp-75363 polypeptide of SEQ ID NO: 132 or a variant thereof having at least 99% sequence identity thereto;
  xi) the *Myrothecium* sp. polypeptide of SEQ ID NO: 133 or a variant thereof having at least 99% sequence identity thereto;
  xii) the *Paraphoma* sp. polypeptide of SEQ ID NO: 134 or a variant thereof having at least 99% sequence identity thereto;
  xiii) the *Penicillium antarcticum* polypeptide of SEQ ID NO: 135 or a variant thereof having at least 99% sequence identity thereto;
  xiv) the *Penicillium concentricum* polypeptide of SEQ ID NO: 136 or a variant thereof having at least 99% sequence identity thereto;
  xv) the *Penicillium roseopurpureum* polypeptide of SEQ ID NO: 139 or a variant thereof having at least 99% sequence identity thereto;
  xvi) the *Penicillium sclerotiorum* polypeptide of SEQ ID NO: 141 or a variant thereof having at least 99% sequence identity thereto;
  xvii) the *Penicillium* sp-52627 polypeptide of SEQ ID NO: 142 or a variant thereof having at least 99% sequence identity thereto;
  xviii) the *Penicillium* sp-72443 polypeptide of SEQ ID NO: 144 or a variant thereof having at least 99% sequence identity thereto;
  xix) the *Penicillium steckii* polypeptide of SEQ ID NO: 145 or a variant thereof having at least 99% sequence identity thereto;
  xx) the *Penicillium vulpinum* polypeptide of SEQ ID NO: 147 or a variant thereof having at least 99% sequence identity thereto;
  xxi) the *Pestalotiopsis* sp-71627 polypeptide of SEQ ID NO: 148 or a variant thereof having at least 99% sequence identity thereto;
  xxii) the *Setophaeosphaeria* sp. NN051506 polypeptide of SEQ ID NO: 149 or a variant thereof having at least 99% sequence identity thereto;
  xxiii) the *Talaromyces sayulitensis* polypeptide of SEQ ID NO: 150 or a variant thereof having at least 99% sequence identity thereto; and
  xxiv) the *Trichocladium asperum* polypeptide of SEQ ID NO: 151 or a variant thereof having at least 99% sequence identity thereto.

\* \* \* \* \*

SEQUENCE LISTING

<160> NUMBER OF SEQ ID NOS: 151

<210> SEQ ID NO 1
<211> LENGTH: 249
<212> TYPE: PRT
<213> ORGANISM: Thermoascus aurantiacus

<400> SEQUENCE: 1

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Asn Tyr Gly Gly Tyr Leu Val Asn Gln Tyr Pro Tyr Met Ser Asn
        35                  40                  45

Pro Pro Glu Val Ile Ala Trp Ser Thr Thr Ala Thr Asp Leu Gly Phe
50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His His Gly Pro Val Ile
            100                 105                 110

Asn Tyr Leu Ala Pro Cys Asn Gly Asp Cys Ser Thr Val Asp Lys Thr
        115                 120                 125

Gln Leu Glu Phe Phe Lys Ile Ala Glu Ser Gly Leu Ile Asn Asp Asp
130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
        195                 200                 205

Ser Asp Asn Pro Ala Gly Thr Leu Gly Thr Ala Leu Tyr His Asp Thr
210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                245

<210> SEQ ID NO 2
<211> LENGTH: 236
<212> TYPE: PRT
<213> ORGANISM: Penicillium emersonii

<400> SEQUENCE: 2

His Gly Phe Val Gln Gly Ile Val Ile Gly Asp Gln Phe Tyr Ser Gly
1               5                   10                  15

Tyr Ile Val Asn Ser Phe Pro Tyr Glu Ser Asn Pro Pro Val Ile
            20                  25                  30

Gly Trp Ala Thr Thr Ala Thr Asp Leu Gly Phe Val Asp Gly Thr Gly
        35                  40                  45

Tyr Gln Gly Pro Asp Ile Ile Cys His Arg Asn Ala Thr Pro Ala Pro
50                  55                  60

Leu Thr Ala Pro Val Ala Ala Gly Gly Thr Val Glu Leu Gln Trp Thr

```
            65                  70                  75                  80
        Pro Trp Pro Asp Ser His His Gly Pro Val Ile Thr Tyr Leu Ala Pro
                            85                  90                  95

Cys Asn Gly Asn Cys Ser Thr Val Asp Lys Thr Thr Leu Glu Phe Phe
                        100                 105                 110

Lys Ile Asp Gln Gln Gly Leu Ile Asp Asp Thr Ser Pro Pro Gly Thr
                        115                 120                 125

Trp Ala Ser Asp Asn Leu Ile Ala Asn Asn Ser Trp Thr Val Thr
                    130                 135                 140

Ile Pro Asn Ser Val Ala Pro Gly Asn Tyr Val Leu Arg His Glu Ile
        145                 150                 155                 160

Ile Ala Leu His Ser Ala Asn Asn Lys Asp Gly Ala Gln Asn Tyr Pro
                        165                 170                 175

Gln Cys Ile Asn Ile Glu Val Thr Gly Gly Ser Asp Ala Pro Glu
                        180                 185                 190

Gly Thr Leu Gly Glu Asp Leu Tyr His Asp Thr Asp Pro Gly Ile Leu
                    195                 200                 205

Val Asp Ile Tyr Glu Pro Ile Ala Thr Tyr Thr Ile Pro Gly Pro Pro
                    210                 215                 220

Glu Pro Thr Phe His His His His His His
        225                 230                 235

<210> SEQ ID NO 3
<211> LENGTH: 208
<212> TYPE: PRT
<213> ORGANISM: Thielavia terrestris

<400> SEQUENCE: 3

His Tyr Thr Trp Pro Arg Val Asn Asp Gly Ala Asp Trp Gln Gln Val
        1               5                   10                  15

Arg Lys Ala Asp Asn Trp Gln Asp Asn Gly Tyr Val Gly Asp Val Thr
                        20                  25                  30

Ser Pro Gln Ile Arg Cys Phe Gln Ala Thr Pro Ser Pro Ala Pro Ser
                    35                  40                  45

Val Leu Asn Thr Thr Ala Gly Ser Thr Val Thr Tyr Trp Ala Asn Pro
        50                  55                  60

Asp Val Tyr His Pro Gly Pro Val Gln Phe Tyr Met Ala Arg Val Pro
        65                  70                  75                  80

Asp Gly Glu Asp Ile Asn Ser Trp Asn Gly Asp Gly Ala Val Trp Phe
                        85                  90                  95

Lys Val Tyr Glu Asp His Pro Thr Phe Gly Ala Gln Leu Thr Trp Pro
                        100                 105                 110

Ser Thr Gly Lys Ser Ser Phe Ala Val Pro Ile Pro Pro Cys Ile Lys
                    115                 120                 125

Ser Gly Tyr Tyr Leu Leu Arg Ala Glu Gln Ile Gly Leu His Val Ala
                    130                 135                 140

Gln Ser Val Gly Gly Ala Gln Phe Tyr Ile Ser Cys Ala Gln Leu Ser
        145                 150                 155                 160

Val Thr Gly Gly Gly Ser Thr Glu Pro Pro Asn Lys Val Ala Phe Pro
                        165                 170                 175

Gly Ala Tyr Ser Ala Thr Asp Pro Gly Ile Leu Ile Asn Ile Tyr Tyr
                        180                 185                 190

Pro Val Pro Thr Ser Tyr Gln Asn Pro Gly Pro Ala Val Phe Ser Cys
                    195                 200                 205
```

<210> SEQ ID NO 4
<211> LENGTH: 250
<212> TYPE: PRT
<213> ORGANISM: Aspergillus fumigatus

<400> SEQUENCE: 4

Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45

Pro Pro Asp Thr Ile Ala Trp Ser Thr Thr Ala Thr Asp Leu Gly Phe
50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Pro Trp Pro Asp Ser His His Gly Pro Val Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
130                 135                 140

Asn Pro Pro Gly Val Trp Ala Ser Asp Glu Leu Ile Ala Asn Asn Asn
145                 150                 155                 160

Thr Trp Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250

<210> SEQ ID NO 5
<211> LENGTH: 229
<212> TYPE: PRT
<213> ORGANISM: Thermoascus crustaceus

<400> SEQUENCE: 5

His Gly Phe Val Gln Asn Ile Val Ile Asp Gly Lys Ser Tyr Gly Gly
1               5                   10                  15

Tyr Ile Val Asn Gln Tyr Pro Tyr Met Ser Asp Pro Pro Glu Val Val
            20                  25                  30

Gly Trp Ser Thr Thr Ala Thr Asp Leu Gly Phe Val Asp Gly Thr Gly
        35                  40                  45

Tyr Gln Gly Pro Asp Ile Ile Cys His Arg Gly Ala Lys Pro Ala Ala
        50                  55                  60

Leu Thr Ala Gln Val Ala Ala Gly Gly Thr Val Lys Leu Glu Trp Thr
65                  70                  75                  80

```
Pro Trp Pro Asp Ser His His Gly Pro Val Ile Asn Tyr Leu Ala Pro
                 85                  90                  95

Cys Asn Gly Asp Cys Ser Thr Val Asp Lys Thr Gln Leu Lys Phe Phe
            100                 105                 110

Lys Ile Ala Gln Ala Gly Leu Ile Asp Asp Asn Ser Pro Pro Gly Ile
        115                 120                 125

Trp Ala Ser Asp Asn Leu Ile Ala Ala Asn Ser Trp Thr Val Thr
    130                 135                 140

Ile Pro Thr Thr Thr Ala Pro Gly Asn Tyr Val Leu Arg His Glu Ile
145                 150                 155                 160

Ile Ala Leu His Ser Ala Gly Asn Lys Asp Gly Ala Gln Asn Tyr Pro
                165                 170                 175

Gln Cys Ile Asn Leu Lys Val Thr Gly Asn Gly Ser Gly Asn Pro Pro
            180                 185                 190

Ala Gly Ala Leu Gly Thr Ala Leu Tyr Lys Asp Thr Asp Pro Gly Ile
        195                 200                 205

Leu Ile Asn Ile Tyr Gln Lys Leu Ser Ser Tyr Val Ile Pro Gly Pro
    210                 215                 220

Ala Leu Tyr Thr Gly
225

<210> SEQ ID NO 6
<211> LENGTH: 228
<212> TYPE: PRT
<213> ORGANISM: Penicillium emersonii

<400> SEQUENCE: 6

His Gly Phe Val Gln Gly Ile Val Ile Gly Asp Gln Phe Tyr Ser Gly
1               5                   10                  15

Tyr Ile Val Asn Ser Phe Pro Tyr Glu Ser Asn Pro Pro Val Ile
            20                  25                  30

Gly Trp Ala Thr Thr Ala Thr Asp Leu Gly Phe Val Asp Gly Thr Gly
        35                  40                  45

Tyr Gln Gly Pro Asp Ile Ile Cys His Arg Asn Ala Thr Pro Ala Pro
50                  55                  60

Leu Thr Ala Pro Val Ala Ala Gly Gly Thr Val Glu Leu Gln Trp Thr
65                  70                  75                  80

Pro Trp Pro Asp Ser His His Gly Pro Val Ile Thr Tyr Leu Ala Pro
                85                  90                  95

Cys Asn Gly Asn Cys Ser Thr Val Asp Lys Thr Thr Leu Glu Phe Phe
            100                 105                 110

Lys Ile Asp Gln Gln Gly Leu Ile Asp Asp Thr Ser Pro Pro Gly Thr
        115                 120                 125

Trp Ala Ser Asp Asn Leu Ile Ala Asn Asn Asn Ser Trp Thr Val Thr
    130                 135                 140

Ile Pro Asn Ser Val Ala Pro Gly Asn Tyr Val Leu Arg His Glu Ile
145                 150                 155                 160

Ile Ala Leu His Ser Ala Asn Asn Lys Asp Gly Ala Gln Asn Tyr Pro
                165                 170                 175

Gln Cys Ile Asn Ile Glu Val Thr Gly Gly Ser Asp Ala Pro Glu
            180                 185                 190

Gly Thr Leu Gly Glu Asp Leu Tyr His Asp Thr Asp Pro Gly Ile Leu
        195                 200                 205

Val Asp Ile Tyr Glu Pro Ile Ala Thr Tyr Thr Ile Pro Gly Pro Pro
    210                 215                 220
```

Glu Pro Thr Phe
225

<210> SEQ ID NO 7
<211> LENGTH: 326
<212> TYPE: PRT
<213> ORGANISM: Thielavia terrestris

<400> SEQUENCE: 7

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 8
<211> LENGTH: 239
<212> TYPE: PRT

<213> ORGANISM: Thielavia terrestris

<400> SEQUENCE: 8

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Pro Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Trp Gly Thr Ala Ile Val Tyr Lys
130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe
225                 230                 235
```

<210> SEQ ID NO 9
<211> LENGTH: 258
<212> TYPE: PRT
<213> ORGANISM: Thielavia terrestris

<400> SEQUENCE: 9

```
Met Leu Leu Thr Ser Val Leu Gly Ser Ala Leu Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
```

```
                    115                 120                 125
Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala

<210> SEQ ID NO 10
<211> LENGTH: 226
<212> TYPE: PRT
<213> ORGANISM: Thielavia terrestris

<400> SEQUENCE: 10

Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
                20                  25                  30

Gln Val Arg Lys Ala Asp Asn Trp Gln Asp Asn Gly Tyr Val Gly Asp
            35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
    115                 120                 125

Trp Pro Ser Thr Gly Lys Ser Ser Phe Ala Val Pro Ile Pro Pro Cys
130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
```

-continued

```
<210> SEQ ID NO 11
<211> LENGTH: 304
<212> TYPE: PRT
<213> ORGANISM: Thielavia terrestris

<400> SEQUENCE: 11

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
    290                 295                 300

<210> SEQ ID NO 12
<211> LENGTH: 317
<212> TYPE: PRT
<213> ORGANISM: Thielavia terrestris

<400> SEQUENCE: 12

Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
```

```
                20                  25                  30
Tyr Gly Ile Arg Asp Pro Ser Tyr Asp Gly Pro Ile Thr Asp Val Thr
             35                  40                  45

Ser Asp Ser Leu Ala Cys Asn Gly Pro Pro Asn Pro Thr Thr Pro Ser
 50                  55                  60

Pro Tyr Ile Ile Asn Val Thr Ala Gly Thr Thr Val Ala Ala Ile Trp
 65                  70                  75                  80

Arg His Thr Leu Thr Ser Gly Pro Asp Asp Val Met Asp Ala Ser His
                 85                  90                  95

Lys Gly Pro Thr Leu Ala Tyr Leu Lys Val Asp Asp Ala Leu Thr
                100                 105                 110

Asp Thr Gly Ile Gly Gly Trp Phe Lys Ile Gln Glu Ala Gly Tyr
                115                 120                 125

Asp Asn Gly Asn Trp Ala Thr Ser Thr Val Ile Thr Asn Gly Gly Phe
     130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Ala
                165                 170                 175

Gln Leu Tyr Met Glu Cys Ala Gln Ile Asn Val Val Gly Gly Ser Gly
                180                 185                 190

Ser Ala Ser Pro Gln Thr Tyr Ser Ile Pro Gly Ile Tyr Gln Ala Thr
                195                 200                 205

Asp Pro Gly Leu Leu Ile Asn Ile Tyr Ser Met Thr Pro Ser Ser Gln
     210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Thr Ala Lys
                245                 250                 255

Pro Thr Thr Thr Thr Ala Ala Thr Thr Thr Ser Ser Ala Ala Pro Thr
                260                 265                 270

Ser Ser Gln Gly Gly Ser Ser Gly Cys Thr Val Pro Gln Trp Gln Gln
         275                 280                 285

Cys Gly Gly Ile Ser Phe Thr Gly Cys Thr Thr Cys Ala Ala Gly Tyr
         290                 295                 300

Thr Cys Lys Tyr Leu Asn Asp Tyr Tyr Ser Gln Cys Gln
305                 310                 315

<210> SEQ ID NO 13
<211> LENGTH: 249
<212> TYPE: PRT
<213> ORGANISM: Thermoascus aurantiacus

<400> SEQUENCE: 13

Met Ser Phe Ser Lys Ile Ile Ala Thr Ala Gly Val Leu Ala Ser Ala
 1               5                  10                  15

Ser Leu Val Ala Gly His Gly Phe Val Gln Asn Ile Val Ile Asp Gly
                 20                  25                  30

Lys Tyr Tyr Gly Gly Tyr Leu Val Asn Gln Tyr Pro Tyr Met Ser Asn
             35                  40                  45

Pro Pro Glu Val Ile Ala Trp Ser Thr Thr Ala Thr Asp Leu Gly Phe
 50                  55                  60

Val Asp Gly Thr Gly Tyr Gln Thr Pro Asp Ile Ile Cys His Arg Gly
 65                  70                  75                  80
```

```
Ala Lys Pro Gly Ala Leu Thr Ala Pro Val Ser Pro Gly Gly Thr Val
            85                  90                  95

Glu Leu Gln Trp Thr Pro Trp Pro Asp Ser His His Gly Pro Val Ile
            100                 105                 110

Asn Tyr Leu Ala Pro Cys Asn Gly Asp Cys Ser Thr Val Asp Lys Thr
            115                 120                 125

Gln Leu Glu Phe Phe Lys Ile Ala Glu Ser Gly Leu Ile Asn Asp Asp
            130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                    165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
            195                 200                 205

Ser Asp Asn Pro Ala Gly Thr Leu Gly Thr Ala Leu Tyr His Asp Thr
210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                    245

<210> SEQ ID NO 14
<211> LENGTH: 249
<212> TYPE: PRT
<213> ORGANISM: Trichoderma reesei

<400> SEQUENCE: 14

Met Lys Ser Cys Ala Ile Leu Ala Ala Leu Gly Cys Leu Ala Gly Ser
1                   5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Tyr Gln Lys Gln Asn Thr Gly
            35                  40                  45

His Phe Pro Asn Val Ala Gly Trp Tyr Ala Glu Asp Leu Asp Leu Gly
50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
            85                  90                  95

Ile Val Phe Gln Trp Gly Pro Val Trp Pro His Pro Tyr Gly Pro
            100                 105                 110

Ile Val Thr Tyr Val Val Glu Cys Ser Gly Ser Cys Thr Thr Val Asn
            115                 120                 125

Lys Asn Asn Leu Arg Trp Val Lys Ile Gln Glu Ala Gly Ile Asn Tyr
            130                 135                 140

Asn Thr Gln Val Trp Ala Gln Asp Leu Ile Asn Gln Gly Asn Lys
145                 150                 155                 160

Trp Thr Val Lys Ile Pro Ser Ser Leu Arg Pro Gly Asn Tyr Val Phe
                    165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
            195                 200                 205
```

```
Lys Ala Leu Pro Ala Gly Thr Pro Ala Thr Gln Leu Tyr Lys Pro Thr
            210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 15
<211> LENGTH: 232
<212> TYPE: PRT
<213> ORGANISM: Myceliophthora thermophila

<400> SEQUENCE: 15

Met Lys Phe Thr Ser Ser Leu Ala Val Leu Ala Ala Gly Ala Gln
1               5                   10                  15

Ala His Tyr Thr Phe Pro Arg Ala Gly Thr Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
130                 135                 140

Thr Ile Pro Ser Cys Ile Asp Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
210                 215                 220

Pro Gly Pro Ala Pro Val Ser Cys
225                 230

<210> SEQ ID NO 16
<211> LENGTH: 235
<212> TYPE: PRT
<213> ORGANISM: Myceliophthora thermophila

<400> SEQUENCE: 16

Met Lys Ala Leu Ser Leu Leu Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Asp Pro Ser Tyr Asp Gly Pro Ile Thr Asp Val Thr
        35                  40                  45
```

```
Ser Asn Asp Val Ala Cys Asn Gly Gly Pro Asn Pro Thr Thr Pro Ser
 50                  55                  60

Ser Asp Val Ile Thr Val Thr Ala Gly Thr Thr Val Lys Ala Ile Trp
 65                  70                  75                  80

Arg His Thr Leu Gln Ser Gly Pro Asp Asp Val Met Asp Ala Ser His
                 85                  90                  95

Lys Gly Pro Thr Leu Ala Tyr Leu Lys Lys Val Gly Asp Ala Thr Lys
                100                 105                 110

Asp Ser Gly Val Gly Gly Trp Phe Lys Ile Gln Glu Asp Gly Tyr
                115                 120                 125

Asn Asn Gly Gln Trp Gly Thr Ser Thr Val Ile Ser Asn Gly Gly Glu
            130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
                180                 185                 190

Ser Val Pro Ser Ser Thr Val Ser Phe Pro Gly Ala Tyr Ser Pro Asn
                195                 200                 205

Asp Pro Gly Leu Leu Ile Asn Ile Tyr Ser Met Ser Pro Ser Ser Ser
210                 215                 220

Tyr Thr Ile Pro Gly Pro Pro Val Phe Lys Cys
225                 230                 235

<210> SEQ ID NO 17
<211> LENGTH: 323
<212> TYPE: PRT
<213> ORGANISM: Myceliophthora thermophila

<400> SEQUENCE: 17

Met Lys Ser Phe Ala Leu Thr Thr Leu Ala Ala Leu Ala Gly Asn Ala
 1               5                  10                  15

Ala Ala His Ala Thr Phe Gln Ala Leu Trp Val Asp Gly Val Asp Tyr
                20                  25                  30

Gly Ala Gln Cys Ala Arg Leu Pro Ala Ser Asn Ser Pro Val Thr Asp
             35                  40                  45

Val Thr Ser Asn Ala Ile Arg Cys Asn Ala Asn Pro Ser Pro Ala Arg
 50                  55                  60

Gly Lys Cys Pro Val Lys Ala Gly Ser Thr Val Thr Val Glu Met His
 65                  70                  75                  80

Gln Gln Pro Gly Asp Arg Ser Cys Ser Ser Glu Ala Ile Gly Gly Ala
                 85                  90                  95

His Tyr Gly Pro Val Met Val Tyr Met Ser Lys Val Ser Asp Ala Ala
                100                 105                 110

Ser Ala Asp Gly Ser Ser Gly Trp Phe Lys Val Phe Glu Asp Gly Trp
                115                 120                 125

Ala Lys Asn Pro Ser Gly Gly Ser Gly Asp Asp Tyr Trp Gly Thr
            130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
```

```
            180                 185                 190
Gln Leu Thr Val Thr Gly Ser Gly Ser Ala Ser Pro Pro Thr Val Ser
            195                 200                 205

Phe Pro Gly Ala Tyr Lys Ala Thr Asp Pro Gly Ile Leu Val Asn Ile
            210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
                260                 265                 270

Gly Ser Thr Ala Thr Ser Ala Pro Gly Gly Gly Gly Cys Thr Val
            275                 280                 285

Gln Lys Tyr Gln Gln Cys Gly Gly Glu Gly Tyr Thr Gly Cys Thr Asn
            290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 18
<211> LENGTH: 310
<212> TYPE: PRT
<213> ORGANISM: Myceliophthora thermophila

<400> SEQUENCE: 18

Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
                20                  25                  30

Lys Gly Val Arg Ala Pro Ser Ser Asn Ser Pro Ile Gln Asn Val Asn
            35                  40                  45

Asp Ala Asn Met Ala Cys Asn Ala Asn Ile Val Tyr His Asp Ser Thr
50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Ser Gly Leu Arg Trp Phe Lys Val Ala Glu
        115                 120                 125

Arg Gly Leu Asn Asn Gly Val Trp Ala Val Asp Glu Leu Ile Ala Asn
130                 135                 140

Asn Gly Trp His Tyr Phe Asp Leu Pro Ser Cys Val Ala Pro Gly Gln
145                 150                 155                 160

Tyr Leu Met Arg Val Glu Leu Leu Ala Leu His Ser Ala Ser Ser Pro
                165                 170                 175

Gly Gly Ala Gln Phe Tyr Met Gly Cys Ala Gln Ile Glu Val Thr Gly
            180                 185                 190

Ser Gly Thr Asn Ser Gly Ser Asp Phe Val Ser Phe Pro Gly Ala Tyr
            195                 200                 205

Ser Ala Asn Asp Pro Gly Ile Leu Leu Ser Ile Tyr Asp Ser Ser Gly
            210                 215                 220

Lys Pro Thr Asn Gly Gly Arg Ser Tyr Pro Ile Pro Gly Pro Arg Pro
```

```
                225                 230                 235                 240
Ile Ser Cys Ser Gly Ser Gly Asp Gly Gly Asn Asn Gly Gly Gly
                245                 250                 255

Asp Asp Asn Asn Asn Asn Gly Gly Asn Asn Gly Gly Gly Gly
            260                 265                 270

Gly Gly Ser Val Pro Leu Tyr Gly Gln Cys Gly Gly Ile Gly Tyr Thr
            275                 280                 285

Gly Pro Thr Thr Cys Ala Gln Gly Thr Cys Lys Val Ser Asn Glu Tyr
            290                 295                 300

Tyr Ser Gln Cys Leu Pro
305                 310

<210> SEQ ID NO 19
<211> LENGTH: 246
<212> TYPE: PRT
<213> ORGANISM: Myceliophthora thermophila

<400> SEQUENCE: 19

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
                20                  25                  30

Ser Leu Thr Gly Leu Arg Ala Pro Asn Asn Asn Pro Val Gln Asp
            35                  40                  45

Val Asn Ser Gln Asp Met Ile Cys Gly Gln Ser Gly Ser Thr Ser Asn
50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
130                 135                 140

Ile Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Ser Phe Thr Pro Pro Ser Thr Val Ser Phe Pro
        195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245

<210> SEQ ID NO 20
<211> LENGTH: 354
<212> TYPE: PRT
<213> ORGANISM: Thermoascus aurantiacus
```

<400> SEQUENCE: 20

Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
                20                  25                  30

Thr Tyr Tyr Gly Gly Tyr Ile Val Thr Gln Tyr Pro Tyr Met Ser Thr
            35                  40                  45

Pro Pro Asp Val Ile Ala Trp Ser Thr Lys Ala Thr Asp Leu Gly Phe
50                      55                  60

Val Asp Pro Ser Ser Tyr Ala Ser Ser Asp Ile Ile Cys His Lys Gly
65                      70                  75                  80

Ala Glu Pro Gly Ala Leu Ser Ala Lys Val Ala Ala Gly Gly Thr Val
                    85                  90                  95

Glu Leu Gln Trp Thr Asp Trp Pro Glu Ser His Lys Gly Pro Val Ile
                100                 105                 110

Asp Tyr Leu Ala Ala Cys Asn Gly Asp Cys Ser Thr Val Asp Lys Thr
                115                 120                 125

Lys Leu Glu Phe Phe Lys Ile Asp Glu Ser Gly Leu Ile Asp Gly Ser
            130                 135                 140

Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
                180                 185                 190

Ala Gln Asn Tyr Pro Gln Cys Ile Asn Leu Glu Val Thr Gly Ser Gly
            195                 200                 205

Thr Asp Thr Pro Ala Gly Thr Leu Gly Thr Glu Leu Tyr Lys Ala Thr
            210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Ser Gly Ser Ser Gly
                245                 250                 255

Ser Ser Asn Thr Ala Lys Ala Thr Thr Ser Thr Ala Ser Ser Ser Ile
            260                 265                 270

Val Thr Pro Thr Pro Val Asn Asn Pro Thr Val Thr Gln Thr Ala Val
            275                 280                 285

Val Asp Val Thr Gln Thr Val Ser Gln Asn Ala Ala Val Ala Thr Thr
290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
                325                 330                 335

Ala Thr Val Asn Trp Leu Leu Ser Asn Lys Lys His Ala Arg Asp Leu
                340                 345                 350

Ser Tyr

<210> SEQ ID NO 21
<211> LENGTH: 322
<212> TYPE: PRT
<213> ORGANISM: Penicillium pinophilum

<400> SEQUENCE: 21

Met Pro Ser Thr Lys Val Ala Ala Leu Ser Ala Val Leu Ala Leu Ala

-continued

```
               1               5                  10                 15
             Ser Thr Val Ala Gly His Gly Phe Val Gln Asn Ile Val Ile Asp Gly
                             20                 25                 30

Lys Ser Tyr Ser Gly Tyr Leu Val Asn Gln Phe Pro Tyr Glu Ser Asn
                             35                 40                 45

Pro Pro Ala Val Ile Gly Trp Ala Thr Thr Ala Thr Asp Leu Gly Phe
                 50                     55                 60

Val Ala Pro Ser Glu Tyr Thr Asn Ala Asp Ile Ile Cys His Lys Asn
              65                 70                 75                 80

Ala Thr Pro Gly Ala Leu Ser Ala Pro Val Ala Gly Gly Thr Val
                             85                 90                 95

Glu Leu Gln Trp Thr Thr Trp Pro Asp Ser His His Gly Pro Val Ile
                            100                105                110

Ser Tyr Leu Ala Asn Cys Asn Gly Asn Cys Ser Thr Val Asp Lys Thr
                            115                120                125

Lys Leu Asp Phe Val Lys Ile Asp Gln Gly Gly Leu Ile Asp Asp Thr
                         130                135                140

Thr Pro Pro Gly Thr Trp Ala Ser Asp Lys Leu Ile Ala Ala Asn Asn
             145                150                155                160

Ser Trp Thr Val Thr Ile Pro Ser Thr Ile Ala Pro Gly Asn Tyr Val
                                165                170                175

Leu Arg His Glu Ile Ile Ala Leu His Ser Ala Gly Asn Ala Asp Gly
                         180                185                190

Ala Gln Asn Tyr Pro Gln Cys Ile Asn Leu Glu Ile Thr Gly Ser Gly
                         195                200                205

Thr Ala Ala Pro Ser Gly Thr Ala Gly Glu Lys Leu Tyr Thr Ser Thr
                 210                215                220

Asp Pro Gly Ile Leu Val Asn Ile Tyr Gln Ser Leu Ser Thr Tyr Val
             225                230                235                240

Ile Pro Gly Pro Thr Leu Trp Ser Gly Ala Ala Asn Gly Ala Val Ala
                             245                250                255

Thr Gly Ser Ala Thr Ala Val Ala Thr Thr Ala Thr Ala Ser Ala Thr
                         260                265                270

Ala Thr Pro Thr Thr Leu Val Thr Ser Val Ala Pro Ala Ser Ser Thr
                         275                280                285

Phe Ala Thr Ala Val Val Thr Thr Val Ala Pro Ala Val Thr Asp Val
                         290                295                300

Val Thr Val Thr Asp Val Val Thr Val Thr Thr Val Ile Thr Thr
             305                310                315                320

Val Leu

<210> SEQ ID NO 22
             <211> LENGTH: 444
             <212> TYPE: PRT
             <213> ORGANISM: Thermoascus sp.

<400> SEQUENCE: 22

Met Leu Ser Phe Ala Ser Ala Lys Ser Ala Val Leu Thr Thr Leu Leu
             1               5                  10                 15

Leu Leu Gly Ser Ala Gln Ala His Thr Leu Met Thr Thr Leu Phe Val
                             20                 25                 30

Asp Gly Val Asn Gln Gly Asp Gly Val Cys Ile Arg Met Asn Asn Asn
                             35                 40                 45

Gly Ser Thr Ala Asn Thr Tyr Ile Gln Pro Val Thr Ser Lys Asp Ile
```

```
            50                  55                  60
Ala Cys Gly Ile Gln Gly Glu Ile Gly Ala Ala Arg Val Cys Pro Ala
 65                  70                  75                  80

Lys Ala Ser Ser Thr Leu Thr Phe Gln Phe Arg Glu Gln Pro Ser Asn
                 85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Gly Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190

Gly Cys Ala Gln Leu Phe Ile Asp Ser Ala Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
        275                 280                 285

Ala Thr Gly Val Pro Val Ala Arg Ser Thr Leu Arg Thr Trp Val Asp
    290                 295                 300

Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
                325                 330                 335

Ile Phe Val Asn Gly Asn Trp Cys Gly Phe Glu Val Pro Asp Tyr Asn
            340                 345                 350

Asp Ala Glu Ser Cys Trp Ala Ala Ser Asp Asn Cys Trp Lys Gln Ser
        355                 360                 365

Asp Ser Cys Trp Asn Gln Thr Gln Pro Thr Gly Tyr Asn Asn Cys Gln
    370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
            420                 425                 430

Ser Tyr Arg Asp Trp Ile Met Lys Arg Lys Gly Ala
        435                 440

<210> SEQ ID NO 23
<211> LENGTH: 253
<212> TYPE: PRT
<213> ORGANISM: Penicillium sp.
```

```
<400> SEQUENCE: 23

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
 50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
        180                 185                 190

Asn Lys Asp Gly Ala Gln Asn Tyr Pro Gln Cys Ile Asn Ile Glu Val
            195                 200                 205

Thr Gly Gly Gly Ser Asp Ala Pro Glu Gly Thr Leu Gly Glu Asp Leu
210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 24
<211> LENGTH: 246
<212> TYPE: PRT
<213> ORGANISM: Thielavia terrestris

<400> SEQUENCE: 24

Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
            20                  25                  30

Leu Leu Thr Gly Leu Arg Ala Pro Ser Asn Asn Pro Val Gln Asp
            35                  40                  45

Val Asn Ser Gln Asn Met Ile Cys Gly Gln Ser Gly Ser Lys Ser Gln
     50                  55                  60

Thr Val Ile Asn Val Lys Ala Gly Asp Arg Ile Gly Ser Leu Trp Gln
65                  70                  75                  80

His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
            100                 105                 110
```

```
Asn Ala Ala Ser Ala Ser Gln Thr Gly Leu Lys Trp Phe Lys Ile Trp
            115                 120                 125

Gln Asp Gly Phe Asp Thr Ser Ser Lys Thr Trp Gly Val Asp Asn Leu
        130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
                180                 185                 190

Val Ser Gly Ser Gly Ser Phe Ser Pro Ser Gln Thr Val Ser Ile Pro
            195                 200                 205

Gly Val Tyr Ser Ala Thr Asp Pro Ser Ile Leu Ile Asn Ile Tyr Gly
        210                 215                 220

Ser Thr Gly Gln Pro Asp Asn Gly Gly Lys Ala Tyr Asn Pro Pro Gly
225                 230                 235                 240

Pro Ala Pro Ile Ser Cys
                245

<210> SEQ ID NO 25
<211> LENGTH: 334
<212> TYPE: PRT
<213> ORGANISM: Thielavia terrestris

<400> SEQUENCE: 25

Met Arg Thr Thr Phe Ala Ala Leu Ala Ala Phe Ala Ala Gln Glu
1               5                   10                  15

Val Ala Gly His Ala Ile Phe Gln Gln Leu Trp His Gly Ser Ser Cys
            20                  25                  30

Val Arg Met Pro Leu Ser Asn Ser Pro Val Thr Asn Val Gly Ser Arg
        35                  40                  45

Asp Met Ile Cys Asn Ala Gly Thr Arg Pro Val Ser Gly Lys Cys Pro
    50                  55                  60

Val Lys Ala Gly Gly Thr Val Thr Val Glu Met His Gln Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Ser Lys Val Glu Asp Ala Ser Thr Ala Asp Gly
            100                 105                 110

Ser Thr Gly Trp Phe Lys Ile Phe Ala Asp Thr Trp Ser Lys Lys Ala
        115                 120                 125

Gly Ser Ser Val Gly Asp Asp Asp Asn Trp Gly Thr Arg Asp Leu Asn
    130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
        195                 200                 205

Tyr Ser Ala Asn Asp Pro Gly Ile His Ile Asn Ile His Ala Ala Val
    210                 215                 220

Ser Asn Tyr Val Ala Pro Gly Pro Ala Val Tyr Ser Gly Gly Thr Thr
```

-continued

```
                225                 230                 235                 240
Lys Val Ala Gly Ser Gly Cys Gln Gly Cys Glu Asn Thr Cys Lys Val
                    245                 250                 255
Gly Ser Ser Pro Thr Ala Thr Ala Pro Ser Gly Lys Ser Gly Ala Gly
                    260                 265                 270
Ser Asp Gly Gly Ala Gly Thr Asp Gly Gly Ser Ser Ser Ser Ser Pro
                    275                 280                 285
Asp Thr Gly Ser Ala Cys Ser Val Gln Ala Tyr Gly Gln Cys Gly Gly
                    290                 295                 300
Asn Gly Tyr Ser Gly Cys Thr Gln Cys Ala Pro Gly Tyr Thr Cys Lys
305                 310                 315                 320
Ala Val Ser Pro Pro Tyr Tyr Ser Gln Cys Ala Pro Ser Ser
                    325                 330

<210> SEQ ID NO 26
<211> LENGTH: 227
<212> TYPE: PRT
<213> ORGANISM: Thielavia terrestris

<400> SEQUENCE: 26

Met Lys Leu Ser Val Ala Ile Ala Val Leu Ala Ser Ala Leu Ala Glu
1               5                   10                  15
Ala His Tyr Thr Phe Pro Ser Ile Gly Asn Thr Ala Asp Trp Gln Tyr
                20                  25                  30
Val Arg Ile Thr Thr Asn Tyr Gln Ser Asn Gly Pro Val Thr Asp Val
            35                  40                  45
Thr Ser Asp Gln Ile Arg Cys Tyr Glu Arg Asn Pro Gly Thr Gly Ala
        50                  55                  60
Gln Gly Ile Tyr Asn Val Thr Ala Gly Gln Thr Ile Asn Tyr Asn Ala
65                  70                  75                  80
Lys Ala Ser Ile Ser His Pro Gly Pro Met Ser Phe Tyr Ile Ala Lys
                85                  90                  95
Val Pro Ala Gly Gln Thr Ala Ala Thr Trp Asp Gly Lys Gly Ala Val
                100                 105                 110
Trp Thr Lys Ile Tyr Gln Asp Met Pro Lys Phe Gly Ser Ser Leu Thr
            115                 120                 125
Trp Pro Thr Met Gly Ala Lys Ser Val Pro Val Thr Ile Pro Arg Cys
        130                 135                 140
Leu Gln Asn Gly Asp Tyr Leu Leu Arg Ala Glu His Ile Ala Leu His
145                 150                 155                 160
Ser Ala Ser Ser Val Gly Gly Ala Gln Phe Tyr Leu Ser Cys Ala Gln
                165                 170                 175
Leu Thr Val Ser Gly Gly Ser Gly Thr Trp Asn Pro Lys Asn Arg Val
                180                 185                 190
Ser Phe Pro Gly Ala Tyr Lys Ala Thr Asp Pro Gly Ile Leu Ile Asn
            195                 200                 205
Ile Tyr Tyr Pro Val Pro Thr Ser Tyr Ser Pro Pro Gly Pro Pro Ala
        210                 215                 220
Glu Thr Cys
225

<210> SEQ ID NO 27
<211> LENGTH: 223
<212> TYPE: PRT
<213> ORGANISM: Thielavia terrestris
```

```
<400> SEQUENCE: 27

Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
        35                  40                  45

Val Thr Ser Leu Ser Ser Asn Asp Leu Arg Cys Asn Val Gly Gly Glu
    50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
            85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
            115                 120                 125

Ala Ser Trp Pro Leu Arg Asp Asn Tyr Gln Tyr Asn Ile Pro Thr Cys
    130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
            165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
            195                 200                 205

Asn Phe His Ser Tyr Thr Val Pro Gly Pro Ala Val Phe Gln Cys
    210                 215                 220

<210> SEQ ID NO 28
<211> LENGTH: 368
<212> TYPE: PRT
<213> ORGANISM: Thielavia terrestris

<400> SEQUENCE: 28

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30

Val Ser Tyr Gln Gly Tyr Asp Pro Thr Ser Phe Pro Tyr Met Gln Asn
        35                  40                  45

Pro Pro Ile Val Val Gly Trp Thr Ala Ala Asp Thr Asp Asn Gly Phe
    50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Ala Gly Asp Lys Ile
            85                  90                  95

Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
            115                 120                 125

Thr Lys Leu Glu Phe Phe Lys Ile Asp Glu Val Gly Leu Val Asp Gly
            130                 135                 140
```

```
Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
            165                 170                 175

Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
            195                 200                 205

Gly Thr Ala Thr Pro Ser Gly Val Pro Gly Thr Ser Leu Tyr Thr Pro
            210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
            245                 250                 255

Ser Ser Ser Ala Ile Thr Ala Ser Gly Thr Ala Leu Thr Gly Ser Ala
            260                 265                 270

Thr Ala Pro Ala Ala Ala Ala Thr Thr Ser Thr Asn Ala
            275                 280                 285

Ala Ala Ala Ala Thr Ser Ala Ala Ala Ala Gly Thr Ser Thr Thr
            290                 295                 300

Thr Thr Ser Ala Ala Val Val Gln Thr Ser Ser Ser Ser Ser
305                 310                 315                 320

Ala Pro Ser Ser Ala Ala Ala Ala Thr Thr Ala Ala Ala Ser
            325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
            355                 360                 365

<210> SEQ ID NO 29
<211> LENGTH: 330
<212> TYPE: PRT
<213> ORGANISM: Thielavia terrestris

<400> SEQUENCE: 29

Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
            35                  40                  45

Asn Tyr Pro Ser Arg Val Gly Trp Ser Thr Gly Ala Val Asp Asp Gly
50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
            85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
            115                 120                 125

Asn Lys Thr Ala Leu Arg Trp Thr Lys Ile Asp Asp Ser Ser Pro Thr
            130                 135                 140

Met Gln Asn Val Ala Gly Ala Gly Thr Gln Gly Glu Gly Thr Pro Gly
145                 150                 155                 160
```

```
Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
            195                 200                 205

Tyr Pro Leu Cys Met Asn Leu Trp Val Asp Ala Ser Gly Asp Asn Ser
        210                 215                 220

Ser Val Ala Ala Thr Thr Ala Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
            260                 265                 270

Thr Val Ala Ala Gly Ala Thr Pro Val Pro Tyr Ala Gln Gln Ser Pro
        275                 280                 285

Ser Val Ser Thr Ala Ala Gly Thr Pro Val Val Thr Arg Thr Ser
        290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330

<210> SEQ ID NO 30
<211> LENGTH: 236
<212> TYPE: PRT
<213> ORGANISM: Thielavia terrestris

<400> SEQUENCE: 30

Met Lys Thr Phe Thr Ala Leu Leu Ala Ala Ala Gly Leu Val Ala Gly
1               5                   10                  15

His Gly Tyr Val Asp Asn Ala Thr Ile Gly Gly Gln Phe Tyr Gln Asn
            20                  25                  30

Pro Ala Val Leu Thr Phe Phe Gln Pro Asp Arg Val Ser Arg Ser Ile
        35                  40                  45

Pro Gly Asn Gly Pro Val Thr Asp Val Thr Leu Ile Asp Leu Gln Cys
    50                  55                  60

Asn Ala Asn Ser Thr Pro Ala Lys Leu His Ala Thr Ala Ala Ala Gly
65                  70                  75                  80

Ser Asp Val Ile Leu Arg Trp Thr Leu Trp Pro Glu Ser His Val Gly
                85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
```

```
                    195                 200                 205
Tyr Lys Gly Ser Asp Pro Gly Ile Thr Tyr Asp Ala Tyr Lys Ala Gln
    210                 215                 220
Thr Tyr Gln Ile Pro Gly Pro Ala Val Phe Thr Cys
225                 230                 235

<210> SEQ ID NO 31
<211> LENGTH: 250
<212> TYPE: PRT
<213> ORGANISM: Thielavia terrestris

<400> SEQUENCE: 31

Met Ala Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
                20                  25                  30

Arg Gly Tyr Asp Pro Phe Thr Pro Ala Ala Asp Gln Ile Gly Gln Pro
            35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

Tyr Ile Pro Ile Arg Ala Gly Glu Asn Ile Thr Ala Val Tyr Trp Tyr
                85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
            115                 120                 125

Trp Glu Ala Gly Leu Leu Ser Gly Pro Asn Leu Ala Glu Gly Met Trp
130                 135                 140

Tyr Gln Lys Ala Phe Gln Asn Trp Asp Gly Ser Pro Asp Leu Trp Pro
145                 150                 155                 160

Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
            180                 185                 190

Cys Ala His Leu Asn Val Thr Gly Gly Gly Asp Leu Leu Pro Pro Asp
            195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250

<210> SEQ ID NO 32
<211> LENGTH: 478
<212> TYPE: PRT
<213> ORGANISM: Thielavia terrestris

<400> SEQUENCE: 32

Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
                20                  25                  30

Gly Val Asp Gln Gly Asp Gly Thr Cys Ile Arg Met Ala Lys Lys Gly
```

```
                35                  40                  45
Ser Val Cys Thr His Pro Ile Ala Gly Gly Leu Asp Ser Pro Asp Met
 50                  55                  60
Ala Cys Gly Arg Asp Gly Gln Gln Ala Val Ala Phe Thr Cys Pro Ala
 65                  70                  75                  80
Pro Ala Gly Ser Lys Leu Ser Phe Glu Phe Arg Met Trp Ala Asp Ala
                 85                  90                  95
Ser Gln Pro Gly Ser Ile Asp Pro Ser His Leu Gly Ser Thr Ala Ile
            100                 105                 110
Tyr Leu Lys Gln Val Ser Asn Ile Ser Ser Asp Ser Ala Ala Gly Pro
            115                 120                 125
Gly Trp Phe Lys Ile Tyr Ala Glu Gly Tyr Asp Thr Ala Ala Lys Lys
            130                 135                 140
Trp Ala Thr Glu Lys Leu Ile Asp Asn Gly Gly Leu Leu Ser Ile Glu
145                 150                 155                 160
Leu Pro Pro Thr Leu Pro Ala Gly Tyr Tyr Leu Ala Arg Ser Glu Ile
                165                 170                 175
Val Thr Ile Gln Asn Val Thr Asn Asp His Val Asp Pro Gln Phe Tyr
            180                 185                 190
Val Gly Cys Ala Gln Leu Phe Val Gln Gly Pro Thr Thr Pro Thr
            195                 200                 205
Val Pro Pro Asp Arg Leu Val Ser Ile Pro Gly His Val His Ala Ser
210                 215                 220
Asp Pro Gly Leu Thr Phe Asn Ile Trp Arg Asp Pro Ser Lys Thr
225                 230                 235                 240
Ala Tyr Thr Val Val Gly Pro Ala Pro Phe Ser Pro Thr Ala Ala Pro
                245                 250                 255
Thr Pro Thr Ser Thr Asn Thr Asn Gly Gln Gln Gln Gln Gln Gln Gln
                260                 265                 270
Gln Ala Ile Lys Gln Thr Asp Gly Val Ile Pro Ala Asp Cys Gln Leu
            275                 280                 285
Lys Asn Ala Asn Trp Cys Gly Ala Glu Val Pro Ala Tyr Ala Asp Glu
            290                 295                 300
Ala Gly Cys Trp Ala Ser Ser Ala Asp Cys Phe Ala Gln Leu Asp Ala
305                 310                 315                 320
Cys Tyr Thr Ser Ala Pro Pro Thr Gly Ser Arg Gly Cys Arg Leu Trp
                325                 330                 335
Glu Asp Trp Cys Thr Gly Ile Gln Gln Gly Cys Arg Ala Gly Arg Trp
            340                 345                 350
Arg Gly Pro Pro Pro Phe His Gly Glu Gly Ala Ala Ala Glu Thr Ala
            355                 360                 365
Ser Ala Gly Arg Gly Gly Ala Arg Ile Ala Ala Val Ala Gly Cys Gly
            370                 375                 380
Gly Gly Thr Gly Asp Met Val Glu Glu Val Phe Leu Phe Tyr Trp Asp
385                 390                 395                 400
Ala Cys Ser Gly Trp Arg Arg Ser Arg Gly Gly Ser Ile Leu Ala
                405                 410                 415
Arg Leu Ile Leu His Val Leu Leu Pro Leu Arg Pro Arg Arg Ala
            420                 425                 430
Pro Arg Val His Leu Leu Phe His Leu Tyr Leu Asn Phe Cys Tyr
            435                 440                 445
Pro Gly Thr Ser Gly Phe Tyr Asn Arg Leu Ser Ile Lys Leu Gly Ile
            450                 455                 460
```

```
Trp Pro Ser Lys Met Ser Pro Asp Val Ala His Tyr Val Lys
465                 470                 475
```

```
<210> SEQ ID NO 33
<211> LENGTH: 230
<212> TYPE: PRT
<213> ORGANISM: Thielavia terrestris

<400> SEQUENCE: 33

Met Gln Leu Leu Val Gly Leu Leu Ala Ala Val Ala Ala Arg Ala
1               5                   10                  15

His Tyr Thr Phe Pro Arg Leu Val Asn Gly Gln Pro Glu Asp Lys
                20                  25                  30

Asp Trp Ser Val Thr Arg Met Thr Lys Asn Ala Gln Ser Lys Gln Gly
            35                  40                  45

Val Gln Asp Pro Thr Ser Pro Asp Ile Arg Cys Tyr Thr Ser Gln Thr
        50                  55                  60

Ala Pro Asn Val Ala Thr Val Pro Ala Gly Ala Thr Val His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Ser Ser Ala Lys Thr Trp Asp Gly Ser Gly Ala
                100                 105                 110

Val Trp Phe Lys Ile Ser Thr Thr Met Pro Tyr Leu Asp Asn Asn Lys
                115                 120                 125

Gln Leu Val Trp Pro Asn Gln Asn Thr Tyr Thr Thr Val Asn Thr Thr
130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
                180                 185                 190

Pro Leu Val Ala Leu Pro Gly Ala Tyr Lys Ser Asn Asp Pro Gly Ile
                195                 200                 205

Leu Val Asn Ile Tyr Ser Met Gln Pro Gly Asp Tyr Lys Pro Pro Gly
210                 215                 220

Pro Pro Val Trp Ser Gly
225                 230
```

```
<210> SEQ ID NO 34
<211> LENGTH: 257
<212> TYPE: PRT
<213> ORGANISM: Thielavia terrestris

<400> SEQUENCE: 34

Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
                20                  25                  30

Thr Pro Glu Trp Lys Tyr Val Arg Asp Val Ala Trp Glu Gly Ala Tyr
            35                  40                  45

Glu Pro Glu Lys Tyr Pro Asn Thr Glu Phe Phe Lys Thr Pro Pro Gln
        50                  55                  60

Thr Asp Ile Asn Asn Pro Asn Ile Thr Cys Gly Arg Asn Ala Phe Asp
65                  70                  75                  80
```

```
Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Thr Pro Thr
            195                 200                 205

Gly Phe Ala Arg Phe Pro Gly Thr Tyr Thr Val Asp Asp Pro Gly Ile
        210                 215                 220

Lys Val Pro Leu Asn Gln Ile Val Asn Ser Gly Glu Leu Pro Gln Asp
225                 230                 235                 240

Gln Leu Arg Leu Leu Glu Tyr Lys Pro Pro Gly Pro Ala Leu Trp Thr
                245                 250                 255

Gly

<210> SEQ ID NO 35
<211> LENGTH: 251
<212> TYPE: PRT
<213> ORGANISM: Thermoascus crustaceus

<400> SEQUENCE: 35

Met Ala Phe Ser Gln Ile Met Ala Ile Thr Gly Val Phe Leu Ala Ser
1               5                   10                  15

Ala Ser Leu Val Ala Gly His Gly Phe Val Gln Asn Ile Val Ile Asp
                20                  25                  30

Gly Lys Ser Tyr Gly Gly Tyr Ile Val Asn Gln Tyr Pro Tyr Met Ser
            35                  40                  45

Asp Pro Pro Glu Val Val Gly Trp Ser Thr Thr Ala Thr Asp Leu Gly
        50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
                85                  90                  95

Val Lys Leu Glu Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Lys Phe Phe Lys Ile Ala Gln Ala Gly Leu Ile Asp Asp
    130                 135                 140

Asn Ser Pro Pro Gly Ile Trp Ala Ser Asp Asn Leu Ile Ala Ala Asn
145                 150                 155                 160

Asn Ser Trp Thr Val Thr Ile Pro Thr Thr Ala Pro Gly Asn Tyr
                165                 170                 175

Val Leu Arg His Glu Ile Ile Ala Leu His Ser Ala Gly Asn Lys Asp
            180                 185                 190
```

```
Gly Ala Gln Asn Tyr Pro Gln Cys Ile Asn Leu Lys Val Thr Gly Asn
            195                 200                 205

Gly Ser Gly Asn Pro Pro Ala Gly Ala Leu Gly Thr Ala Leu Tyr Lys
        210                 215                 220

Asp Thr Asp Pro Gly Ile Leu Ile Asn Ile Tyr Gln Lys Leu Ser Ser
225                 230                 235                 240

Tyr Val Ile Pro Gly Pro Ala Leu Tyr Thr Gly
            245                 250

<210> SEQ ID NO 36
<211> LENGTH: 349
<212> TYPE: PRT
<213> ORGANISM: Thermoascus crustaceus

<400> SEQUENCE: 36

Met Ser Phe Ser Lys Ile Leu Ala Ile Ala Gly Ala Ile Thr Tyr Ala
1               5                   10                  15

Ser Ser Ala Ala Ala His Gly Tyr Val Gln Gly Ile Val Val Asp Gly
            20                  25                  30

Ser Tyr Tyr Gly Gly Tyr Met Val Thr Gln Tyr Pro Tyr Thr Ala Gln
        35                  40                  45

Pro Pro Glu Leu Ile Ala Trp Ser Thr Lys Ala Thr Asp Leu Gly Phe
    50                  55                  60

Val Asp Gly Ser Gly Tyr Thr Ser Pro Asp Ile Ile Cys His Lys Gly
65                  70                  75                  80

Ala Glu Pro Gly Ala Gln Ser Ala Lys Val Ala Ala Gly Gly Thr Val
                85                  90                  95

Glu Leu Gln Trp Thr Ala Trp Pro Glu Ser His Lys Gly Pro Val Ile
            100                 105                 110

Asp Tyr Leu Ala Ala Cys Asp Gly Asp Cys Ser Ser Val Asp Lys Thr
        115                 120                 125

Ala Leu Lys Phe Phe Lys Ile Asp Glu Ser Gly Leu Ile Asp Gly Asn
    130                 135                 140

Gly Ala Gly Thr Trp Ala Ser Asp Thr Leu Ile Lys Asn Asn Asn Ser
145                 150                 155                 160

Trp Thr Val Thr Ile Pro Ser Thr Ile Ala Ser Gly Asn Tyr Val Leu
                165                 170                 175

Arg His Glu Ile Ile Ala Leu His Ser Ala Gly Asn Lys Asp Gly Ala
            180                 185                 190

Gln Asn Tyr Pro Gln Cys Ile Asn Leu Glu Val Thr Gly Ser Gly Thr
        195                 200                 205

Glu Asn Pro Ala Gly Thr Leu Gly Thr Ala Leu Tyr Thr Asp Thr Asp
    210                 215                 220

Pro Gly Leu Leu Val Asn Ile Tyr Gln Gly Leu Ser Asn Tyr Ser Ile
225                 230                 235                 240

Pro Gly Pro Ala Leu Tyr Ser Gly Asn Ser Asp Asn Ala Gly Ser Leu
                245                 250                 255

Asn Pro Thr Thr Thr Pro Ser Ile Gln Asn Ala Ala Ala Pro Ser
            260                 265                 270

Thr Ser Thr Ala Ser Val Val Thr Asp Ser Ser Ser Thr Gln Thr
        275                 280                 285

Ala Ser Val Ala Ala Thr Thr Pro Ala Ser Thr Ser Ala Val Thr Ala
    290                 295                 300

Ser Pro Ala Pro Asp Thr Gly Ser Asp Val Thr Lys Tyr Leu Asp Ser
```

```
            305                 310                 315                 320
Met Ser Ser Asp Glu Val Leu Thr Leu Val Arg Gly Thr Leu Ser Trp
                    325                 330                 335

Leu Val Ser Asn Lys Lys His Ala Arg Asp Leu Ser His
                340                 345

<210> SEQ ID NO 37
<211> LENGTH: 436
<212> TYPE: PRT
<213> ORGANISM: Thermoascus crustaceus

<400> SEQUENCE: 37

Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
                20                  25                  30

Asp Gly Val Asn Gln Gly Asp Gly Val Cys Ile Arg Met Asn Asn Asp
            35                  40                  45

Gly Gly Thr Ala Asn Thr Tyr Ile Gln Pro Ile Thr Ser Lys Asp Ile
        50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Ser Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Trp Glu Thr Pro Leu Ala Leu Pro Tyr Pro Met Tyr
225                 230                 235                 240

Gly Pro Pro Val Tyr Thr Pro Gly Ser Gly Ser Gly Ser Val Arg Ala
                245                 250                 255

Thr Ser Ser Ser Ala Val Pro Thr Ala Thr Glu Ser Ser Phe Val Glu
            260                 265                 270

Glu Arg Ala Asn Pro Val Thr Ala Asn Ser Val Tyr Ser Ala Arg Gly
        275                 280                 285

Lys Phe Lys Thr Trp Ile Asp Lys Leu Ser Trp Arg Gly Lys Val Arg
    290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
                325                 330                 335
```

```
Gly Phe Glu Val Pro Asp Tyr Asn Asp Ala Glu Ser Cys Trp Ala Ala
            340                 345                 350

Ser Asp Asn Cys Trp Lys Gln Ser Asp Ala Cys Trp Asn Lys Thr Gln
            355                 360                 365

Pro Thr Gly Tyr Asn Asn Cys Gln Ile Trp Gln Asp Lys Lys Cys Lys
            370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
                405                 410                 415

Asp Thr Phe Ser Lys Arg Thr Ile Gly Tyr Arg Asp Trp Ile Val Arg
            420                 425                 430

Arg Arg Gly Ala
        435

<210> SEQ ID NO 38
<211> LENGTH: 344
<212> TYPE: PRT
<213> ORGANISM: Aspergillus aculeatus

<400> SEQUENCE: 38

Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
        35                  40                  45

Tyr Glu Pro Thr Lys Tyr Thr Ser Thr Phe Asp Asn Leu Thr Pro Ser
    50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu
                85                  90                  95

Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
            115                 120                 125

Trp Phe Lys Ile Trp Glu Lys Thr Leu Cys Asn Thr Asp Gly Asp Leu
        130                 135                 140

Thr Thr Glu Ala Trp Cys Thr Trp Gly Met Ser Gln Phe Glu Phe Gln
145                 150                 155                 160

Ile Pro Ala Ala Thr Pro Ala Gly Glu Tyr Leu Val Arg Ala Glu His
                165                 170                 175

Ile Gly Leu His Gly Ala Gln Ala Asn Glu Ala Glu Phe Phe Tyr Ser
            180                 185                 190

Cys Ala Gln Ile Lys Val Thr Gly Ser Gly Thr Gly Ser Pro Ser Leu
            195                 200                 205

Thr Tyr Gln Ile Pro Gly Leu Tyr Asn Asp Thr Met Thr Leu Phe Asn
    210                 215                 220

Gly Leu Asn Leu Trp Thr Asp Ser Ala Glu Lys Val Gln Leu Asp Phe
225                 230                 235                 240

Leu Glu Thr Pro Ile Gly Asp Asp Val Trp Ser Gly Ala Gly Ser Gly
                245                 250                 255

Ser Pro Ser Ala Ala Thr Ser Ser Ser Gly Ala Thr Leu Ala Ala
            260                 265                 270
```

```
Gln Gly Thr Thr Thr Ser Ala Ala His Ala Gln Ala Gln Thr Thr Ile
            275                 280                 285

Thr Thr Ser Thr Ser Thr Ile Thr Ser Leu Glu Ser Ala Ser Ser Thr
            290                 295                 300

Asp Leu Val Ala Gln Tyr Gly Gln Cys Gly Gly Leu Asn Trp Ser Gly
305                 310                 315                 320

Pro Thr Glu Cys Glu Thr Pro Tyr Thr Cys Val Gln Gln Asn Pro Tyr
            325                 330                 335

Tyr His Gln Cys Val Asn Ser Cys
            340

<210> SEQ ID NO 39
<211> LENGTH: 400
<212> TYPE: PRT
<213> ORGANISM: Aspergillus aculeatus

<400> SEQUENCE: 39

Met Ser Val Ala Lys Phe Ala Gly Val Ile Leu Gly Ser Ala Ala Leu
1               5                   10                  15

Val Ala Gly His Gly Tyr Val Ser Gly Ala Val Val Asp Gly Thr Tyr
            20                  25                  30

Tyr Gly Gly Tyr Ile Val Thr Ser Tyr Pro Tyr Ser Ser Asp Pro Pro
        35                  40                  45

Glu Thr Ile Gly Trp Ser Thr Glu Ala Thr Asp Leu Gly Phe Val Asp
    50                  55                  60

Gly Ser Glu Tyr Ala Asp Ala Asp Ile Ile Cys His Lys Ser Ala Lys
65                  70                  75                  80

Pro Gly Ala Ile Ser Ala Glu Val Lys Ala Gly Gly Thr Val Glu Leu
                85                  90                  95

Gln Trp Thr Thr Trp Pro Asp Ser His His Gly Pro Val Leu Thr Tyr
            100                 105                 110

Leu Ala Asn Cys Asn Gly Asp Cys Ser Ser Val Thr Lys Thr Asp Leu
        115                 120                 125

Glu Phe Phe Lys Ile Asp Glu Ser Gly Leu Ile Asn Asp Asp Asp Val
    130                 135                 140

Pro Gly Thr Trp Ala Ser Asp Asn Leu Ile Ala Asn Asn Asn Ser Trp
145                 150                 155                 160

Thr Val Thr Ile Pro Ser Asp Ile Ala Ala Gly Asn Tyr Val Leu Arg
                165                 170                 175

His Glu Ile Ile Ala Leu His Ser Ala Gly Asn Lys Asp Gly Ala Gln
            180                 185                 190

Asn Tyr Pro Gln Cys Leu Asn Leu Lys Val Thr Gly Gly Gly Asp Leu
        195                 200                 205

Ala Pro Ser Gly Thr Ala Gly Glu Ser Leu Tyr Lys Asp Thr Asp Ala
    210                 215                 220

Gly Ile Leu Val Asn Ile Tyr Gln Ser Leu Ser Ser Tyr Asp Ile Pro
225                 230                 235                 240

Gly Pro Ala Met Tyr Asn Ala Thr Ser Ser Ser Ser Ser Ser Ser Ser
                245                 250                 255

Ser Ser Ser Ser Ser Ser Ser Ser Ser Gly Ser Ser Ser Ser
            260                 265                 270

Ala Ala Ala Ser Ser Ser Ser Ser Ser Ser Thr Thr Ala Ala Ala
        275                 280                 285

Ala Ala Ala Thr Ser Ala Ala Ser Ser Val Thr Ser Ala Ala Gly Ser
```

```
                290                 295                 300
Val Val Thr Gln Thr Ala Thr Val Glu Thr Asp Thr Ala Thr Ala
305                 310                 315                 320

Tyr Gln Thr Ser Thr Glu Val Ala Gln Val Thr Val Thr Gly Ser Ala
                325                 330                 335

Pro Gln Gln Thr Tyr Val Ala Thr Pro Ser Ser Ser Ser Ala Ser
                340                 345                 350

Ser Ser Ser Ser Ala Ser Val Ser Thr Ser Thr Ser Leu Thr Ser Tyr
            355                 360                 365

Phe Glu Ser Leu Ser Ala Asp Gln Phe Leu Ser Val Leu Lys Gln Thr
            370                 375                 380

Phe Thr Trp Leu Val Ser Glu Lys Lys His Ala Arg Asp Leu Ser Ala
385                 390                 395                 400
```

<210> SEQ ID NO 40
<211> LENGTH: 389
<212> TYPE: PRT
<213> ORGANISM: Aspergillus aculeatus

<400> SEQUENCE: 40

```
Met Lys Ser Ser Thr Phe Gly Met Leu Ala Leu Ala Ala Ala Lys
1               5                   10                  15

Met Val Asp Ala His Thr Thr Val Phe Ala Val Trp Ile Asn Gly Glu
                20                  25                  30

Asp Gln Gly Leu Gly Asn Ser Ala Ser Gly Tyr Ile Arg Ser Pro Pro
            35                  40                  45

Ser Asn Ser Pro Val Lys Asp Val Thr Ser Thr Asp Ile Thr Cys Asn
        50                  55                  60

Val Asn Gly Asp Gln Ala Ala Ala Lys Thr Leu Ser Val Lys Gly Gly
65                  70                  75                  80

Asp Val Val Thr Phe Glu Trp His His Asp Ser Arg Asp Ala Ser Asp
                    85                  90                  95

Asp Ile Ile Ala Ser Ser His Lys Gly Pro Val Met Val Tyr Met Ala
                100                 105                 110

Pro Thr Thr Ala Gly Ser Ser Gly Lys Asn Trp Val Lys Ile Ala Glu
            115                 120                 125

Asp Gly Tyr Ser Asp Gly Thr Trp Ala Val Asp Thr Leu Ile Ala Asn
        130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                    165                 170                 175

Gly Ala Gln Phe Tyr Met Glu Cys Val Gln Phe Lys Val Thr Ser Asp
                180                 185                 190

Gly Ala Asn Thr Leu Pro Asp Gly Val Ser Leu Pro Gly Ala Tyr Ser
            195                 200                 205

Ala Thr Asp Pro Gly Ile Leu Phe Asn Met Tyr Gly Ser Phe Asp Ser
        210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ala Ala Ala
                    245                 250                 255

Val Val Ala Thr Ser Ser Ser Ser Ser Ala Ser Ile Glu Ala Val
            260                 265                 270
```

```
Thr Thr Lys Gly Ala Val Ala Val Ser Thr Ala Ala Val Ala
        275                 280             285

Pro Thr Thr Thr Thr Ala Ala Pro Thr Thr Phe Ala Thr Ala Val Ala
290             295                 300

Ser Thr Lys Lys Ala Thr Ala Cys Arg Asn Lys Thr Lys Ser Ser Ser
305             310                 315                 320

Ala Ala Thr Thr Ala Ala Ala Val Ala Glu Thr Thr Ser Ser Thr Ala
            325                 330                 335

Ala Ala Thr Ala Ala Ser Ser Ala Ser Ser Ala Ser Gly Thr Ala
            340                 345                 350

Gly Lys Tyr Glu Arg Cys Gly Gly Gln Gly Trp Thr Gly Ala Thr Thr
        355                 360                 365

Cys Val Asp Gly Trp Thr Cys Lys Gln Trp Asn Pro Tyr Tyr Tyr Gln
    370                 375                 380

Cys Val Glu Ser Ala
385

<210> SEQ ID NO 41
<211> LENGTH: 406
<212> TYPE: PRT
<213> ORGANISM: Aspergillus aculeatus

<400> SEQUENCE: 41

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

Ile Ser Pro Ser Asp Tyr Gly Thr Asp Ile Ile Cys His Gln Asn
65                  70                  75                  80

Ala Thr Asn Ala Gln Ala His Ile Val Val Ala Ala Gly Asp Lys Ile
                85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
    130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
            180                 185                 190

Ala Gln Asn Tyr Pro Gln Cys Phe Asn Leu Gln Val Thr Gly Ser Gly
        195                 200                 205

Thr Asp Glu Pro Ala Gly Thr Leu Gly Thr Lys Leu Tyr Thr Glu Asp
    210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255
```

```
Thr Ser Ala Ile Thr Ser Thr Gly Thr Ala Val Val Gly Ser Gly Ser
            260                 265                 270

Ala Val Ala Thr Ser Ala Ala Ala Thr Thr Ser Ala Ala Ala Ser
        275                 280                 285

Ser Ala Ala Ala Thr Thr Ala Ala Val Thr Ser Ala Asn Ala
290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Thr Ser Ser Ser Gly Ala
        355                 360                 365

Ala Gln Ser Leu Tyr Gly Gln Cys Gly Gly Ile Asn Trp Thr Gly Ala
370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
                405

<210> SEQ ID NO 42
<211> LENGTH: 427
<212> TYPE: PRT
<213> ORGANISM: Aspergillus aculeatus

<400> SEQUENCE: 42

Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
                20                  25                  30

Tyr Gly Gly Tyr Leu Val Asp Thr Tyr Tyr Glu Ser Asp Pro Pro
            35                  40                  45

Glu Leu Ile Ala Trp Ser Thr Asn Ala Thr Asp Asp Gly Tyr Val Ser
50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
                85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
        115                 120                 125

Glu Phe Phe Lys Ile Asp Ala Gly Gly Leu Ile Asp Asp Thr Asp Val
        130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
                180                 185                 190

Asn Tyr Pro Gln Cys Ile Asn Leu Glu Val Thr Gly Ser Glu Thr Ala
        195                 200                 205

Thr Pro Ser Gly Thr Leu Gly Thr Ala Leu Tyr Lys Glu Thr Asp Pro
```

-continued

```
                    210                 215                 220
Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala Ala
                    245                 250                 255

Ala Asp Thr Thr Thr Thr Ser Ala Gly Thr Thr Ala Glu Ala Thr Thr
                260                 265                 270

Ala Ala Ala Ala Val Ser Thr Thr Ala Asp Ala Val Pro Thr Glu Ser
                275                 280                 285

Ser Ala Pro Ser Glu Thr Ser Ala Thr Thr Ala Asn Pro Ala Arg Pro
            290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                    325                 330                 335

Thr Thr Thr Thr Thr Ser Val Ala Thr Ala Ser Ser Ala Asp Ser
                340                 345                 350

Ser Thr Thr Ser Gly Val Leu Ser Gly Ala Cys Ser Gln Glu Gly Tyr
            355                 360                 365

Trp Tyr Cys Asn Gly Gly Thr Ala Phe Gln Arg Cys Val Asn Gly Glu
370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Thr Arg Arg Asp Ala
                405                 410                 415

Met Arg Arg His Leu Ala Arg Pro Lys Arg His
                420                 425

<210> SEQ ID NO 43
<211> LENGTH: 267
<212> TYPE: PRT
<213> ORGANISM: Aspergillus aculeatus

<400> SEQUENCE: 43

Met Leu Val Lys Leu Ile Ser Phe Leu Ser Ala Ala Thr Ser Val Ala
1               5                   10                  15

Ala His Gly His Val Ser Asn Ile Val Ile Asn Gly Val Ser Tyr Arg
                20                  25                  30

Gly Trp Asp Ile Asn Ser Asp Pro Tyr Asn Ser Asn Pro Val Val
            35                  40                  45

Val Ala Trp Gln Thr Pro Asn Thr Ala Asn Gly Phe Ile Ser Pro Asp
50                  55                  60

Ala Tyr Asp Thr Asp Val Ile Cys His Leu Ser Thr Asn Ala
65                  70                  75                  80

Arg Gly His Ala Val Val Ala Ala Gly Asp Lys Ile Ser Leu Gln Trp
                85                  90                  95

Thr Thr Trp Pro Asp Ser His His Gly Pro Val Ile Ser Tyr Leu Ala
                100                 105                 110

Asn Cys Gly Ser Ser Cys Glu Thr Val Asp Lys Thr Thr Leu Glu Phe
            115                 120                 125

Phe Lys Ile Asp Gly Val Gly Leu Val Asp Glu Ser Asn Pro Pro Gly
        130                 135                 140

Ile Trp Gly Asp Asp Glu Leu Ile Ala Asn Asn Asn Ser Trp Leu Val
145                 150                 155                 160
```

```
Glu Ile Pro Ala Ser Ile Ala Pro Gly Tyr Tyr Val Leu Arg His Glu
                165                 170                 175

Leu Ile Ala Leu His Gly Ala Gly Ser Glu Asn Gly Ala Gln Asn Tyr
            180                 185                 190

Met Gln Cys Phe Asn Leu Gln Val Thr Gly Thr Gly Thr Val Gln Pro
            195                 200                 205

Ser Gly Val Leu Gly Thr Glu Leu Tyr Lys Pro Thr Asp Ala Gly Ile
        210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                245                 250                 255

Thr Ala Ser Gly Thr Ala Val Thr Thr Thr Ala
            260                 265
```

<210> SEQ ID NO 44
<211> LENGTH: 273
<212> TYPE: PRT
<213> ORGANISM: Aspergillus aculeatus

<400> SEQUENCE: 44

```
Met Lys Tyr Leu Ala Ile Phe Ala Ala Ala Ala Gly Leu Ala Arg
1               5                   10                  15

Pro Thr Ala Ala His Tyr Ile Phe Ser Lys Leu Ile Leu Asp Gly Glu
                20                  25                  30

Val Ser Glu Asp Trp Gln Tyr Ile Arg Lys Thr Thr Arg Glu Thr Cys
            35                  40                  45

Tyr Leu Pro Thr Lys Phe Thr Asp Thr Phe Asp Asn Leu Thr Pro Asn
50                  55                  60

Asp Gln Asp Phe Arg Cys Asn Leu Gly Ser Phe Ser Asn Ala Ala Lys
65                  70                  75                  80

Thr Glu Val Ala Glu Val Glu Ala Gly Ser Thr Ile Gly Met Gln Leu
                85                  90                  95

Phe Ala Gly Ser His Met Arg His Pro Gly Pro Ala Gln Val Phe Met
            100                 105                 110

Ser Lys Ala Pro Ser Gly Asn Val Gln Ser Tyr Glu Gly Asp Gly Ser
        115                 120                 125

Trp Phe Lys Ile Trp Glu Arg Thr Leu Cys Asp Lys Ser Gly Asp Leu
    130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
            180                 185                 190

Cys Ala Gln Val Lys Val Thr Gly Asn Gly Thr Gly Val Pro Ser Gln
        195                 200                 205

Thr Tyr Gln Ile Pro Gly Met Tyr Asn Asp Arg Ser Glu Leu Phe Asn
    210                 215                 220

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255

Ser Glu Ser His Val Pro Lys Tyr Lys Lys Ser His Ala Cys Arg Val
            260                 265                 270
```

Tyr

<210> SEQ ID NO 45
<211> LENGTH: 322
<212> TYPE: PRT
<213> ORGANISM: Aurantiporus alborubescens

<400> SEQUENCE: 45

| | | | | | | | | | | | | | | | |
|---|---|---|---|---|---|---|---|---|---|---|---|---|---|---|---|
| Met | Arg | Thr | Ile | Ala | Thr | Phe | Val | Thr | Leu | Val | Ala | Ser | Val | Leu | Pro |
| 1 | | | | 5 | | | | | 10 | | | | | 15 | |
| Ala | Val | Leu | Ala | His | Gly | Gly | Val | Leu | Ser | Tyr | Ser | Asn | Gly | Gly | Asn |
| | | | 20 | | | | | 25 | | | | | 30 | | |
| Trp | Tyr | Trp | Gly | Trp | Lys | Pro | Tyr | Asn | Ser | Pro | Asp | Gly | Gln | Thr | Thr |
| | | | 35 | | | | | 40 | | | | | 45 | | |
| Ile | Gln | Arg | Pro | Trp | Ala | Thr | Tyr | Asn | Pro | Ile | Thr | Asp | Ala | Thr | Asp |
| | 50 | | | | | 55 | | | | | 60 | | | | |
| Pro | Thr | Ile | Ala | Cys | Asn | Asn | Asp | Gly | Thr | Ser | Gly | Ala | Leu | Gln | Leu |
| 65 | | | | | 70 | | | | | 75 | | | | | 80 |
| Thr | Ala | Thr | Val | Ala | Ala | Gly | Ser | Ala | Ile | Thr | Ala | Tyr | Trp | Asn | Gln |
| | | | | 85 | | | | | 90 | | | | | 95 | |
| Val | Trp | Pro | His | Asp | Lys | Gly | Pro | Met | Thr | Thr | Tyr | Leu | Ala | Gln | Cys |
| | | | 100 | | | | | 105 | | | | | 110 | | |
| Pro | Gly | Ser | Thr | Cys | Thr | Gly | Val | Asn | Ala | Lys | Thr | Leu | Lys | Trp | Phe |
| | | | 115 | | | | | 120 | | | | | 125 | | |
| Lys | Ile | Asp | His | Ala | Gly | Leu | Leu | Ser | Gly | Thr | Val | Tyr | Ser | Gly | Ser |
| | 130 | | | | | 135 | | | | | 140 | | | | |
| Trp | Ala | Ser | Gly | Lys | Met | Ile | Ala | Gln | Asn | Ser | Thr | Trp | Thr | Thr | Thr |
| 145 | | | | | 150 | | | | | 155 | | | | | 160 |
| Ile | Pro | Ala | Thr | Val | Pro | Ser | Gly | Asn | Tyr | Leu | Ile | Arg | Phe | Glu | Thr |
| | | | | 165 | | | | | 170 | | | | | 175 | |
| Ile | Ala | Leu | His | Ser | Leu | Pro | Ala | Gln | Phe | Tyr | Pro | Glu | Cys | Ala | Gln |
| | | | 180 | | | | | 185 | | | | | 190 | | |
| Ile | Gln | Ile | Thr | Gly | Gly | Gly | Ser | Arg | Ala | Pro | Thr | Ala | Ala | Glu | Leu |
| | | | 195 | | | | | 200 | | | | | 205 | | |
| Val | Ser | Phe | Pro | Gly | Ala | Tyr | Ser | Asn | Asn | Asp | Pro | Gly | Val | Asn | Ile |
| | 210 | | | | | 215 | | | | | 220 | | | | |
| Asp | Ile | Tyr | Ser | Asn | Ala | Ala | Gln | Ser | Ala | Thr | Thr | Tyr | Val | Ile | Pro |
| 225 | | | | | 230 | | | | | 235 | | | | | 240 |
| Gly | Pro | Pro | Leu | Tyr | Gly | Gly | Ala | Ser | Gly | Ser | Gly | Pro | Ser | Ser | Ala |
| | | | | 245 | | | | | 250 | | | | | 255 | |
| Pro | Pro | Ser | Ser | Thr | Pro | Gly | Ser | Ser | Ser | Thr | Ser | His | Gly | Pro | Thr |
| | | | 260 | | | | | 265 | | | | | 270 | | |
| Ser | Val | Ser | Thr | Ser | Ser | Ser | Ala | Ala | Pro | Ser | Thr | Thr | Gly | Thr | Val |
| | | | 275 | | | | | 280 | | | | | 285 | | |
| Thr | Gln | Tyr | Gly | Gln | Cys | Gly | Gly | Ile | Gly | Trp | Ala | Gly | Ala | Thr | Gly |
| | 290 | | | | | 295 | | | | | 300 | | | | |
| Cys | Ile | Ser | Pro | Phe | Lys | Cys | Thr | Val | Ile | Asn | Asp | Tyr | Tyr | Tyr | Gln |
| 305 | | | | | 310 | | | | | 315 | | | | | 320 |
| Cys | Leu | | | | | | | | | | | | | | |

<210> SEQ ID NO 46
<211> LENGTH: 234
<212> TYPE: PRT
<213> ORGANISM: Aurantiporus alborubescens

<400> SEQUENCE: 46

Met Lys Ala Ile Leu Ala Ile Phe Ser Ala Leu Ala Pro Leu Ala Ala
1               5                   10                  15

Ala His Tyr Thr Phe Pro Asp Phe Ile Val Asn Gly Thr Thr Thr Ala
            20                  25                  30

Asp Trp Val Tyr Ile Arg Glu Thr Ala Asn His Tyr Ser Asn Gly Pro
        35                  40                  45

Val Thr Asn Val Asn Asp Pro Glu Phe Arg Cys Tyr Glu Leu Asp Leu
    50                  55                  60

Gln Asn Thr Ala Ala Ser Thr Leu Thr Ala Thr Val Ser Ala Gly Ser
65                  70                  75                  80

Ser Val Gly Phe Lys Ala Asn Ser Ala Leu Tyr His Pro Gly Tyr Leu
                85                  90                  95

Asp Val Tyr Met Ser Lys Ala Thr Pro Ala Ala Asn Ser Pro Ser Ala
            100                 105                 110

Gly Thr Asp Gln Ser Trp Phe Lys Val Tyr Glu Ser Ala Pro Val Phe
        115                 120                 125

Ala Asn Gly Ala Leu Ser Phe Pro Ser Glu Asn Ile Gln Ser Phe Thr
    130                 135                 140

Phe Thr Ile Pro Lys Ser Leu Pro Ser Gly Gln Tyr Leu Ile Arg Val
145                 150                 155                 160

Glu His Ile Ala Leu His Ser Ala Ser Ser Tyr Gly Gly Ala Gln Phe
                165                 170                 175

Tyr Ile Ser Cys Ala Gln Val Asn Val Val Asn Gly Gly Asn Gly Asn
            180                 185                 190

Pro Gly Pro Leu Val Lys Ile Pro Gly Val Tyr Thr Gly Asn Glu Pro
        195                 200                 205

Gly Ile Leu Ile Asn Ile Tyr Ser Phe Pro Pro Gly Phe Ser Gly Tyr
    210                 215                 220

Gln Ser Pro Gly Pro Ala Val Trp Arg Gly
225                 230

<210> SEQ ID NO 47
<211> LENGTH: 233
<212> TYPE: PRT
<213> ORGANISM: Trichophaea saccata

<400> SEQUENCE: 47

Met Thr Pro Leu Lys Leu Arg Pro Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
    50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
            100                 105                 110

Asp Gly Asn Gly Asp Trp Phe Lys Ile Trp Glu Lys Gly Pro Thr Ser
        115                 120                 125

```
Ile Thr Ser Ser Gly Ile Thr Trp Asp Val Thr Asp Thr Gln Trp Thr
130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
                180                 185                 190

Pro Gly Pro Thr Ile Lys Phe Pro Gly Gly Tyr Ser Ala Thr Asp Pro
                195                 200                 205

Gly Ile Leu Ile Asn Ile Tyr Tyr Pro Ile Pro Thr Ser Tyr Thr Ile
210                 215                 220

Pro Gly Pro Pro Val Trp Thr Gly Lys
225                 230
```

```
<210> SEQ ID NO 48
<211> LENGTH: 237
<212> TYPE: PRT
<213> ORGANISM: Trichophaea saccata

<400> SEQUENCE: 48

Met Lys Cys Leu Leu Ser Leu Leu Leu Ala Ala Thr Ala Val Ser Ala
1               5                   10                  15

His Thr Ile Phe Gln Glu Ile Gly Ile Asn Gly Val Met Gln Ala Arg
                20                  25                  30

Tyr Asp Tyr Met Arg Leu Pro Ser Tyr Asp Gly Pro Ile Thr Asp Val
                35                  40                  45

Thr Ser Thr Tyr Met Ala Cys Asn Gly Gly Pro Asn Pro Leu Val Gln
50                  55                  60

Ile Ser Asn Asp Val Ala Phe Val Lys Ala Gly Asp Ser Ile Thr Leu
65                  70                  75                  80

Gln Trp Ala Gln Thr Leu Thr Thr Asp Phe Asn Thr Gly Leu Ile Ile
                85                  90                  95

Asp Pro Ser His Leu Gly Pro Val Met Val Tyr Met Ala Lys Val Pro
                100                 105                 110

Ser Ala Thr Gly Pro Ile Pro Asn Ser Gly Trp Phe Lys Ile Tyr Glu
                115                 120                 125

Asp Gly Tyr Asp Pro Thr Thr Lys Thr Trp Ala Val Thr Lys Leu Ile
                130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
                165                 170                 175

Thr Tyr Pro Gly Ala Gln Phe Tyr Met Glu Cys Ala Gln Leu Arg Leu
                180                 185                 190

Thr Ser Gly Gly Thr Lys Met Pro Thr Thr Tyr Asn Ile Pro Gly Ile
                195                 200                 205

Tyr Ser Pro Thr Asp Pro Gly Val Thr Phe Asn Leu Tyr Asn Gly Phe
                210                 215                 220

Thr Ser Tyr Thr Ile Pro Gly Pro Arg Pro Phe Thr Cys
225                 230                 235
```

```
<210> SEQ ID NO 49
<211> LENGTH: 484
<212> TYPE: PRT
<213> ORGANISM: Penicillium thomii
```

<400> SEQUENCE: 49

```
Met Ser Leu Ser Lys Ile Ser Gly Leu Ile Leu Gly Ser Ala Ala Leu
1               5                   10                  15

Val Ala Gly His Gly Tyr Val Ser Gly Ile Val Asp Asp Thr Tyr
            20                  25                  30

Tyr Gly Gly Tyr Leu Val Thr Gln Tyr Pro Tyr Glu Ser Asp Ala Pro
        35                  40                  45

Glu Leu Ile Ala Trp Ser Gln Glu Thr Asp Leu Gly Tyr Ile Asp
    50                  55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Gly Ser Val Glu Leu
                85                  90                  95

Gln Trp Thr Thr Trp Pro Thr Ser His His Gly Pro Val Ile Thr Tyr
                100                 105                 110

Met Ala Asn Cys Asn Gly Asp Cys Asp Val Asp Lys Thr Thr Leu
            115                 120                 125

Gln Phe Phe Lys Ile Asp Gln Gly Leu Ile Ser Asp Thr Thr Glu
    130                 135                 140

Pro Gly Thr Trp Ala Thr Asp Asn Leu Ile Ala Asn Asn Ser Arg
145             150                 155                 160

Thr Val Thr Val Pro Ser Asp Ile Ala Asp Gly Asn Tyr Val Leu Arg
                165                 170                 175

His Glu Ile Ile Ala Leu His Ser Ala Gly Glu Thr Asn Gly Ala Gln
            180                 185                 190

Asn Tyr Pro Gln Cys Ile Asn Leu Lys Val Thr Gly Gly Ser Ala
        195                 200                 205

Thr Pro Ser Gly Thr Leu Gly Thr Ala Leu Tyr Lys Asn Thr Asp Pro
    210                 215                 220

Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Thr Ala Ala Ser
            245                 250                 255

Thr Ala Ala Ser Ser Thr Ala Ala Val Thr Thr Ala Asp Ala Val
            260                 265                 270

Thr Thr Ala Ala Ala Val Thr Ser Ser Ala Ser Val Glu Val Val
    275                 280                 285

Pro Thr Thr Thr Pro Ser Ser Ser Ile Val Ser Ala Phe Pro Thr Trp
                290                 295                 300

Ser Pro Ser Ser Thr Pro Pro Phe Ser Asn Ser Ser Asn Gly Trp Arg
305                 310                 315                 320

Pro Ser Phe Ser Arg Gly Pro Gly Pro Arg Phe Thr Ser Ala Pro
            325                 330                 335

Ala Pro Gln Phe Ser Ala Pro Ser Gly Ala Gln Gln Lys Gln Ser Ala
                340                 345                 350

Thr Ala Thr Pro Ile Val Ala Thr Pro Val Val Ile Thr Met Thr Glu
    355                 360                 365

Thr Ser Thr Ser Trp Val Thr Glu Met Val Thr Leu Thr Asp Lys Ser
    370                 375                 380

Val Val Gln Thr Thr Ser Ala Val Pro Val Val Ala Ala Thr Thr
385                 390                 395                 400

Thr Leu Thr Glu Gly Ser Glu Pro Ala Gln Thr Ala Ser Pro Ser Val
```

-continued

```
                405                 410                 415
Val Ser Gly Ser Ser Ser Gly Ser Ser Ser Ser Thr Thr Thr
            420                 425                 430

Thr Ser Lys Thr Ser Thr Gly Ser Asp Tyr Val Ser Ser Asp Trp Met
        435                 440                 445

Ser Tyr Leu Ser Ser Leu Ser Ala Ala Glu Val Leu Gln Met Leu Arg
    450                 455                 460

Gln Thr Phe Arg Trp Met Val Ser Asn Asp Lys Val His Ala Arg Asp
465                 470                 475                 480

Ile Thr Ile Asn

<210> SEQ ID NO 50
<211> LENGTH: 320
<212> TYPE: PRT
<213> ORGANISM: Talaromyces stipitatus

<400> SEQUENCE: 50

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Thr Gly Tyr Leu Val Asn Gln Tyr Pro Tyr Gln Ser Asn
        35                  40                  45

Pro Pro Ala Val Ile Gly Trp Ser Thr Thr Ala Thr Asp Leu Gly Phe
    50                  55                  60

Val Asp Gly Ser Gly Tyr Thr Asn Pro Asp Ile Ile Cys His Lys Asn
65                  70                  75                  80

Ala Lys Pro Gly Gln Leu Ser Ala Pro Val Ala Gly Gly Lys Val
                85                  90                  95

Glu Leu Glu Trp Thr Thr Trp Pro Glu Ser His His Gly Pro Val Ile
            100                 105                 110

Ser Tyr Leu Ala Asn Cys Asn Gly Asp Cys Thr Thr Val Asp Lys Thr
        115                 120                 125

Lys Leu Glu Phe Val Lys Ile Asp Gln Arg Gly Leu Ile Asp Asp Ser
    130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
            180                 185                 190

Ala Gln Asn Tyr Pro Gln Cys Ile Asn Leu Gln Ile Thr Gly Ser Gly
        195                 200                 205

Thr Ala Asn Pro Ser Gly Thr Pro Gly Glu Lys Leu Tyr Thr Pro Thr
    210                 215                 220

Asp Pro Gly Ile Leu Val Asn Ile Tyr Gln Ser Leu Ser Ser Tyr Val
225                 230                 235                 240

Ile Pro Gly Pro Thr Leu Trp Ser Gly Ala Ala Ala His Val Val Ala
                245                 250                 255

Thr Ala Ala Gly Ser Ala Thr Gly Val Ala Ser Ala Thr Ala Thr Pro
            260                 265                 270

Thr Thr Leu Val Thr Ala Val Ser Ser Pro Thr Gly Ala Pro Ser Val
        275                 280                 285

Val Thr Pro Glu Ala Pro Ser Val Thr Ser Phe Ala Pro Val Val Thr
```

```
                 290                 295                 300
Val Thr Asp Val Val Thr Val Thr Thr Val Ile Thr Thr Ile Ser
305                 310                 315                 320

<210> SEQ ID NO 51
<211> LENGTH: 272
<212> TYPE: PRT
<213> ORGANISM: Thermomyces lanuginosus

<400> SEQUENCE: 51

Met Lys Gly Ser Ser Ala Ala Ser Val Leu Thr Phe Leu Ala Gly
1               5                   10                  15

Ile Ser Arg Thr Ser Ala His Gly Tyr Val Ser Asn Leu Val Ile Asn
                20                  25                  30

Gly Val Tyr Tyr Arg Gly Trp Leu Pro Gly Glu Asp Pro Tyr Asn Pro
                35                  40                  45

Asp Pro Pro Ile Gly Val Gly Trp Glu Thr Pro Asn Leu Gly Asn Gly
            50                  55                  60

Phe Val Thr Pro Ser Glu Ala Ser Thr Asp Ala Val Ile Cys His Lys
65              70                  75                  80

Glu Ala Thr Pro Ala Arg Gly His Val Ser Val Lys Ala Gly Asp Lys
                85                  90                  95

Ile Tyr Ile Gln Trp Gln Pro Asn Pro Trp Pro Asp Ser His His Gly
                100                 105                 110

Pro Val Leu Asp Tyr Leu Ala Pro Cys Asn Gly Pro Cys Glu Ser Val
                115                 120                 125

Asp Lys Thr Ser Leu Arg Phe Phe Lys Ile Asp Gly Val Gly Leu Ile
                130                 135                 140

Asp Gly Ser Ser Pro Pro Gly Tyr Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Ser Ala Gly Asn
                180                 185                 190

Pro Asp Gly Ala Gln Leu Tyr Pro Gln Cys Phe Asn Leu Glu Ile Thr
                195                 200                 205

Gly Ser Gly Thr Val Glu Pro Glu Gly Val Pro Ala Thr Glu Phe Tyr
                210                 215                 220

Ser Pro Asp Asp Pro Gly Ile Leu Val Asn Ile Tyr Glu Pro Leu Ser
225                 230                 235                 240

Thr Tyr Glu Val Pro Gly Pro Ser Leu Ile Pro Gln Ala Val Gln Ile
                245                 250                 255

Glu Gln Ser Ser Ser Ala Ile Thr Ala Thr Gly Thr Thr Pro Ala
                260                 265                 270

<210> SEQ ID NO 52
<211> LENGTH: 327
<212> TYPE: PRT
<213> ORGANISM: Thermomyces lanuginosus

<400> SEQUENCE: 52

Met Ala Phe Ser Thr Val Thr Val Phe Val Thr Phe Leu Ala Phe Ile
1               5                   10                  15

Ser Ile Ala Ser Ala His Gly Phe Val Thr Lys Ile Thr Val Leu Gly
                20                  25                  30

Asp Asn Asn Lys Asp Tyr Pro Gly Phe Asp Pro Ser Thr Pro Lys Glu
```

```
                  35                  40                  45
Val Pro Pro Gly Leu Asp Val Ala Trp Ser Thr Ser Ala Ser Asp Gln
 50                  55                  60

Gly Tyr Met Ser Ser Ser Asn Ala Ser Tyr His Ser Lys Asp Phe Ile
 65                  70                  75                  80

Cys His Arg Asn Ala Lys Pro Ala Pro Asp Ala Ala Gln Val His Ala
                 85                  90                  95

Gly Asp Lys Val Gln Leu His Trp Thr Gln Trp Pro Gly Pro Glu Asp
                100                 105                 110

His Gln Gly Pro Ile Leu Asp Tyr Leu Ala Ser Cys Asn Gly Pro Cys
                115                 120                 125

Ser Asn Val Glu Lys Ala Ser Leu Lys Trp Thr Lys Ile Asp Glu Ala
130                 135                 140

Gly Arg Phe Pro Asn Gly Thr Trp Ala Thr Asp Leu Leu Arg Asn Gly
145                 150                 155                 160

Gly Asn Thr Trp Asn Val Thr Ile Pro Ser Asp Leu Ala Pro Gly Glu
                165                 170                 175

Tyr Val Leu Arg Asn Glu Ile Ile Ala Leu His Ser Ala Arg Asn Met
                180                 185                 190

Gly Gly Ala Gln His Tyr Met Gln Cys Val Asn Leu Asn Val Thr Gly
                195                 200                 205

Thr Gly His Arg Glu Leu Gln Gly Val Ser Ala Ala Glu Phe Tyr Asn
210                 215                 220

Pro Thr Asp Pro Gly Ile Leu Ile Asn Val Trp Gln Thr Gln Ser Leu
225                 230                 235                 240

Ser Ser Tyr His Ile Pro Gly Pro Thr Leu Leu Ala Ala Asp Thr Gly
                245                 250                 255

Asn Asp Gly Gly His Ser Ala Ser Thr Leu Ala Thr Val Thr Ser
                260                 265                 270

Arg Arg Leu Ser Thr Pro Ser Asp Ala Met Pro Gly Asn Gly Ser Tyr
                275                 280                 285

Gly Ala Ile Ser Pro Pro Leu Lys Pro Ala Lys Gly Phe His Pro Val
                290                 295                 300

Cys Asn Ala Arg Phe Arg His Gly Ser Thr Phe Thr Leu Thr Thr Leu
305                 310                 315                 320

Val Ala Pro Pro Ala Arg Thr
                325

<210> SEQ ID NO 53
<211> LENGTH: 274
<212> TYPE: PRT
<213> ORGANISM: Thermomyces lanuginosus

<400> SEQUENCE: 53

Met Lys Gly Ser Thr Thr Ala Ser Leu Leu Leu Pro Leu Leu Ala Ser
 1               5                  10                  15

Val Thr Arg Thr Ser Ala His Gly Phe Val Ser Asn Leu Val Ile Asn
                 20                  25                  30

Gly Val Phe Tyr Arg Gly Trp Leu Pro Thr Glu Asp Pro Tyr Lys Ala
                 35                  40                  45

Asp Pro Pro Ile Gly Val Gly Trp Glu Thr Pro Asn Leu Gly Asn Gly
 50                  55                  60

Phe Val Leu Pro Glu Glu Ala Ser Thr Asp Ala Ile Val Cys His Lys
 65                  70                  75                  80
```

-continued

Glu Ala Glu Pro Ala Arg Gly Tyr Ala Ser Val Ala Ala Gly Asp Lys
                85                  90                  95

Ile Tyr Ile Gln Trp Gln Pro Asn Pro Trp Pro Glu Ser His His Gly
            100                 105                 110

Pro Val Ile Asp Tyr Leu Ala Pro Cys Asn Gly Asp Cys Ser Thr Val
            115                 120                 125

Asn Lys Thr Ser Leu Glu Phe Phe Lys Ile Asp Gly Val Gly Leu Ile
        130                 135                 140

Asp Gly Ser Ser Pro Pro Gly Lys Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Ala Phe Asn
            180                 185                 190

Gln Asn Gly Ala Gln Ile Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
                245                 250                 255

Glu Gln Ser Ser Ser Ala Val Thr Ala Thr Gly Thr Pro Thr Pro Ala
            260                 265                 270

Ala Ala

<210> SEQ ID NO 54
<211> LENGTH: 227
<212> TYPE: PRT
<213> ORGANISM: Humicola insolens

<400> SEQUENCE: 54

Met Lys Leu Ser Val Val Leu Thr Gly Leu Ala Ala Ala Leu Ala Glu
1               5                   10                  15

Ala His Tyr Thr Phe Pro Ser Val Gly Asn Thr Ala Asp Trp Gln Val
            20                  25                  30

Val Arg Gln Thr Thr Asn Phe Gln Ser Asn Gly Pro Val Thr Asp Val
        35                  40                  45

Asn Ser Asp Gln Ile Arg Cys Tyr Glu Arg Phe Pro Gly Gln Gly Ala
    50                  55                  60

Pro Gly Ile Tyr Asn Val Thr Ala Gly Gln Thr Ile Ser Tyr Asn Ala
65                  70                  75                  80

Lys Ala Ser Ile Ser His Pro Gly Pro Met Ala Phe Tyr Ile Ala Lys
                85                  90                  95

Val Pro Ala Gly Tyr Thr Ala Ala Asn Trp Asp Gly Arg Gly Ala Val
            100                 105                 110

Trp Ser Lys Ile Tyr Gln Asp Met Pro Arg Ile Ala Gly Ser Leu Thr
        115                 120                 125

Trp Pro Thr Asn Gly Ala Arg Ser Val Ser Val Thr Ile Pro Arg Cys
    130                 135                 140

Leu Gln Asp Gly His Tyr Leu Leu Arg Ala Glu His Ile Gly Leu His
145                 150                 155                 160

Ser Ala Ser Gly Val Gly Gly Ala Gln Phe Tyr Ile Ser Cys Ala Gln
                165                 170                 175

-continued

Leu Tyr Val Ser Gly Gly Thr Gly Thr Trp Asn Pro Arg Asn Lys Val
            180                 185                 190

Ala Phe Pro Gly Ala Tyr Ser Pro Thr His Pro Gly Ile Met Ile Asn
        195                 200                 205

Ile Tyr Trp Pro Val Pro Thr Ser Tyr Thr Pro Pro Gly Pro Pro Val
    210                 215                 220

Glu Thr Cys
225

<210> SEQ ID NO 55
<211> LENGTH: 257
<212> TYPE: PRT
<213> ORGANISM: Humicola insolens

<400> SEQUENCE: 55

Met Arg Pro Phe Leu Ala Ala Leu Ala Ala Ala Thr Thr Val His Ala
1               5                   10                  15

His Gly Trp Val Asp Asn Ala Thr Ile Asp Gly Val Phe Tyr Gln Leu
            20                  25                  30

Tyr His Pro Tyr Met Asp Pro Tyr Met Gly Glu Phe Ala Pro Pro Arg
        35                  40                  45

Ile Ser Arg Lys Leu Val Trp Asn Gly Tyr Val Asn Asp Val Thr Ser
    50                  55                  60

Ile Asp Leu Gln Cys Gly Gly His Thr Ala Glu Gly Gln Ile Gly Thr
65                  70                  75                  80

Glu Pro Ala Pro Leu His Ala Pro Ala Thr Ala Gly Ser Thr Val Asn
                85                  90                  95

Leu Arg Trp Thr Leu Trp Pro Asp Ser His Met Gly Pro Ile Met Thr
            100                 105                 110

Tyr Met Ala Arg Cys Pro Asp Glu Gly Cys Asp Lys Trp Leu Pro Val
        115                 120                 125

Trp Phe Lys Ile His Glu Ala Gly Arg Tyr Thr Thr Asp Lys Ser Tyr
    130                 135                 140

Pro Asp Asp Ile Trp Glu Val Thr Arg Leu Met Tyr Pro Ala Asn Glu
145                 150                 155                 160

Gly Tyr Asn Tyr Thr Ile Pro Ala Cys Leu Ala Ser Gly His Tyr Leu
                165                 170                 175

Val Arg His Glu Ile Ile Ala Leu His Ser Ala Trp Ala Lys Gly Glu
            180                 185                 190

Ala Gln Phe Tyr Pro Ser Cys His Gln Leu Thr Val Thr Ser Ile Gly
        195                 200                 205

Gly Asn Val Arg Glu Ala Pro Ala Glu Tyr Arg Val Ser Phe Pro Gly
    210                 215                 220

Ala Tyr Lys Asp Asp Pro Gly Ile Phe Ile Asn Val Trp Asn Pro
225                 230                 235                 240

Gly Pro Tyr Thr Ile Pro Gly Pro Val Trp Thr Cys Pro Glu Ser
                245                 250                 255

Glu

<210> SEQ ID NO 56
<211> LENGTH: 246
<212> TYPE: PRT
<213> ORGANISM: Humicola insolens

<400> SEQUENCE: 56

Met Arg Leu Ser Leu Thr Thr Leu Leu Ala Ser Ala Leu Ser Val Gln

```
            1               5                  10                 15
         Gly His Ala Ile Phe Gln Arg Val Thr Val Asn Gly Gln Asp Gln Gly
                        20                  25                  30

Ser Leu Thr Gly Leu Arg Ala Pro Asn Asn Asn Pro Val Gln Asn
                     35                  40                  45

Val Asn Ser Gln Asp Ile Ile Cys Gly Ala Pro Gly Ser Arg Ser Gln
                 50                  55                  60

Ser Val Ile Asn Val Asn Ala Gly Asp Arg Ile Gly Ala Trp Tyr Gln
         65                  70                  75                  80

His Val Ile Gly Gly Ala Gln Phe Pro Gly Asp Pro Asp Asn Pro Ile
                             85                  90                  95

Ala Arg Ser His Lys Gly Pro Ile Ser Val Tyr Leu Ala Lys Val Asp
                         100                 105                 110

Asn Ala Ala Thr Ala Asn His Gln Gly Leu Gln Trp Phe Lys Ile Trp
                     115                 120                 125

His Asp Gly Phe Asn Pro Ser Thr Arg Gln Trp Ala Val Asp Thr Met
                 130                 135                 140

Ile Asn Asn Asn Gly Trp Val Tyr Phe Asn Leu Pro Gln Cys Ile Ala
         145                 150                 155                 160

Pro Gly His Tyr Leu Met Arg Val Glu Leu Leu Ala Leu His Ser Ala
                             165                 170                 175

Thr Tyr Gln Gly Gln Ala Gln Phe Tyr Ile Ser Cys Ala Gln Ile Asn
                         180                 185                 190

Val Gln Ser Gly Gly Asn Phe Thr Pro Trp Gln Thr Val Ser Phe Pro
                     195                 200                 205

Gly Ala Tyr Gln Ala Asn His Pro Gly Ile Gln Val Asn Ile Tyr Gly
                 210                 215                 220

Ala Met Gly Gln Pro Asp Asn Gly Gly Arg Pro Tyr Gln Ile Pro Gly
         225                 230                 235                 240

Pro Glu Pro Ile Gln Cys
                         245

<210> SEQ ID NO 57
<211> LENGTH: 265
<212> TYPE: PRT
<213> ORGANISM: Humicola insolens

<400> SEQUENCE: 57

Met Gly Pro Thr Trp Ala Val Ile Leu Gly Leu Ile Ala Pro Ser Val
1               5                   10                  15

Leu Asn Ile His Gly Ile Leu Leu Val Asn Gly Thr Glu Thr Pro Glu
                20                  25                  30

Trp Lys Tyr Val Leu Asp Val Ala Pro Ala Val Pro Ile Ser Asn Pro
            35                  40                  45

Asp Ser Leu Pro Pro Gly Tyr Gln Gly Tyr Lys Val Asp Pro Ile Ile
        50                  55                  60

Gly Ser Gly Asn Pro Asn Ile Thr Cys Gly Arg Leu Ala Phe Asp Ser
65                  70                  75                  80

Ala Pro Lys Thr Gln Ile Ala Asp Val Leu Ala Gly Ser Glu Val Gly
                85                  90                  95

Phe Arg Val Ser Ala Asp Gly Leu Gly Asn Arg Asp Leu Glu Lys Gly
                100                 105                 110

Tyr Ile Pro Thr Phe Trp His Pro Gly Pro Ala Gln Ala Tyr Leu Ser
            115                 120                 125
```

Arg Ala Pro Asn Asp Asp Leu Tyr Ser Tyr Lys Gly Asp Gly Asp Trp
130                 135                 140

Phe Lys Ile Ala Tyr Ala Gly Pro Val Asp Asp Leu Thr Trp Ser Leu
145                 150                 155                 160

Trp Pro Gly Val Ser Asp Phe Asn Phe Thr Ile Pro Leu Ser Thr Pro
                165                 170                 175

Pro Gly Lys Tyr Leu Leu Arg Ile Glu Asn Phe Met Pro Thr Ala Ser
            180                 185                 190

Thr Gly Tyr Leu Gln Phe Tyr Val Asn Cys Ala Phe Val Asn Ile Ile
        195                 200                 205

Gly Pro Gly Gly Gly Thr Pro Thr Glu Phe Ile Arg Ile Pro Gly Asp
210                 215                 220

Tyr Thr Asp Glu Asp Pro Gly Phe Leu Val Pro Pro Glu Gln Ser Ser
225                 230                 235                 240

Leu Asp Gly Arg Val Pro Arg Asp Gln Leu Lys Leu Met Ser Tyr Thr
                245                 250                 255

Pro Pro Gly Pro Ala Val Trp Thr Gly
            260                 265

<210> SEQ ID NO 58
<211> LENGTH: 310
<212> TYPE: PRT
<213> ORGANISM: Humicola insolens

<400> SEQUENCE: 58

Met Lys Ala Leu Thr Leu Leu Ala Ala Ala Thr Ala Ala Ser Ala His
1               5                   10                  15

Thr Ile Phe Val Gln Leu Glu Ala Asp Gly Thr Arg Tyr Pro Val Ser
                20                  25                  30

His Gly Val Arg Thr Pro Gln Tyr Asp Gly Pro Ile Thr Asp Val Ser
            35                  40                  45

Ser Asn Asp Leu Ala Cys Asn Gly Gly Pro Asn Pro Thr Met Lys Thr
50                  55                  60

Asp Lys Ile Ile Thr Val Thr Ala Gly Ser Thr Val Lys Ala Ile Trp
65                  70                  75                  80

Arg His Thr Leu Gln Ser Gly Pro Asn Asp Val Met Asp Pro Ser His
                85                  90                  95

Lys Gly Pro Thr Leu Ala Tyr Leu Lys Lys Val Asp Asn Ala Leu Thr
            100                 105                 110

Asp Ser Gly Val Gly Gly Gly Trp Phe Lys Ile Gln Glu Asp Gly His
        115                 120                 125

Ser Asn Gly Asn Trp Gly Thr Leu Lys Val Ile Asn Asn Gln Gly Ile
130                 135                 140

His Tyr Ile Asp Ile Pro Asp Cys Ile Asp Ser Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Glu Ile Val Gly Gly Lys Gly
            180                 185                 190

Thr Val Lys Pro Gln Thr Tyr Ser Ile Pro Gly Ile Tyr Lys Ser Asn
        195                 200                 205

Asp Pro Gly Ile Leu Ile Asn Ile Tyr Ser Met Ser Pro Ser Ser Gln
210                 215                 220

Tyr Ile Ile Pro Gly Pro Pro Leu Phe Thr Cys Asn Gly Gly Gly Gly
225                 230                 235                 240

```
Ser Asn Asn Gly Gly Gly Asn Gly Gly Ser Asn Pro Pro Val Gln
            245                 250                 255

Gln Pro Pro Ala Thr Thr Leu Thr Thr Ala Ile Ala Gln Pro Thr Pro
            260                 265                 270

Ile Cys Ser Val Gln Gln Trp Gly Gln Cys Gly Gly Gln Gly Tyr Ser
            275                 280                 285

Gly Cys Thr Thr Cys Ala Ser Pro Tyr Arg Cys Asn Glu Ile Asn Ala
            290                 295                 300

Trp Tyr Ser Gln Cys Leu
305                 310

<210> SEQ ID NO 59
<211> LENGTH: 354
<212> TYPE: PRT
<213> ORGANISM: Humicola insolens

<400> SEQUENCE: 59

Met Ala Pro Lys Thr Ser Thr Phe Leu Ala Ser Leu Thr Gly Ala Ala
1               5                   10                  15

Leu Val Ala Ala His Gly His Val Ser His Ile Ile Val Asn Gly Val
            20                  25                  30

Gln Tyr Arg Asn Tyr Asp Pro Thr Thr Asp Phe Tyr Ser Gly Asn Pro
            35                  40                  45

Pro Thr Val Ile Gly Trp Ser Ala Leu Asn Gln Asp Asn Gly Phe Ile
        50                  55                  60

Glu Pro Asn Asn Phe Gly Thr Pro Asp Ile Ile Cys His Lys Ser Ala
65                  70                  75                  80

Lys Pro Gly Gly Gly His Val Thr Val Arg Ala Gly Asp Lys Ile Ser
                85                  90                  95

Ile Val Trp Thr Pro Glu Trp Pro Glu Ser His Val Gly Pro Val Ile
            100                 105                 110

Asp Tyr Leu Ala Ala Cys Asn Gly Asp Cys Glu Thr Val Asp Lys Thr
        115                 120                 125

Ser Leu Arg Phe Phe Lys Ile Asp Gly Ala Gly Tyr Asp Ala Ala Ala
    130                 135                 140

Gly Arg Trp Ala Ala Asp Ala Leu Arg Ala Asn Gly Asn Ser Trp Leu
145                 150                 155                 160

Val Gln Ile Pro Ala Asp Leu Lys Ala Gly Asn Tyr Val Leu Arg His
                165                 170                 175

Glu Ile Ile Ala Leu His Gly Ala Ala Asn Pro Asn Gly Ala Gln Ala
            180                 185                 190

Tyr Pro Gln Cys Ile Asn Ile Arg Val Thr Gly Gly Gly Asn Asn Gln
        195                 200                 205

Pro Ser Gly Val Pro Gly Thr Gln Leu Tyr Lys Ala Ser Asp Pro Gly
    210                 215                 220

Ile Leu Phe Asn Pro Trp Val Ala Asn Pro Gln Tyr Pro Val Pro Gly
225                 230                 235                 240

Pro Ala Leu Ile Pro Gly Ala Val Ser Ser Ile Pro Gln Ser Arg Ser
                245                 250                 255

Thr Ala Thr Ala Thr Gly Thr Ala Thr Arg Pro Gly Ala Asp Thr Asp
            260                 265                 270

Pro Thr Gly Val Pro Pro Val Val Thr Thr Ser Ala Pro Ala Gln
        275                 280                 285

Val Thr Thr Thr Thr Ser Ser Arg Thr Thr Ser Leu Pro Gln Ile Thr
```

```
            290                 295                 300
Thr Thr Phe Ala Thr Ser Thr Thr Pro Pro Pro Ala Ala Thr Gln
305                 310                 315                 320

Ser Lys Trp Gly Gln Cys Gly Gly Asn Gly Trp Thr Gly Pro Thr Val
                325                 330                 335

Cys Ala Pro Gly Ser Ser Cys Asn Lys Leu Asn Asp Trp Tyr Ser Gln
            340                 345                 350

Cys Ile
```

<210> SEQ ID NO 60
<211> LENGTH: 267
<212> TYPE: PRT
<213> ORGANISM: Humicola insolens

<400> SEQUENCE: 60

```
Met Tyr Leu Leu Pro Ile Ala Ala Ala Leu Ala Phe Thr Thr Thr
1               5                   10                  15

Ala Tyr Ala His Ala Gln Val Tyr Gly Leu Arg Val Asn Asp Gln His
                20                  25                  30

Gln Gly Asp Gly Arg Asn Lys Tyr Ile Arg Ser Pro Ser Asn Ser
            35                  40                  45

Pro Ile Arg Trp Asp His Val Thr His Pro Phe Leu Ile Cys Asn Ile
50                  55                  60

Arg Asp Asp Asn Gln Pro Pro Gly Pro Ala Pro Asp Phe Val Arg Ala
65                  70                  75                  80

Phe Ala Gly Asp Arg Val Ala Phe Gln Trp Tyr His Ala Arg Pro Asn
                85                  90                  95

Asp Pro Thr Asp Tyr Val Leu Asp Ser Ser His Leu Gly Val Leu Val
            100                 105                 110

Thr Trp Ile Ala Pro Tyr Thr Asp Gly Pro Gly Thr Gly Pro Ile Trp
            115                 120                 125

Thr Lys Ile His Gln Asp Gly Trp Asn Gly Thr His Trp Ala Thr Ser
    130                 135                 140

Arg Leu Ile Ser Asn Gly Gly Phe Val Glu Phe Arg Leu Pro Gly Ser
145                 150                 155                 160

Leu Lys Pro Gly Lys Tyr Leu Val Arg Gln Glu Ile Ile Ala Leu His
                165                 170                 175

Gln Ala Asp Met Pro Gly Pro Asn Arg Gly Pro Glu Phe Tyr Pro Ser
            180                 185                 190

Cys Ala Gln Leu Glu Val Phe Gly Ser Gly Glu Ala Ala Pro Pro Gln
        195                 200                 205

Gly Tyr Asp Ile Asn Lys Gly Tyr Ala Glu Ser Gly Asp Lys Leu Trp
    210                 215                 220

Phe Asn Ile Tyr Ile Asn Lys Asn Asp Glu Phe Lys Met Pro Gly Pro
225                 230                 235                 240

Glu Val Trp Asp Gly Gly Cys Arg Phe Gly Arg Trp Ala Thr Glu
                245                 250                 255

Glu Pro Gly Lys Pro Lys Val Asn Gln His Gly
            260                 265
```

<210> SEQ ID NO 61
<211> LENGTH: 237
<212> TYPE: PRT
<213> ORGANISM: Humicola insolens

<400> SEQUENCE: 61

```
Met Lys Leu Leu Ala Pro Leu Met Leu Ala Gly Ala Ala Ser Ala His
1               5                   10                  15

Thr Ile Phe Thr Ser Leu Glu Val Asp Gly Arg Asn Tyr Gly Thr Gly
            20                  25                  30

Asn Gly Val Arg Val Pro Ser Tyr Asn Gly Pro Val Glu Asp Val Thr
            35                  40                  45

Ser Asn Ser Ile Ala Cys Asn Gly Pro Pro Asn Pro Thr Ser Pro Thr
50                  55                  60

Asp Thr Val Ile Thr Val Gln Ala Gly Gln Asn Val Thr Ala Ile Trp
65                  70                  75                  80

Arg Tyr Met Leu Asn Thr Gln Gly Thr Ser Pro Asn Asp Ile Met Asp
                85                  90                  95

Ser Ser His Lys Gly Pro Thr Leu Ala Tyr Leu Lys Lys Val Asn Asp
                100                 105                 110

Ala Arg Thr Asp Ser Gly Val Gly Asp Gly Trp Phe Lys Ile Gln His
            115                 120                 125

Asp Gly Phe Asp Gly Thr Thr Trp Gly Thr Glu Arg Val Ile Phe Gly
            130                 135                 140

Gln Gly Arg His Thr Ile Lys Ile Pro Glu Cys Ile Glu Pro Gly Gln
145                 150                 155                 160

Tyr Leu Leu Arg Ala Glu Met Ile Ala Leu His Gly Ala Gln Asn Tyr
                165                 170                 175

Pro Gly Ala Gln Phe Tyr Met Glu Cys Ala Gln Leu Asn Ile Val Gly
            180                 185                 190

Gly Thr Gly Thr Lys Lys Pro Ser Thr Val Ser Phe Pro Gly Ala Tyr
            195                 200                 205

Lys Gly Thr Asp Pro Gly Val Lys Leu Ser Ile Trp Trp Pro Pro Val
            210                 215                 220

Thr Asn Tyr Val Ile Pro Gly Pro Asp Val Phe Lys Cys
225                 230                 235

<210> SEQ ID NO 62
<211> LENGTH: 234
<212> TYPE: PRT
<213> ORGANISM: Humicola insolens

<400> SEQUENCE: 62

Met Lys Leu Leu Ser Thr Leu Ala Ala Ile Ala Ala Thr Leu Ala Thr
1               5                   10                  15

Ala Asp Ala His Tyr Ile Phe Asn Ile Leu Tyr Val Asn Gly Gln Arg
            20                  25                  30

Met Gly Gly Glu Tyr Thr Tyr Val Arg Arg Asn Ser Asn Ser Tyr Phe
            35                  40                  45

Pro Val Phe Pro Asp Ile Leu Asn Ser Asn Asp Met Arg Cys Asn Val
50                  55                  60

Gly Ala Arg Pro Gly Asn Thr Gln Thr Ala Thr Val Arg Ala Gly Asp
65                  70                  75                  80

Arg Ile Gly Phe Lys Val Phe Asn Asn Glu Val Ile Glu His Pro Gly
                85                  90                  95

Pro Gly Phe Ile Tyr Met Ser Lys Ala Pro Gly Ser Val Asn Asn Tyr
                100                 105                 110

Asp Gly Ser Gly Asp Trp Phe Lys Val Tyr Glu Thr Gly Leu Cys Arg
            115                 120                 125

Gly Gly Gly Asn Val Asp Thr Asn Trp Cys Ser Tyr Tyr Lys Asp Arg
```

```
                130                 135                 140
Leu Glu Phe Thr Ile Pro Pro Lys Thr Pro Pro Gly Glu Tyr Leu Val
145                 150                 155                 160

Arg Ile Glu His Ile Gly Leu His Glu Gly His Val Asn Arg Ala Gln
                165                 170                 175

Phe Tyr Ile Thr Cys Ala Gln Leu Lys Ile Glu Gly Pro Gly Gly Gly
                180                 185                 190

Asn Pro Asn Pro Leu Val Lys Ile Pro Gly Ile Tyr Arg Ala Asn Asp
                195                 200                 205

Pro Gly Ile Ala Tyr Asn Lys Trp Thr Asn Asn Pro Ala Pro Tyr Ile
            210                 215                 220

Met Pro Gly Pro Lys Val Trp Asp Gly Asn
225                 230

<210> SEQ ID NO 63
<211> LENGTH: 226
<212> TYPE: PRT
<213> ORGANISM: Humicola insolens

<400> SEQUENCE: 63

Met Leu Gly Ser Ala Leu Leu Leu Gly Thr Ala Leu Gly Ala Thr
1               5                   10                  15

Ala His Tyr Thr Phe Pro Arg Ile Asn Ser Gly Gly Asp Trp Gln Tyr
                20                  25                  30

Val Arg Arg Ala Asp Asn Trp Gln Asp Asn Gly Phe Val Gly Asn Val
            35                  40                  45

Asn Ser Pro Gln Ile Arg Cys Phe Gln Ser Arg His Gln Ala Ala Pro
        50                  55                  60

Ala Thr Leu Asn Val Thr Ala Gly Ser Thr Val Thr Tyr Tyr Ala Asn
65                  70                  75                  80

Pro Asn Val Tyr His Pro Gly Pro Met Ala Phe Tyr Met Ala Arg Val
                85                  90                  95

Pro Asp Gly Gln Asp Ile Asn Ser Trp Thr Gly Glu Gly Ala Val Trp
                100                 105                 110

Phe Lys Ile Tyr His Glu Gln Pro Thr Gly Leu Gly Gln Gln Leu Arg
                115                 120                 125

Trp Ser Ser Asp Gly Lys Asn Ser Phe Gln Val Gln Ile Pro Arg Cys
            130                 135                 140

Ile Arg Ser Gly Tyr Tyr Leu Leu Arg Ala Glu His Ile Gly Leu His
145                 150                 155                 160

Ser Ala Gly Ser Pro Gly Gly Ala Gln Phe Tyr Ile Ser Cys Ala Gln
                165                 170                 175

Leu Ala Val Asn Gly Gly Ser Thr Glu Pro Pro Asn Lys Val Ser
                180                 185                 190

Phe Pro Gly Ala Tyr Ser Pro Ser Asp Pro Gly Ile Gln Ile Asn Ile
            195                 200                 205

Tyr Trp Pro Val Pro Thr Ser Tyr Lys Asn Pro Gly Pro Pro Val Phe
            210                 215                 220

Gln Cys
225

<210> SEQ ID NO 64
<211> LENGTH: 231
<212> TYPE: PRT
<213> ORGANISM: Humicola insolens
```

<400> SEQUENCE: 64

```
Met Lys Leu Leu Pro Gly Leu Leu Ala Ala Thr Ala Ala Gln Ala
1               5                  10                  15

His Tyr Thr Phe Pro Arg Leu Val Val Asn Gly Gln Pro Glu Glu Arg
            20                  25                  30

Asp Trp Ser Val Thr Arg Met Thr Lys Asn His Gln Ser Lys Ser Gly
                35                  40                  45

Ile Glu Asn Pro Thr Ser Pro Asp Ile Arg Cys Tyr Ser Ser Gln Thr
 50                  55                  60

Ala Pro Asn Val Ala Ile Val Pro Ala Gly Ser Thr Ile His Tyr Ile
 65                  70                  75                  80

Ser Thr Gln Gln Ile Asn His Pro Gly Pro Thr Gln Tyr Tyr Leu Ala
                85                  90                  95

Lys Val Pro Ala Gly Gln Ser Ala Lys Thr Trp Asp Gly Ser Gly Asn
            100                 105                 110

Val Trp Phe Lys Ile Ala Thr Ser Met Pro Glu Tyr Asp Gln Asn Arg
        115                 120                 125

Gln Leu Val Trp Pro Gly His Asn Thr Tyr Gln Thr Ile Asn Ala Thr
    130                 135                 140

Ile Pro Ala Asn Thr Pro Ser Gly Glu Tyr Leu Leu Arg Val Glu Gln
145                 150                 155                 160

Ile Ala Leu His Met Ala Ser Gln Pro Asn Lys Ala Gln Phe Tyr Ile
                165                 170                 175

Ser Cys Ser Gln Ile Gln Ile Thr Asn Gly Gly Asn Gly Thr Pro Gly
            180                 185                 190

Pro Leu Val Ala Phe Pro Gly Ala Tyr Arg Ser Asn Asp Pro Gly Ile
        195                 200                 205

Leu Val Asn Leu Tyr Ser Gly Met Gln Pro Ser Gln Tyr Gln Pro Pro
    210                 215                 220

Gly Pro Ala Val Trp Arg Gly
225                 230
```

<210> SEQ ID NO 65
<211> LENGTH: 248
<212> TYPE: PRT
<213> ORGANISM: Humicola insolens

<400> SEQUENCE: 65

```
Met Leu Leu Asn Ser Val Ile Gly Ser Ala Val Leu Leu Ala Thr Gly
1               5                  10                  15

Ala Ala Ala His Gly Ala Val Thr Ser Tyr Val Ile Ala Gly Lys Asn
            20                  25                  30

Tyr Pro Gly Tyr Asn Gly Tyr Ala Pro Ser Thr Thr Pro Asn Thr Ile
        35                  40                  45

Gln Trp Gln Trp Ser Thr Tyr Asp Pro Ile Tyr Ser Ala Thr Asp Pro
    50                  55                  60

Lys Leu Arg Cys Asn Gly Gly Arg Ser Ala Thr Gln Ser Ala Pro Ala
65                  70                  75                  80

Ala Pro Gly Asp Asn Ile Thr Ala Ile Trp Gln Gln Trp Thr His Ser
                85                  90                  95

Gln Gly Pro Ile Leu Val Trp Met Tyr Lys Cys Pro Gly Ala Phe Ser
            100                 105                 110

Ser Cys Asp Gly Ser Gly Gln Gly Trp Phe Lys Ile Asp Glu Ala Gly
        115                 120                 125
```

```
Phe Asn Gly Asp Gly Lys Thr Val Phe Leu Asp Thr Glu Arg Pro Ser
    130                 135                 140

Gly Trp Glu Ile Ala Lys Leu Val Gly Gly Asn Lys Gly Trp Thr Ser
145                 150                 155                 160

Thr Ile Pro Lys Asn Leu Ala Pro Gly Asn Tyr Leu Val Arg His Glu
                165                 170                 175

Leu Ile Ala Leu His Gln Ala Asn Ala Pro Gln Trp Tyr Pro Glu Cys
                180                 185                 190

Ala Gln Val Val Ile Thr Gly Ser Gly Thr Lys Glu Pro Pro Ala Ser
                195                 200                 205

Tyr Lys Ala Ala Ile Pro Gly Tyr Cys Asn Gln Asn Asp Pro Asn Ile
210                 215                 220

Arg Val Pro Ile Asn Asp His Ser Ile Pro Gln Thr Tyr Lys Ile Pro
225                 230                 235                 240

Gly Pro Pro Val Trp Arg Gly Glu
                245

<210> SEQ ID NO 66
<211> LENGTH: 233
<212> TYPE: PRT
<213> ORGANISM: Humicola insolens

<400> SEQUENCE: 66

Met Lys Leu Thr Thr Ser Ile Ala Leu Leu Ala Ala Gly Ala Gln
1               5                   10                  15

Ala His Tyr Thr Phe Pro Arg Thr Lys Val Asp Gly Val Thr Ser Gly
                20                  25                  30

Glu Trp Glu Thr Ile Arg Ile Thr Glu Asn His Trp Ser His Gly Pro
            35                  40                  45

Val Thr Asp Val Thr Ser Gln Ala Met Thr Cys Tyr Glu Lys Thr Pro
        50                  55                  60

Gly Gln Gly Ala Pro Lys Thr Val Asn Val Lys Ala Gly Gly Thr Val
65                  70                  75                  80

Thr Phe Thr Val Asp Thr Asp Val Gly His Pro Gly Pro Leu His Phe
                85                  90                  95

Tyr Leu Ala Lys Val Pro Ala Gly Lys Thr Ala Ala Thr Phe Asp Gly
                100                 105                 110

Lys Gly Ala Val Trp Phe Lys Ile Tyr Gln Asp Gly Pro Gly Gly Leu
            115                 120                 125

Gly Thr Ser Ser Leu Thr Trp Pro Ser Phe Gly Lys Lys Glu Val Ser
130                 135                 140

Val Gln Ile Pro Pro Cys Val Gln Asp Gly Glu Tyr Leu Leu Arg Val
145                 150                 155                 160

Glu His Ile Ala Leu His Ser Ala Ala Ser Val Gly Gly Ala Gln Leu
                165                 170                 175

Tyr Ile Ser Cys Ala Gln Ile Asn Val Thr Gly Gly Thr Gly Thr Leu
                180                 185                 190

Asn Pro Gly Gln Leu Val Ser Phe Pro Gly Ala Tyr Lys Pro Thr Asp
            195                 200                 205

Pro Gly Ile Leu Phe Gln Leu Tyr Trp Pro Pro Thr Gln Tyr Ile
    210                 215                 220

Asn Pro Gly Pro Ala Pro Val Lys Cys
225                 230

<210> SEQ ID NO 67
```

```
<211> LENGTH: 243
<212> TYPE: PRT
<213> ORGANISM: Humicola insolens

<400> SEQUENCE: 67

Met Lys Thr Leu Ala Ser Ala Leu Ile Ala Ala Gly Leu Leu Ala Gln
1               5                   10                  15

Tyr Ala Ala His Ala Ile Phe Gln Phe Ala Ser Ser Gly Gly Thr
            20                  25                  30

Asp Phe Gly Thr Ser Cys Val Arg Met Pro Pro Asn Asn Ser Pro Val
        35                  40                  45

Thr Ser Val Thr Ser Ser Asp Met Ala Cys Asn Val Gly Gly Ser Arg
50                  55                  60

Gly Val Ser Gly Ile Cys Glu Val Asn Ala Gly Ser Asp Phe Thr Val
65                  70                  75                  80

Glu Met His Ala Gln Pro Asn Asp Arg Ser Cys Ala Ser Glu Ala Ile
                85                  90                  95

Gly Gly Asn His Phe Gly Pro Val Met Val Tyr Met Ala Lys Val Asp
            100                 105                 110

Asp Ala Thr Arg Ala Asp Gly Ala Ser Ala Ser Trp Phe Lys Val Asp
        115                 120                 125

Glu Phe Gly Tyr Asp Ala Gly Ser Lys Thr Trp Gly Thr Asp Met Leu
    130                 135                 140

Asn Lys Asn Cys Gly Lys Arg Thr Phe Arg Ile Pro Ser Lys Ile Pro
145                 150                 155                 160

Ser Gly Asp Tyr Leu Val Arg Ala Glu Ala Ile Ala Leu His Thr Ala
                165                 170                 175

Gly Gln Pro Ser Gly Ala Gln Phe Tyr Met Ser Cys Tyr Gln Val Arg
            180                 185                 190

Ile Lys Gly Ser Asn Asn Gly Gln Leu Pro Ala Gly Val Arg Ile Pro
        195                 200                 205

Gly Ala Tyr Ser Ala Thr Asp Pro Gly Ile Leu Val Asp Ile Trp Gly
    210                 215                 220

Asn Gly Phe Ser Gln Tyr Thr Ile Pro Gly Pro Arg Val Ile Asp Gly
225                 230                 235                 240

Ser Phe Phe

<210> SEQ ID NO 68
<211> LENGTH: 363
<212> TYPE: PRT
<213> ORGANISM: Humicola insolens

<400> SEQUENCE: 68

Met Pro Arg Phe Thr Lys Ser Ile Val Ser Ala Leu Ala Gly Ala Ser
1               5                   10                  15

Leu Val Ala Ala His Gly His Val Thr His Ile Val Ile Asn Gly Val
            20                  25                  30

Leu Tyr Pro Asn Phe Asp Pro Thr Ser His Pro Tyr Leu Gln Asn Pro
        35                  40                  45

Pro Thr Val Val Gly Trp Thr Ala Ala Asn Thr Asp Asn Gly Phe Val
    50                  55                  60

Ala Pro Asp Gln Phe Ala Ser Gly Asp Ile Ile Cys His Asn Gln Ala
65                  70                  75                  80

Thr Asn Ala Gly Gly His Ala Val Val Ala Ala Gly Asp Lys Ile Trp
                85                  90                  95
```

```
Ile Gln Trp Asp Gln Trp Pro Glu Ser His His Gly Pro Val Leu Asp
            100                 105                 110

Tyr Leu Ala Ser Cys Gly Ser Ser Gly Cys Glu Ser Val Asn Lys Leu
            115                 120                 125

Asp Leu Glu Phe Phe Lys Ile Gly Glu Lys Gly Leu Ile Asp Gly Ser
            130                 135                 140

Ser Ala Pro Gly Arg Trp Ala Ser Asp Glu Leu Ile Ala Asn Asn Ala
145                 150                 155                 160

Gly Trp Leu Val Gln Ile Pro Ala Asp Ile Ala Pro Gly His Tyr Val
                165                 170                 175

Leu Arg His Glu Ile Ile Ala Leu His Ala Ala Gly Gln Pro Asn Gly
            180                 185                 190

Ala Gln Asn Tyr Pro Gln Cys Phe Asn Leu Leu Val Thr Gly Ser Gly
            195                 200                 205

Thr Ala Arg Pro Gln Gly Val Lys Gly Thr Ala Leu Tyr Thr Pro Asn
            210                 215                 220

Asp Lys Gly Ile Leu Ala Gly Ile Tyr Asn Ala Pro Val Ser Tyr Glu
225                 230                 235                 240

Ile Pro Gly Pro Ala Leu Tyr Ser Gly Ala Ala Arg Asn Leu Gln Gln
                245                 250                 255

Ser Ser Ser Gln Ala Thr Ser Thr Ala Thr Leu Thr Gly Asp Ala
            260                 265                 270

Val Pro Val Pro Thr Gln Ala Pro Val Thr Thr Thr Ser Ser Ser Ser
                275                 280                 285

Ala Asp Ala Ala Thr Ala Thr Ser Thr Thr Val Gln Pro Pro Gln Gln
            290                 295                 300

Thr Thr Leu Thr Thr Ala Ile Ala Thr Ser Thr Ala Ala Ala Ala Pro
305                 310                 315                 320

Thr Thr Thr Ala Gly Ser Gly Asn Gly Gly Asn Arg Pro Phe Pro Thr
                325                 330                 335

Arg Cys Pro Gly Leu Ala Gly Leu Gly Phe Asp Lys Arg Arg Arg Gln
            340                 345                 350

Leu Arg Ala Glu Glu Gly Val Gln Val Val Ala
            355                 360

<210> SEQ ID NO 69
<211> LENGTH: 296
<212> TYPE: PRT
<213> ORGANISM: Humicola insolens

<400> SEQUENCE: 69

Met Lys Gly Leu Leu Ser Ile Ala Ala Leu Ser Leu Ala Val Gly Glu
1               5                   10                  15

Ala Ser Ala His Tyr Ile Phe Gln Gln Leu Ser Thr Gly Gly Thr Lys
            20                  25                  30

His Pro Met Trp Lys Tyr Ile Arg Gln His Thr Asn Tyr Asn Ser Pro
            35                  40                  45

Val Ile Asp Leu Asp Ser Asn Asp Leu Arg Cys Asn Val Gly Ala Arg
            50                  55                  60

Gly Ala Gly Thr Glu Thr Val Thr Val Ala Ala Gly Ser Ser Leu Thr
65                  70                  75                  80

Phe His Leu Asp Thr Pro Val Tyr His Gln Gly Pro Val Ser Val Tyr
                85                  90                  95

Met Ser Lys Ala Pro Gly Ser Val Ser Asp Tyr Asp Gly Ser Gly Gly
            100                 105                 110
```

```
Trp Phe Lys Ile Gln Asp Trp Gly Pro Thr Phe Thr Gly Ser Gly Ala
        115                 120                 125

Thr Trp Lys Leu Asp Asp Ser Tyr Thr Phe Asn Ile Pro Ser Cys Ile
130                 135                 140

Pro Asp Gly Glu Tyr Leu Val Arg Ile Gln Ser Leu Gly Ile His Asn
145                 150                 155                 160

Pro Trp Pro Ala Gly Ile Pro Gln Phe Tyr Ile Ser Cys Ala Gln Val
                165                 170                 175

Arg Val Thr Gly Gly Asn Ala Asn Pro Ser Pro Gln Val Ser Ile
        180                 185                 190

Pro Gly Ala Phe Lys Glu Thr Asp Pro Gly Tyr Thr Ala Asn Ile Tyr
        195                 200                 205

Asn Asn Phe Arg Ser Tyr Thr Val Pro Gly Pro Ser Val Phe Thr Cys
210                 215                 220

Ser Gly Asn Ser Gly Gly Ser Asn Pro Ser Asn Pro Asn Pro Pro
225                 230                 235                 240

Thr Pro Thr Thr Phe Thr Thr Gln Val Thr Thr Pro Thr Pro Ala Ser
                245                 250                 255

Pro Pro Ser Cys Thr Val Ala Lys Trp Gly Gln Cys Gly Gly Gln Gly
        260                 265                 270

Tyr Ser Gly Cys Thr Asn Cys Glu Ala Gly Ser Thr Cys Arg Gln Gln
        275                 280                 285

Asn Ala Tyr Tyr Ser Gln Cys Ile
        290                 295

<210> SEQ ID NO 70
<211> LENGTH: 318
<212> TYPE: PRT
<213> ORGANISM: Humicola insolens

<400> SEQUENCE: 70

Met Arg Pro Phe Ser Leu Val Ala Leu Ala Thr Ala Val Ser Gly His
1               5                   10                  15

Ala Ile Phe Gln Arg Val Ser Val Asn Gly Val Asp Gln Gly Gln Leu
            20                  25                  30

Lys Gly Val Arg Ala Pro Ser Ser Asn Tyr Pro Ile Glu Asn Val Asn
        35                  40                  45

His Pro Asp Phe Ala Cys Asn Thr Asn Ile Gln His Arg Asp Gly Thr
    50                  55                  60

Val Ile Lys Ile Pro Ala Gly Ala Thr Val Gly Ala Trp Trp Gln His
65                  70                  75                  80

Glu Ile Gly Gly Pro Ser Phe Pro Gly Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Asn Gly Leu Arg Trp Phe Lys Ile Ala Glu
        115                 120                 125

Lys Gly Leu Ser Gly Gly Val Trp Ala Val Asp Glu Met Ile Arg Asn
130                 135                 140

Asn Gly Trp His Tyr Phe Thr Met Pro Gln Cys Ile Ala Pro Gly His
145                 150                 155                 160

Tyr Leu Met Arg Val Glu Leu Leu Ala Leu His Ser Ala Ser Phe Pro
                165                 170                 175

Gly Gly Ala Gln Phe Tyr Met Glu Cys Ala Gln Ile Glu Val Thr Gly
```

```
            180                 185                 190
Ser Gly Asn Phe Ser Pro Ser Glu Thr Val Ser Phe Pro Gly Ala Tyr
            195                 200                 205

Pro Ala Asn His Pro Gly Ile Val Val Ser Ile Tyr Asp Ala Gln Gly
            210                 215                 220

Asn Ala Asn Asn Gly Gly Arg Glu Tyr Gln Ile Pro Gly Pro Arg Pro
225                 230                 235                 240

Ile Thr Cys Ser Gly Gly Ser Asn Gly Gly Gly Asn Asn
            245                 250                 255

Gly Gly Gly Asn Asn Asn Gly Gly Asn Asn Gly Gly Gly Asn
                260                 265                 270

Asn Asn Gly Gly Gly Asn Thr Gly Gly Ser Ala Pro Leu Trp Gly
            275                 280                 285

Gln Cys Gly Gly Asn Gly Tyr Thr Gly Pro Thr Thr Cys Ala Glu Gly
            290                 295                 300

Thr Cys Lys Lys Gln Asn Asp Trp Tyr Ser Gln Cys Thr Pro
305                 310                 315

<210> SEQ ID NO 71
<211> LENGTH: 259
<212> TYPE: PRT
<213> ORGANISM: Humicola insolens

<400> SEQUENCE: 71

Met Val Leu Arg Ser Leu Ser Ile Leu Ala Phe Val Ala Arg Gly Val
1               5                   10                  15

Phe Ala His Gly Gly Leu Ser Asn Tyr Thr Val Gly Asp Thr Trp Tyr
                20                  25                  30

Ser Gly Tyr Asp Pro Phe Thr Pro Ala Ala Gln Leu Ser Gln Pro
            35                  40                  45

Trp Leu Ile Gln Arg Gln Trp Thr Ser Ile Asp Pro Leu Phe Ser Pro
50                  55                  60

Thr Ser Pro Tyr Leu Ala Cys Asn Phe Pro Gly Thr Ala Pro Pro Ser
65                  70                  75                  80

Tyr Ile Pro Leu Arg Ala Gly Asp Ile Leu Thr Ala Val Tyr Trp Phe
                85                  90                  95

Trp Leu His Pro Val Gly Pro Met Ser Val Trp Leu Ala Arg Cys Ala
                100                 105                 110

Gly Asp Cys Arg Asp Glu Asp Val Thr Arg Ala Arg Trp Phe Lys Ile
            115                 120                 125

Trp His Ala Gly Phe Leu Glu Gly Pro Asn Leu Glu Leu Gly Met Trp
130                 135                 140

Tyr Gln Lys Lys Phe Gln Arg Trp Asp Gly Pro Ala Leu Trp Arg
145                 150                 155                 160

Val Arg Ile Pro Arg Gly Leu Lys Lys Gly Leu Tyr Met Val Arg His
                165                 170                 175

Glu Ile Leu Ser Ile His Val Gly Gly Arg Pro Gln Phe Tyr Pro Glu
                180                 185                 190

Cys Ala His Leu Asn Val Thr Glu Gly Gly Glu Val Val Pro Gly
            195                 200                 205

Glu Trp Thr Arg Arg Phe Pro Gly Ala Tyr Asp Asp Asp Lys Ser
            210                 215                 220

Val Phe Ile Asp Ile Tyr Arg Pro Glu His Glu Asn Arg Thr Asp Tyr
225                 230                 235                 240
```

```
Glu Ile Pro Gly Gly Pro Ile Trp Glu Ser Leu Gly Glu Met Glu Leu
                245                 250                 255

Trp Pro Glu

<210> SEQ ID NO 72
<211> LENGTH: 325
<212> TYPE: PRT
<213> ORGANISM: Humicola insolens

<400> SEQUENCE: 72

Met Arg Thr Val Phe Ala Ala Leu Ala Ala Leu Ala Ala Arg Glu
1               5                   10                  15

Val Ala Gly His Ala Thr Phe Gln Gln Leu Trp Val Asp Gly Thr Asp
                20                  25                  30

Tyr Gly Ser Thr Cys Val Arg Leu Pro Ala Ser Asn Ser Pro Leu Thr
            35                  40                  45

Asp Val Thr Ser Ser Asp Phe Ala Cys Asn Ile Gly Gly Arg Arg Gly
        50                  55                  60

Val Gly Gly Lys Cys Pro Val Lys Ala Gly Gly Val Val Thr Ile Glu
65                  70                  75                  80

Met His Gln Gln Pro Asn Asp Arg Asn Cys Arg Ser Glu Ala Ile Gly
                85                  90                  95

Gly Met His Trp Gly Pro Val Gln Val Tyr Leu Ser Lys Val Pro Asp
            100                 105                 110

Ala Ser Thr Ala Glu Pro Thr Gln Val Gly Trp Phe Lys Ile Phe Ser
        115                 120                 125

Asn Ala Trp Ala Lys Lys Pro Gly Gly Asn Ser Gly Asp Asp Asp Tyr
130                 135                 140

Trp Gly Thr Arg Glu Leu Asn Gly Cys Cys Gly Arg Met Asp Val Pro
145                 150                 155                 160

Ile Pro Thr Asp Leu Glu Asp Gly Asp Tyr Leu Leu Arg Ala Glu Ala
                165                 170                 175

Leu Ala Leu His Ala Met Pro Gly Gln Phe Tyr Met Ser Cys Tyr Gln
            180                 185                 190

Ile Thr Ile Thr Gly Gly Thr Gly Thr Ala Lys Pro Ala Thr Val Arg
        195                 200                 205

Phe Pro Gly Ala Tyr Thr Asn Asn Asp Ala Gly Ile Arg Ala Asn Ile
210                 215                 220

His Ala Pro Leu Ser Thr Tyr Ile Ala Pro Gly Pro Glu Val Tyr Ser
225                 230                 235                 240

Gly Gly Thr Thr Arg Ala Pro Gly Glu Gly Cys Pro Gly Cys Ala Thr
                245                 250                 255

Thr Cys Gln Val Gly Ser Ser Pro Ser Ala Gln Ala Pro Gly His Gly
            260                 265                 270

Thr Ala Val Gly Gly Gly Ala Gly Gly Pro Ser Ala Cys Thr Val Gln
        275                 280                 285

Ala Tyr Gly Gln Cys Gly Gly Gln Gly Tyr Thr Gly Cys Thr Glu Cys
        290                 295                 300

Ala Asp Gly Phe Val Cys Arg Asp Val Ser Ala Pro Trp Tyr Ser Gln
305                 310                 315                 320

Cys Gln Pro Ala Phe
                325

<210> SEQ ID NO 73
<211> LENGTH: 298
```

```
<212> TYPE: PRT
<213> ORGANISM: Humicola insolens

<400> SEQUENCE: 73
```

| | | | | | | | | | | | | | | | |
|---|---|---|---|---|---|---|---|---|---|---|---|---|---|---|---|
|Met|Arg|Leu|Pro|Gln|Val|Ala|Ser|Val|Leu|Ala|Leu|Ala|Ala|Gln|Val|
|1| | | |5| | | | |10| | | | |15| |
|His|Gly|His|Gly|Tyr|Ile|Tyr|Arg|Val|Thr|Ala|Asp|Asn|Ile|Val|Tyr|
| | | |20| | | | |25| | | | |30| | |
|Pro|Gly|Tyr|Asp|Ile|Tyr|Val|Asp|Pro|Leu|Leu|Gln|Pro|Pro|Pro|Tyr|
| | | | |35| | | | |40| | | | |45| |
|Arg|Ile|Ala|Tyr|Gly|Gly|Gln|Thr|Gly|Pro|Val|Tyr|Asp|Ile|Asn| |
| | |50| | | | |55| | | | |60| | | |
|Ser|Lys|Asp|Ile|Ala|Cys|Gln|Arg|Val|His|Ser|Pro|Ala|Pro|Gly|Leu|
|65| | | | |70| | | | |75| | | | |80|
|Ile|Ala|Gln|Ala|Arg|Ala|Gly|Ser|Asn|Ile|Thr|Phe|Trp|Trp|Ser|Arg|
| | | | |85| | | | |90| | | | |95| |
|Trp|Leu|Tyr|Ser|His|Lys|Gly|Pro|Ile|Ser|Ala|Trp|Met|Ala|Pro|Tyr|
| | | |100| | | | |105| | | | |110| | |
|Glu|Gly|Asp|Ile|Ala|Asn|Val|Asp|Val|Asn|Gln|Leu|Glu|Phe|Phe|Lys|
| | | | |115| | | | |120| | | | |125| |
|Ile|Gly|Glu|Glu|Phe|His|Asp|Glu|Thr|Gly|Lys|Trp|Ala|Thr|Glu|Lys|
| | |130| | | | |135| | | | |140| | | |
|Leu|Val|Asp|Asp|Pro|Glu|Gly|Lys|Trp|Thr|Val|Lys|Ile|Pro|Ala|Asp|
|145| | | | |150| | | | |155| | | | |160|
|Ile|Lys|Pro|Gly|Leu|Tyr|Val|Val|Arg|Asn|Glu|Ile|Ile|Ala|Leu|His|
| | | | |165| | | | |170| | | | |175| |
|Phe|Ala|Val|Arg|Met|Pro|Pro|Phe|Ala|Ala|Phe|Thr|Pro|Leu|Gly| |
| | | |180| | | | |185| | | | |190| | |
|Pro|Gln|Phe|Tyr|Met|Thr|Cys|Phe|Ala|Phe|Asn|Ile|Thr|Gly|Asp|Gly|
| | | |195| | | | |200| | | | |205| | |
|Thr|Ala|Thr|Pro|Gln|Gly|Tyr|Lys|Phe|Pro|Gly|Ala|Tyr|Ser|Lys|Asp|
| | |210| | | | |215| | | | |220| | | |
|Asp|Pro|Ala|Leu|Trp|Trp|Asp|Leu|Glu|Glu|Asn|Lys|Asn|Pro|Tyr|Pro|
|225| | | | |230| | | | |235| | | | |240|
|Gly|Ala|Gly|Pro|Lys|Pro|His|Val|Ser|Ala|Tyr|Asp|Val|Asp|Leu|Val|
| | | | |245| | | | |250| | | | |255| |
|Pro|Asn|Glu|Leu|Tyr|Ile|Val|Ser|Pro|Thr|Asn|Asn|Ala|Thr|Ala|Asp|
| | | |260| | | | |265| | | | |270| | |
|Glu|Leu|Tyr|Trp|Glu|Ala|Gln|Arg|Gln|Ala|Leu|Ala|Ala|Gln|Ala|Ala|
| | |275| | | | |280| | | | |285| | | |
|Thr|Thr|Glu|Tyr|Phe|Asp|Ser|Ile|Gly|Gly| | | | | | |
| | |290| | | | |295| | | | | | | | |

```
<210> SEQ ID NO 74
<211> LENGTH: 298
<212> TYPE: PRT
<213> ORGANISM: Humicola insolens

<400> SEQUENCE: 74
```

| | | | | | | | | | | | | | | | |
|---|---|---|---|---|---|---|---|---|---|---|---|---|---|---|---|
|Met|His|Val|Gln|Ser|Leu|Leu|Ala|Gly|Ala|Leu|Ala|Leu|Ala|Pro|Ser|
|1| | | |5| | | | |10| | | | |15| |
|Ala|Ser|Ala|His|Phe|Leu|Phe|Pro|His|Leu|Met|Leu|Asn|Gly|Val|Arg|
| | | |20| | | | |25| | | | |30| | |
|Thr|Gly|Ala|Tyr|Glu|Tyr|Val|Arg|Glu|His|Asp|Phe|Gly|Phe|Met|Pro|
| | | | |35| | | | |40| | | | |45| |

His Asn Asn Asp Trp Ile Asn Ser Pro Asp Phe Arg Cys Asn Glu Gly
 50                  55                  60

Ser Trp Arg His Arg Arg Glu Pro Lys Thr Ala Val Thr Ala Gly
65                  70                  75                  80

Val Asp Val Val Gly Phe Asn Leu His Leu Asp Phe Asp Leu Tyr His
                85                  90                  95

Pro Gly Pro Val Thr Ile Tyr Leu Ser Arg Ala Pro Gly Asp Val Arg
            100                 105                 110

Asp Tyr Asp Gly Ser Gly Asp Trp Phe Lys Val Tyr Gln Leu Gly Thr
            115                 120                 125

Arg Gln Pro Phe Asn Gly Thr Asp Glu Gly Trp Ala Thr Trp Lys Met
130                 135                 140

Lys Asn Trp Gln Phe Arg Leu Pro Ala Glu Ile Pro Ala Gly Glu Tyr
145                 150                 155                 160

Leu Met Arg Ile Glu Gln Met Ser Val His Pro Pro Tyr Arg Gln Lys
                165                 170                 175

Glu Trp Tyr Val Gln Cys Ala His Leu Lys Ile Asn Ser Asn Tyr Asn
            180                 185                 190

Gly Pro Ala Pro Gly Pro Thr Ile Lys Ile Pro Gly Gly Tyr Lys Ile
            195                 200                 205

Ser Asp Pro Ala Ile Gln Tyr Asp Gln Trp Ala Gln Pro Pro Thr
210                 215                 220

Tyr Ala Pro Met Pro Gly Pro Leu Trp Pro Asn Asn Asn Pro Gln
225                 230                 235                 240

Gln Gly Asn Pro Asn Gln Gly Gly Asn Gly Gly Gly Asn Gln Gly
                245                 250                 255

Gly Gly Asn Gly Gly Cys Thr Val Pro Lys Trp Gly Gln Cys Gly Gly
            260                 265                 270

Gln Gly Tyr Ser Gly Cys Arg Asn Cys Glu Ser Gly Ser Thr Cys Arg
            275                 280                 285

Ala Gln Asn Asp Trp Tyr Ser Gln Cys Leu
            290                 295

<210> SEQ ID NO 75
<211> LENGTH: 344
<212> TYPE: PRT
<213> ORGANISM: Humicola insolens

<400> SEQUENCE: 75

Met Pro Pro Pro Leu Leu Ala Thr Val Leu Ser Leu Leu Ala Leu Thr
1               5                   10                  15

Arg Gly Ala Leu Ser His Ser His Leu Ala His Val Ile Ile Asn Gly
                20                  25                  30

Gln Leu Tyr His Gly Phe Asp Pro Arg Pro Asn Gln Asn Asn His Pro
            35                  40                  45

Ala Arg Val Gly Trp Ser Thr Thr Ala Thr Asp Asp Gly Phe Val Thr
        50                  55                  60

Pro Gly Asn Tyr Ser His Pro Asp Ile Ile Cys His Arg Gly Gly Val
65                  70                  75                  80

Ser Pro Arg Ala His Ala Pro Val Thr Ala Gly Gly Lys Val Gln Val
                85                  90                  95

Gln Trp Asn Gly Trp Pro Ile Gly His Val Gly Pro Ile Leu Thr Tyr
            100                 105                 110

Ile Ala Pro Cys Gly Gly Leu Pro Gly Ala Glu Glu Gly Cys Thr Gly
        115                 120                 125

Val Asp Lys Thr Asp Leu Arg Trp Thr Lys Ile Asp Ser Met Pro
                130                 135                 140

Pro Phe Arg Phe Thr Asp Ala Thr Lys Pro Val Ser Gly Arg Ala Gln
145                 150                 155                 160

Phe Pro Ile Gly Gln Val Trp Ala Thr Asp Ala Leu Val Glu Ala Asn
                165                 170                 175

Asn Ser Trp Ser Val Val Ile Pro Arg Asn Ile Pro Pro Gly Pro Tyr
                180                 185                 190

Val Leu Arg Gln Glu Ile Val Ala Leu His Tyr Ala Ala Lys Leu Asn
                195                 200                 205

Gly Ala Gln Asn Tyr Pro Leu Cys Leu Asn Leu Trp Val Glu Lys Gly
                210                 215                 220

Gln Gln Asp Gln Gly Glu Pro Phe Lys Phe Asp Ala Tyr Asp Ala Arg
225                 230                 235                 240

Glu Phe Tyr Ser Glu Asp His Pro Gly Val Leu Ile Asp Val Met Thr
                245                 250                 255

Met Val Gly Pro Arg Ala Val Tyr Arg Ile Pro Gly Pro Thr Val Ala
                260                 265                 270

Ser Gly Ala Thr Arg Ile Pro His Ser Leu Gln Thr Ser Ala Glu Thr
                275                 280                 285

Trp Val Glu Gly Thr Pro Val Ala Val Thr Arg Ala Thr Glu Thr Val
                290                 295                 300

Gln Met Glu Ile Thr Thr Thr Pro Ala Gly Gln Gly Ala Gly Val Arg
305                 310                 315                 320

Thr Ala Thr Pro Ala Met Pro Thr Pro Thr Val Thr Lys Arg Trp Lys
                325                 330                 335

Gly Arg Phe Glu Met Gly Arg Pro
                340

<210> SEQ ID NO 76
<211> LENGTH: 330
<212> TYPE: PRT
<213> ORGANISM: Humicola insolens

<400> SEQUENCE: 76

Met Lys Ser Leu Thr Tyr Ala Ala Leu Ala Ala Leu Trp Ala Gln Gln
1               5                   10                  15

Thr Ala Ala His Ala Thr Phe Gln Gln Leu Trp Val Asp Gly Val Asp
                20                  25                  30

Tyr Gly Ser Gln Cys Ala Arg Leu Pro Pro Ser Asn Ser Pro Ile Ala
                35                  40                  45

Ser Val Thr Ser Thr Ala Met Arg Cys Asn Asn Gly Pro Arg Ala Ala
                50                  55                  60

Ala Lys Cys Pro Val Lys Ala Gly Gly Thr Val Thr Ile Glu Met His
65                  70                  75                  80

Gln Gln Pro Gly Asp Arg Ser Cys Asn Gln Asp Ala Ile Gly Gly Ala
                85                  90                  95

His His Gly Pro Val Met Val Tyr Met Ser Lys Val Ser Asp Ala Phe
                100                 105                 110

Thr Ala Asp Gly Ser Ser Gly Trp Phe Lys Ile Phe Gln Asp Gly Trp
                115                 120                 125

Ala Lys Asn Pro Asn Gly Arg Val Gly Asp Asp Phe Trp Gly Thr
                130                 135                 140

Lys Asp Leu Asn Thr Cys Cys Gly Lys Met Asn Val Lys Ile Pro Ala

-continued

```
            145                 150                 155                 160
        Asp Ile Ala Pro Gly Asp Tyr Leu Leu Arg Ala Glu Ala Ile Ala Leu
                        165                 170                 175

His Ala Ala Gly Pro Ser Gly Gly Ala Gln Pro Tyr Val Thr Cys Tyr
                        180                 185                 190

Gln Leu Thr Val Thr Gly Gly Asn Ala Asn Pro Thr Val Asn
                        195                 200                 205

Phe Pro Gly Ala Tyr Ser Glu Arg Asp Pro Gly Ile Ala Val Ser Ile
                        210                 215                 220

His Gly Ala Leu Ser Asn Tyr Val Val Pro Gly Pro Val Tyr Ser
        225                 230                 235                 240

Gly Gly Ser Glu Lys Arg Ala Gly Ser Pro Cys Glu Gly Cys Glu Ala
                        245                 250                 255

Thr Cys Lys Val Gly Ser Ser Pro Ser Gln Thr Leu Ala Pro Ser Asn
                        260                 265                 270

Pro Ala Pro Thr Ser Pro Ala Asn Gly Gly Gly Asn Asn Gly Gly Gly
                        275                 280                 285

Asn Thr Gly Gly Gly Cys Thr Val Pro Lys Trp Gln Gln Cys Gly Gly
                        290                 295                 300

Gln Gly Tyr Ser Gly Cys Thr Val Cys Glu Ser Gly Ser Thr Cys Arg
        305                 310                 315                 320

Ala Gln Asn Gln Trp Tyr Ser Gln Cys Val
                        325                 330

<210> SEQ ID NO 77
<211> LENGTH: 216
<212> TYPE: PRT
<213> ORGANISM: Humicola insolens

<400> SEQUENCE: 77

Met Lys Leu Leu Leu Pro Ala Leu Leu Ala Leu Ala Ala Glu Ser Val
        1               5                   10                  15

Ser Ala His Tyr Ile Phe Gln Gln Leu Thr Val Ala Gly Thr Lys Tyr
                        20                  25                  30

Pro Val Trp Lys Tyr Ile Arg Arg Asn Ser Asn Pro Ala Trp Leu Gln
                        35                  40                  45

Asn Gly Pro Val Thr Asp Leu Ala Ser Thr Asp Leu Arg Cys Asn Val
                        50                  55                  60

Gly Gly Gln Val Ser Asn Gly Thr Glu Thr Leu Thr Val Arg Ala Gly
        65                  70                  75                  80

Asp Gln Phe Thr Phe His Leu Asp Thr Ala Val Tyr His Gln Gly Pro
                        85                  90                  95

Thr Ser Leu Tyr Met Ser Arg Ala Pro Gly Lys Val Glu Asp Tyr Asp
                        100                 105                 110

Gly Ser Gly Pro Trp Phe Lys Ile Tyr Asp Trp Gly Pro Thr Gly Asn
                        115                 120                 125

Asn Trp Val Met Arg Asp Ser Tyr Thr Tyr Asn Ile Pro Arg Cys Ile
                        130                 135                 140

Pro Asp Gly Glu Tyr Leu Leu Arg Ile Gln Gln Leu Gly Leu His Asn
        145                 150                 155                 160

Pro Gly Ala Ala Pro Gln Phe Tyr Ile Ser Cys Ala Gln Ile Lys Val
                        165                 170                 175

Thr Gly Gly Gly Thr Thr Asn Pro Thr Pro Thr Ala Leu Ile Pro Gly
                        180                 185                 190
```

```
Ala Phe Arg Ala Thr Asp Pro Gly Tyr Thr Val Asn Val Ser Gln Thr
            195                 200                 205

Leu Ser Asn Ser Ile Ser Thr Ser
    210                 215

<210> SEQ ID NO 78
<211> LENGTH: 490
<212> TYPE: PRT
<213> ORGANISM: Humicola insolens

<400> SEQUENCE: 78

Met Arg Ser Val Ser Leu Leu Ala Ala Phe Ala Pro Leu Ala Thr
1               5                   10                  15

Ala His Thr Val Phe Thr Ala Leu Phe Ile Asn Asn Val His Gln Gly
                20                  25                  30

Asp Gly Thr Cys Val Arg Met Ala Lys Gln Gly Asn Leu Ala Thr His
            35                  40                  45

Pro Val Ser Leu Asn Ser Asn Glu Met Ala Cys Gly Arg Asp Gly Gln
    50                  55                  60

Gln Pro Val Ala Phe Thr Cys Pro Ala Pro Ala Gly Ala Lys Leu Thr
65                  70                  75                  80

Leu Leu Phe Arg Met Trp Ala Asp Gly Ser Gln Pro Gly Ser Ile Asp
                85                  90                  95

Lys Ser His Val Gly Pro Met Ser Ile Tyr Leu Lys Lys Val Ser Asp
                100                 105                 110

Met Asn Thr Asp Ser Ala Ala Gly Pro Gly Trp Phe Lys Ile Trp Ser
            115                 120                 125

Glu Gly Tyr Asp Ala Ala Thr Lys Lys Trp Ala Thr Glu Lys Leu Ile
    130                 135                 140

Ala Asn Asn Gly Leu Leu Ser Val Asn Leu Pro Pro Gly Leu Pro Ala
145                 150                 155                 160

Gly Tyr Tyr Leu Ala Arg His Glu Ile Val Thr Leu Gln Asn Val Thr
                165                 170                 175

Asn Asn Lys Ala Asp Pro Gln Phe Tyr Val Gly Cys Ala Gln Leu Phe
            180                 185                 190

Val Gln Gly Leu Gly Thr Ala Ala Ser Val Pro Ala Asp Lys Thr Val
    195                 200                 205

Ser Ile Pro Gly His Leu Asn Pro Asn Asp Pro Ala Leu Val Phe Asn
210                 215                 220

Pro Tyr Thr Gln Asn Ala Ala Thr Tyr Pro Ser Phe Gly Pro Pro Leu
225                 230                 235                 240

Phe Phe Pro Asn Ala Ala Ser Ala Gly Ser Asn Lys Ala Gln Ser Thr
                245                 250                 255

Leu Lys Gln Thr Ser Gly Val Ile Pro Ser Asp Cys Leu Ile Lys Asn
            260                 265                 270

Ala Asn Trp Cys Gly Arg Glu Val Pro Asp Tyr Thr Asn Glu Ala Gly
    275                 280                 285

Cys Trp Thr Ala Ala Gly Asn Cys Trp Glu Gln Ala Asp Gln Cys Tyr
290                 295                 300

Lys Thr Ala Pro Pro Ser Gly His Lys Gly Cys Lys Thr Trp Glu Glu
305                 310                 315                 320

Gln Lys Cys Asn Val Ile Gln Asn Ser Cys Glu Ala Lys Arg Phe Ser
                325                 330                 335

Gly Pro Pro Asn Arg Gly Val Lys Phe Ala Asp Met Asp Val Asn Gln
            340                 345                 350
```

```
Leu Val Pro Gly Ala Ile Pro Glu Ala Val Asn Ala Gly Gln Asn Gly
            355                 360                 365

Glu Ala Val Val Val Asp Gly Thr Thr Ser Ser Ala Asp Glu Lys Ala
    370                 375                 380

Ser Val Asp Leu Thr Thr Ser Ser Leu Pro Thr Pro Thr Pro Ala Ala
385                 390                 395                 400

Glu Glu Asn Gly Lys Glu Asp Glu Arg Leu Ala Leu Asp Pro Thr Leu
                405                 410                 415

Thr Glu Asp Glu Ser Phe Phe Ser Val Glu Pro Thr Ser Glu Pro Thr
            420                 425                 430

Gly Val Gln Val Glu Val Pro Leu Thr Thr Val Val Leu Leu Pro Thr
            435                 440                 445

Leu Thr Ser Ser Leu Asn Pro Leu Pro Thr Pro Thr Ser Ile Ser Gln
    450                 455                 460

Pro Ala His Pro Gly Arg Pro Cys Thr Gly Arg Arg Arg Pro Arg
465                 470                 475                 480

Pro Gly Phe Pro Lys His Pro Arg Asp Phe
                485                 490

<210> SEQ ID NO 79
<211> LENGTH: 306
<212> TYPE: PRT
<213> ORGANISM: Humicola insolens

<400> SEQUENCE: 79

Met Phe Phe Arg Asn Ala Ala Thr Leu Ala Leu Ala Tyr Ala Thr Thr
1               5                   10                  15

Gly Val Ser Ala His Ala Leu Met Tyr Gly Val Trp Val Asn Gly Val
                20                  25                  30

Asp Gln Gly Asp Gly Arg Asn Val Tyr Ile Arg Thr Pro Pro Asn Asn
            35                  40                  45

Ser Pro Val Lys Asp Leu Ala Ser Pro Asp Ile Val Cys Asn Val Asn
    50                  55                  60

Gly Gly Arg Ala Val Pro Asp Phe Val Gln Ala Ser Ala Gly Asp Thr
65                  70                  75                  80

Leu Thr Phe Glu Trp Leu His Asn Thr Arg Gly Asp Asp Ile Ile Asp
                85                  90                  95

Arg Ser His Leu Gly Pro Ile Ile Thr Tyr Ile Ala Pro Phe Thr Thr
                100                 105                 110

Gly Asn Pro Thr Gly Pro Val Trp Thr Lys Ile Ala Glu Gln Gly Phe
            115                 120                 125

Asn Pro Ser Thr Arg Arg Trp Ala Val Asp Asp Leu Ile Asp Asn Gly
    130                 135                 140

Gly Lys Thr Asp Phe Val Leu Pro Ala Ser Leu Ala Pro Gly Arg Tyr
145                 150                 155                 160

Ile Ile Arg Gln Glu Ile Ile Ala His His Glu Ser Glu Thr Thr Phe
                165                 170                 175

Glu Ser Asn Pro Ala Arg Gly Ala Gln Phe Tyr Pro Ser Cys Val Gln
            180                 185                 190

Ile Gln Val Ser Ser Gly Ser Gly Thr Ala Val Pro Asp Gln Asn Phe
    195                 200                 205

Asp Phe Asn Thr Gly Tyr Thr Tyr Ala Asp Pro Gly Ile His Phe Asn
    210                 215                 220

Ile Tyr Thr Ser Phe Asn Ser Tyr Ser Ile Pro Gly Pro Glu Val Trp
```

```
            225                 230                 235                 240
Thr Gly Ala Ser Thr Gly Gly Asn Gly Asn Gly Asn Gly
                245                 250                 255

Asn Ala Thr Pro Thr Gln Pro Thr Pro Thr Pro Thr Val Thr Pro Thr
                260                 265                 270

Pro Ile Glu Thr Ala Gln Pro Val Thr Thr Thr Thr Ser Thr Arg
                275                 280                 285

Pro Phe Pro Thr Arg Cys Pro Gly Arg Arg Leu Lys Arg Glu Glu Pro
                290                 295                 300

Lys Ala
305

<210> SEQ ID NO 80
<211> LENGTH: 339
<212> TYPE: PRT
<213> ORGANISM: Humicola insolens

<400> SEQUENCE: 80

Met Ala His Pro Trp Ala Arg Cys Val Tyr Thr Ala Ile Trp Leu Ala
1               5                   10                  15

Ala Ser Ala Ser Gly His Ser Arg Val Trp Ser Val Ser Val Asn Gly
                20                  25                  30

Arg Tyr Gln Gly Pro Gly Val Asp Asp Tyr Leu Arg Ala Pro Pro Ser
            35                  40                  45

Asp Ser Pro Val Val Asp Leu Asp Ser Pro Thr Leu Asn Cys Asn Val
        50                  55                  60

Asn Gly Asn Lys Pro Val Pro Gly Phe Val Glu Val Ser Ala Gly Asp
65                  70                  75                  80

Ser Leu Glu Trp Lys Trp Tyr Tyr Ile Asn Pro Tyr Asn Pro Ser Asp
                85                  90                  95

Met Ile Ile Ala Ala Glu His Arg Gly Pro Ile Ile Thr Tyr Ile Thr
            100                 105                 110

Asn Tyr Thr Asp Gly Gln Pro Gln Gly Ala Val Trp Thr Lys Ile Asp
        115                 120                 125

His Glu Gly Tyr Asp Pro Val Thr Asp Arg Phe Ala Val Asp Asn Leu
        130                 135                 140

Ile Ala Asn Arg Gly Trp Lys Ala Ile Lys Leu Pro Met Leu Ala Asp
145                 150                 155                 160

Gly Lys Tyr Ile Leu Arg Gln Glu Ile Ile Ala Leu His Ser Ala His
                165                 170                 175

Asn Gln Gly Gly Ala Gln Leu Tyr Pro Asn Cys Ile Gln Ile Lys Val
            180                 185                 190

Val Gly Gly Lys Gly Ser Ala Val Pro Asn Gln Asn Phe Asp Leu Asn
        195                 200                 205

Lys Gly Tyr Thr Ser Asp His Pro Gly Leu Arg Phe Asn Leu Trp Gln
    210                 215                 220

Pro Phe Asn Asn Tyr Thr Ile Pro Gly Pro Glu Val Trp Lys Gly Val
225                 230                 235                 240

Val Val Ala Ser Asn Gly Thr Thr Asn Ser Thr Thr Asn Leu Thr Asn
                245                 250                 255

Asn Thr Gly Thr Gly Phe Ala Asn Ser Thr Met Ala Thr Gly Glu Thr
            260                 265                 270

Arg Thr Glu Arg Ser Phe Met Thr Leu Thr Ala Ser His Ser Asp Thr
        275                 280                 285
```

```
Gly Val Pro Ala Lys Ser His Thr Val Ala Val Ser Trp Thr Thr Ser
    290                 295                 300

Ala Ala Val Val Gly Ser Pro Ile Ser Val Thr Thr Thr Phe Ser Ser
305                 310                 315                 320

Phe Thr Thr Thr Pro Val Pro Thr Asn Ser Thr Gly Ala Tyr Leu Tyr
                325                 330                 335

Arg Tyr Lys

<210> SEQ ID NO 81
<211> LENGTH: 334
<212> TYPE: PRT
<213> ORGANISM: Malbranchea cinnamomea

<400> SEQUENCE: 81

Met Ser Pro Ser Phe Lys Ser Thr Ala Ile Leu Gly Ala Val Ala Leu
1               5                   10                  15

Ala Ala Arg Val Arg Ala His Gly Tyr Val Ser Gly Ile Val Val Asp
                20                  25                  30

Gly Ala Tyr His Gly Gly Tyr Ile Val Asp Lys Tyr Pro Tyr Met Pro
            35                  40                  45

Asn Pro Pro Asp Val Val Gly Trp Ser Thr Thr Ala Thr Asp Leu Gly
50                  55                  60

Phe Val Ala Pro Asp Ala Phe Gly Asp Pro Asp Ile Ile Cys His Arg
65                  70                  75                  80

Asp Gly Ala Pro Gly Ala Ile His Ala Lys Val Asn Ala Gly Ala Thr
                85                  90                  95

Ile Glu Leu Gln Trp Asn Thr Trp Pro Glu Ser His His Gly Pro Val
            100                 105                 110

Ile Asp Tyr Leu Ala Asn Cys Asn Gly Asp Cys Ser Ser Val Asp Lys
        115                 120                 125

Thr Ser Leu Lys Phe Phe Lys Ile Ser Glu Ala Gly Leu Asn Asp Gly
130                 135                 140

Ser Asn Ala Pro Gly Gln Trp Ala Ser Asp Asp Leu Ile Ala Asn Asn
145                 150                 155                 160

Asn Ser Trp Thr Val Thr Ile Pro Lys Ser Ile Ala Pro Gly Asn Tyr
                165                 170                 175

Val Leu Arg His Glu Ile Ile Ala Leu His Ser Ala Gly Asn Gln Asn
            180                 185                 190

Gly Ala Gln Asn Tyr Pro Gln Cys Phe Asn Leu Glu Ile Thr Ser Asn
        195                 200                 205

Gly Ser Asp Asn Pro Glu Gly Val Leu Gly Thr Glu Leu Tyr Lys Ala
210                 215                 220

Asp Asp Pro Gly Ile Leu Phe Asn Ile Tyr Gln Pro Met Asp Ser Tyr
225                 230                 235                 240

Pro Ile Pro Gly Pro Ala Leu Tyr Thr Gly Gly Ser Ser Pro Ser Pro
                245                 250                 255

Asn Pro Pro Thr Ser Thr Gln Ser Pro Val Pro Gln Pro Thr Gln Ser
            260                 265                 270

Pro Pro Ser Gly Ser Asn Pro Gly Asn Gly Asn Gly Asp Asp Asp Asn
        275                 280                 285

Asp Asn Gly Asn Glu Thr Pro Ser Pro Ser Leu Pro Val Glu Ile Pro
            290                 295                 300

Asp Asp Leu Thr Ser Arg Glu Leu Leu Leu Val Ala Gln Glu Ile Ile
305                 310                 315                 320
```

Ala Arg Leu Leu Glu Leu Gln Asn Gln Leu Val Val Ser Asn
            325                 330

<210> SEQ ID NO 82
<211> LENGTH: 366
<212> TYPE: PRT
<213> ORGANISM: Talaromyces leycettanus

<400> SEQUENCE: 82

Met His Gln His Phe Arg Tyr Thr Ala Leu Leu Thr Ala Leu Leu Ser
1               5                   10                  15

Ala Ser Thr Arg Val Ala Ser His Gly His Val Ser Asn Ile Val Ile
            20                  25                  30

Asn Gly Val Pro Tyr Gln Gly Trp Asp Ile Asp Ser Met Pro Tyr Glu
        35                  40                  45

Ser Asp Pro Pro Val Val Ala Trp Glu Thr Pro Asn Thr Ser Asn
    50                  55                  60

Gly Phe Ile Thr Pro Asp Gln Tyr Gly Thr Ser Asp Ile Ile Cys His
65                  70                  75                  80

Leu Asn Ala Thr Asn Ala Lys Gly His Ala Val Val Ala Ala Gly Asp
                85                  90                  95

Lys Ile Ser Ile Gln Trp Thr Ala Trp Pro Ser Ser His His Gly Pro
            100                 105                 110

Val Ile Ser Tyr Leu Ala Asn Cys Gly Ala Ser Cys Glu Thr Val Asp
        115                 120                 125

Lys Thr Thr Leu Gln Phe Phe Lys Ile Asp Asn Ile Gly Phe Ile Asp
130                 135                 140

Asp Ser Ser Pro Pro Gly Ile Trp Ala Ala Asp Gln Leu Glu Ala Asn
145                 150                 155                 160

Asn Asn Thr Trp Leu Val Glu Ile Pro Pro Thr Ile Ala Pro Gly Tyr
                165                 170                 175

Tyr Val Leu Arg Asn Glu Ile Ile Ala Leu His Gly Ala Glu Asn Gln
            180                 185                 190

Asp Gly Ala Gln Asn Tyr Pro Gln Cys Phe Asn Leu Gln Val Thr Gly
        195                 200                 205

Ser Gly Thr Asp Lys Pro Ala Gly Val Leu Gly Thr Gln Leu Tyr Ser
    210                 215                 220

Pro Thr Asp Pro Gly Ile Leu Val Asn Ile Tyr Thr Ser Leu Ser Thr
225                 230                 235                 240

Tyr Ile Val Pro Gly Pro Thr Pro Tyr Ser Gly Trp Val Ser Val Val
                245                 250                 255

Gln Ser Ser Ser Ala Ile Thr Ala Ser Gly Thr Pro Val Thr Gly Thr
            260                 265                 270

Gly Gly Val Ser Pro Thr Thr Ala Thr Thr Ser Ser Ser His
        275                 280                 285

Ser Thr Thr Ser Thr Thr Thr Gly Pro Thr Val Thr Ser Thr Ser His
    290                 295                 300

Thr Thr Thr Thr Thr Thr Pro Thr Thr Leu Arg Thr Thr Thr Thr Thr
305                 310                 315                 320

Ala Ala Gly Gly Gly Ala Thr Gln Thr Val Tyr Gly Gln Cys Gly Gly
                325                 330                 335

Ser Gly Trp Thr Gly Ala Thr Ala Cys Ala Ala Gly Ala Thr Cys Ser
            340                 345                 350

Thr Leu Asn Pro Tyr Tyr Ala Gln Cys Leu Pro Thr Gly Ala
        355                 360                 365

<210> SEQ ID NO 83
<211> LENGTH: 364
<212> TYPE: PRT
<213> ORGANISM: Chaetomium thermophilum
<220> FEATURE:
<221> NAME/KEY: misc_feature
<222> LOCATION: (174)..(176)
<223> OTHER INFORMATION: Xaa can be any naturally occurring amino acid

<400> SEQUENCE: 83

Met Pro Ser Phe Ala Ser Lys Thr Leu Ile Ser Ala Leu Gly Ala
1               5                   10                  15

Ala Ser Val Ala Ala His Gly His Val Lys Asn Phe Val Ile Asn Gly
            20                  25                  30

Leu Ser Tyr Gln Ala Tyr Asp Pro Thr Val Phe Pro Tyr Met Gln Asn
        35                  40                  45

Pro Pro Ile Val Ala Gly Trp Thr Ala Ser Asn Thr Asp Asn Gly Phe
    50                  55                  60

Val Gly Pro Glu Ser Tyr Ser Ser Pro Asp Ile Ile Cys His Lys Ser
65                  70                  75                  80

Ala Thr Asn Ala Lys Gly His Ala Val Ile Lys Ala Gly Asp Ser Val
                85                  90                  95

Tyr Ile Gln Trp Asp Thr Trp Pro Glu Ser His His Gly Pro Val Ile
            100                 105                 110

Asp Tyr Leu Ala Ser Cys Gly Ser Ala Gly Cys Glu Thr Val Asp Lys
        115                 120                 125

Thr Gln Leu Glu Phe Phe Lys Ile Ala Glu Ala Gly Leu Ile Asp Gly
    130                 135                 140

Ser Gln Ala Pro Gly Lys Trp Ala Ala Asp Gln Leu Ile Ala Gln Asn
145                 150                 155                 160

Asn Ser Trp Leu Val Thr Ile Pro Glu Asn Ile Lys Pro Xaa Xaa Xaa
                165                 170                 175

Gly Ser Tyr Val Leu Arg His Glu Ile Ile Ala Leu His Ser Ala Gly
            180                 185                 190

Gln Thr Asn Gly Ala Gln Asn Tyr Pro Val Cys Ile Asn Leu Glu Val
        195                 200                 205

Thr Gly Gly Gly Ser Asp Val Pro Ser Gly Val Lys Gly Thr Glu Leu
    210                 215                 220

Tyr Lys Pro Thr Asp Pro Gly Ile Leu Ile Asn Ile Tyr Gln Ser Leu
225                 230                 235                 240

Ser Asn Tyr Thr Ile Pro Gly Pro Ala Leu Met Pro Gly Ala Lys Pro
                245                 250                 255

Val Thr Gln His Thr Ser Ala Ile Ile Gly Ser Thr Thr Ala Ile Thr
            260                 265                 270

Gly Thr Ala Thr Ala Ala Pro Ala Ala Pro Thr Ser Thr Ala Ala Ala
        275                 280                 285

Ile Thr Thr Ser Ser Ala Asn Ala Asn Pro Ala Pro Thr Thr Thr Arg
    290                 295                 300

Gly Asn Ala Asn Pro Val Pro Thr Thr Thr Leu Arg Thr Ser Thr Ile
305                 310                 315                 320

Ala Pro Gln Pro Thr Ala Ala Pro Ile Gln Thr Pro Thr Ser Ser Val
                325                 330                 335

Gly Arg Pro Pro Arg Pro Thr Arg Cys Pro Gly Leu Asp Asn Phe Lys
            340                 345                 350

Arg Ala Arg Arg His Ala Arg Asp Leu Ala Ala His
        355                 360

<210> SEQ ID NO 84
<211> LENGTH: 344
<212> TYPE: PRT
<213> ORGANISM: Trichoderma reesei

<400> SEQUENCE: 84

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
    130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
            260                 265                 270

Ser Gly Pro Thr Ser Arg Thr Thr Thr Ala Arg Thr Thr Gln Ala
        275                 280                 285

Ser Ser Arg Pro Ser Ser Thr Pro Pro Ala Thr Ser Ala Pro Ala
    290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340

<210> SEQ ID NO 85

-continued

```
<211> LENGTH: 252
<212> TYPE: PRT
<213> ORGANISM: Acrophialophora fusispora

<400> SEQUENCE: 85

Met Arg Ile Glu Ala Ile Thr Gly Leu Val Leu Ala Ser Ala Gly Ala
1               5                   10                  15

Val Ser Ala His Gly Trp Val Asp Val Trp Ala Ile Gly Gly Lys Asn
            20                  25                  30

Tyr Thr Gly Phe Asn Pro Thr Val Ala Pro Trp Val Pro Asp Gln Gly
        35                  40                  45

Thr Ile Ala Trp Pro Ala Trp Asn Thr Asp Thr Gly Pro Val Tyr Ser
    50                  55                  60

Lys Asp Val Asn Thr Thr Asp Ile Ile Cys Ser Ile Asn Ala Thr Asn
65                  70                  75                  80

Ala Lys Ile Tyr Ser Asp Pro Ile Ala Gly Asn Val Ile Asn Leu
                85                  90                  95

His Trp Thr Val Trp Pro Asp Ser His His Gly Pro Ile Leu Ser Tyr
            100                 105                 110

Leu Ala Ala Cys Asn Gly Asp Cys Ala Lys Ala Asp Lys Thr Lys Leu
        115                 120                 125

Lys Trp Phe Lys Ile Ala His Ala Gly Gln Ile Ser Leu Gly Thr Gly
    130                 135                 140

Gly Gly Gln Val Gly Tyr Trp Ala Ser Asp Lys Leu Gln Asp Asp Asn
145                 150                 155                 160

Gly Thr Trp Pro Val Thr Ile Pro Ala Ser Ile Lys Pro Gly Asn Tyr
                165                 170                 175

Val Leu Arg Asn Glu Ile Ile Ala Leu His Ser Ala Tyr Asp Val Gly
            180                 185                 190

Ala Ala Gln Leu Tyr Pro Gln Cys Val Asn Ile Lys Ile Thr Gly Asn
        195                 200                 205

Gly Arg Val Thr Pro Ala Gly Val Val Gly Thr Lys Leu Tyr Lys Glu
    210                 215                 220

Thr Asp Pro Gly Leu His Tyr Asn Ile Tyr Asn Asp Glu Ser Lys Pro
225                 230                 235                 240

Val Tyr Gln Ile Pro Gly Pro Ala Leu Cys Lys Cys
                245                 250

<210> SEQ ID NO 86
<211> LENGTH: 344
<212> TYPE: PRT
<213> ORGANISM: Corynascus sepedonium

<400> SEQUENCE: 86

Met Ser Lys Thr Ser Ala Leu Leu Ala Gly Leu Thr Gly Ala Ala Leu
1               5                   10                  15

Val Ala Ala His Gly His Val Ser His Ile Ile Val Asn Gly Val Tyr
            20                  25                  30

Tyr Glu Asn Tyr Asp Pro Thr Thr His Trp Tyr Gln Pro Asn Pro Pro
        35                  40                  45

Thr Val Ile Gly Trp Thr Ala Ala Gln Gln Asp Asn Gly Phe Ile Glu
    50                  55                  60

Pro Asn Asn Phe Gly Thr Ser Asp Ile Ile Cys His Lys Ser Gly Ser
65                  70                  75                  80

Pro Gly Gly Gly His Ala Thr Val Ala Ala Gly Asp Lys Ile Asn Ile
                85                  90                  95
```

```
Val Trp Thr Pro Glu Trp Pro Asp Ser His Ile Gly Pro Val Ile Asp
            100                 105                 110

Tyr Leu Ala Ala Cys Asn Gly Asp Cys Glu Thr Val Asn Lys Glu Ser
            115                 120                 125

Leu Arg Phe Phe Lys Ile Asp Gly Ala Gly Tyr Asp Lys Ala Ala Gly
            130                 135                 140

Arg Trp Ala Ala Glu Thr Leu Arg Gln Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gly Ser Ala Asn Gly Ala Gln Ala Tyr
            180                 185                 190

Pro Gln Cys Ile Asn Leu Arg Val Thr Gly Gly Gly Ser Ser Val Pro
            195                 200                 205

Ser Gly Val Ala Gly Thr Ser Leu Tyr Lys Ala Ser Asp Ala Gly Ile
            210                 215                 220

Leu Phe Asn Pro Tyr Val Ala Ser Pro Asp Tyr Pro Val Pro Gly Pro
225                 230                 235                 240

Ala Leu Ile Ala Gly Ala Ala Ser Ser Ile Val Gln Ser Thr Ser Ala
                245                 250                 255

Val Thr Ala Thr Ala Ser Ala Thr Ala Pro Gly Gly Gly Gly Ala Asn
            260                 265                 270

Pro Asn Pro Thr Pro Thr Thr Thr Ser Ser Ser Asn Pro Ala Pro Ser
            275                 280                 285

Thr Thr Leu Arg Thr Thr Thr Ser Ala Ala Gln Thr Thr Pro Pro Pro
            290                 295                 300

Thr Asn Gly Asn Val Gln Thr Lys Tyr Gly Gln Cys Gly Gly Arg Asp
305                 310                 315                 320

Trp Ser Gly Pro Thr Ala Cys Ala Ala Gly Ser Ser Cys Ser Val Leu
                325                 330                 335

Asn Asp Trp Tyr Ser Gln Cys Val
            340

<210> SEQ ID NO 87
<211> LENGTH: 347
<212> TYPE: PRT
<213> ORGANISM: Corynascus sepedonium

<400> SEQUENCE: 87

Met Pro Ser Ser Thr Ser Lys Gly Leu Phe Ser Ala Leu Met Gly Ala
1               5                   10                  15

Ala Ser Val Ala Ala His Gly His Val Thr Asn Ile Val Ile Asn Gly
            20                  25                  30

Val Ser Tyr Gln Asn Tyr Asp Pro Thr Ser Phe Pro Tyr Met Gln Asn
            35                  40                  45

Pro Pro Thr Val Val Gly Trp Thr Ala Ser Asn Thr Asp Asn Gly Phe
            50                  55                  60

Val Ala Pro Asp Ala Phe Ala Ser Gly Asp Ile Ile Cys His Arg Asp
65                  70                  75                  80

Ala Thr Asn Ala Gly Gly His Ala Val Val Ala Ala Gly Asp Lys Val
                85                  90                  95

Phe Ile Gln Trp Asp Thr Trp Pro Glu Ser His His Gly Pro Val Leu
            100                 105                 110

Asp Tyr Leu Ala Ser Cys Gly Asp Ala Gly Cys Glu Thr Val Asp Lys
```

```
            115                 120                 125
Asn Thr Leu Glu Phe Phe Lys Ile Gly Glu Ala Gly Leu Ile Asp Gly
    130                 135                 140

Ser Ser Ala Pro Gly Lys Trp Ala Ser Asp Gln Leu Ile Glu Asn Asn
145                 150                 155                 160

Asn Ser Trp Met Val Gln Ile Pro Ala Asn Leu Ala Pro Gly Asn Tyr
                    165                 170                 175

Val Leu Arg His Glu Ile Ile Ala Leu His Ser Ala Gly Gln Ala Asn
                180                 185                 190

Gly Ala Gln Asn Tyr Pro Gln Cys Phe Asn Leu Gln Val Thr Gly Ser
            195                 200                 205

Gly Thr Asp Lys Pro Ala Gly Val Leu Gly Thr Glu Leu Tyr Thr Pro
    210                 215                 220

Thr Asp Ala Gly Ile Leu Ala Asn Ile Tyr Thr Ser Pro Val Gln Tyr
225                 230                 235                 240

Glu Ile Pro Gly Pro Ala Leu Ile Ser Gly Ala Ser Ala Val Glu Gln
                    245                 250                 255

Ser Ser Ser Ala Ile Thr Ala Ser Ala Ser Glu Thr Gly Ser Ala
                260                 265                 270

Thr Ala Pro Pro Ala Gly Ser Ala Thr Ala Ala Pro Thr Thr Thr Thr
            275                 280                 285

Thr Thr Ala Gly Ser Asp Ala Ser Ala Thr Pro Ser Ser Ser Ser Ser
    290                 295                 300

Ser Gly Ala Ser Thr Thr Ala Glu Pro Thr Pro Ser Ala Thr Thr Thr
305                 310                 315                 320

Ala Gly Gly Ser Thr Pro Arg Pro Thr Arg Cys Pro Gly Leu Lys Arg
                    325                 330                 335

Arg Arg His Ala Arg Asp Val Lys Leu Ala Leu
                340                 345

<210> SEQ ID NO 88
<211> LENGTH: 342
<212> TYPE: PRT
<213> ORGANISM: Myceliophthora thermophila

<400> SEQUENCE: 88

Met Ser Lys Ala Ser Ala Leu Leu Ala Gly Leu Thr Gly Ala Ala Leu
1               5                   10                  15

Val Ala Ala His Gly His Val Ser His Ile Val Asn Gly Val Tyr
                20                  25                  30

Tyr Arg Asn Tyr Asp Pro Thr Thr Asp Trp Tyr Gln Pro Asn Pro Pro
            35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                    85                  90                  95

Val Trp Thr Pro Glu Trp Pro Glu Ser His Ile Gly Pro Val Ile Asp
                100                 105                 110

Tyr Leu Ala Ala Cys Asn Gly Asp Cys Glu Thr Val Asp Lys Ser Ser
            115                 120                 125

Leu Arg Trp Phe Lys Ile Asp Gly Ala Gly Tyr Asp Lys Ala Ala Gly
    130                 135                 140
```

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
            165                 170                 175

Ile Ile Ala Leu His Gly Ala Gln Ser Pro Asn Gly Ala Gln Ala Tyr
        180                 185                 190

Pro Gln Cys Ile Asn Leu Arg Val Thr Gly Gly Ser Asn Leu Pro
    195                 200                 205

Ser Gly Val Ala Gly Thr Ser Leu Tyr Lys Ala Thr Asp Pro Gly Ile
    210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
            245                 250                 255

Ala Thr Ala Thr Gly Thr Ala Thr Val Pro Gly Gly Gly Ala Asn
            260                 265                 270

Pro Thr Ala Thr Thr Ala Ala Thr Ser Ala Ala Pro Ser Thr Thr
    275                 280                 285

Leu Arg Thr Thr Thr Thr Ser Ala Ala Gln Thr Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
            325                 330                 335

Trp Tyr Ser Gln Cys Leu
            340

<210> SEQ ID NO 89
<211> LENGTH: 254
<212> TYPE: PRT
<213> ORGANISM: Talaromyces emersonii

<400> SEQUENCE: 89

Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
            20                  25                  30

Ile Val Ile Gly Asp Gln Phe Tyr Ser Gly Tyr Ile Val Asn Glu Phe
        35                  40                  45

Pro Tyr Glu Ser Asn Pro Pro Val Ile Gly Trp Ala Thr Thr Ala
    50                  55                  60

Thr Asp Leu Gly Phe Val Asp Gly Thr Glu Tyr Gln Gly Pro Asp Ile
65                  70                  75                  80

Ile Cys His Arg Asn Ala Thr Pro Ala Leu Leu Thr Ala Pro Val Ala
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Asn Gly Asn Cys Ser
        115                 120                 125

Thr Val Asp Lys Thr Gln Leu Glu Phe Phe Lys Ile Asp Gln Ser Gly
    130                 135                 140

Leu Ile Asn Asp Thr Asp Pro Pro Gly Thr Trp Ala Ser Asp Asn Leu
145                 150                 155                 160

Ile Ala Asn Asn Asn Ser Trp Thr Val Thr Ile Pro Ser Thr Leu Glu
                165                 170                 175

```
Pro Gly Asn Tyr Val Leu Arg His Glu Ile Ile Ala Leu His Ser Ala
            180                 185                 190

Gly Asn Lys Asp Gly Ala Gln Asn Tyr Pro Gln Cys Ile Asn Ile Glu
            195                 200                 205

Val Thr Gly Gly Gly Ser Val Glu Pro Thr Gly Thr Leu Gly Glu Asp
    210                 215                 220

Leu Tyr His Asp Thr Asp Pro Gly Ile Leu Ile Asp Ile Tyr Glu Pro
225                 230                 235                 240

Ile Ala Thr Tyr Thr Ile Pro Gly Pro Pro Glu Pro Thr Phe
                245                 250

<210> SEQ ID NO 90
<211> LENGTH: 272
<212> TYPE: PRT
<213> ORGANISM: Talaromyces thermophilus

<400> SEQUENCE: 90

Met Lys Ala Pro Ser Ala Ala Ser Ile Leu Leu Pro Phe Leu Ala Ser
1               5                   10                  15

Ile Thr Arg Thr Ser Ala His Gly Phe Val Ser Asn Ile Val Ile Asn
            20                  25                  30

Gly Val Ser Tyr Arg Gly Trp Leu Pro Asn Glu Asp Pro Tyr Lys Pro
        35                  40                  45

Glu Pro Pro Ile Gly Val Gly Trp Glu Thr Pro Asn Leu Ser Asn Gly
    50                  55                  60

Phe Val Thr Pro Glu Glu Ala Leu Thr Asp Ala Ile Val Cys His Lys
65                  70                  75                  80

Glu Ala Lys Pro Ala Arg Gly Tyr Ala Ser Val Ala Ala Gly Asp Lys
                85                  90                  95

Ile Tyr Ile Gln Trp Gln Pro Ile Pro Trp Pro Glu Ser His His Gly
            100                 105                 110

Pro Val Leu Asp Tyr Leu Ala Pro Cys Asn Gly Asp Cys Gln Asn Val
        115                 120                 125

Asn Lys Ser Ser Leu Glu Phe Phe Lys Ile Asp Gly Lys Gly Leu Ile
    130                 135                 140

Asp Gly Ser Ser Pro Pro Gly Phe Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Gly Phe Asn
            180                 185                 190

Gln Asn Gly Ala Gln Leu Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
                245                 250                 255

Glu Gln Ser Ser Ser Ala Val Thr Ala Thr Gly Thr Pro Thr Pro Ala
            260                 265                 270

<210> SEQ ID NO 91
<211> LENGTH: 272
<212> TYPE: PRT
```

<213> ORGANISM: Talaromyces thermophilus

<400> SEQUENCE: 91

Met Lys Gly Ser Ser Ala Ala Ser Val Leu Ala Leu Leu Ala Gly
1               5                   10                  15

Ile Thr Arg Thr Ser Ala His Gly Tyr Val Ser Asn Ile Val Asn
                20                  25                  30

Gly Val Tyr Tyr Arg Gly Trp Leu Pro Gly Glu Asp Pro Tyr Asn Pro
            35                  40                  45

Asp Pro Pro Ile Gly Val Gly Trp Glu Thr Pro Asn Leu Gly Asn Gly
        50                  55                  60

Phe Val Thr Pro Glu Glu Ala Ser Thr Asp Ala Ile Ile Cys His Lys
65                  70                  75                  80

Glu Ala Lys Pro Ala Arg Gly His Ala Thr Val Lys Ala Gly Asp Lys
                85                  90                  95

Ile Tyr Ile Gln Trp Gln Pro Ile Pro Trp Pro Glu Ser His His Gly
            100                 105                 110

Pro Val Leu Asp Tyr Leu Ala Ala Cys Asn Gly Asp Cys Glu Thr Val
        115                 120                 125

Asp Lys Thr Ser Leu Arg Phe Phe Lys Ile Ser Asn Lys Gly Leu Ile
130                 135                 140

Asp Gly Ser Ser Pro Pro Gly Tyr Trp Ala Asp Asp Gln Leu Ile Glu
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Ala Ala Gly Asn
            180                 185                 190

Pro Asn Gly Ala Gln Leu Tyr Pro Gln Cys Phe Asn Leu His Ile Thr
        195                 200                 205

Gly Ser Gly Thr Val Glu Pro Gln Gly Ile Pro Ala Thr Glu Leu Tyr
210                 215                 220

Ser Pro Asp Asp Pro Gly Ile Leu Ile Asn Ile Tyr Gln Pro Leu Thr
225                 230                 235                 240

Thr Tyr Glu Val Pro Gly Pro Thr Pro Ile Pro Gln Ala Val Glu Ile
                245                 250                 255

Glu Gln Ser Ser Ser Ala Ile Thr Ala Thr Gly Thr Pro Thr Pro Ala
            260                 265                 270

<210> SEQ ID NO 92
<211> LENGTH: 863
<212> TYPE: PRT
<213> ORGANISM: Aspergillus fumigatus

<400> SEQUENCE: 92

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu

```
                    85                  90                  95
Gly Ile Arg Phe Ser Asp Leu Asn Ser Ala Phe Pro Ala Gly Thr Asn
                100                 105                 110
Val Ala Ala Thr Trp Asp Lys Thr Leu Ala Tyr Leu Arg Gly Lys Ala
                115                 120                 125
Met Gly Glu Glu Phe Asn Asp Lys Gly Val Asp Ile Leu Leu Gly Pro
                130                 135                 140
Ala Ala Gly Pro Leu Gly Lys Tyr Pro Asp Gly Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
                180                 185                 190
Ile Leu Asn Glu Gln Glu His Phe Arg Gln Val Gly Glu Ala Gln Gly
                195                 200                 205
Tyr Gly Tyr Asn Ile Thr Glu Thr Ile Ser Ser Asn Val Asp Asp Lys
                210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
                260                 265                 270
Gly Phe Gln Gly Phe Val Met Ser Asp Trp Ser Ala His His Ser Gly
                275                 280                 285
Val Gly Ala Ala Leu Ala Gly Leu Asp Met Ser Met Pro Gly Asp Ile
                290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
                340                 345                 350
Pro Pro Asn Phe Ser Ser Trp Thr Arg Asp Glu Tyr Gly Trp Glu His
                355                 360                 365
Ser Ala Val Ser Glu Gly Ala Trp Thr Lys Val Asn Asp Phe Val Asn
                370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
                450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Phe
                500                 505                 510
```

```
Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 93
<211> LENGTH: 208
<212> TYPE: PRT
<213> ORGANISM: Myceliophthora thermophila

<400> SEQUENCE: 93

His Tyr Thr Leu Pro Arg Val Gly Thr Gly Ser Asp Trp Gln His Val
1               5                   10                  15

Arg Arg Ala Asp Asn Trp Gln Asn Asn Gly Phe Val Gly Asp Val Asn
```

```
            20                  25                  30
Ser Glu Gln Ile Arg Cys Phe Gln Ala Thr Pro Ala Gly Ala Gln Asp
            35                  40                  45

Val Tyr Thr Val Gln Ala Gly Ser Thr Val Thr Tyr His Ala Asn Pro
50                  55                  60

Ser Ile Tyr His Pro Gly Pro Met Gln Phe Tyr Leu Ala Arg Val Pro
65                  70                  75                  80

Asp Gly Gln Asp Val Lys Ser Trp Thr Gly Glu Gly Ala Val Trp Phe
                85                  90                  95

Lys Val Tyr Glu Glu Gln Pro Gln Phe Gly Ala Gln Leu Thr Trp Pro
            100                 105                 110

Ser Asn Gly Lys Ser Ser Phe Glu Val Pro Ile Pro Ser Cys Ile Arg
            115                 120                 125

Ala Gly Asn Tyr Leu Leu Arg Ala Glu His Ile Ala Leu His Val Ala
            130                 135                 140

Gln Ser Gln Gly Gly Ala Gln Phe Tyr Ile Ser Cys Ala Gln Leu Gln
145                 150                 155                 160

Val Thr Gly Gly Gly Ser Thr Glu Pro Ser Gln Lys Val Ser Phe Pro
                165                 170                 175

Gly Ala Tyr Lys Ser Thr Asp Pro Gly Ile Leu Ile Asn Ile Asn Tyr
            180                 185                 190

Pro Val Pro Thr Ser Tyr Gln Asn Pro Gly Pro Ala Val Phe Arg Cys
            195                 200                 205

<210> SEQ ID NO 94
<211> LENGTH: 225
<212> TYPE: PRT
<213> ORGANISM: Myceliophthora thermophila

<400> SEQUENCE: 94

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Gly Phe Val Gly Asp Val
            35                  40                  45

Asn Ser Glu Gln Ile Arg Cys Phe Gln Ala Thr Pro Ala Gly Ala Gln
50                  55                  60

Asp Val Tyr Thr Val Gln Ala Gly Ser Thr Val Thr Tyr His Ala Asn
65                  70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Thr Gly Glu Gly Ala Val Trp
            100                 105                 110

Phe Lys Val Tyr Glu Glu Gln Pro Gln Phe Gly Ala Gln Leu Thr Trp
            115                 120                 125

Pro Ser Asn Gly Lys Ser Ser Phe Glu Val Pro Ile Pro Ser Cys Ile
            130                 135                 140

Arg Ala Gly Asn Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Gln Val Thr Gly Gly Gly Ser Thr Glu Pro Ser Gln Lys Val Ser Phe
            180                 185                 190
```

```
Pro Gly Ala Tyr Lys Ser Thr Asp Pro Gly Ile Leu Ile Asn Ile Asn
            195                 200                 205

Tyr Pro Val Pro Thr Ser Tyr Gln Asn Pro Gly Pro Ala Val Phe Arg
210                 215                 220

Cys
225

<210> SEQ ID NO 95
<211> LENGTH: 515
<212> TYPE: PRT
<213> ORGANISM: Bacillus thermoaerophilus

<400> SEQUENCE: 95

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335
```

```
Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
515

<210> SEQ ID NO 96
<211> LENGTH: 356
<212> TYPE: PRT
<213> ORGANISM: Dictyogllomus thermophilum

<400> SEQUENCE: 96

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Lys Glu Glu Ala Lys
            20                  25                  30

Gly Met Glu Ile Pro Ser Leu Lys Glu Val Tyr Lys Asp Tyr Phe Thr
        35                  40                  45

Ile Gly Ala Ala Val Ser His Leu Asn Ile Tyr His Tyr Glu Asn Leu
    50                  55                  60

Leu Lys Lys His Phe Asn Ser Leu Thr Pro Glu Asn Gln Met Lys Trp
65                  70                  75                  80

Glu Val Ile His Pro Lys Pro Tyr Val Tyr Asp Phe Gly Pro Ala Asp
                85                  90                  95

Glu Ile Val Asp Phe Ala Met Lys Asn Gly Met Lys Val Arg Gly His
            100                 105                 110

Thr Leu Val Trp His Asn Gln Thr Pro Gly Trp Val Tyr Ala Gly Thr
        115                 120                 125

Lys Asp Glu Ile Leu Ala Arg Leu Lys Glu His Ile Lys Glu Val Val
    130                 135                 140

Gly His Tyr Lys Gly Lys Val Tyr Ala Trp Asp Val Val Asn Glu Ala
145                 150                 155                 160

Leu Ser Asp Asn Pro Asn Glu Phe Leu Arg Arg Ala Pro Trp Tyr Asp
                165                 170                 175

Ile Cys Gly Glu Glu Val Ile Glu Lys Ala Phe Ile Trp Ala His Glu
```

```
                180                 185                 190
Val Asp Pro Ala Lys Leu Phe Tyr Asn Asp Tyr Asn Leu Glu Asp
            195                 200                 205

Pro Ile Lys Arg Glu Lys Ala Tyr Lys Leu Val Lys Lys Leu Lys Asp
        210                 215                 220

Lys Gly Val Pro Ile His Gly Ile Gly Ile Gln Gly His Trp Thr Leu
225                 230                 235                 240

Ala Trp Pro Thr Pro Lys Met Leu Glu Asp Ser Ile Lys Arg Phe Ala
                245                 250                 255

Glu Leu Gly Val Glu Val Gln Val Thr Glu Phe Asp Ile Ser Ile Tyr
            260                 265                 270

Tyr Asp Arg Asn Glu Asn Asn Phe Lys Val Pro Pro Glu Asp Arg
        275                 280                 285

Leu Glu Arg Gln Ala Gln Leu Tyr Lys Glu Ala Phe Glu Ile Leu Arg
        290                 295                 300

Lys Tyr Lys Gly Ile Val Thr Gly Val Thr Phe Trp Gly Val Ala Asp
305                 310                 315                 320

Asp Tyr Thr Trp Leu Tyr Phe Trp Pro Val Arg Gly Arg Glu Asp Tyr
                325                 330                 335

Pro Leu Leu Phe Asp Lys Asn His Asn Pro Lys Lys Ala Phe Trp Glu
                340                 345                 350

Ile Val Lys Phe
            355

<210> SEQ ID NO 97
<211> LENGTH: 203
<212> TYPE: PRT
<213> ORGANISM: Dictyogllomus thermophilum

<400> SEQUENCE: 97

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Gly Thr Tyr Asp Ile Tyr Arg Thr Thr
        115                 120                 125

Arg Val Asn Gln Pro Ser Ile Val Gly Thr Ala Thr Phe Asp Gln Tyr
        130                 135                 140

Trp Ser Val Arg Thr Ser Lys Arg Thr Ser Gly Thr Val Thr Val Thr
145                 150                 155                 160

Asp His Phe Arg Ala Trp Ala Asn Arg Gly Leu Asn Leu Gly Thr Ile
                165                 170                 175

Asp Gln Ile Thr Leu Cys Val Glu Gly Tyr Gln Ser Ser Gly Ser Ala
            180                 185                 190
```

```
              Asn Ile Thr Gln Asn Thr Phe Ser Gln Gly Ser
                      195                 200
```

<210> SEQ ID NO 98
<211> LENGTH: 383
<212> TYPE: PRT
<213> ORGANISM: Rasomsonia byssochlamydoides

<400> SEQUENCE: 98

```
Asp Gly Leu Asn Thr Ala Ala Lys Ala Ile Gly Lys Leu Tyr Phe Gly
1               5                   10                  15

Thr Ala Thr Asp Asn Pro Glu Leu Ser Asp Val Ala Tyr Glu Thr Gln
            20                  25                  30

Leu Asn Asn Thr Gln Asp Phe Gly Gln Ile Thr Pro Ala Asn Ser Met
        35                  40                  45

Lys Trp Asp Ala Thr Glu Pro Glu Gln Asn Thr Phe Thr Phe Ala Ala
50                  55                  60

Gly Asp Gln Ile Ala Asp Leu Ala Glu Ala Asn Gly Gln Ile Leu Arg
65                  70                  75                  80

Cys His Asn Leu Val Trp Tyr Asn Gln Leu Pro Ser Trp Val Thr Ser
                85                  90                  95

Gly Ser Trp Thr Asn Glu Thr Leu Leu Ala Ala Met Lys Asn His Ile
            100                 105                 110

Thr Asn Val Val Thr His Tyr Lys Gly Arg Cys Tyr Ala Trp Asp Val
        115                 120                 125

Val Asn Glu Ala Leu Asn Asp Asp Gly Thr Tyr Arg Asp Asn Val Phe
130                 135                 140

Tyr Gln Tyr Ile Gly Glu Ala Tyr Ile Pro Ile Ala Phe Glu Thr Ala
145                 150                 155                 160

Ala Ala Ala Asp Pro Asn Val Lys Leu Tyr Tyr Asn Asp Tyr Asn Ile
                165                 170                 175

Glu Tyr Ala Gly Val Lys Ala Thr Ala Ala Gln Asn Ile Val Lys Leu
            180                 185                 190

Val Gln Ser Tyr Gly Ala Arg Ile Asp Gly Val Gly Leu Gln Ser His
        195                 200                 205

Phe Ile Val Gly Glu Thr Pro Ser Thr Ser Thr Gln Ala Ser Asn Met
210                 215                 220

Ala Ser Phe Thr Ala Leu Gly Val Glu Val Ala Ile Thr Glu Leu Asp
225                 230                 235                 240

Ile Arg Met Gln Leu Pro Glu Thr Thr Ala Leu Leu Thr Gln Gln Ser
                245                 250                 255

Thr Asp Tyr Gln Ser Thr Val Gln Ala Cys Val Asn Thr Pro Gly Cys
            260                 265                 270

Val Gly Ile Thr Leu Trp Asp Trp Thr Asp Lys Tyr Ser Trp Val Pro
        275                 280                 285

Ser Thr Phe Ser Gly Tyr Gly Asp Ala Cys Pro Trp Asp Asp Asn Tyr
290                 295                 300

Gln Lys Lys Pro Ala Tyr Tyr Gly Ile Leu Thr Ala Leu Gly Gly Ser
305                 310                 315                 320

Ala Ser Thr Thr Thr Val Gly Thr Gly Thr Thr Thr Ser Thr Ala
                325                 330                 335

Thr Thr Ser Ser Thr Gly Ser Ser Gly Thr Gly Val Ala Gln His Trp
            340                 345                 350

Gly Gln Cys Gly Gly Ile Gly Trp Thr Gly Pro Thr Val Cys Ala Ser
        355                 360                 365
```

Gly Tyr Thr Cys Thr Val Val Asn Pro Tyr Tyr Ser Gln Cys Leu
            370                 375                 380

<210> SEQ ID NO 99
<211> LENGTH: 385
<212> TYPE: PRT
<213> ORGANISM: Talaromyces leycettanus

<400> SEQUENCE: 99

Ala Gly Leu Asn Thr Ala Ala Lys Ala Ile Gly Lys Leu Tyr Phe Gly
1               5                   10                  15

Thr Ala Thr Asp Asn Pro Glu Leu Ser Asp Ser Thr Tyr Met Gln Glu
            20                  25                  30

Thr Asp Asn Thr Asp Asp Phe Gly Gln Leu Thr Pro Ala Asn Ser Met
        35                  40                  45

Lys Trp Asp Ala Thr Glu Pro Ser Gln Asn Thr Phe Thr Phe Thr Asn
    50                  55                  60

Gly Asp Gln Ile Ala Asn Leu Ala Lys Ser Asn Gly Gln Met Leu Arg
65                  70                  75                  80

Cys His Asn Leu Val Trp Tyr Asn Gln Leu Pro Ser Trp Val Thr Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Gln Cys Tyr Ala Trp Asp Val
        115                 120                 125

Val Asn Glu Ala Leu Asn Asp Asp Gly Thr Tyr Arg Ser Asn Val Phe
    130                 135                 140

Tyr Gln Tyr Ile Gly Glu Ala Tyr Ile Pro Ile Ala Phe Ala Thr Ala
145                 150                 155                 160

Ala Ala Ala Asp Pro Asn Ala Lys Leu Tyr Tyr Asn Asp Tyr Asn Ile
                165                 170                 175

Glu Tyr Pro Gly Ala Lys Ala Thr Ala Ala Gln Asn Ile Val Lys Met
            180                 185                 190

Val Lys Ala Tyr Gly Ala Lys Ile Asp Gly Val Gly Leu Gln Ser His
        195                 200                 205

Phe Ile Val Gly Ser Thr Pro Ser Gln Ser Gln Gln Ser Asn Met
    210                 215                 220

Ala Ala Phe Thr Ala Leu Gly Val Glu Val Ala Ile Thr Glu Leu Asp
225                 230                 235                 240

Ile Arg Met Thr Leu Pro Ser Thr Ser Ala Leu Leu Ala Gln Gln Ser
                245                 250                 255

Thr Asp Tyr Gln Ser Thr Val Ser Ala Cys Val Asn Thr Pro Lys Cys
            260                 265                 270

Ile Gly Ile Thr Leu Trp Asp Trp Thr Asp Lys Tyr Ser Trp Val Pro
        275                 280                 285

Asn Thr Phe Ser Gly Gln Gly Asp Ala Cys Pro Trp Asp Ser Asn Tyr
    290                 295                 300

Gln Lys Lys Pro Ala Tyr Tyr Gly Ile Leu Thr Ala Leu Gly Gly Ser
305                 310                 315                 320

Ala Ser Thr Ser Thr Thr Thr Thr Leu Val Ser Thr Arg Thr Ser
                325                 330                 335

Thr Thr Thr Ser Thr Ser Ala Thr Ser Thr Ser Thr Gly Val Ala Gln
            340                 345                 350

His Trp Gly Gln Cys Gly Gly Ile Gly Trp Thr Gly Pro Thr Thr Cys

```
            355                 360                 365
Ala Ser Pro Tyr Thr Cys Gln Glu Leu Asn Pro Tyr Tyr Gln Cys
    370                 375                 380

Leu
385

<210> SEQ ID NO 100
<211> LENGTH: 378
<212> TYPE: PRT
<213> ORGANISM: Aspergillus fumigatus

<400> SEQUENCE: 100

Ala Gly Leu Asn Thr Ala Ala Lys Ala Lys Gly Leu Lys Tyr Phe Gly
1               5                   10                  15

Ser Ala Thr Asp Asn Pro Glu Leu Thr Asp Ser Ala Tyr Val Ala Gln
            20                  25                  30

Leu Ser Asn Thr Asp Asp Phe Gly Gln Ile Thr Pro Gly Asn Ser Met
        35                  40                  45

Lys Trp Asp Ala Thr Glu Pro Ser Gln Asn Ser Phe Ser Phe Ala Asn
    50                  55                  60

Gly Asp Ala Val Val Asn Leu Ala Asn Lys Asn Gly Gln Leu Met Arg
65                  70                  75                  80

Cys His Thr Leu Val Trp His Ser Gln Leu Pro Asn Trp Val Ser Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Lys Cys Tyr Ala Trp Asp Val
        115                 120                 125

Val Asn Glu Ala Leu Asn Glu Asp Gly Thr Phe Arg Asn Ser Val Phe
    130                 135                 140

Tyr Gln Ile Ile Gly Pro Ala Tyr Ile Pro Ile Ala Phe Ala Thr Ala
145                 150                 155                 160

Ala Ala Ala Asp Pro Asp Val Lys Leu Tyr Tyr Asn Asp Tyr Asn Ile
                165                 170                 175

Glu Tyr Ser Gly Ala Lys Ala Thr Ala Ala Gln Asn Ile Val Lys Met
            180                 185                 190

Ile Lys Ala Tyr Gly Ala Lys Ile Asp Gly Val Gly Leu Gln Ala His
        195                 200                 205

Phe Ile Val Gly Ser Thr Pro Ser Gln Ser Asp Leu Thr Thr Val Leu
    210                 215                 220

Lys Gly Tyr Thr Ala Leu Gly Val Glu Val Ala Tyr Thr Glu Leu Asp
225                 230                 235                 240

Ile Arg Met Gln Leu Pro Ser Thr Ala Ala Lys Leu Ala Gln Gln Ser
                245                 250                 255

Thr Asp Phe Gln Gly Val Ala Ala Cys Val Ser Thr Thr Gly Cys
            260                 265                 270

Val Gly Val Thr Ile Trp Asp Trp Thr Asp Lys Tyr Ser Trp Val Pro
        275                 280                 285

Ser Val Phe Gln Gly Tyr Gly Ala Pro Leu Pro Trp Asp Glu Asn Tyr
    290                 295                 300

Val Lys Lys Pro Ala Tyr Asp Gly Leu Met Ala Gly Leu Gly Ala Ser
305                 310                 315                 320

Gly Ser Gly Thr Thr Thr Thr Thr Thr Thr Ser Thr Thr Thr Gly
                325                 330                 335
```

Gly Thr Asp Pro Thr Gly Val Ala Gln Lys Trp Gly Gln Cys Gly Gly
                340                 345                 350

Ile Gly Trp Thr Gly Pro Thr Thr Cys Val Ser Gly Thr Cys Gln
            355                 360                 365

Lys Leu Asn Asp Trp Tyr Ser Gln Cys Leu
        370                 375

<210> SEQ ID NO 101
<211> LENGTH: 409
<212> TYPE: PRT
<213> ORGANISM: Talaromyces leycettanus

<400> SEQUENCE: 101

Met Lys Phe Ser Asn Val Ile Leu Ala Ala Ser Ala Ser Ser Leu Val
1               5                   10                  15

Leu Ala Ala Pro Lys Ser Lys Thr Lys Arg Thr Ser Ala Phe Gln Trp
            20                  25                  30

Phe Gly Ala Asn Glu Ser Gly Ala Glu Phe Gly Asn Gln Asn Ile Pro
        35                  40                  45

Gly Thr Leu Gly Thr Asp Tyr Thr Trp Pro Asp Thr Ser Thr Ile Gln
    50                  55                  60

Thr Leu Arg Asn Ala Gly Met Asn Ile Phe Arg Val Pro Phe Leu Met
65                  70                  75                  80

Glu Arg Leu Val Pro Asn Gln Met Thr Gly Ser Pro Asp Pro Thr Tyr
                85                  90                  95

Leu Ala Asp Leu Lys Ser Thr Val Asn Phe Ile Thr Gly Thr Gly Ala
            100                 105                 110

Tyr Ala Val Val Asp Pro His Asn Tyr Gly Arg Tyr Tyr Asn Asn Ile
        115                 120                 125

Ile Thr Ser Thr Ser Asp Phe Ala Ala Phe Trp Thr Thr Val Ala Ser
    130                 135                 140

Gln Phe Ala Ser Asn Pro Arg Val Ile Phe Asp Thr Asn Asn Glu Tyr
145                 150                 155                 160

Asn Asn Met Asp Gln Thr Leu Val Leu Asn Leu Asn Gln Ala Ala Ile
                165                 170                 175

Asn Ala Ile Arg Ala Ala Gly Ala Thr Ser Gln Tyr Ile Phe Ala Glu
            180                 185                 190

Gly Asn Ser Trp Thr Gly Ala Trp Thr Trp Thr Ser Val Asn Asp Asn
        195                 200                 205

Met Lys Gln Leu Thr Asp Pro Ser Asn Lys Leu Val Tyr Glu Met His
    210                 215                 220

Gln Tyr Leu Asp Ser Asp Gly Ser Gly Thr Ser Asp Gln Cys Val Asn
225                 230                 235                 240

Ser Thr Ile Gly Tyr Asp Arg Ile Val Ser Ala Thr Gln Trp Leu Gln
                245                 250                 255

Ala Asn Gly Lys Val Ala Phe Leu Gly Glu Phe Ala Gly Gly Ser Asn
            260                 265                 270

Ser Val Cys Glu Ala Ala Val Thr Gly Met Leu Asp Tyr Met Glu Gln
        275                 280                 285

Asn Ser Asp Val Trp Leu Gly Ala Glu Trp Trp Ala Ala Gly Pro Trp
    290                 295                 300

Trp Gly Asn Tyr Ile Tyr Ser Met Glu Pro Pro Ser Gly Ile Ala Tyr
305                 310                 315                 320

Gln Asn Tyr Leu Ser Ile Leu Glu Pro Tyr Phe Pro Gly Gly Ser Tyr
                325                 330                 335

```
Ser Gly Gly Thr Gly Ser Gly Ser Thr Thr Thr Ala Thr
            340             345             350

Thr Thr Thr Thr Lys Val Pro Pro Thr Ser Thr Ser Ala Ser
        355             360             365

Ser Thr Gly Thr Gly Val Ala Gln His Trp Gly Gln Cys Gly Gly Gln
    370             375             380

Gly Trp Thr Gly Pro Thr Thr Cys Val Ser Pro Tyr Thr Cys Gln Glu
385             390             395             400

Leu Asn Pro Tyr Tyr Tyr Gln Cys Leu
                405
```

<210> SEQ ID NO 102
<211> LENGTH: 334
<212> TYPE: PRT
<213> ORGANISM: Penicillium capsulatum

<400> SEQUENCE: 102

```
Met Lys Phe Ser Asn Leu Val Ala Leu Ala Ala Ala Ser Ser Ala
1               5                   10                  15

Met Ala Leu Pro Leu Thr Lys Lys His Ala Lys Arg Ala Ser Ser Phe
            20                  25                  30

Glu Trp Phe Gly Ser Asn Glu Ser Gly Ala Glu Phe Gly Ser Gly Asn
        35                  40                  45

Ile Pro Gly Val Tyr Gly Thr Asp Tyr Ile Phe Pro Ser Thr Ser Ala
    50                  55                  60

Ile Gln Thr Leu Ile Asn Asn Gly Met Asn Ile Phe Arg Val Thr Phe
65                  70                  75                  80

Met Met Glu Arg Leu Val Pro Asn Thr Met Thr Gly Ser Phe Asp Ala
                85                  90                  95

Glu Tyr Leu Ser Asn Leu Thr Ser Val Val Asn Tyr Ile Thr Glu Ala
            100                 105                 110

Gly Ala His Ala Val Ile Asp Pro His Asn Tyr Gly Arg Tyr Tyr Gly
        115                 120                 125

Ser Ile Ile Ser Ser Thr Ser Asp Phe Gln Thr Phe Trp Lys Asn Val
    130                 135                 140

Ala Gly Gln Phe Lys Ser Asn Ser Leu Val Ile Phe Asp Thr Asn Asn
145                 150                 155                 160

Glu Tyr His Asp Met Asp Gln Thr Leu Val Leu Asn Leu Asn Gln Ala
                165                 170                 175

Ala Ile Asn Gly Ile Arg Ala Ala Gly Ala Thr Ser Gln Tyr Ile Phe
            180                 185                 190

Val Glu Gly Asn Ser Tyr Thr Gly Ala Trp Thr Trp Ala Asp Val Asn
        195                 200                 205

Asp Asn Leu Lys Asn Leu Thr Asp Pro Gln Asn Lys Ile Val Tyr Glu
210                 215                 220

Met His Gln Tyr Leu Asp Ser Asp Gly Ser Gly Thr Ser Ala Thr Cys
225                 230                 235                 240

Val Ser Thr Thr Ile Gly Lys Glu Arg Val Thr Ser Ala Thr Gln Trp
                245                 250                 255

Leu Gln Lys Asn Gly Lys Val Gly Ile Leu Gly Glu Phe Ala Gly Gly
            260                 265                 270

Val Asn Asp Gln Cys Lys Thr Ala Ile Thr Gly Met Leu Ser Tyr Leu
        275                 280                 285

Glu Asp Asn Ser Asp Val Trp Arg Gly Ala Met Trp Trp Ala Ala Gly
```

```
                290             295             300
Pro Trp Trp Gly Asp Tyr Ile Phe Ser Leu Glu Pro Pro Ser Gly Thr
305                 310             315                 320

Ala Tyr Thr Gly Met Trp Ser Thr Leu Lys Ser Tyr Leu Ala
                325             330

<210> SEQ ID NO 103
<211> LENGTH: 394
<212> TYPE: PRT
<213> ORGANISM: Trichophaea saccata

<400> SEQUENCE: 103

Met His Ser Phe Phe Ser Leu Ala Leu Ala Val Ala Gly Leu Pro Ala
1               5                   10                  15

Leu Ile Asn Ala Gln Gln Ser Ala Trp Gly Gln Cys Gly Gly Val Gly
                20                  25                  30

Trp Thr Gly Ala Thr Thr Cys Val Ser Gly Tyr Tyr Cys Ser Lys Leu
            35                  40                  45

Asn Asp Tyr Tyr Ser Gln Cys Ile Pro Gly Thr Ala Ser Thr Thr Thr
    50                  55                  60

Ser Ala Val Ser Thr Thr Thr Ala Thr Ser Pro Thr Gly Ser Val
65                  70                  75                  80

Cys Ser Gly Asn Arg Thr Lys Phe Lys Tyr Phe Gly Val Asn Glu Ser
                85                  90                  95

Gly Ala Glu Phe Gly Asn Asn Val Val Pro Gly Thr Leu Gly Lys Asp
                100                 105                 110

Tyr Thr Trp Pro Thr Thr Asp Ser Val Asp Phe Leu Gly Lys Gly
            115                 120                 125

Met Asn Thr Phe Arg Ile Ala Phe Leu Met Glu Arg Leu Ser Pro Pro
130                 135                 140

Ala Gly Gly Leu Thr Gly Thr Phe Asp Pro Thr Tyr Leu Ala Ser Leu
145                 150                 155                 160

Lys Asn Ile Ala Ser Tyr Ile Thr Gly Lys Gly Tyr Ala Ile Ile
                165                 170                 175

Asp Pro His Asn Tyr Gly Arg Tyr Asn Gly Asn Ile Ile Thr Asp Tyr
            180                 185                 190

Thr Ser Phe Gly Thr Trp Cys Lys Asn Leu Ala Ser Gln Phe Lys Ser
    195                 200                 205

Asp Ser His Ile Ile Phe Asp Thr Asn Asn Glu Tyr His Asp Met Asp
210                 215                 220

Glu Thr Leu Val Phe Asn Leu Asn Gln Ala Cys Ile Asn Gly Ile Arg
225                 230                 235                 240

Ala Ala Gly Ala Thr Ser Gln Leu Ile Leu Ile Glu Gly Asn Ser Trp
                245                 250                 255

Thr Gly Ala Trp Thr Trp Ile Ser Ser Gly Asn Ala Ala Ser Leu Ile
            260                 265                 270

Asn Leu Thr Asp Pro Asn Asn Asn Ile Ala Tyr Glu Met His Gln Tyr
    275                 280                 285

Leu Asp Ser Asp Gly Ser Gly Thr Ser Pro Thr Cys Val Ser Ser Thr
290                 295                 300

Ile Gly Ala Glu Arg Leu Ala Ala Ala Thr Ala Trp Leu Gln Ala Asn
305                 310                 315                 320

Asn Lys Lys Gly Phe Leu Gly Ile Gly Ala Gly Ser Asn Asp Asp
                325                 330                 335
```

-continued

```
Cys Ile Ala Ala Val Lys Gly Ala Leu Cys Ser Met Gln Glu Ala Gly
                340                 345                 350

Gly Val Trp Leu Gly Ala Leu Trp Trp Ala Ala Gly Pro Trp Trp Gly
            355                 360                 365

Asp Tyr Tyr Gln Ser Ile Glu Pro Pro Asp Gly Ala Ala Ile Ala Arg
        370                 375                 380

Ile Leu Pro Glu Ala Leu Leu Pro Phe Leu
385                 390

<210> SEQ ID NO 104
<211> LENGTH: 294
<212> TYPE: PRT
<213> ORGANISM: Sordaria fimicola

<400> SEQUENCE: 104

Met Arg Ser Ser Thr Ile Leu Gln Thr Gly Leu Val Ala Val Leu Pro
1               5                   10                  15

Phe Ala Val Gln Ala Ala Ser Gly Ser Gly Lys Ser Thr Arg Tyr Trp
            20                  25                  30

Asp Cys Cys Lys Pro Ser Cys Ala Trp Ser Gly Lys Ala Ser Val Asn
        35                  40                  45

Arg Pro Val Leu Ala Cys Asp Ala Asn Asn Asn Pro Leu Asn Asp Ala
    50                  55                  60

Asn Val Lys Ser Gly Cys Asp Gly Gly Ser Ala Tyr Thr Cys Ala Asn
65                  70                  75                  80

Asn Ser Pro Trp Ala Val Asn Asp Asn Leu Ala Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ser Gly Lys Thr Leu Val Val
        115                 120                 125

Gln Ser Thr Ser Thr Gly Gly Asp Leu Gly Ser Asn His Phe Asp Leu
    130                 135                 140

Asn Met Pro Gly Gly Gly Val Gly Leu Phe Asp Gly Cys Lys Arg Glu
145                 150                 155                 160

Phe Gly Gly Leu Pro Gly Ala Gln Tyr Gly Gly Ile Ser Ser Arg Ser
                165                 170                 175

Glu Cys Asp Ser Phe Pro Ala Ala Leu Lys Pro Gly Cys Gln Trp Arg
            180                 185                 190

Phe Asp Trp Phe Lys Asn Ala Asp Asn Pro Glu Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Ala Phe Thr Pro Pro Ser Gly Gly Gly Ser
225                 230                 235                 240

Asn Pro Ser Thr Pro Thr Thr Pro Pro Ser Ser Gly Gly Gly Gly Ser
                245                 250                 255

Gly Cys Ala Ala Ala Met Tyr Ala Gln Cys Gly Gly Ser Gly Phe Ser
            260                 265                 270

Gly Cys Thr Asn Cys Pro Ser Gly Ser Thr Cys Lys Ala Ile Asn Asp
        275                 280                 285

Tyr Tyr His Gln Cys Ala
    290

<210> SEQ ID NO 105
```

<211> LENGTH: 278
<212> TYPE: PRT
<213> ORGANISM: Thielavia terrestris

<400> SEQUENCE: 105

```
Ala Ser Gly Ser Gly Gln Ser Thr Arg Tyr Trp Asp Cys Cys Lys Pro
1               5                   10                  15
Ser Cys Ala Trp Pro Gly Lys Ala Ala Val Ser Gln Pro Val Tyr Ala
            20                  25                  30
Cys Asp Ala Asn Phe Gln Arg Leu Ser Asp Phe Asn Val Gln Ser Gly
        35                  40                  45
Cys Asn Gly Gly Ser Ala Tyr Ser Cys Ala Asp Gln Thr Pro Trp Ala
    50                  55                  60
Val Asn Asp Asn Leu Ala Tyr Gly Phe Ala Ala Thr Ser Ile Ala Gly
65                  70                  75                  80
Gly Ser Glu Ser Ser Trp Cys Cys Ala Cys Tyr Ala Leu Thr Phe Thr
                85                  90                  95
Ser Gly Pro Val Ala Gly Lys Thr Met Val Val Gln Ser Thr Ser Thr
            100                 105                 110
Gly Gly Asp Leu Gly Ser Asn His Phe Asp Ile Ala Met Pro Gly Gly
        115                 120                 125
Gly Val Gly Ile Phe Asn Gly Cys Ser Ser Gln Phe Gly Gly Leu Pro
    130                 135                 140
Gly Ala Gln Tyr Gly Gly Ile Ser Ser Arg Asp Gln Cys Asp Ser Phe
145                 150                 155                 160
Pro Ala Pro Leu Lys Pro Gly Cys Gln Trp Arg Phe Asp Trp Phe Gln
                165                 170                 175
Asn Ala Asp Asn Pro Thr Phe Thr Phe Gln Gln Val Gln Cys Pro Ala
            180                 185                 190
Glu Ile Val Ala Arg Ser Gly Cys Lys Arg Asn Asp Asp Ser Ser Phe
        195                 200                 205
Pro Val Phe Thr Pro Pro Ser Gly Gly Asn Gly Thr Gly Thr Pro
    210                 215                 220
Thr Ser Thr Ala Pro Gly Ser Gly Gln Thr Ser Pro Gly Gly Gly Ser
225                 230                 235                 240
Gly Cys Thr Ser Gln Lys Trp Ala Gln Cys Gly Gly Ile Gly Phe Ser
                245                 250                 255
Gly Cys Thr Thr Cys Val Ser Gly Thr Thr Cys Gln Lys Leu Asn Asp
            260                 265                 270
Tyr Tyr Ser Gln Cys Leu
        275
```

<210> SEQ ID NO 106
<211> LENGTH: 595
<212> TYPE: PRT
<213> ORGANISM: Penicillium oxalicum

<400> SEQUENCE: 106

```
Arg Pro Asp Pro Lys Gly Gly Asn Leu Thr Pro Phe Ile His Lys Glu
1               5                   10                  15
Gly Glu Arg Ser Leu Gln Gly Ile Leu Asp Asn Leu Gly Gly Arg Gly
            20                  25                  30
Lys Lys Thr Pro Gly Thr Ala Ala Gly Leu Phe Ile Ala Ser Pro Asn
        35                  40                  45
Thr Glu Asn Pro Asn Tyr Tyr Tyr Thr Trp Thr Arg Asp Ser Ala Leu
    50                  55                  60
```

```
Thr Ala Lys Cys Leu Ile Asp Leu Phe Glu Asp Ser Arg Ala Lys Phe
 65                  70                  75                  80

Pro Ile Asp Arg Lys Tyr Leu Glu Thr Gly Ile Arg Asp Tyr Lys Ser
                 85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480
```

```
Ser Ser Lys Thr Lys Cys Val Pro Ala Lys Asp Ile Val Pro Ile Thr
            485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
            515                 520                 525

Leu Thr Ala Asn Leu Tyr Thr Gln Asp Gln Asn Leu Trp Phe Ala Ser
            530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 107
<211> LENGTH: 863
<212> TYPE: PRT
<213> ORGANISM: Aspergillus fumigatus

<400> SEQUENCE: 107

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255
```

```
Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
            275                 280                 285

Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Met Ala Val
                325                 330                 335

Arg Ile Met Thr Ala Tyr Tyr Lys Val Gly Arg Asp Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670
```

Ser Ala Tyr Val Pro Thr Ser Gly Glu Thr Lys Pro Ala Pro Thr Tyr
                675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Gln Pro Leu Leu Lys Ala Gly
            740                 745                 750

Gly Ala Pro Gly Gly Asn Pro Thr Leu Tyr Gln Asp Leu Val Arg Val
                755                 760                 765

Ser Ala Thr Ile Thr Asn Thr Gly Asn Val Ala Gly Tyr Glu Val Pro
            770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
                835                 840                 845

Ser Ser Arg Lys Leu Pro Leu Arg Ala Pro Leu Pro Arg Val Tyr
            850                 855                 860

<210> SEQ ID NO 108
<211> LENGTH: 253
<212> TYPE: PRT
<213> ORGANISM: Penicillium emersonii

<400> SEQUENCE: 108

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
        50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
            195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 109
<211> LENGTH: 532
<212> TYPE: PRT
<213> ORGANISM: Aspergillus fumigatus

<400> SEQUENCE: 109

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr

```
                305                 310                 315                 320
Asp Asp Gly Thr Ser Ser Gly Thr Leu Lys Glu Ile Lys Arg Phe Tyr
                    325                 330                 335

Val Gln Asn Gly Lys Val Ile Pro Asn Ser Glu Ser Thr Trp Thr Gly
                    340                 345                 350

Val Ser Gly Asn Ser Ile Thr Thr Glu Tyr Cys Thr Ala Gln Lys Ser
                    355                 360                 365

Leu Phe Gln Asp Gln Asn Val Phe Glu Lys His Gly Gly Leu Glu Gly
                    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                    405                 410                 415

Thr Ala Ser Ser Thr Thr Pro Gly Val Ala Arg Gly Thr Cys Asp Ile
                    420                 425                 430

Ser Ser Gly Val Pro Ala Asp Val Glu Ala Asn His Pro Asp Ala Tyr
                    435                 440                 445

Val Val Tyr Ser Asn Ile Lys Val Gly Pro Ile Gly Ser Thr Phe Asn
                    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Ala Gly Asn Pro Gly Gly Thr Gly
                    485                 490                 495

Val Ala Gln His Tyr Gly Gln Cys Gly Gly Ile Gly Trp Thr Gly Pro
                    500                 505                 510

Thr Thr Cys Ala Ser Pro Tyr Thr Cys Gln Lys Leu Asn Asp Tyr Tyr
                    515                 520                 525

Ser Gln Cys Leu
        530

<210> SEQ ID NO 110
<211> LENGTH: 454
<212> TYPE: PRT
<213> ORGANISM: Aspergillus fumigatus

<400> SEQUENCE: 110

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
                    20                  25                  30

Ser Gly Pro Thr Ser Cys Val Ala Gly Ala Ala Cys Ser Thr Leu Asn
                35                  40                  45

Pro Tyr Tyr Ala Gln Cys Ile Pro Gly Ala Thr Ala Thr Ser Thr Thr
        50                  55                  60

Leu Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                    85                  90                  95

Gly Asn Pro Phe Ser Gly Tyr Gln Leu Tyr Ala Asn Pro Tyr Tyr Ser
                    100                 105                 110

Ser Glu Val His Thr Leu Ala Met Pro Ser Leu Pro Ser Ser Leu Gln
                    115                 120                 125

Pro Lys Ala Ser Ala Val Ala Glu Val Pro Ser Phe Val Trp Leu Asp
        130                 135                 140
```

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
            165                 170                 175

Val Tyr Asp Leu Pro Asp Arg Asp Cys Ala Ala Leu Ala Ser Asn Gly
        180                 185                 190

Glu Tyr Ser Ile Ala Asn Asn Gly Val Ala Asn Tyr Lys Ala Tyr Ile
    195                 200                 205

Asp Ala Ile Arg Ala Gln Leu Val Lys Tyr Ser Asp Val His Thr Ile
210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
            245                 250                 255

Tyr Ala Leu Lys Gln Leu Asn Leu Pro Asn Val Ala Met Tyr Leu Asp
        260                 265                 270

Ala Gly His Ala Gly Trp Leu Gly Trp Pro Ala Asn Leu Gly Pro Ala
    275                 280                 285

Ala Thr Leu Phe Ala Lys Val Tyr Thr Asp Ala Gly Ser Pro Ala Ala
290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
            325                 330                 335

Lys Tyr Ile Asn Ala Met Ala Pro Leu Leu Lys Glu Ala Gly Phe Asp
        340                 345                 350

Ala His Phe Ile Met Asp Thr Ser Arg Asn Gly Val Gln Pro Thr Lys
    355                 360                 365

Gln Asn Ala Trp Gly Asp Trp Cys Asn Val Ile Gly Thr Gly Phe Gly
370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
            405                 410                 415

Pro Arg Tyr Asp Ala His Cys Gly Tyr Ser Asp Ala Leu Gln Pro Ala
        420                 425                 430

Pro Glu Ala Gly Thr Trp Phe Gln Ala Tyr Phe Glu Gln Leu Leu Thr
    435                 440                 445

Asn Ala Asn Pro Ser Phe
    450

<210> SEQ ID NO 111
<211> LENGTH: 412
<212> TYPE: PRT
<213> ORGANISM: Pyrococcus furiosus

<400> SEQUENCE: 111

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
            85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 112
<211> LENGTH: 177
<212> TYPE: PRT
<213> ORGANISM: Thermoascus aurantiacus

<400> SEQUENCE: 112

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Ala Asp Ala Ala

```
                    20                  25                  30
Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
        130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 113
<211> LENGTH: 583
<212> TYPE: PRT
<213> ORGANISM: Synthetic construct

<400> SEQUENCE: 113

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
```

```
              210                 215                 220
Tyr Gln Lys Tyr Leu Pro Ser Leu Ile Asn Tyr Pro Met Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 114
<211> LENGTH: 330
<212> TYPE: PRT
<213> ORGANISM: Streptomyces coelicolor

<400> SEQUENCE: 114
```

His Gly Val Ala Met Met Pro Gly Ser Arg Thr Tyr Leu Cys Gln Leu
1               5                   10                  15

Asp Ala Lys Thr Gly Thr Gly Ala Leu Asp Pro Thr Asn Pro Ala Cys
            20                  25                  30

Gln Ala Ala Leu Asp Gln Ser Gly Ala Thr Ala Leu Tyr Asn Trp Phe
                35                  40                  45

Ala Val Leu Asp Ser Asn Ala Gly Gly Arg Gly Ala Gly Tyr Val Pro
50                  55                  60

Asp Gly Thr Leu Cys Ser Ala Gly Asp Arg Ser Pro Tyr Asp Phe Ser
65                  70                  75                  80

Ala Tyr Asn Ala Ala Arg Ser Asp Trp Pro Arg Thr His Leu Thr Ser
                85                  90                  95

Gly Ala Thr Ile Pro Val Glu Tyr Ser Asn Trp Ala Ala His Pro Gly
                100                 105                 110

Asp Phe Arg Val Tyr Leu Thr Lys Pro Gly Trp Ser Pro Thr Ser Glu
            115                 120                 125

Leu Gly Trp Asp Leu Glu Leu Ile Gln Thr Val Thr Asn Pro Pro
        130                 135                 140

Gln Gln Gly Ser Pro Gly Thr Asp Gly Gly His Tyr Tyr Trp Asp Leu
145                 150                 155                 160

Ala Leu Pro Ser Gly Arg Ser Gly Asp Ala Leu Ile Phe Met Gln Trp
                165                 170                 175

Val Arg Ser Asp Ser Gln Glu Asn Phe Ser Cys Ser Asp Val Val
                180                 185                 190

Phe Asp Gly Gly Asn Gly Glu Val Thr Gly Ile Arg Gly Ser Gly Ser
            195                 200                 205

Thr Pro Asp Pro Asp Pro Thr Pro Thr Pro Thr Asp Pro Thr Thr Pro
210                 215                 220

Pro Thr His Thr Gly Ser Cys Met Ala Val Tyr Ser Val Glu Asn Ser
225                 230                 235                 240

Trp Ser Gly Gly Phe Gln Gly Ser Val Glu Val Met Asn His Gly Thr
                245                 250                 255

Glu Pro Leu Asn Gly Trp Ala Val Gln Trp Gln Pro Gly Gly Gly Thr
            260                 265                 270

Thr Leu Gly Gly Val Trp Asn Gly Ser Leu Thr Ser Gly Ser Asp Gly
            275                 280                 285

Thr Val Thr Val Arg Asn Val Asp His Asn Arg Val Val Pro Pro Asp
290                 295                 300

Gly Ser Val Thr Phe Gly Phe Thr Ala Thr Ser Thr Gly Asn Asp Phe
305                 310                 315                 320

Pro Val Asp Ser Ile Gly Cys Val Ala Pro
                325                 330

<210> SEQ ID NO 115
<211> LENGTH: 362
<212> TYPE: PRT
<213> ORGANISM: Synthetic protein

<400> SEQUENCE: 115

Met Ala Leu Arg Ser Arg Leu Val Ser Leu Ala Val Leu Ala Thr
1               5                   10                  15

Leu Leu Gly Gly Leu Gly Leu Ser Phe Leu Trp Gln Lys Asp Ala Gln
            20                  25                  30

Ala His Gly Val Ala Met Met Pro Gly Ser Arg Thr Tyr Leu Cys Gln
        35                  40                  45

Leu Asp Ala Val Thr Gly Thr Gly Ala Leu Asp Pro Thr Asn Pro Ala
            50                  55                  60

Cys Lys Ala Ala Leu Asn Gln Ser Gly Ala Thr Ala Leu Tyr Asn Trp
 65                  70                  75                  80

Phe Ala Val Leu Asp Ser Gln Ala Gly Gly Arg Gly Gln Gly Tyr Val
                85                  90                  95

Pro Asp Gly Thr Leu Cys Ser Ala Gly Asp Arg Ser Pro Tyr Asp Phe
                100                 105                 110

Ser Ala Tyr Asn Ala Ala Arg Ser Asp Trp Pro Arg Thr His Leu Thr
                115                 120                 125

Ser Gly Ser Thr Ile Lys Val Gln Tyr Ser Asn Trp Ala Ala His Pro
            130                 135                 140

Gly Asp Phe Arg Val Tyr Ile Thr Lys Pro Gly Trp Ser Pro Thr Ser
145                 150                 155                 160

Gln Leu Gly Trp Asn Asp Leu Glu Leu Ile Gln Thr Val Thr Asp Pro
                165                 170                 175

Pro Gln Gln Gly Ser Pro Gly Ala Asn Gly Gly His Tyr Tyr Trp Asn
                180                 185                 190

Leu Gln Leu Pro Ser Gly Arg Ser Gly Asp Ala Leu Ile Phe Met Gln
            195                 200                 205

Trp Val Arg Ser Asp Ser Lys Glu Asn Phe Phe Ser Cys Ser Asp Val
            210                 215                 220

Val Phe Asp Gly Gly Asn Gly Glu Val Thr Gly Ile Arg Gly Ser Gly
225                 230                 235                 240

Thr Asp Pro Gly Thr Asp Pro Thr Pro Asp Thr Asp Pro Thr Asp
                245                 250                 255

Pro Pro His Thr Gly Glu Cys Met Ala Val Tyr Ser Val Thr Asn Ser
                260                 265                 270

Trp Ser Gly Gly Phe Gln Gly Ser Val Glu Val Met Asn His Gly Thr
            275                 280                 285

Ser Pro Leu Asn Gly Trp Ala Val Gln Trp Lys Pro Gly Gln Gly Thr
            290                 295                 300

Thr Ile Gly Ser Ala Trp Asn Gly Thr Leu Thr Lys Gly Ser Asp Gly
305                 310                 315                 320

Thr Val Thr Val Arg Asn Ala Asp His Asn Arg Val Ile Pro Pro Asp
                325                 330                 335

Gly Ser Val Ser Phe Gly Phe Thr Ala Thr Ser Ser Gly Asn Asn Phe
                340                 345                 350

Pro Val Gly Thr Ile Gly Cys Val Asn Pro
            355                 360

<210> SEQ ID NO 116
<211> LENGTH: 362
<212> TYPE: PRT
<213> ORGANISM: Streptomyces sp.

<400> SEQUENCE: 116

Met Ala Arg Arg Ser Arg Leu Ile Ser Leu Ala Ala Val Leu Ala Thr
1               5                   10                  15

Leu Leu Gly Ala Leu Gly Leu Thr Ala Leu Trp Pro Gly Lys Ala Glu
                20                  25                  30

Ala His Gly Val Ala Met Thr Pro Gly Ser Arg Thr Tyr Leu Cys Gln
            35                  40                  45

Leu Asp Ala Leu Ser Gly Thr Gly Ala Leu Asn Pro Thr Asn Pro Ala

```
                50                  55                  60
    Cys Arg Asp Ala Leu Ser Gln Ser Gly Ala Asn Ala Leu Tyr Asn Trp
    65                  70                  75                  80

Phe Ala Val Leu Asp Ser Asn Ala Gly Gly Arg Gly Ala Gly Tyr Val
                        85                  90                  95

Pro Asp Gly Ser Leu Cys Ser Ala Gly Asp Arg Ser Pro Tyr Asp Phe
                    100                 105                 110

Ser Ala Tyr Asn Ala Ala Arg Ala Asp Trp Pro Arg Thr His Leu Thr
                115                 120                 125

Ser Gly Ala Thr Leu Lys Val Gln Tyr Ser Asn Trp Ala Ala His Pro
            130                 135                 140

Gly Asp Phe Arg Val Tyr Leu Thr Lys Pro Gly Trp Ala Pro Thr Ser
    145                 150                 155                 160

Glu Leu Ala Trp Asp Asp Leu Gln Leu Val Gln Thr Val Ser Asn Pro
                        165                 170                 175

Pro Gln Gln Gly Gly Ala Gly Thr Asn Gly Gly His Tyr Tyr Trp Asp
                    180                 185                 190

Leu Ala Leu Pro Ser Gly Arg Ser Gly Asp Ala Leu Met Phe Ile Gln
                195                 200                 205

Trp Val Arg Ser Asp Ser Gln Glu Asn Phe Phe Ser Cys Ser Asp Ile
            210                 215                 220

Val Phe Asp Gly Gly Asn Gly Glu Val Thr Gly Ile Gly Gly Thr Gly
    225                 230                 235                 240

Thr Pro Thr Pro Thr Pro Thr Pro Thr Pro Thr Pro Thr Pro Thr Asp
                        245                 250                 255

Pro Glu His Ser Gly Ser Cys Met Ala Val Tyr Asn Val Val Ser Ser
                    260                 265                 270

Trp Ala Gly Gly Phe Gln Ala Ser Val Glu Val Met Asn His Gly Thr
                275                 280                 285

Glu Pro Arg Asn Gly Trp Ala Val Gln Trp Lys Pro Gly Ser Gly Thr
    290                 295                 300

Gln Ile Asn Ser Val Trp Asn Gly Ser Leu Ser Thr Gly Ser Asp Gly
    305                 310                 315                 320

Thr Val Thr Val Arg Asp Val Asp His Asn Arg Val Ile Ala Pro Asp
                        325                 330                 335

Gly Ser Val Thr Phe Gly Phe Thr Ala Thr Ser Thr Gly Asn Asp Tyr
                    340                 345                 350

Pro Ala Gly Thr Ile Gly Cys Val Thr Ser
                355                 360

<210> SEQ ID NO 117
<211> LENGTH: 364
<212> TYPE: PRT
<213> ORGANISM: Synthetic protein

<400> SEQUENCE: 117

Met Ala Arg Gly Lys Arg Leu Leu Val Ser Leu Thr Ala Val Phe Ala
    1               5                   10                  15

Thr Leu Leu Gly Gly Ile Ala Leu Thr Leu Phe Gly Gln Gly Asn Ala
                        20                  25                  30

Gln Ala His Gly Val Thr Met Thr Pro Gly Ser Arg Thr Tyr Leu Cys
                    35                  40                  45

Trp Leu Asp Ala Lys Thr Ser Thr Gly Ser Leu Asp Pro Thr Asn Pro
                50                  55                  60
```

Ala Cys Lys Ala Ala Leu Ser Glu Ser Gly Ser Asn Ala Leu Tyr Asn
 65                  70                  75                  80

Trp Phe Ala Val Leu Asp Ser Asn Ala Gly Gly Arg Gly Ala Gly Tyr
                 85                  90                  95

Val Pro Asp Gly Lys Leu Cys Ser Ala Gly Asp Arg Ser Pro Tyr Asn
            100                 105                 110

Phe Thr Gly Tyr Asn Ala Ala Arg Ser Asp Trp Pro Arg Thr His Leu
        115                 120                 125

Thr Ala Gly Arg Thr Ile Gln Val Lys His Ser Asn Trp Ala Ala His
130                 135                 140

Pro Gly Ser Phe Arg Val Tyr Leu Ser Lys Pro Gly Tyr Ser Pro Ser
145                 150                 155                 160

Thr Glu Leu Gly Trp Asp Asp Leu Glu Leu Ile Glu Thr Val Thr Asn
                165                 170                 175

Pro Pro Gln Thr Gly Ser Pro Gly Thr Asp Gly Gly His Tyr Tyr Trp
            180                 185                 190

Asn Leu Asp Leu Pro Ser Gly Arg Ser Gly Asp Ala Val Met Phe Ile
        195                 200                 205

Gln Trp Val Arg Ser Asp Ser Gln Glu Asn Phe Phe Ser Cys Ser Asp
210                 215                 220

Val Val Phe Asp Gly Gly Asn Gly Glu Val Thr Gly Ile Arg Gly Ser
225                 230                 235                 240

Gly Ser Thr Pro Asp Pro Thr Pro Thr Pro Thr Pro Asp Pro Thr Pro
                245                 250                 255

Thr Pro Thr Asp Pro His Ser Gly Cys Met Ala Val Tyr Arg Val Thr
            260                 265                 270

Asn Tyr Trp Ser Gly Gly Phe Gln Gly Ser Val Glu Val Met Asn His
        275                 280                 285

Ser Thr Thr Ala Arg Asp Gly Trp Ala Val Lys Trp Thr Pro Gly Ala
290                 295                 300

Gly Ala Lys Val Ser Ser Val Trp Asn Gly Ala Leu Thr Thr Gly Ser
305                 310                 315                 320

Asp Gly Ala Val Thr Val Arg Ser Leu Asp Tyr Asn Arg Ser Ile Pro
                325                 330                 335

Pro Asp Gly Ser Val Thr Phe Gly Phe Thr Ala Thr Ser Thr Gly Asn
            340                 345                 350

Asn Leu Pro Val Gly Ser Ile Gly Cys Val Asn Pro
        355                 360

<210> SEQ ID NO 118
<211> LENGTH: 399
<212> TYPE: PRT
<213> ORGANISM: Acremonium alcalophilum

<400> SEQUENCE: 118

His Met Glu Ile Ser Trp Pro Pro Leu Arg Ser Lys Tyr Asn Pro
1               5                   10                  15

Phe Ala Gly Gly Asp Ile Asp Tyr Ser Met Thr Ser Pro Leu Ser Ala
                 20                  25                  30

Ser Gly Ser Asp Phe Pro Cys Lys Gly Ser Leu Ser Leu Leu Gly Ser
             35                  40                  45

Asp Ala Ala Leu Pro Val Thr Ser Tyr Glu Ala Gly Gln Thr Tyr Asn
 50                  55                  60

Met Thr Ile Thr Gly Gly Ala His His Asn Gly Gly Ser Cys Gln Ala
 65                  70                  75                  80

```
Ser Leu Ser Phe Asp Gly Gly Asn Thr Phe Ser Val Ile His Ser Tyr
                85                  90                  95

Ile Gly Gly Cys Pro Pro Ala Gly Thr Ser Ser Tyr Asp Phe Thr Ile
            100                 105                 110

Pro Ala Asp Ala Pro Ser Ala Asp Asn Ala Ile Phe Ala Trp Thr Trp
        115                 120                 125

Phe Asn Gln Ile Gly Asn Arg Glu Met Tyr Met Asn Cys Ala Val Val
    130                 135                 140

Ser Ile Gln Gly Ser Gly Thr Ser Thr Ser Ser Leu Ala Gly Arg Pro
145                 150                 155                 160

Glu Ile Met Ile Ala Asn Val Gly Asn Gly Cys Ser Thr Thr Glu Gly
                165                 170                 175

Thr Asp Val Glu Phe Pro Asn Pro Gly Pro Asp Val Thr Val Ala Gly
            180                 185                 190

Ser Ala Thr Thr Pro Pro Leu Gly Ser Cys Gly Gly Ser Gly Gly
        195                 200                 205

Gly Asn Ser Gly Gly Asp Asn Gly Asp Gly Asn Arg Ser Asn Pro
    210                 215                 220

Asp Glu Gly Ser Asn Pro Gly Val Pro Thr Ile Gln Pro Asp Gln Pro
225                 230                 235                 240

Ala Ile Lys Pro Asp Gln Pro Val Pro Glu Leu Pro Lys Thr Thr Thr
                245                 250                 255

Ser Leu Pro Gly Gly Val Phe Ile Pro Leu Pro Ser Glu Ala Pro Pro
            260                 265                 270

Ala Glu Arg Leu Ser Thr Leu Thr Thr Val Thr Ile Pro Thr Thr Thr
        275                 280                 285

Ala Pro Pro Ser Gln Pro Thr Ser Ser Pro Gly Glu Glu Ala Cys
    290                 295                 300

Asp Asp Val Glu Asp Gly Val Glu Asp Gly Val Gln Asp Asp Val Gln
305                 310                 315                 320

Asp Gly Val Glu Asp Gly Val Glu Asp Gly Val Gln Asp Gly Ala Gln
                325                 330                 335

Asn Pro Gly Thr Ala Cys Ala Asn Glu Gly Gln Trp Asn Cys Leu Gly
            340                 345                 350

Gly Thr His Phe Gln Arg Cys Ala Ser Gly Val Trp Ser Gln Leu Met
        355                 360                 365

Gln Met Ala Ala Gly Thr Thr Cys Glu Ala Gly Leu Ser Glu Thr Leu
    370                 375                 380

Ile Met Ile Arg Lys Arg Gly Gly Ala Arg Arg Phe Leu Ile Leu
385                 390                 395

<210> SEQ ID NO 119
<211> LENGTH: 400
<212> TYPE: PRT
<213> ORGANISM: Aspergillus terreus

<400> SEQUENCE: 119

Met Leu Leu Thr Val Leu Ala Val Val Gly Cys Phe Thr Ala Val Asn
1               5                   10                  15

Gly His Gly Tyr Leu Thr Ile Pro Ala Ser Arg Thr Arg Leu Gly Phe
            20                  25                  30

Glu Thr Gly Ile Asp Thr Cys Pro Glu Cys Ser Ile Leu Glu Pro Val
        35                  40                  45

Thr Ala Trp Pro Asp Leu Glu Ala Ala Gln Val Gly Arg Ser Gly Pro
```

```
            50                  55                  60
Cys Gly Tyr Asn Ala Arg Val Ser Val Asp Tyr Asn Gln Pro Ser Glu
 65                  70                  75                  80

Tyr Trp Gly Asn Glu Pro Val Val Thr Tyr Thr Ser Gly Glu Val Val
                 85                  90                  95

Glu Val Gln Trp Cys Val Asp Ala Asn Gly Asp His Gly Gly Met Phe
            100                 105                 110

Thr Tyr Gly Ile Cys Gln Asn Gln Thr Leu Val Asp Lys Phe Leu Thr
            115                 120                 125

Pro Gly Tyr Leu Pro Thr Asn Glu Glu Lys Gln Ala Ala Glu Asp Cys
        130                 135                 140

Phe Leu Asp Gly Glu Leu Lys Cys Thr Asp Val Ser Gly Gln Thr Cys
145                 150                 155                 160

Gly Tyr Asn Pro Asp Cys Thr Glu Gly Ala Ala Cys Trp Arg Asn Asp
                165                 170                 175

Trp Phe Thr Cys Asn Ala Phe Gln Ala Asn Thr Ala Arg Ala Cys Gln
            180                 185                 190

Gly Val Asp Gly Ala Ser Leu Asn Ser Cys Lys Thr Thr Ile Ala Gly
        195                 200                 205

Gly Tyr Thr Val Thr Lys Arg Ile Lys Ile Pro Asp Tyr Ser Ser Asp
        210                 215                 220

His Thr Leu Leu Arg Phe Arg Trp Asn Ser Phe Gln Thr Ala Gln Val
225                 230                 235                 240

Tyr Leu His Cys Ala Asp Ile Ala Ile Ala Gly Ser Gly Gly Gly Thr
                245                 250                 255

Thr Ser Lys Ser Thr Thr Ser Thr Thr Ser Thr Thr Ser Thr Ser Arg
            260                 265                 270

Ser Thr Ser Thr Ser Ala Pro Thr Thr Thr Ser Ser Ala Ser Thr Ala
        275                 280                 285

Thr Pro Ile Cys Thr Thr Gln Ala Ser Leu Ile Pro Val Thr Phe Gln
        290                 295                 300

Glu Phe Val Thr Thr Met Trp Gly Glu Asn Val Phe Val Thr Gly Ser
305                 310                 315                 320

Ile Ser Gln Leu Gly Ser Trp Ser Thr Asp Lys Ala Val Ala Leu Ser
                325                 330                 335

Ala Thr Gly Tyr Thr Ala Ser Asn Pro Leu Trp Thr Thr Thr Ile Asp
            340                 345                 350

Leu Pro Ala Gly Thr Thr Phe Glu Tyr Lys Phe Ile Lys Lys Glu Thr
        355                 360                 365

Asp Gly Ser Ile Ile Trp Glu Ser Asp Pro Asn Arg Ser Tyr Thr Val
        370                 375                 380

Pro Thr Gly Cys Ser Gly Thr Thr Ala Thr Ala Ala Ser Trp Arg
385                 390                 395                 400

<210> SEQ ID NO 120
<211> LENGTH: 389
<212> TYPE: PRT
<213> ORGANISM: Aspergillus lentulus

<400> SEQUENCE: 120

Met Ile Phe Ser Ile Leu Val Ala Ala Gly Cys Phe Ala Ser Ala Tyr
  1               5                  10                  15

Gly His Gly Tyr Leu Thr Ile Pro Ala Ser Arg Thr Arg Leu Gly Phe
             20                  25                  30
```

Glu Ala Gly Ile Asp Thr Cys Pro Glu Cys Ser Ile Leu Glu Pro Val
            35                  40                  45

Thr Ala Trp Pro Asp Leu Glu Glu Ala Gln Val Gly Arg Ser Gly Pro
    50                  55                  60

Cys Gly Tyr Asn Ala Arg Val Ser Val Asp Tyr Asn Gln Pro Ser Asp
65                  70                  75                  80

His Trp Gly Asn Glu Pro Val Val Thr Tyr Thr Ser Gly Glu Val Val
                85                  90                  95

Glu Val Gln Trp Cys Val Asp Ala Asn Gly Asp His Gly Gly Met Phe
            100                 105                 110

Thr Tyr Gly Ile Cys Gln Asn Gln Thr Leu Val Asp Lys Phe Leu Thr
        115                 120                 125

Pro Gly Tyr Leu Pro Thr Asn Ala Glu Lys Gln Ala Ala Glu Asp Cys
    130                 135                 140

Phe Leu Glu Gly Glu Leu Lys Cys Thr Asp Val Ser Gly Gln Thr Cys
145                 150                 155                 160

Gly Tyr Asn Pro Asp Cys Thr Glu Gly Lys Ala Cys Trp Arg Asn Asp
                165                 170                 175

Trp Phe Thr Cys Asn Ala Phe Gln Ala Asn Thr Ala Arg Ala Cys Glu
            180                 185                 190

Gly Val Asp Arg Ala Pro Leu Asn Ser Cys Lys Thr Thr Ile Ala Gly
        195                 200                 205

Gly Tyr Thr Val Thr Lys Arg Ile Lys Ile Pro Asn Tyr Ser Ser Asn
    210                 215                 220

His Thr Leu Leu Arg Phe Arg Trp Asn Ser Phe Gln Thr Ala Gln Val
225                 230                 235                 240

Tyr Leu His Cys Ala Asp Ile Ala Ile Ser Gly Ser Gly Ser Thr Thr
                245                 250                 255

Thr Ser Thr Ser Thr Ser Ala Thr Thr Ser Lys Thr Thr Ser Thr Thr
            260                 265                 270

Ser Thr Ser Thr Ser Thr Ser Cys Thr Ala Thr Ala Ser Leu Ile
        275                 280                 285

Pro Val Thr Phe Asn Glu Leu Val Thr Thr Thr Tyr Gly Glu Asn Ile
    290                 295                 300

Phe Ile Thr Gly Ser Ile Ser Gln Leu Gly Ser Trp Ser Thr Asn Asn
305                 310                 315                 320

Ala Val Ala Leu Ser Ala Ser Arg Tyr Ser Ala Ser Asn Pro Leu Trp
                325                 330                 335

Ile Thr Thr Ile Asn Leu Pro Ala Gly Thr Thr Phe Glu Tyr Lys Phe
            340                 345                 350

Ile Lys Lys Glu Thr Asp Gly Ser Val Ile Trp Glu Ser Gly Pro Asn
        355                 360                 365

Arg Ser Tyr Thr Val Pro Thr Gly Cys Ser Gly Thr Thr Ala Thr Ala
    370                 375                 380

Thr Ala Ser Trp Arg
385

<210> SEQ ID NO 121
<211> LENGTH: 386
<212> TYPE: PRT
<213> ORGANISM: Aspergillus lentulus

<400> SEQUENCE: 121

Met Ile Phe Ser Ile Leu Val Ala Ala Gly Cys Phe Ala Ser Ala Tyr
1               5                   10                  15

Gly His Gly Tyr Leu Thr Ile Pro Ala Ser Arg Thr Arg Leu Gly Phe
            20                  25                  30

Glu Ala Gly Ile Asp Thr Cys Pro Glu Cys Ser Ile Leu Glu Pro Val
            35                  40                  45

Thr Ala Trp Pro Asp Leu Glu Glu Ala Gln Val Gly Arg Ser Gly Pro
 50                  55                  60

Cys Gly Tyr Asn Ala Arg Val Ser Val Asp Tyr Asn Gln Pro Ser Asp
 65                  70                  75                  80

His Trp Gly Asn Glu Pro Val Val Thr Tyr Thr Ser Gly Glu Val Val
                 85                  90                  95

Glu Val Gln Trp Cys Val Asp Ala Asn Gly Asp His Gly Gly Met Phe
            100                 105                 110

Thr Tyr Gly Ile Cys Gln Asn Gln Thr Leu Val Asp Lys Phe Leu Thr
            115                 120                 125

Pro Gly Tyr Leu Pro Thr Asn Ala Glu Lys Gln Ala Ala Glu Asp Cys
130                 135                 140

Phe Leu Glu Gly Glu Leu Lys Cys Thr Asp Val Ser Gly Gln Thr Cys
145                 150                 155                 160

Gly Tyr Asn Pro Asp Cys Thr Glu Gly Lys Ala Cys Trp Arg Asn Asp
                165                 170                 175

Trp Phe Thr Cys Asn Ala Phe Gln Ala Asn Thr Ala Arg Ala Cys Glu
            180                 185                 190

Gly Val Asp Arg Ala Pro Leu Asn Ser Cys Lys Thr Thr Ile Ala Gly
            195                 200                 205

Gly Tyr Thr Val Thr Lys Arg Ile Lys Ile Pro Asn Tyr Ser Ser Asn
            210                 215                 220

His Thr Leu Leu Arg Phe Arg Trp Asn Ser Phe Gln Thr Ala Gln Val
225                 230                 235                 240

Tyr Leu His Cys Ala Asp Ile Ala Ile Ser Gly Ser Gly Ser Thr Thr
                245                 250                 255

Thr Ser Thr Ser Thr Ser Ala Thr Thr Ser Lys Thr Thr Ser Thr Thr
            260                 265                 270

Ser Thr Ser Thr Ser Thr Ser Cys Thr Ala Thr Ala Ser Leu Ile
            275                 280                 285

Pro Val Thr Phe Asn Glu Leu Val Thr Thr Tyr Gly Glu Asn Ile
            290                 295                 300

Phe Ile Thr Gly Ser Ile Ser Gln Leu Gly Ser Trp Ser Thr Asn Asn
305                 310                 315                 320

Ala Val Ala Leu Ser Ala Ser Arg Tyr Ser Ala Ser Asn Pro Leu Trp
                325                 330                 335

Ile Thr Thr Ile Asn Leu Pro Ala Gly Thr Thr Phe Glu Tyr Lys Phe
            340                 345                 350

Ile Lys Lys Glu Thr Asp Gly Ser Val Ile Trp Glu Ser Gly Pro Asn
            355                 360                 365

Arg Ser Tyr Thr Val Pro Thr Gly Cys Ser Gly Thr Thr Ala Thr Ala
            370                 375                 380

Thr Ala
385

<210> SEQ ID NO 122
<211> LENGTH: 381
<212> TYPE: PRT
<213> ORGANISM: Aspergillus fischerianus

```
<400> SEQUENCE: 122

Met Ile Phe Ser Ile Leu Val Ala Ala Gly Cys Phe Ala Ser Ala Tyr
1               5                   10                  15

Gly His Gly Tyr Leu Thr Ile Pro Ala Ser Arg Thr Arg Leu Gly Phe
            20                  25                  30

Glu Ala Gly Ile Asp Thr Cys Pro Glu Cys Ser Ile Leu Glu Pro Val
        35                  40                  45

Thr Ala Trp Pro Asp Leu Glu Glu Ala Gln Val Gly Arg Ser Gly Pro
    50                  55                  60

Cys Gly Tyr Asn Ala Arg Val Ser Val Asp Tyr Asn Gln Pro Ser Asp
65                  70                  75                  80

His Trp Gly Asn Glu Pro Val Val Thr Tyr Thr Ser Gly Glu Val Val
                85                  90                  95

Glu Val Gln Trp Cys Val Asp Ala Asn Gly Asp His Gly Met Phe
            100                 105                 110

Thr Tyr Gly Ile Cys Gln Asn Gln Thr Leu Val Asp Lys Phe Leu Thr
            115                 120                 125

Pro Gly Tyr Leu Pro Thr His Gly Glu Lys Gln Ala Ala Glu Asp Cys
    130                 135                 140

Phe Leu Glu Gly Glu Leu Lys Cys Thr Asp Val Ser Gly Gln Thr Cys
145                 150                 155                 160

Gly Tyr Asn Pro Asp Cys Thr Glu Gly Ala Ala Cys Trp Arg Asn Asp
                165                 170                 175

Trp Phe Thr Cys Asn Ala Phe Gln Ala Asn Thr Ala Arg Ala Cys Gln
            180                 185                 190

Gly Val Asp Gly Ala Pro Leu Asn Ser Cys Lys Thr Thr Ile Ala Gly
        195                 200                 205

Gly Tyr Thr Val Thr Lys Arg Ile Lys Ile Pro Asn Tyr Ser Ser Asn
    210                 215                 220

His Thr Leu Leu Arg Phe Arg Trp Asn Ser Phe Gln Thr Ala Gln Val
225                 230                 235                 240

Tyr Leu His Cys Ala Asp Ile Ala Ile Ser Gly Ser Gly Ser Thr Thr
                245                 250                 255

Thr Ser Thr Thr Thr Ser Thr Thr Ser Thr Ser Thr Ser Thr Ser Thr
            260                 265                 270

Cys Thr Ala Thr Ala Ser Leu Ile Pro Val Thr Phe Asn Glu Leu Val
        275                 280                 285

Thr Thr Thr Tyr Gly Glu Asn Val Phe Ile Thr Gly Ser Ile Ser Gln
    290                 295                 300

Leu Gly Ser Trp Ser Thr Asp Asn Ala Val Ala Leu Ser Ala Ser Arg
305                 310                 315                 320

Tyr Thr Thr Ser Asn Pro Leu Trp Ile Thr Ile Asn Leu Pro Ala
                325                 330                 335

Gly Thr Thr Phe Gln Tyr Lys Phe Ile Lys Lys Glu Thr Asp Gly Ser
            340                 345                 350

Val Ile Trp Glu Ser Asp Pro Asn Arg Ser Tyr Thr Val Pro Thr Gly
            355                 360                 365

Cys Ser Gly Thr Thr Ala Thr Ala Thr Ala Ser Trp Arg
    370                 375                 380

<210> SEQ ID NO 123
<211> LENGTH: 385
<212> TYPE: PRT
<213> ORGANISM: Aspergillus nidulans
```

<400> SEQUENCE: 123

```
Met Lys Ser Leu Leu Ala Leu Val Ala Gly Asn Leu Val Thr Ala Val
1               5                   10                  15

Ser Gly His Gly Tyr Leu Thr Val Pro Ala Ser Arg Thr Arg Leu Gly
            20                  25                  30

Phe Glu Ala Gly Ile Asp Thr Cys Pro Glu Cys Ser Ile Leu Glu Pro
            35                  40                  45

Val Ser Ala Trp Pro Asp Leu Thr Ala Ala Gln Val Gly Arg Ser Gly
50                  55                  60

Pro Cys Gly Tyr Asn Ala Arg Val Ser Val Asp Tyr Asn Gln Pro Gly
65                  70                  75                  80

Asp Tyr Trp Gly Asn Glu Pro Val Val Ser Tyr Thr Ala Gly Asp Val
                85                  90                  95

Val Glu Val Gln Trp Cys Val Asp His Asn Gly Asp His Gly Gly Met
            100                 105                 110

Phe Thr Tyr Gly Ile Cys Gln Asn Gln Thr Leu Val Asp Leu Phe Leu
            115                 120                 125

Thr Pro Gly Tyr Leu Pro Thr Asn Glu Glu Lys Gln Ala Ala Glu Asp
    130                 135                 140

Cys Phe Leu Glu Gly Glu Leu Ser Cys Leu His Val Pro Gly Gln Thr
145                 150                 155                 160

Cys Asn Tyr Asn Pro Asp Cys Ser Ala Gly Glu Pro Cys Tyr Gln Asn
                165                 170                 175

Asp Trp Phe Thr Cys Asn Ala Phe Gln Ala Asp Asn Asn Arg Ala Cys
            180                 185                 190

Gln Gly Val Asp Gly Ala Ala Leu Asn Ser Cys Met Thr Thr Ile Ala
            195                 200                 205

Gly Gly Tyr Thr Val Thr Lys Lys Ile Lys Ile Pro Asp Tyr Ser Ser
    210                 215                 220

Ser His Thr Leu Leu Arg Phe Arg Trp Asn Ser Phe Gln Thr Ala Gln
225                 230                 235                 240

Val Tyr Leu His Cys Ala Asp Ile Ala Ile Val Gly Gly Ser Gly Ser
                245                 250                 255

Ser Pro Ser Pro Thr Ser Thr Ser Thr Ala Thr Ser Thr Thr Thr
            260                 265                 270

Pro Ser Ser Thr Ser Cys Ala Ser Ala Ile Ser Ile Pro Val Thr Phe
    275                 280                 285

Asn Ala Leu Val Thr Thr Thr Tyr Gly Glu Asn Val Tyr Leu Ala Gly
    290                 295                 300

Ser Ile Ser Gln Leu Gly Ser Trp Ser Thr Ser Ser Ala Val Ala Leu
305                 310                 315                 320

Ser Ala Ser Lys Tyr Ser Ser Ser Pro Leu Trp Thr Val Thr Val
                325                 330                 335

Asp Leu Pro Val Gly Ala Thr Phe Glu Tyr Lys Tyr Ile Lys Lys Glu
            340                 345                 350

Ser Asp Gly Ser Ile Val Trp Glu Ser Gly Pro Asn Arg Ser Tyr Thr
            355                 360                 365

Val Pro Thr Gly Cys Ser Gly Thr Thr Ala Thr Glu Ser Gly Ala Trp
    370                 375                 380

Arg
385
```

<210> SEQ ID NO 124
<211> LENGTH: 392
<212> TYPE: PRT
<213> ORGANISM: Penicillium polonicum

<400> SEQUENCE: 124

```
Met Lys Ala Phe Ser Ile Leu Thr Leu Ala Gly Leu Phe Ser Ser Val
1               5                   10                  15

Asn Ala His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
        35                  40                  45

Val Ala Pro Trp Pro Asp Leu Glu Gly Pro Gln Val Gly Arg Ser Gly
    50                  55                  60

Pro Cys Gly Tyr Asn Ala Arg Val Ser Val Asp Tyr Asn Gln Pro Ala
65                  70                  75                  80

Ala His Trp Gly Asn Ser Val Val Ala Thr Tyr Thr Ala Asn Gln Ile
                85                  90                  95

Val Asp Val Gln Trp Cys Val Asp His Asn Gly Asp His Gly Gly Met
            100                 105                 110

Phe Thr Tyr Gly Leu Cys Gln Asn Gln Thr Leu Val Asp Leu Phe Leu
        115                 120                 125

Asp Pro Thr Tyr Leu Pro Thr Asn Asp Glu Lys Gln Ala Ala Glu Asp
    130                 135                 140

Cys Phe Leu Glu Gly Glu Leu Lys Cys Thr Asp Val Ala Gly Gln Thr
145                 150                 155                 160

Cys Gly Tyr Ser Pro Asp Cys Thr Ala Gly Gln Ala Cys Trp Arg Asn
                165                 170                 175

Asp Trp Phe Thr Cys Asn Ala Phe Ser Ala Asp Ser Asn Arg Gly Cys
            180                 185                 190

Gln Gly Val Asp Gly Ala Pro Leu Asn Ser Cys Lys Thr Thr Ile Ala
        195                 200                 205

Gly Gly Tyr Thr Val Thr Lys Lys Ile Lys Ile Pro Asp Tyr Asp Ser
    210                 215                 220

Ala His Thr Leu Leu Arg Phe Arg Trp Asn Ser Phe Gln Thr Gly Gln
225                 230                 235                 240

Val Tyr Leu Asn Cys Ala Asp Ile Ala Val Ala Gly Thr Gly Gly Gly
                245                 250                 255

Ser Thr Ser Thr Thr Ser Ser Ala Thr Ser Thr Thr Ser Lys Thr Ser
            260                 265                 270

Thr Ile Thr Thr Ser Thr Thr Thr Thr Ala Cys Ala Thr Thr Val
        275                 280                 285

Thr Thr Val Pro Val Thr Phe Lys Glu Leu Val Thr Thr Ser Tyr Gly
    290                 295                 300

Gln Asn Val Phe Val Thr Gly Ser Ile Ser Gln Leu Gly Ser Trp Ser
305                 310                 315                 320

Thr Ser Ser Ala Val Ala Leu Ser Ala Gly Ser Tyr Thr Thr Ser Asn
                325                 330                 335

Pro Leu Trp Thr Ala Ser Ile Asp Leu Pro Ala Gly Thr Thr Phe Glu
            340                 345                 350

Tyr Lys Phe Phe Lys Lys Gly Ser Asp Gly Thr Ile Thr Trp Glu Ser
        355                 360                 365

Glu Pro Asn Arg Ser Tyr Thr Val Pro Thr Gly Cys Ser Gly Thr Thr
    370                 375                 380
```

```
Gly Thr Ala Ser Ala Thr Trp Arg
385                 390
```

<210> SEQ ID NO 125
<211> LENGTH: 405
<212> TYPE: PRT
<213> ORGANISM: Penicillium oxalicum

<400> SEQUENCE: 125

```
Met Leu Leu Ser Ser Leu Leu Ala Val Pro Trp Leu Ala Ser Leu Val
1               5                   10                  15

Thr Ala His Gly Tyr Leu Thr Val Pro Phe Ser Arg Thr Arg Leu Gly
            20                  25                  30

Phe Glu Ala Gly Ile Asp Thr Cys Pro Glu Cys Ser Ile Leu Glu Pro
        35                  40                  45

Val Thr Ala Trp Pro Asp Val Glu Ala Ala Pro Val Gly Arg Ser Gly
50                  55                  60

Pro Cys Gly Tyr Asn Ala Arg Val Gly Val Asp Tyr Asn Gln Pro Ser
65                  70                  75                  80

Ala His Trp Gly Gln Ser Val Val Ala Thr Tyr Thr Ala Asn Gln Val
                85                  90                  95

Val Glu Val Gln Trp Cys Val Asp Asn Asn Gly Asp His Gly Gly Met
            100                 105                 110

Phe Thr Tyr Gly Ile Cys Arg Asn Gln Thr Leu Val Asp Leu Phe Thr
        115                 120                 125

Asn Pro Asn Tyr Leu Pro Thr Asn Ala Glu Lys Gln Ala Ala Glu Asp
    130                 135                 140

Cys Phe Leu Asp Gly Glu Leu Lys Cys Thr Asp Val Thr Gly Gln Thr
145                 150                 155                 160

Cys Gly Tyr Asn Pro Asp Cys Gln Pro Gly Gln Pro Cys Tyr Arg Asn
                165                 170                 175

Asp Trp Phe Thr Cys Asn Ala Phe Asn Gly Asp Ser Ser Gly Gly Val
            180                 185                 190

Arg Gly Cys Gln Gly Val Asp Ala Ala Pro Leu Asn Ser Cys Lys Thr
        195                 200                 205

Thr Ile Ala Gly Gly Tyr Thr Val Thr Lys Lys Ile Arg Ile Pro Asp
    210                 215                 220

Tyr Asp Ser Lys His Thr Leu Leu Arg Phe Arg Trp Asn Ser Phe Gln
225                 230                 235                 240

Thr Ala Gln Val Tyr Leu His Cys Ala Asp Ile Ala Ile Ser Gly Ser
                245                 250                 255

Gly Ser Gly Ser Gly Ser Gly Ser Ser Thr Thr Ser Lys Thr Thr Leu
            260                 265                 270

Thr Thr Lys Ala Thr Thr Ala Thr Ser Lys Thr Ser Thr Thr Thr Ala
        275                 280                 285

Ala Ala Thr Thr Thr Thr Thr Gly Thr Cys Ser Pro Ala Ser Ala Val
    290                 295                 300

Pro Val Thr Phe Asn Glu Leu Ala Thr Thr Thr Tyr Gly Glu Asn Ile
305                 310                 315                 320

Tyr Leu Val Gly Ser Ile Ser Gln Leu Gly Ser Trp Ala Thr Ser Ser
                325                 330                 335

Ala Ile Ala Leu Ser Ala Ser Tyr Thr Thr Ser Asn Pro Leu Trp
            340                 345                 350

Thr Thr Thr Val Asn Leu Pro Ala Gly Thr Ser Phe Gln Tyr Lys Phe
        355                 360                 365
```

```
Ile Arg Lys Lys Ser Asp Gly Ser Val Val Trp Glu Ser Asp Pro Asn
    370                 375                 380

Arg Ser Tyr Ser Val Pro Thr Gly Cys Ser Gly Ile Lys Ala Thr Ala
385                 390                 395                 400

Ser Gly Thr Trp Arg
                405

<210> SEQ ID NO 126
<211> LENGTH: 391
<212> TYPE: PRT
<213> ORGANISM: Penicillium arizonense

<400> SEQUENCE: 126

Met Lys Thr Thr Ser Val Leu Ala Leu Ala Gly Leu Leu Thr Ser Val
1               5                   10                  15

Asn Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Thr Ala Trp Pro Asp Val Glu Ala Ala Gln Val Gly Arg Ser Gly
50                  55                  60

Pro Cys Gly Tyr Asn Ala Arg Val Ser Val Asp Tyr Asn Gln Pro Gly
65                  70                  75                  80

Asp Tyr Trp Gly Asn Ser Val Val Ala Thr Tyr Ala Asn Asp Ile
                85                  90                  95

Val Glu Val Gln Trp Cys Val Asp Asn Asn Gly Asp His Gly Gly Met
                100                 105                 110

Phe Thr Tyr Gly Val Cys Gln Asn Gln Thr Leu Val Asp Leu Phe Leu
            115                 120                 125

Thr Pro Gly Tyr Leu Pro Thr Thr Glu Glu Lys Gln Ala Ala Glu Asp
130                 135                 140

Cys Phe Leu Asp Gly Glu Leu Lys Cys Thr Asp Val Asp Gly Gln Ser
145                 150                 155                 160

Cys Gly Tyr Asn Pro Asp Cys Thr Ser Asp Gln Ala Cys Tyr Arg Asn
                165                 170                 175

Asp Trp Phe Thr Cys Asn Ala Phe Asn Ala Asp Ser Asn Arg Gly Cys
            180                 185                 190

Gln Gly Val Asp Gly Ala Ala Leu Asn Ser Cys Lys Thr Thr Ile Ala
            195                 200                 205

Gly Gly Tyr Thr Val Thr Lys Lys Ile Lys Ile Pro Asp Tyr Ser Ser
210                 215                 220

Asp His Thr Leu Leu Arg Phe Arg Trp Asn Ser Phe Gln Thr Ala Gln
225                 230                 235                 240

Val Tyr Leu His Cys Ala Asp Ile Ala Ile Ser Gly Ser Gly Ser Gly
                245                 250                 255

Ser Thr Ser Ser Thr Ser Ser Thr Ser Thr Ile Ala Thr Ser Ala
            260                 265                 270

Thr Lys Thr Ser Thr Thr Ala Ser Ser Thr Cys Thr Ala Ala Thr
            275                 280                 285

Ser Val Ala Val Thr Phe Asn Glu Leu Val Thr Thr Tyr Gly Glu
            290                 295                 300

Asp Val Tyr Val Val Gly Ser Ile Ser Gln Leu Gly Ser Trp Ser Thr
305                 310                 315                 320

Ser Ser Ala Ile Ala Leu Ser Ala Ser Ser Tyr Thr Ser Ser Asn Pro
```

```
            325                 330                 335
Leu Trp Thr Ala Thr Ile Ser Leu Pro Val Gly Thr Thr Phe Glu Tyr
            340                 345                 350

Lys Phe Ile Lys Lys Glu Ser Asp Gly Ser Ile Val Trp Glu Ser Asp
            355                 360                 365

Pro Asn Arg Ser Tyr Thr Val Pro Thr Gly Cys Ser Gly Thr Thr Ala
            370                 375                 380

Thr Ala Ser Ala Thr Trp Arg
385                 390

<210> SEQ ID NO 127
<211> LENGTH: 382
<212> TYPE: PRT
<213> ORGANISM: Mycothermus thermophilus

<400> SEQUENCE: 127

Met Lys Phe Thr Ala Thr Gly Leu Phe Met Ser Leu Pro Arg Ile Val
1               5                   10                  15

Leu Gly His Gly Tyr Leu Thr Val Pro Phe Ser Arg Thr Arg Leu Gly
            20                  25                  30

Ala Glu Ala Gly Ile Asp Ser Cys Pro Glu Cys Ser Ile Leu Glu Pro
            35                  40                  45

Val Leu Ala Trp Pro Asn Leu Asp Ala Ala Pro Val Gly Arg Ser Gly
50                  55                  60

Pro Cys Gly Tyr Asn Ala Arg Val Ser Val Asp Tyr Asn Gln Pro Ser
65                  70                  75                  80

Ser His Trp Gly Thr Thr Pro Val Ala Thr Tyr Ser Pro Gly Gln Ile
                85                  90                  95

Val Glu Val Glu Trp Cys Val Asp His Asn Gly Asp His Gly Gly Met
            100                 105                 110

Phe Ser Tyr Arg Ile Cys Gln Asn Gln Thr Leu Val Asp Lys Phe Leu
            115                 120                 125

Thr Pro Gly Tyr Leu Pro Thr Glu Ala Glu Lys Gln Glu Ala Glu Asp
            130                 135                 140

Cys Phe Glu Ala Gly Leu Leu Pro Cys Thr Asp Val Ser Gly Gln Ser
145                 150                 155                 160

Cys Glu Tyr Ser Pro Asp Cys Thr Pro Gly Gln Ala Cys Trp Arg Lys
                165                 170                 175

Asp Trp Phe Thr Cys Asn Ala Phe Gln Ala Asp Ser Arg Arg Ala Cys
            180                 185                 190

Gln Gly Val Asp Asn Ala Pro Arg Gly Ser Cys Tyr Thr Ser Ile Ala
            195                 200                 205

Gly Gly Tyr Pro Val Thr Lys Lys Ile Arg Ile Pro Asn Tyr Leu Ser
        210                 215                 220

Lys His Thr Leu Leu Ser Phe Lys Trp Asn Ser Tyr Gln Thr Gly Gln
225                 230                 235                 240

Ile Tyr Leu Ser Cys Ala Asp Ile Ala Ile Ile Pro Gly Ser Asp Pro
                245                 250                 255

Thr Thr Pro Thr Ser Thr Thr Ser Glu Ala Ser Ala Thr Ala Thr Pro
            260                 265                 270

Thr Ala Ser Cys Thr Pro Val Ser Thr Val Thr Leu Thr Phe Ser Glu
            275                 280                 285

Arg Val Val Thr Thr Trp Gly Gln Ser Ile Lys Leu Val Gly Ser Ile
        290                 295                 300
```

```
Pro Glu Leu Gly Ser Trp Asn Leu Ser Ala Ala Pro Thr Leu Ser Ser
305                 310                 315                 320

Ser Glu Tyr Thr Ser Thr Asn Pro Val Trp Thr His Thr Ile Met Leu
                325                 330                 335

Pro Val Gly Thr Ser Phe Gln Tyr Lys Phe Val Arg Val Glu Ala Asn
            340                 345                 350

Gly Ala Val Thr Trp Glu Ser Asp Pro Asn Arg Leu Tyr Thr Val Pro
        355                 360                 365

Ser Gly Cys Ala Thr Ser Ile Arg Val Thr Ser Glu Trp Arg
    370                 375                 380

<210> SEQ ID NO 128
<211> LENGTH: 381
<212> TYPE: PRT
<213> ORGANISM: Acremonium sp. XZ1982

<400> SEQUENCE: 128

Met Lys Pro Ala Ser Phe Phe Ala His Met Gly Leu Val Ser Ser Val
1               5                   10                  15

Leu Gly His Gly Tyr Leu Thr Ile Pro Arg Ser Arg Thr Arg Leu Gly
            20                  25                  30

Ala Glu Ala Gly Ile Asp Thr Cys Pro Glu Cys Thr Ile Arg Glu Pro
        35                  40                  45

Val Thr Ala Trp Pro Asp Leu Asp Gln Ala Thr Val Gly Arg Ser Gly
    50                  55                  60

Pro Cys Gly Phe Asn Ala Arg Val Ser Val Asp Tyr Asn Gln Pro Ser
65                  70                  75                  80

Ala Asn Trp Gly Ser Ala Pro Val Ala Thr Tyr Thr Arg Gly Gln Thr
                85                  90                  95

Val Thr Val Glu Trp Cys Val Asp Asn Gly Asp His Gly Gly Met
            100                 105                 110

Phe Thr Tyr Arg Ile Cys Gln Asp Gln Ala Leu Val Asp Lys Leu Leu
            115                 120                 125

Thr Pro Gly Tyr Leu Pro Thr Glu Ala Glu Lys Glu Ala Ala Glu Arg
130                 135                 140

Cys Phe Gln Arg Gly Thr Leu Pro Cys Thr Asp Val Ser Gly Gln Ser
145                 150                 155                 160

Cys Gly Tyr Asn Pro Asp Cys Gln Gln Gly Gln Ala Cys Trp Arg Asn
                165                 170                 175

Asp Trp Phe Thr Cys Asn Ala Phe Gln Ala Asp Ser Arg Arg Gly Cys
            180                 185                 190

Gln Gly Val Asp Ala Ala Pro Leu Gly Ser Cys Tyr Thr Ser Ile Ala
        195                 200                 205

Gly Gly Tyr Arg Val Thr Lys Gln Ile Lys Ile Pro Asp Tyr Val Ser
    210                 215                 220

Asn His Thr Leu Leu Ser Phe Lys Trp Asn Ser Phe Gln Thr Pro Gln
225                 230                 235                 240

Ile Tyr Leu Ser Cys Ala Asp Ile Ala Ile Thr Gly Thr Gly Ala
                245                 250                 255

Pro Asn Pro Gly Thr Thr Thr Thr Arg Met Thr Ala Pro Thr Asn
            260                 265                 270

Thr Ala Cys Ala Ala Ala Ser Ser Val Ala Val Thr Phe Asn Gln Val
        275                 280                 285

Ala Thr Thr Ser Pro Gly Gln Thr Ile Lys Leu Val Gly Ser Ile Gln
    290                 295                 300
```

Gln Leu Gly Ser Trp Asn Pro Ser Ala Ala Pro Ala Leu Ser Ala Ser
305                 310                 315                 320

Gln Tyr Thr Ser Ala Lys Pro Leu Trp Ser Tyr Val Thr Leu Ala
            325                 330                 335

Ala Gly Ser Thr Phe Gln Tyr Lys Phe Val Asn Val Gln Ala Asp Gly
            340                 345                 350

Thr Ile Arg Trp Glu Ser Asp Pro Asn Arg Ser Tyr Thr Val Pro Arg
            355                 360                 365

Gly Cys Asp Gln Arg Val Thr Val Glu Ser Thr Trp Arg
            370                 375                 380

<210> SEQ ID NO 129
<211> LENGTH: 380
<212> TYPE: PRT
<213> ORGANISM: Acrostalagmus luteoalbus

<400> SEQUENCE: 129

Met Lys Thr Ser Gly Ile Leu Ser Ala Leu Ser Leu Ala Ser Ser Val
1               5                   10                  15

Leu Gly His Gly Tyr Leu Thr Ile Pro Lys Ser Arg Thr Arg Leu Gly
            20                  25                  30

Gln Glu Ala Gly Ile Asp Thr Cys Pro Glu Cys Thr Ile Leu Glu Pro
        35                  40                  45

Val His Ala Trp Pro Gly Leu Asp Gln Ala Val Val Gly Arg Ser Gly
    50                  55                  60

Pro Cys Gly Tyr Asn Ala Arg Val Ser Val Asp Tyr Asn Gln Pro Gly
65                  70                  75                  80

Ser Ala Trp Gly Ser Ala Pro Val Val Thr Tyr Ser Pro Gly Gln Thr
                85                  90                  95

Val Thr Val Glu Trp Cys Val Asp Asn Asn Gly Asp His Gly Gly Met
            100                 105                 110

Phe Ala Tyr Arg Ile Cys Gln Asp Gln Asp Ile Val Asn Lys Leu Ile
        115                 120                 125

Thr Pro Gly Tyr Leu Pro Thr Glu Ala Glu Lys Gln Glu Ala Glu Asp
    130                 135                 140

Cys Phe Glu Glu Gly Thr Leu Pro Cys Thr Asp Val Ser Gly Gln Ser
145                 150                 155                 160

Cys Gly Tyr Ser Pro Asp Cys Gln Pro Gly Gln Pro Cys Trp Arg Asn
                165                 170                 175

Asp Trp Phe Thr Cys Asn Ala Phe Asp Ala Gly Ser Arg Arg Gly Cys
            180                 185                 190

Gln Gly Val Asp Asn Ala Pro Ile Gly Ser Cys Tyr Thr Ser Ile Ala
        195                 200                 205

Gly Gly Tyr Lys Val Thr Lys Gln Ile Arg Ile Pro Asp Tyr Val Ser
    210                 215                 220

Glu His Thr Leu Leu Ser Phe Lys Trp Asn Ala Phe Gln Thr Pro Gln
225                 230                 235                 240

Ile Tyr Leu Ser Cys Ala Asp Ile Arg Ile Ser Ser Gly Gly Asn Pro
                245                 250                 255

Asn Pro Asn Pro Thr Thr Thr Ser Thr Ser Ala Gly Pro Ser Pro Thr
            260                 265                 270

Asp Cys Thr Val Ala Ser Asn Val Ala Val Thr Phe Asn Gln Leu Val
        275                 280                 285

Asn Thr Val Pro Gly Gln Thr Ile Lys Ile Ala Gly Ser Ile Pro Gln

```
                290                 295                 300
Leu Gly Asn Trp Ser Pro Ala Ser Ala Pro Ala Leu Ser Ala Ala Gln
305                 310                 315                 320

Tyr Thr Ser Ser Arg Pro Leu Trp Gly His Thr Val Thr Leu Pro Ala
                325                 330                 335

Gly Thr Thr Phe Gln Tyr Lys Tyr Ile Asn Val Gln Ser Asp Gly Gln
                340                 345                 350

Val Arg Trp Glu Ser Asp Pro Asn Arg Ser Tyr Thr Val Pro Arg Ser
            355                 360                 365

Cys Ala Gln Ser Val Val Val Asp Thr Thr Trp Arg
370                 375                 380

<210> SEQ ID NO 130
<211> LENGTH: 386
<212> TYPE: PRT
<213> ORGANISM: Aspergillus insuetus

<400> SEQUENCE: 130

Met Ser Pro Met Lys Thr Tyr Leu Leu Leu Val Ala Ser Asn Leu Leu
1               5                   10                  15

Gly Thr Ala Tyr Gly His Gly Tyr Leu Thr Ile Pro Ser Ser Arg Thr
                20                  25                  30

Arg Leu Gly Phe Glu Ala Gly Ile Asp Thr Cys Pro Glu Cys Ser Ile
            35                  40                  45

Leu Glu Pro Val Ser Ala Trp Pro Asp Leu Thr Ala Val Gln Val Gly
        50                  55                  60

Arg Ser Gly Pro Cys Gly Tyr Asn Ala Arg Val Ser Val Asp Tyr Asn
65                  70                  75                  80

Gln Pro Thr Asp Tyr Trp Gly Asn Glu Pro Val Val Thr Tyr Ser Ala
                85                  90                  95

Gly Asp Ile Ile Glu Ile Gln Trp Cys Val Asp Asn Gly Asp His
                100                 105                 110

Gly Gly Met Phe Thr Tyr Gly Ile Cys Gln Asp Gln Thr Leu Val Asp
            115                 120                 125

Leu Phe Leu Thr Pro Gly Tyr Ile Pro Thr Asn Glu Glu Lys Gln Ala
        130                 135                 140

Ala Glu Asp Cys Phe Leu Glu Gly Leu Ser Cys Thr Asp Val Pro
145                 150                 155                 160

Gly Gln Ser Cys Gly Tyr Asn Pro Asp Cys Thr Ala Gly Gln Ala Cys
                165                 170                 175

Tyr Arg Asn Asp Trp Phe Thr Cys Asn Ala Phe Gln Ala Ser Ser Asn
            180                 185                 190

Arg Gly Cys Gln Gly Val Asp Ala Ala Pro Leu Asn Ser Cys Ala Thr
        195                 200                 205

Thr Ile Ser Gly Gly Tyr Thr Val Thr Lys Lys Ile Lys Ile Pro Asp
210                 215                 220

Tyr Asp Ser Ala His Thr Leu Leu Arg Phe Arg Trp Asn Ser Phe Gln
225                 230                 235                 240

Thr Ala Gln Val Tyr Leu Gly Cys Ala Asp Ile Ala Ile Ser Gly Ser
                245                 250                 255

Gly Gly Ser Pro Thr Ser Ser Thr Ala Thr Ser Thr Thr Thr
            260                 265                 270

Thr Ser Pro Ser Ser Cys Ala Ala Ala Thr Ser Ile Pro Val Thr
        275                 280                 285
```

```
Phe Asp Ala Lys Val Thr Thr Ser Trp Gly Glu Lys Val Tyr Leu Val
    290                 295                 300

Gly Ser Ile Ser Gln Leu Gly Ser Trp Ser Thr Gly Ser Ala Val Ala
305                 310                 315                 320

Leu Asn Ala Asp Lys Tyr Thr Ser Ser Asn Pro Val Trp Ser Val Thr
                325                 330                 335

Leu Asp Ile Pro Val Gly Thr Ser Phe Glu Tyr Lys Tyr Ile Lys Lys
            340                 345                 350

Glu Ser Asp Gly Ser Val Val Trp Glu Ser Asp Pro Asn Arg Ser Tyr
        355                 360                 365

Thr Val Pro Ser Gly Cys Gln Gly Ala Lys Val Asn Glu Ser Gly Ser
370                 375                 380

Trp Arg
385

<210> SEQ ID NO 131
<211> LENGTH: 387
<212> TYPE: PRT
<213> ORGANISM: Cladosporium gossypiicola

<400> SEQUENCE: 131

Met Lys Thr Thr Thr Leu Ala Gly Leu Ala Ala Ser Leu Ala Ala Thr
1               5                   10                  15

Val Asn Ala His Gly Tyr Leu Thr Ile Pro Ser Ser Arg Thr Ser Leu
            20                  25                  30

Asn Phe Leu Lys Gly Asn Asp Thr Cys Pro Glu Cys Thr Ile Leu Glu
        35                  40                  45

Pro Val Thr Thr Phe Pro Asn Leu Asp Ser Ala Leu Val Gly Arg Ser
    50                  55                  60

Gly Pro Cys Gly Tyr Asn Ala Arg Val Ser Thr Asp Tyr Asn Thr Pro
65                  70                  75                  80

Gly Asn Val Trp Gly Thr Ser Pro Val Ala Thr Tyr Ser Pro Gly Gln
                85                  90                  95

Ile Val Asp Val Glu Trp Cys Val Asp Asn Asn Gly Asp His Gly Gly
            100                 105                 110

Met Phe Ser Tyr Arg Ile Cys Gln Asp Gln Leu Val Asn Lys Leu
        115                 120                 125

Ile Thr Pro Gly Tyr Ile Pro Thr Gln Ala Glu Lys Gln Ala Ala Glu
    130                 135                 140

Ala Cys Phe Glu Ala Gly Thr Leu Asp Cys Thr Asp Val Pro Gly Gln
145                 150                 155                 160

Asn Cys Gly Ile Asn Pro Asp Cys Gln Asp Ser Ala Cys Lys Arg Thr
                165                 170                 175

Asp Trp Phe Thr Cys Asn Ala Phe Gln Ala Asp Thr Arg Arg Ala Cys
            180                 185                 190

Gln Gly Val Asp Ser Ser Ala Leu Gly Ser Cys Lys Thr Thr Ile Ala
        195                 200                 205

Gly Gly Tyr Thr Val Thr Lys Lys Ile Lys Ile Pro Asp Tyr Val Ser
    210                 215                 220

Glu His Thr Leu Leu Ser Phe Lys Trp Asn Ser Trp Gln Thr Pro Gln
225                 230                 235                 240

Ile Tyr Leu Gly Cys Ala Asp Ile Ala Ile Lys Gly Ser Gly Thr Thr
                245                 250                 255

Pro Pro Ser Ser Thr Thr Ser Lys Ala Ser Thr Thr Ser Thr Gly
            260                 265                 270
```

```
Thr Thr Thr Ser Ser Thr Ser Thr Ala Thr Asn Cys Pro Ala Lys Val
            275                 280                 285

Ala Val Thr Phe Ser Glu Lys Arg Ala Thr Asn Tyr Gly Asp Thr Val
290                 295                 300

Lys Val Val Gly Ser Ile Ala Glu Leu Gly Asn Trp Asn Val Gln Asn
305                 310                 315                 320

Ala Pro Ser Leu Ser Ala Thr Gly Tyr Thr Ala Ser Asn Pro Val Trp
                325                 330                 335

Lys Gln Thr Ile Gln Leu Pro Ala Gly Ser Ser Phe Thr Tyr Lys Phe
            340                 345                 350

Ala Ile Val Ser Ser Gly Ala Val Thr Trp Glu Ser Asp Pro Asn
            355                 360                 365

Arg Ser Tyr Thr Val Pro Ala Cys Gln Gln Ser Ala Glu Val Ser Ala
370                 375                 380

Thr Trp Arg
385

<210> SEQ ID NO 132
<211> LENGTH: 253
<212> TYPE: PRT
<213> ORGANISM: Fusarium sp_75363

<400> SEQUENCE: 132

Met Phe Tyr Ser Ser Ile Ile Thr Ile Val Thr Leu Ser Thr Lys Val
1               5                   10                  15

Tyr Gly His Gly Tyr Leu Ser Gln Pro Met Ser Arg Thr Gly Leu Asn
            20                  25                  30

Ala Glu Ala Gly Pro Asp Thr Cys Pro Glu Cys Ala Ile Leu Glu Pro
        35                  40                  45

Val Thr Ala Trp Pro Asp Leu Asp Ala Ala Lys Val Gly Arg Ser Gly
50                  55                  60

Pro Cys Gly Tyr Asn Ala Arg Val Ser Val Asp Tyr Asn Arg Pro Gly
65                  70                  75                  80

Ala Asn Trp Gly Lys Glu Pro Val Thr Thr Tyr Ser Pro Gly Glu Val
                85                  90                  95

Ile Asp Val Gln Trp Cys Val Asp Asn Asn Gly Asp His Gly Gly Met
            100                 105                 110

Phe Thr Tyr Arg Ile Cys Gln Asp Gln Ala Ile Val Asp Lys Phe Leu
        115                 120                 125

Asp Pro Asp Tyr Ile Pro Thr Glu Ala Glu Lys Gln Glu Ala Glu Asp
130                 135                 140

Cys Phe Glu Ala Gly Ile Leu Pro Cys Thr Asp Val Asp Gly Gln Ser
145                 150                 155                 160

Cys Glu Tyr Ser Pro Asp Cys Thr Pro Asp Gln Pro Cys Trp Arg Asn
                165                 170                 175

Asp Trp Phe Thr Cys Lys Ser Phe Gln Gly Asn Asp Gly Lys Gly
            180                 185                 190

Cys Arg Gly Val Asp Asp Ser Pro Ile Asn Ser Cys Tyr Thr Ser Ile
        195                 200                 205

Ala Gly Gly Tyr Thr Val Ser Ser Lys Ile Lys Ile Pro Asp Tyr Val
            210                 215                 220

Ser Glu His Thr Leu Leu Ser Phe Lys Trp Asn Ser Phe Gln Thr Pro
225                 230                 235                 240

Gln Val Tyr Leu Thr Cys Ala Asp Ile Ala Ile Lys Ala
                245                 250
```

```
                245                 250

<210> SEQ ID NO 133
<211> LENGTH: 377
<212> TYPE: PRT
<213> ORGANISM: Myrothecium sp.

<400> SEQUENCE: 133

Met Lys Thr Thr Thr Ile Val Pro Phe Leu Ser Leu Val Ser Gln Val
1               5                   10                  15

Val Gly His Gly Tyr Met Val Ile Pro Ser Ser Arg Thr Arg Leu Gly
            20                  25                  30

Ala Glu Ala Lys Leu Asp Ser Cys Pro Glu Cys Thr Ile Leu Glu Pro
        35                  40                  45

Val Ser Ala Trp Pro Asp Leu Asp Val Ala Gln Val Gly Arg Ser Gly
    50                  55                  60

Pro Cys Gly Tyr Asn Ala Arg Val Ser Ile Asp Tyr Asn Arg Pro Ser
65                  70                  75                  80

Ala Asn Trp Gly Thr Lys Pro Val Ala Thr Tyr Thr Pro Gly Gln Thr
                85                  90                  95

Val Asp Val Gln Trp Cys Val Asp Asn Asn Gly Asp His Gly Gly Met
            100                 105                 110

Phe Ser Trp Arg Val Cys His Asp Gln Ala Ile Val Asp Lys Leu Leu
        115                 120                 125

Asp Pro Asp Arg Thr Pro Thr Asp Ala Glu Lys Gln Ala Ala Glu Asp
    130                 135                 140

Cys Phe Glu Ala Gly Leu Leu Pro Cys Thr Asp Val Ser Gly Gln Ser
145                 150                 155                 160

Cys Gly Tyr Ser Pro Asp Cys Thr Gln Gly Gln Ala Cys Trp Arg Asn
                165                 170                 175

Asp Trp Phe Thr Cys Asn Ala Phe Ser Gly Asp Ser Gly Lys Arg Gly
            180                 185                 190

Cys Gln Gly Val Asp Gly Ser Ala Leu Gly Ser Cys Tyr Thr Ser Ile
        195                 200                 205

Ala Gly Gly Tyr Thr Val Thr Lys Lys Val Lys Met Pro Glu Ile Val
    210                 215                 220

Ser Asn His Thr Leu Leu Ser Leu Arg Trp Asn Ser Phe Gln Thr Gly
225                 230                 235                 240

Gln Val Tyr Leu Thr Cys Ala Asp Ile Ala Ile Thr Asp Ser Gly Ser
                245                 250                 255

Gly Gly Thr Pro Thr Asn Pro Asn Pro Pro Thr Thr Thr Thr Cys Ala
            260                 265                 270

Ala Gly Ala Ser Val Lys Val Thr Phe Asn Glu Gln Val Lys Thr Val
        275                 280                 285

Val Gly Asp Ser Val Arg Leu Val Gly Ser Thr Ala Gln Leu Gly Ser
    290                 295                 300

Trp Asp Ala Thr Lys Gly Val Ala Leu Ser Ala Asp Lys Tyr Thr Asp
305                 310                 315                 320

Ala Lys Pro Leu Trp Ser Ala Thr Val Glu Met Ala Pro Gly Thr Gln
                325                 330                 335

Phe Ser Tyr Lys Phe Val Lys Val Ala Ser Gly Gly Ala Val Thr Trp
            340                 345                 350

Glu Ser Asp Pro Asn Arg Ala Tyr Thr Val Pro Thr Asp Cys Ser Lys
        355                 360                 365
```

```
Ala Tyr Thr Leu Glu Ser Thr Trp Lys
    370                 375

<210> SEQ ID NO 134
<211> LENGTH: 388
<212> TYPE: PRT
<213> ORGANISM: Paraphoma sp.

<400> SEQUENCE: 134

Met Arg Ser Ser Val Ala Phe Leu Ser Ala Phe Val Ala Ser Val Gln
1               5                   10                  15

Ala His Gly Tyr Leu Ser Ser Pro Met Ser Arg Thr Gly Leu Asn Ala
            20                  25                  30

Gln Ala Gly Ala Asp Thr Cys Pro Glu Cys Thr Ile Leu Glu Pro Val
        35                  40                  45

Thr Ala Trp Pro Asp Leu Asp Ser Ala Ala Val Gly Arg Ser Gly Pro
    50                  55                  60

Cys Gly Tyr Asn Ala Arg Val Ser Val Asp Tyr Asn Gln Pro Gly Pro
65                  70                  75                  80

Arg Trp Gly Ser Gln Pro Val Ile Thr Tyr Thr Ala Gly Asp Thr Val
                85                  90                  95

Asp Val Gln Trp Cys Val Asp Asn Asn Gly Asp His Gly Gly Met Phe
            100                 105                 110

Ala Tyr Arg Ile Cys Gln Asn Gln Ala Leu Val Asp Lys Leu Leu Thr
        115                 120                 125

Pro Gly Tyr Leu Pro Thr Asp Ala Glu Lys Gln Ala Ala Glu Asp Cys
    130                 135                 140

Phe Glu Ala Gly Thr Leu Lys Cys Thr Asp Val Asn Gly Gln Ser Cys
145                 150                 155                 160

Gly Phe Asn Pro Asp Cys Gln Gln Gly Gln Ala Cys Trp Arg Asn Asp
                165                 170                 175

Trp Phe Thr Cys Gly Gly Phe Gln Glu Gly Thr Lys Cys Arg Gly Val
            180                 185                 190

Asp Asn Ala Pro Ile Asn Ser Cys Tyr Thr Ser Ile Ala Gly Gly Tyr
        195                 200                 205

Thr Val Thr Lys Arg Ile Lys Ile Pro Asn Tyr Ala Ser Asn His Thr
    210                 215                 220

Leu Leu Ser Leu Lys Trp Asn Ser Phe Gln Thr Pro Gln Ile Tyr Leu
225                 230                 235                 240

Thr Cys Ala Asp Ile Lys Ile Asn Gly Ala Gly Gly Thr Thr Pro Asn
                245                 250                 255

Pro Pro Thr Ser Ser Arg Pro Ala Thr Ser Thr Thr Thr Thr Ser Ala
            260                 265                 270

Thr Ser Ser Ala Val Ala Thr Gly Cys Ala Thr Pro Ala Ala Thr Val
        275                 280                 285

Ala Val Thr Phe Asn Ser Lys Thr Thr Val Val Gly Gln Thr Ile
    290                 295                 300

Lys Ile Ala Gly Ser Ile Ser Gln Leu Gly Ser Trp Asn Thr Ala Asn
305                 310                 315                 320

Ala Pro Ala Leu Ser Ala Ser Ala Tyr Thr Ser Ser Asn Pro Leu Trp
                325                 330                 335

Ser Thr Thr Ile Asn Leu Pro Ala Gly Thr Ser Phe Glu Tyr Lys Phe
            340                 345                 350

Ile Lys Val Glu Ser Ser Gly Thr Val Thr Tyr Glu Ser Gly Ala Asn
        355                 360                 365
```

Arg Ala Tyr Thr Val Pro Arg Asp Cys Thr Gly Lys Ala Thr Val Asp
370                 375                 380

Thr Gln Trp Lys
385

<210> SEQ ID NO 135
<211> LENGTH: 391
<212> TYPE: PRT
<213> ORGANISM: Penicillium antarcticum

<400> SEQUENCE: 135

Met Lys Thr Thr Ser Val Leu Ala Leu Ala Gly Leu Leu Thr Ser Val
1               5                   10                  15

Asn Ala His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
        35                  40                  45

Val Thr Ala Trp Pro Asp Val Glu Ala Ala Gln Val Gly Arg Ser Gly
    50                  55                  60

Pro Cys Gly Tyr Asn Ser Arg Val Ser Val Asp Tyr Asn Gln Pro Gly
65                  70                  75                  80

Asp Tyr Trp Gly Asn Ser Val Val Ala Thr Tyr Thr Ala Asn Asp Ile
                85                  90                  95

Val Glu Val Gln Trp Cys Val Asp Asn Asn Gly Asp His Gly Gly Met
            100                 105                 110

Phe Thr Tyr Gly Val Cys Gln Asn Gln Thr Leu Val Asp Leu Phe Leu
        115                 120                 125

Thr Pro Gly Tyr Leu Pro Thr Thr Ala Glu Lys Gln Ala Ala Glu Asp
    130                 135                 140

Cys Phe Leu Asp Gly Glu Leu Lys Cys Thr Asp Val Asp Gly Gln Ala
145                 150                 155                 160

Cys Gly Tyr Asn Pro Asp Cys Thr Ser Asp Gln Ala Cys Tyr Arg Asn
                165                 170                 175

Asp Trp Phe Thr Cys Asn Ala Phe Ser Ala Asp Ser Asn Arg Gly Cys
            180                 185                 190

Gln Gly Val Asp Gly Ala Ala Leu Asn Ser Cys Lys Thr Thr Ile Ala
        195                 200                 205

Gly Gly Tyr Thr Val Thr Lys Gln Ile Lys Ile Pro Asn Tyr Ser Ser
    210                 215                 220

Asp His Thr Leu Leu Arg Phe Arg Trp Asn Ser Phe Gln Thr Ala Gln
225                 230                 235                 240

Val Tyr Leu His Cys Ala Asp Ile Ala Ile Thr Gly Ser Gly Leu Ala
                245                 250                 255

Ser Thr Ser Thr Thr Thr Ser Thr Lys Ser Thr Thr Thr Thr Ser Ala
            260                 265                 270

Thr Lys Thr Ser Thr Thr Ala Ser Ser Ile Thr Cys Thr Ala Ala Thr
        275                 280                 285

Ser Leu Ala Val Thr Phe Asn Glu Leu Val Thr Thr Tyr Gly Glu
    290                 295                 300

Asn Val Tyr Val Ile Gly Ser Ile Ser Gln Leu Gly Ser Trp Ser Thr
305                 310                 315                 320

Ser Ser Ala Ile Ser Leu Ser Ala Ser Tyr Thr Ser Ser Asn Pro
                325                 330                 335

Leu Trp Thr Ala Thr Ile Ser Leu Pro Val Gly Thr Thr Phe Glu Tyr

```
                340                 345                 350
Lys Phe Ile Lys Lys Asp Ser Asp Gly Ser Ile Val Trp Glu Ser Asp
            355                 360                 365

Pro Asn Arg Ser Tyr Thr Val Pro Thr Gly Cys Ser Gly Ala Thr Ala
        370                 375                 380

Thr Ala Ser Ala Ile Trp Arg
385                 390

<210> SEQ ID NO 136
<211> LENGTH: 387
<212> TYPE: PRT
<213> ORGANISM: Penicillium concentricum

<400> SEQUENCE: 136

Met Lys Ala Ser Ser Ile Leu Thr Trp Ala Gly Leu Leu Ala Ser Val
1               5                   10                  15

Asn Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Ser Pro Trp Pro Asp Leu Glu Gly Pro Gln Val Gly Arg Ser Gly
50                  55                  60

Pro Cys Gly Tyr Asn Ala Arg Val Ser Val Asp Tyr Asn Gln Pro Ser
65                  70                  75                  80

Ala His Trp Gly Asp Val Val Ala Thr Tyr Thr Ala Asn Gln Ile Val
                85                  90                  95

Glu Val Gln Trp Cys Val Asp Asn Gly Asp His Gly Gly Met Phe
            100                 105                 110

Thr Tyr Gly Ile Cys Gln Asp Gln Ala Leu Val Asp Lys Phe Leu Asp
        115                 120                 125

Pro Asp Tyr Leu Pro Thr Asn Ala Glu Lys Gln Ala Ala Glu Asp Cys
    130                 135                 140

Phe Leu Lys Gly Glu Leu Lys Cys Thr Asp Val Ala Gly Gln Asp Cys
145                 150                 155                 160

Gly Tyr Ser Pro Asp Cys Ser Pro Gly Gln Leu Cys Trp Arg Asn Asp
                165                 170                 175

Trp Phe Thr Cys Asn Ala Phe Ser Ala Asp Asn Arg Arg Gly Cys Gln
            180                 185                 190

Gly Val Asp Gly Ala Pro Leu Asn Ser Cys Lys Thr Thr Ile Ala Gly
        195                 200                 205

Gly Tyr Thr Val Thr Lys Lys Ile Lys Ile Pro Asp Tyr Asp Ser Ala
    210                 215                 220

His Thr Leu Leu Arg Phe Arg Trp Asn Ser Phe Gln Thr Gly Gln Ala
225                 230                 235                 240

Tyr Leu His Cys Ala Asp Ile Ser Ile Gly Gly Gly Ser Gly Gly Gly
                245                 250                 255

Pro Thr Thr Thr Asn Thr Ala Thr Thr Leu Thr Thr Thr Thr Thr Lys
            260                 265                 270

Thr Thr Thr Thr Gly Ala Cys Ala Thr Pro Ala Thr Ser Val Ser Val
        275                 280                 285

Thr Phe Asn Glu Leu Val Thr Thr Tyr Gly Gln Asn Ile Phe Leu
    290                 295                 300

Val Gly Ser Ile Ser Gln Leu Gly Ser Trp Ser Thr Ser Ser Ala Ile
305                 310                 315                 320
```

```
Ala Leu Ser Ala Gly Ser Tyr Thr Ser Ser Asn Pro Leu Trp Thr Ala
                325                 330                 335

Ser Val Ser Leu Pro Val Gly Thr Thr Phe Thr Tyr Lys Phe Phe Lys
            340                 345                 350

Lys Gly Ala Asp Gly Ser Ile Thr Trp Glu Ser Asp Pro Asn Arg Ser
        355                 360                 365

Tyr Thr Val Pro Ala Ala Cys Ala Gly Thr Ala Val Thr Glu Ser Thr
    370                 375                 380

Thr Trp Arg
385

<210> SEQ ID NO 137
<211> LENGTH: 397
<212> TYPE: PRT
<213> ORGANISM: Penicillium hoeksii

<400> SEQUENCE: 137

Met Lys Ala Val Thr Ile Leu Thr Leu Ala Ser Leu Leu Ser Ser Val
1               5                   10                  15

Ser Gly His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
        35                  40                  45

Val Ala Ala Trp Pro Asp Leu Glu Glu Ala Gln Val Gly Arg Ser Gly
    50                  55                  60

Pro Cys Gly Tyr Asn Ala Arg Val Ser Val Asp Tyr Asn Gln Pro Ser
65                  70                  75                  80

Asp Tyr Trp Gly Asn Ser Val Val Ala Thr Tyr Thr Ala Asp Glu Ile
                85                  90                  95

Val Glu Val Gln Trp Cys Val Asp Asn Gly Asp His Gly Gly Met
            100                 105                 110

Phe Thr Tyr Gly Ile Cys Gln Asn Gln Thr Leu Val Asp Leu Phe Leu
        115                 120                 125

Asp Pro Asp Tyr Leu Pro Thr Thr Asp Glu Lys Gln Ala Ala Glu Asp
    130                 135                 140

Cys Phe Leu Glu Gly Glu Leu Lys Cys Thr Asp Val Ser Gly Gln Thr
145                 150                 155                 160

Cys Gly Tyr Asn Pro Asp Cys Thr Ser Asp Glu Ala Cys Tyr Arg Asn
                165                 170                 175

Asp Trp Phe Thr Cys Asn Ala Phe Asn Ala Asp Thr Asn Arg Ala Cys
            180                 185                 190

Gln Gly Val Asp Gly Ala Ala Glu Tyr Ser Cys Thr Thr Ile Ser
        195                 200                 205

Gly Gly Tyr Thr Val Thr Lys Lys Ile Lys Ile Pro Asp Tyr Asp Ser
    210                 215                 220

Asp His Thr Leu Leu Arg Leu Arg Trp Asn Ser Tyr Gln Thr Thr Gln
225                 230                 235                 240

Val Tyr Leu His Cys Ala Asp Ile Ala Ile Ser Gly Ser Gly Ser Ser
                245                 250                 255

Ser Ser Ser Ser Ser Ser Ser Ser Thr Ser Ser Thr Lys
            260                 265                 270

Ala Ser Thr Thr Leu Thr Thr Thr Thr Ser Ala Thr Ser Thr Ala
        275                 280                 285

Thr Cys Thr Ala Ala Thr Thr Ile Ala Val Thr Phe Asn Glu Leu Val
    290                 295                 300
```

```
Thr Thr Thr Tyr Gly Glu Asn Val Phe Ile Ala Gly Ser Ile Ser Gln
305                 310                 315                 320

Leu Gly Ser Trp Ser Thr Ser Ser Ala Ile Ala Leu Ser Ala Ser Ser
                325                 330                 335

Tyr Thr Ser Asn Pro Leu Trp Thr Thr Ile Ser Leu Pro Val
                340                 345                 350

Gly Thr Thr Phe Glu Tyr Lys Phe Ile Lys Lys Glu Thr Asn Gly Ser
                355                 360                 365

Ile Val Trp Glu Ser Asp Pro Asn Arg Ser Tyr Thr Val Pro Thr Gly
        370                 375                 380

Cys Ser Gly Ala Thr Ala Thr Ala Thr Ser Thr Trp Arg
385                 390                 395
```

<210> SEQ ID NO 138
<211> LENGTH: 400
<212> TYPE: PRT
<213> ORGANISM: Penicillium paxilli

<400> SEQUENCE: 138

```
Met Asn Thr Ala Leu Leu Leu Ala Leu Phe Gly Thr Ser Ser Leu Val
1               5                   10                  15

Asp Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Ala Ala Trp Pro Asp Leu Glu Ala Ala Gln Val Gly Arg Ser Gly
50                  55                  60

Pro Cys Gly Tyr Asn Ala Arg Val Ser Val Asp Tyr Asn Lys Pro Gly
65                  70                  75                  80

Asp Tyr Trp Gly Asn Ser Val Val Ala Thr Tyr Thr Gly Gly Asp Ile
                85                  90                  95

Val Glu Val Glu Trp Cys Val Asp Asn Gly Asp His Gly Gly Met
                100                 105                 110

Phe Thr Tyr Gly Ile Cys Gln Asn Gln Thr Leu Val Asp Leu Phe Leu
            115                 120                 125

Asp Pro Asp Tyr Leu Pro Ser Thr Asp Glu Lys Gln Ala Ala Glu Asp
130                 135                 140

Cys Phe Leu Asp Gly Glu Leu Lys Cys Thr Asp Val Asp Gly Gln Thr
145                 150                 155                 160

Cys Gly Tyr Asn Pro Asp Cys Ser Ser Asp Glu Ala Cys Tyr Arg Asn
                165                 170                 175

Asp Trp Phe Thr Cys Asn Ala Phe Ser Ala Asp Thr Asn Arg Ala Cys
            180                 185                 190

Gln Gly Val Asp Gly Ala Ala Leu Asn Ser Cys Thr Thr Ile Ala
        195                 200                 205

Gly Gly Tyr Thr Val Thr Lys Lys Ile Lys Ile Pro Asp Tyr Ser Ser
        210                 215                 220

Asp His Thr Leu Leu Arg Phe Arg Trp Asn Ser Tyr Gln Thr Glu Gln
225                 230                 235                 240

Val Tyr Leu His Cys Ala Asp Ile Ala Ile Ser Gly Ser Gly Ser Gly
                245                 250                 255

Ser Ser Ser Ser Ser Ser Ser Ser Ser Arg Thr Ser Thr Ser Thr
                260                 265                 270

Ser Ser Ala Ser Ser Thr Thr Lys Thr Thr Thr Thr Ser Ala Thr Thr
```

```
                   275                 280                 285
Thr Thr Ser Thr Cys Ala Ala Ala Ser Ser Ile Ser Val Gln Phe Asn
    290                 295                 300

Glu Leu Val Thr Thr Thr Tyr Gly Glu Asn Ile Tyr Ile Ser Gly Ser
305                 310                 315                 320

Ile Ser Gln Leu Gly Ser Trp Asp Thr Ser Ala Ile Ala Leu Ser
                325                 330                 335

Ser Ser Ser Tyr Thr Thr Ser Asn Pro Leu Trp Thr Thr Ile Ser
            340                 345                 350

Leu Pro Val Gly Thr Ser Phe Glu Tyr Lys Phe Ile Lys Lys Glu Ser
                355                 360                 365

Asp Gly Ser Val Val Trp Glu Ser Asp Pro Asn Arg Ser Tyr Thr Val
370                 375                 380

Pro Thr Gly Cys Ser Gly Ala Thr Ser Thr Val Thr Ala Ser Trp Gln
385                 390                 395                 400

<210> SEQ ID NO 139
<211> LENGTH: 390
<212> TYPE: PRT
<213> ORGANISM: Penicillium roseopurpureum

<400> SEQUENCE: 139

Met Lys Ser Thr Thr Ile Ile Ser Leu Ala Gly Leu Val Thr Trp Val
1               5                   10                  15

Asp Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Thr Ala Trp Pro Asp Leu Glu Glu Ala Gln Val Gly Arg Ser Gly
    50                  55                  60

Pro Cys Gly Tyr Asn Ala Arg Val Ser Val Asp Tyr Asn Gln Pro Gly
65                  70                  75                  80

Asp Tyr Trp Gly Asn Ser Val Val Ala Ser Tyr Thr Ala Asp Glu Ile
                85                  90                  95

Val Glu Val Gln Trp Cys Val Asp Asn Gly Asp His Gly Gly Met
            100                 105                 110

Phe Thr Tyr Gly Ile Cys Gln Asn Gln Thr Leu Val Asp Leu Phe Leu
        115                 120                 125

Thr Pro Gly Tyr Leu Pro Thr Thr Glu Glu Lys Gln Ala Ala Glu Asp
    130                 135                 140

Cys Phe Leu Asp Gly Glu Leu Lys Cys Thr Asp Val Asp Gly Gln Asn
145                 150                 155                 160

Cys Gly Tyr Ser Pro Asp Cys Thr Ser Asp Glu Ala Cys Tyr Arg Asn
                165                 170                 175

Asp Trp Phe Thr Cys Asn Ala Phe Ser Ala Ser Thr Asn Arg Gly Cys
            180                 185                 190

Gln Gly Val Asp Gly Ala Ala Leu Gly Ser Cys Ala Thr Thr Ile Ala
        195                 200                 205

Gly Gly Tyr Thr Val Thr Lys Lys Ile Lys Ile Pro Asn Tyr Gln Ser
    210                 215                 220

Asp His Thr Leu Leu Arg Phe Arg Trp Asn Ser Tyr Gln Thr Ala Gln
225                 230                 235                 240

Val Tyr Leu His Cys Ala Asp Ile Ala Ile Ala Gly Ser Gly Ser Gly
                245                 250                 255
```

```
Ser Ser Ser Ser Ser Thr Thr Thr Ser Lys Ser Ser Thr Ser Lys
            260                 265                 270

Thr Ile Met Thr Thr Ala Thr Thr Ala Thr Cys Thr Ala Ala Met Ser
        275                 280                 285

Leu Ser Val Val Phe Asn Glu Leu Ala Thr Thr Tyr Gly Glu Asn
    290                 295                 300

Ile Tyr Leu Val Gly Ser Ile Ser Gln Leu Gly Ser Trp Asp Thr Ser
305                 310                 315                 320

Ser Ala Ile Ala Leu Ser Ala Ser Ser Tyr Thr Thr Ser Asn Pro Leu
                325                 330                 335

Trp Thr Gly Thr Val Thr Leu Pro Val Gly Thr Ser Phe Glu Tyr Lys
            340                 345                 350

Phe Ile Lys Lys Glu Thr Asp Gly Ser Ile Thr Trp Glu Ser Asp Pro
            355                 360                 365

Asp Arg Ser Tyr Thr Val Pro Ser Gly Cys Ser Gly Ala Thr Ala Thr
            370                 375                 380

Val Thr Ala Thr Trp Arg
385                 390

<210> SEQ ID NO 140
<211> LENGTH: 389
<212> TYPE: PRT
<213> ORGANISM: Penicillium samsonianum

<400> SEQUENCE: 140

Met Lys Ala Val Ser Ile Leu Thr Leu Ala Gly Leu Leu Ser Ser Val
1               5                   10                  15

Asn Ala His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
        35                  40                  45

Val Thr Ala Trp Pro Asp Leu Glu Gly Pro Gln Val Gly Arg Ser Gly
    50                  55                  60

Pro Cys Gly Tyr Asn Ala Arg Val Ser Val Asp Tyr Asn Gln Pro Gly
65                  70                  75                  80

Ala His Trp Gly Asn Ser Val Val Ala Thr Tyr Ala Asn Gln Ile
                85                  90                  95

Val Glu Val Gln Trp Cys Val Asp His Asn Gly Asp His Gly Gly Met
            100                 105                 110

Phe Thr Tyr Gly Ile Cys Gln Asn Gln Thr Leu Val Asp Leu Phe Leu
        115                 120                 125

Asp Pro Asn Tyr Leu Pro Thr Asn Ala Glu Lys Gln Ala Ala Glu Asp
    130                 135                 140

Cys Phe Leu Glu Gly Glu Leu Lys Cys Thr Asp Val Pro Gly Gln Thr
145                 150                 155                 160

Cys Gly Tyr Ser Pro Asp Cys Thr Ser Asp Gln Pro Cys Trp Arg Asn
                165                 170                 175

Asp Trp Phe Thr Cys Asn Ala Phe Asn Ala Asp Ser Asn Arg Gly Cys
            180                 185                 190

Gln Gly Val Asp Gly Ala Pro Leu Asn Ser Cys Lys Thr Thr Ile Ala
        195                 200                 205

Gly Gly Tyr Thr Val Thr Lys Lys Ile Lys Ile Pro Glu Tyr Asp Ser
    210                 215                 220

Ala His Thr Leu Leu Arg Phe Arg Trp Asn Ser Phe Gln Thr Ala Gln
225                 230                 235                 240
```

Ala Tyr Leu His Cys Ala Asp Ile Ala Ile Gly Gly Thr Gly Ser Gly
            245                 250                 255

Ser Thr Ser Ala Thr Ser Ser Thr Ser Lys Thr Ser Thr Ala Thr
            260                 265                 270

Thr Ser Thr Thr Thr Thr Thr Ala Cys Ala Thr Thr Ala Thr Thr Val
            275                 280                 285

Pro Val Thr Phe Lys Glu Leu Val Thr Thr Thr Tyr Gly Gln Asn Val
            290                 295                 300

Phe Val Thr Gly Ser Ile Ser Gln Leu Gly Ser Trp Ser Thr Ser Ser
305                 310                 315                 320

Ala Ile Ala Leu Ser Ala Gly Ser Tyr Thr Thr Ser Asn Pro Leu Trp
            325                 330                 335

Thr Ala Ser Ile Asp Leu Pro Ala Gly Thr Thr Phe Glu Tyr Lys Phe
            340                 345                 350

Phe Lys Lys Gly Ser Asp Gly Ser Ile Thr Trp Glu Ser Asp Pro Asn
            355                 360                 365

Arg Ser Tyr Thr Val Pro Thr Gly Cys Ser Gly Ile Thr Gly Thr Ala
            370                 375                 380

Ser Ala Thr Trp Arg
385

<210> SEQ ID NO 141
<211> LENGTH: 386
<212> TYPE: PRT
<213> ORGANISM: Penicillium sclerotiorum

<400> SEQUENCE: 141

Met Arg Phe Ala Gln Phe Leu Ala Ile Ser Gly Thr Val Thr Gly Val
1               5                   10                  15

Ala Ala His Gly Tyr Leu Thr Ile Pro Ser Ser Arg Thr Arg Leu Gly
            20                  25                  30

Phe Glu Ala Gly Val Asp Thr Cys Pro Glu Cys Ser Ile Leu Glu Pro
            35                  40                  45

Val Glu Ser Trp Pro Asp Leu Glu Ala Ala Gln Val Gly Arg Ser Gly
50                  55                  60

Pro Cys Gly Tyr Asn Ser Arg Val Ser Val Asp Tyr Asn Gln Pro Ser
65                  70                  75                  80

Asp Tyr Trp Gly Asn Ser Val Val Ala Thr Tyr Ala Ala Gly Asp Thr
            85                  90                  95

Ile Glu Val Gln Trp Cys Val Asp Asn Asn Gly Asp His Gly Gly Met
            100                 105                 110

Phe Thr Tyr Gly Ile Cys Gln Asn Gln Thr Leu Val Asp Leu Phe Leu
            115                 120                 125

Asp Pro Asp Tyr Leu Pro Thr Thr Glu Lys Gln Leu Ala Glu Asp
            130                 135                 140

Cys Phe Leu Glu Gly Glu Leu Lys Cys Thr Asp Val Asp Gly Gln Thr
145                 150                 155                 160

Cys Gly Tyr Asn Pro Asp Cys Thr Ser Asp Glu Ala Cys Tyr Arg Asn
            165                 170                 175

Asp Trp Phe Thr Cys Asn Ala Phe Ala Ala Ser Thr Asn Arg Gly Cys
            180                 185                 190

Glu Gly Val Asp Gly Ala Ala Glu Phe Ser Cys Thr Thr Thr Ile Ser
            195                 200                 205

Gly Gly Tyr Thr Val Thr Lys Lys Ile Lys Ile Pro Asn Tyr Glu Ser

```
            210                 215                 220
Asp His Thr Leu Leu Arg Phe Arg Trp Asn Ser Tyr Gln Thr Gly Gln
225                 230                 235                 240

Val Tyr Leu His Cys Ala Asp Ile Ala Ile Ala Glu Ser Gly Ser Gly
                245                 250                 255

Ser Gly Ala Ser Ser Thr Ile Ser Thr Thr Ala Thr Thr Thr Thr Thr
            260                 265                 270

Ala Thr Thr Thr Ser Thr Cys Ser Ala Ala Ser Val Ser Val Thr
        275                 280                 285

Phe Thr Glu Leu Val Thr Thr Thr Tyr Gly Glu Asn Val Phe Ile Val
    290                 295                 300

Gly Ser Ile Thr Gln Leu Gly Ser Trp Asp Thr Ser Ser Ala Val Ala
305                 310                 315                 320

Leu Ser Ala Ser Ser Tyr Thr Ser Ser Asn Pro Leu Trp Lys Thr Thr
                325                 330                 335

Ile Ser Leu Pro Ala Gly Thr Ser Phe Glu Tyr Lys Phe Ile Lys Lys
                340                 345                 350

Glu Ser Asp Gly Ser Ile Val Trp Glu Asp Pro Asn Arg Thr Phe
            355                 360                 365

Thr Val Pro Thr Gly Cys Ser Gly Ala Thr Ala Thr Glu Ser Ala Thr
370                 375                 380

Trp Lys
385

<210> SEQ ID NO 142
<211> LENGTH: 392
<212> TYPE: PRT
<213> ORGANISM: Penicillium sp-52627

<400> SEQUENCE: 142

Met Lys Phe Thr Cys Leu Leu Ala Leu Ala Gly Thr Leu Ala Thr Val
1               5                   10                  15

Asp Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Glu Ser Trp Pro Asp Leu Glu Ala Ala Gln Val Gly Arg Ser Gly
    50                  55                  60

Pro Cys Gly Tyr Asn Ala Arg Val Ser Val Asp Tyr Asn Gln Pro Gly
65                  70                  75                  80

Asp Tyr Trp Gly Asn Ser Val Val Ala Thr Tyr Thr Gly Gly Asp Thr
                85                  90                  95

Val Glu Val Gln Trp Cys Val Asp Asn Gly Asp His Gly Gly Met
            100                 105                 110

Phe Thr Tyr Gly Ile Cys Gln Asn Gln Thr Leu Val Asp Leu Phe Leu
        115                 120                 125

Asp Pro Asp Tyr Leu Pro Ser Thr Asp Glu Lys Gln Leu Ala Glu Asp
    130                 135                 140

Cys Phe Leu Glu Gly Glu Leu Lys Cys Thr Asp Val Asp Gly Gln Thr
145                 150                 155                 160

Cys Gly Tyr Asn Pro Asp Cys Thr Ser Asp Glu Ala Cys Tyr Arg Asn
                165                 170                 175

Asp Trp Phe Thr Cys Asn Ala Phe Ala Ala Thr Thr Asn Arg Gly Cys
            180                 185                 190
```

```
Glu Gly Val Asp Gly Ala Ala Glu Tyr Ser Cys Thr Thr Thr Ile Ser
            195                 200                 205

Gly Gly Tyr Thr Val Thr Lys Lys Ile Lys Ile Pro Asp Tyr Glu Ser
    210                 215                 220

Asp His Thr Leu Leu Arg Phe Arg Trp Asn Ser Tyr Gln Thr Gly Gln
225                 230                 235                 240

Ile Tyr Leu His Cys Ala Asp Ile Ala Ile Ser Gly Ser Gly Ser Gly
                245                 250                 255

Ser Asp Ser Ser Thr Thr Ser Ser Thr Ala Thr Thr Ser Lys Ala
            260                 265                 270

Thr Ser Thr Thr Ser Thr Ala Thr Thr Thr Ser Thr Cys Thr Ala Ala
            275                 280                 285

Thr Ser Ile Ser Val Thr Phe Asp Glu Leu Val Thr Thr Tyr Gly
            290                 295                 300

Glu Asn Val Tyr Ile Ser Gly Ser Ile Ser Gln Leu Gly Ser Trp Asp
305                 310                 315                 320

Thr Ser Ser Ala Val Ala Leu Ser Ala Ser Ser Tyr Thr Ser Ser Asn
                325                 330                 335

Pro Leu Trp Met Ala Thr Ile Ser Leu Pro Val Gly Thr Ser Phe Glu
            340                 345                 350

Tyr Lys Phe Ile Lys Lys Glu Thr Asp Gly Ser Ile Val Trp Glu Ser
            355                 360                 365

Asp Pro Asn Arg Ser Tyr Thr Val Pro Thr Gly Cys Ser Gly Ala Thr
    370                 375                 380

Ala Thr Val Ser Ala Thr Trp Arg
385                 390

<210> SEQ ID NO 143
<211> LENGTH: 395
<212> TYPE: PRT
<213> ORGANISM: Penicillium sp-54569

<400> SEQUENCE: 143

Met Lys Ala Thr Ser Ile Leu Thr Leu Ala Ser Phe Leu Ser Ser Val
1               5                   10                  15

Asn Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Thr Ala Trp Pro Asp Leu Glu Glu Ala Gln Val Gly Arg Ser Gly
    50                  55                  60

Pro Cys Gly Tyr Asn Ala Arg Val Ser Val Asp Tyr Asn Gln Pro Gly
65                  70                  75                  80

Asp Tyr Trp Gly Asn Ser Val Val Ala Thr Tyr Thr Ala Asp Glu Val
                85                  90                  95

Val Glu Val Gln Trp Cys Val Asp Asn Gly Asp His Gly Gly Met
            100                 105                 110

Phe Thr Tyr Gly Ile Cys Gln Asn Gln Thr Leu Val Asp Leu Phe Leu
            115                 120                 125

Thr Pro Gly Tyr Leu Pro Thr Asp Glu Lys Gln Ala Ala Glu Asp
    130                 135                 140

Cys Phe Leu Glu Gly Glu Leu Lys Cys Thr Asp Val Asp Gly Gln Thr
145                 150                 155                 160

Cys Gly Tyr Asn Pro Asp Cys Thr Ser Asp Glu Ala Cys Tyr Arg Asn
                165                 170                 175
```

```
Asp Trp Phe Thr Cys Asn Ala Phe Asn Ala Asp Ser Asn Arg Ala Cys
            180                 185                 190

Gln Gly Val Asp Gly Ala Ala Glu Gly Ser Cys Thr Thr Ile Ser
            195                 200                 205

Gly Gly Tyr Thr Val Thr Lys Lys Ile Lys Ile Pro Asp Tyr Asp Ser
            210                 215                 220

Asp His Thr Leu Leu Arg Phe Arg Trp Asn Ser Tyr Gln Thr Ala Gln
225                 230                 235                 240

Val Tyr Leu His Cys Ala Asp Ile Ala Ile Ser Gly Ser Gly Ser Gly
                245                 250                 255

Ser Thr Ser Ser Ser Ser Ser Ala Ser Ser Thr Ser Ser Thr Thr
            260                 265                 270

Asn Thr Leu Thr Thr Thr Lys Ser Thr Thr Thr Ser Ser Ala Thr Cys
            275                 280                 285

Thr Ala Ala Thr Thr Ile Ser Val Thr Phe Asn Glu Leu Val Thr Thr
            290                 295                 300

Thr Tyr Gly Glu Asn Ile Phe Ile Ser Gly Ser Ile Ser Gln Leu Ser
305                 310                 315                 320

Ser Trp Ser Thr Ser Ser Ala Ile Ala Leu Ser Ala Ser Ser Tyr Thr
                325                 330                 335

Ser Ser Asn Pro Leu Trp Thr Val Thr Ile Ser Leu Pro Val Gly Ser
            340                 345                 350

Thr Phe Glu Tyr Lys Phe Ile Lys Lys Glu Thr Asp Gly Ser Ile Val
            355                 360                 365

Trp Glu Ser Asp Pro Asn Arg Ser Tyr Thr Val Pro Ala Gly Cys Ser
            370                 375                 380

Gly Ala Thr Ala Thr Ala Thr Ala Thr Trp Arg
385                 390                 395

<210> SEQ ID NO 144
<211> LENGTH: 394
<212> TYPE: PRT
<213> ORGANISM: Penicillium sp-72443

<400> SEQUENCE: 144

Met Lys Ala Ala Phe Ile Ser Thr Leu Gln Cys Leu Leu Thr Leu Val
1               5                   10                  15

Asn Ala His Gly Tyr Leu Thr Ile Pro Ser Ser Arg Thr Arg Leu Gly
                20                  25                  30

Phe Glu Ala Gly Ile Asp Thr Cys Pro Glu Cys Ser Ile Leu Glu Pro
            35                  40                  45

Val Thr Ala Trp Pro Asp Leu Glu Ala Ala Gln Val Gly Arg Ser Gly
            50                  55                  60

Pro Cys Gly Tyr Asn Ala Arg Val Ser Val Asp Tyr Asn Gln Pro Gly
65                  70                  75                  80

Asp Tyr Trp Gly Asn Ser Val Val Ala Thr Tyr Thr Ala Asn Asp Ile
                85                  90                  95

Val Glu Val Gln Trp Cys Val Asp Asn Asn Gly Asp His Gly Gly Met
            100                 105                 110

Phe Thr Tyr Gly Ile Cys Gln Asn Gln Thr Leu Val Asp Leu Phe Leu
            115                 120                 125

Thr Pro Gly Tyr Leu Pro Thr Thr Glu Glu Lys Gln Ala Ala Glu Asp
            130                 135                 140

Cys Phe Leu Glu Gly Glu Leu Lys Cys Thr Asp Val Ser Gly Gln Thr
```

```
                145                 150                 155                 160
        Cys Gly Tyr Asn Pro Asp Cys Thr Ser Asp Gln Ala Cys Tyr Arg Thr
                        165                 170                 175

Asp Trp Phe Thr Cys Asn Ala Phe Asn Asp Thr Asn Arg Ala Cys
                        180                 185                 190

Gln Gly Val Asp Gly Ala Ala Leu Asn Ser Cys Thr Thr Ile Ala
                        195                 200                 205

Gly Gly Tyr Thr Val Thr Lys Lys Ile Lys Ile Pro Asp Tyr Ser Ser
                210                 215                 220

Asp His Thr Leu Leu Arg Phe Arg Trp Asn Ser Tyr Gln Thr Ala Gln
        225                 230                 235                 240

Val Tyr Leu His Cys Ala Asp Ile Ala Ile Ser Gly Ser Gly Ser Gly
                        245                 250                 255

Ser Ser Ser Thr Leu Ser Thr Gly Ser Thr Ser Thr Ala Ala Thr
                        260                 265                 270

Ser Thr Val Thr Lys Thr Ser Thr Thr Ala Ser Thr Thr Cys Ile
                        275                 280                 285

Ser Ala Thr Thr Val Pro Val Val Phe Asp Glu Leu Val Thr Thr Thr
                290                 295                 300

Tyr Gly Glu Asn Ile Tyr Ile Thr Gly Ser Ile Gly Gln Leu Ser Ser
        305                 310                 315                 320

Trp Ser Thr Leu Ser Ala Ile Ala Leu Ser Ala Ser Tyr Thr Ser
                        325                 330                 335

Ser Asn Pro Leu Trp Thr Val Thr Ile Asp Leu Pro Ala Gly Thr Thr
                        340                 345                 350

Phe Glu Tyr Lys Phe Ile Lys Lys Glu Thr Asp Gly Ser Ile Ile Trp
                        355                 360                 365

Glu Ser Asp Pro Asn Arg Ser Tyr Thr Val Pro Thr Gly Cys Ser Gly
                        370                 375                 380

Leu Thr Ala Thr Ala Ser Ala Thr Trp Arg
        385                 390

<210> SEQ ID NO 145
<211> LENGTH: 390
<212> TYPE: PRT
<213> ORGANISM: Penicillium steckii

<400> SEQUENCE: 145

Met Lys Leu Lys Ser Phe Ala Ile Ile Leu Asn Leu Val Thr Trp Ala
        1               5                   10                  15

Asn Ala His Gly Tyr Leu Thr Ile Pro Ser Ser Arg Thr Arg Leu Gly
                        20                  25                  30

Phe Glu Ala Gly Ile Asp Thr Cys Pro Glu Cys Ser Ile Leu Glu Pro
                        35                  40                  45

Val Thr Ala Trp Pro Asp Leu Glu Glu Ala Gln Val Gly Arg Ser Gly
                50                  55                  60

Pro Cys Gly Tyr Asn Ala Arg Val Ser Val Asp Tyr Asn Gln Pro Gly
        65                  70                  75                  80

Asp Tyr Trp Gly Asn Ser Val Val Ala Thr Tyr Thr Ala Gly Asp Ile
                        85                  90                  95

Val Glu Val Gln Trp Cys Val Asp Asn Gly Asp His Gly Gly Met
                        100                 105                 110

Phe Thr Tyr Gly Ile Cys Gln Asn Gln Thr Leu Val Asp Leu Phe Leu
                        115                 120                 125
```

```
Thr Pro Gly Tyr Leu Pro Thr Asn Glu Glu Lys Gln Ala Ala Glu Asp
    130                 135                 140

Cys Phe Leu Asp Gly Glu Leu Lys Cys Thr Asp Val Asp Gly Gln Thr
145                 150                 155                 160

Cys Gly Tyr Asn Pro Asp Cys Ala Ser Asp Glu Ala Cys Tyr Arg Asn
                165                 170                 175

Asp Trp Phe Thr Cys Asn Glu Phe Ser Ala Ser Ser Asn Arg Gly Cys
            180                 185                 190

Gln Gly Val Asp Gly Ala Ala Leu Asn Ser Cys Thr Thr Ile Ala
        195                 200                 205

Gly Gly Tyr Thr Val Thr Lys Lys Ile Lys Ile Pro Asn Tyr Ser Ser
210                 215                 220

Asp His Thr Leu Leu Arg Phe Arg Trp Asn Ser Tyr Gln Thr Ala Gln
225                 230                 235                 240

Val Tyr Leu His Cys Ala Asp Ile Ala Ile Ser Gly Ser Gly Ser Gly
                245                 250                 255

Thr Thr Ser Ser Ser Thr Thr Lys Ser Thr Thr Ser Ala Thr Ser Lys
                260                 265                 270

Thr Ser Thr Thr Thr Ser Gln Ser Thr Thr Thr Cys Thr Ala Ala Thr
            275                 280                 285

Ser Leu Ala Val Thr Phe Thr Glu Leu Val Thr Thr Thr Tyr Gly Glu
        290                 295                 300

Asn Val Tyr Ile Ser Gly Ser Ile Ser Gln Leu Gly Ser Trp Asp Thr
305                 310                 315                 320

Ser Ser Ala Ile Ala Leu Ser Ala Asp Ser Tyr Thr Thr Ser Asn Pro
                325                 330                 335

Leu Trp Lys Thr Thr Leu Asn Leu Pro Val Gly Thr Thr Phe Glu Tyr
            340                 345                 350

Lys Phe Ile Lys Lys Glu Thr Asp Gly Thr Val Val Trp Glu Ser Asp
        355                 360                 365

Pro Asn Arg Ser Tyr Thr Val Pro Ser Gly Cys Ser Gly Ala Thr Ala
    370                 375                 380

Thr Ala Thr Ala Thr Trp
385                 390

<210> SEQ ID NO 146
<211> LENGTH: 389
<212> TYPE: PRT
<213> ORGANISM: Penicillium viticola

<400> SEQUENCE: 146

Met Lys Phe Thr Asn Val Leu Ala Ile Ala Gly Thr Leu Thr Ser Val
1               5                   10                  15

Ala Ala His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
        35                  40                  45

Val Glu Ala Trp Pro Asp Leu Glu Ala Ala Gln Val Gly Arg Ser Gly
    50                  55                  60

Pro Cys Gly Tyr Asn Ser Arg Val Ser Val Asp Tyr Asn Gln Pro Ser
65                  70                  75                  80

Asp Tyr Trp Gly Asn Ser Val Val Ala Thr Tyr Ser Ala Gly Asp Ile
                85                  90                  95

Val Glu Val Gln Trp Cys Val Asp Asn Asn Gly Asp His Gly Gly Met
            100                 105                 110
```

```
Phe Thr Tyr Gly Ile Cys Gln Asn Gln Thr Leu Val Asp Leu Phe Leu
            115                 120                 125

Asp Pro Asp Tyr Leu Pro Thr Thr Ala Glu Lys Gln Leu Ala Glu Asp
    130                 135                 140

Cys Phe Leu Glu Gly Glu Leu Lys Cys Thr Asp Val Asp Gly Gln Thr
145                 150                 155                 160

Cys Gly Tyr Asn Pro Asp Cys Thr Ser Asp Glu Ala Cys Tyr Arg Asn
                165                 170                 175

Asp Trp Phe Thr Cys Asn Ala Phe Ala Ala Thr Thr Asn Arg Gly Cys
            180                 185                 190

Glu Gly Val Asp Gly Ala Ala Glu Phe Ser Cys Thr Thr Thr Ile Ser
            195                 200                 205

Gly Gly Tyr Thr Val Thr Lys Lys Ile Lys Ile Pro Asp Tyr Asp Ser
            210                 215                 220

Asp His Thr Leu Leu Arg Phe Arg Trp Asn Ser Tyr Gln Thr Gly Gln
225                 230                 235                 240

Val Tyr Leu His Cys Ala Asp Ile Ser Ile Gly Ser Gly Ser Gly Thr
                245                 250                 255

Thr Thr Ser Ser Ser Ser Thr Thr Thr Thr Ser Ser Thr Thr Thr Gln
            260                 265                 270

Thr Thr Ala Thr Thr Thr Thr Ser Thr Cys Ser Ala Ala Ala Ser Val
            275                 280                 285

Ser Val Thr Phe Ala Glu Leu Val Thr Thr Thr Tyr Gly Glu Asn Val
            290                 295                 300

Tyr Ile Ala Gly Ser Ile Ser Gln Leu Gly Ser Trp Asp Thr Ser Ser
305                 310                 315                 320

Ala Val Ala Leu Ser Ala Ser Ser Tyr Thr Ser Ser Asn Pro Leu Trp
                325                 330                 335

Gln Ala Thr Ile Ser Leu Pro Val Gly Thr Thr Phe Glu Tyr Lys Phe
            340                 345                 350

Ile Lys Lys Glu Ser Asp Gly Ser Ile Val Trp Glu Ser Asp Pro Asn
            355                 360                 365

Arg Ser Tyr Thr Val Pro Thr Gly Cys Ser Gly Ala Thr Ala Thr Val
            370                 375                 380

Ser Gly Thr Trp Arg
385

<210> SEQ ID NO 147
<211> LENGTH: 397
<212> TYPE: PRT
<213> ORGANISM: Penicillium vulpinum

<400> SEQUENCE: 147

Met Lys Thr Ser Ser Ile Leu Thr Leu Ala Gly Leu Leu Ala Thr Val
1               5                   10                  15

Asn Ala His Gly Tyr Leu Thr Ile Pro Ser Ser Arg Thr Arg Leu Gly
            20                  25                  30

Phe Glu Ala Gly Ile Asp Thr Cys Pro Glu Cys Ser Ile Leu Glu Pro
            35                  40                  45

Val Ala Ala Trp Pro Asp Leu Glu Ala Ala Gln Val Gly Arg Ser Gly
            50                  55                  60

Pro Cys Gly Tyr Asn Ala Arg Val Ser Val Asp Tyr Asn Gln Pro Ser
65                  70                  75                  80

Ala His Trp Gly Asn Ser Val Val Ala Thr Tyr Thr Ala Asn Asp Ile
```

-continued

```
                85                  90                  95
Val Glu Val Gln Trp Cys Val Asp Asn Asn Gly Asp His Gly Gly Met
            100                 105                 110
Phe Thr Tyr Gly Ile Cys Gln Asn Gln Thr Leu Val Asp Leu Phe Leu
            115                 120                 125
Asp Pro Asn Tyr Leu Pro Thr Asn Ala Glu Lys Gln Ala Ala Glu Asp
            130                 135                 140
Cys Phe Leu Asp Gly Glu Leu Lys Cys Thr Asp Val Thr Gly Gln Thr
145                 150                 155                 160
Cys Gly Tyr Ser Pro Asp Cys Thr Ser Asp Gln Pro Cys Trp Arg Asn
                165                 170                 175
Asp Trp Phe Thr Cys Asn Lys Phe Ser Ala Asp Thr Asn Arg Gly Cys
            180                 185                 190
Gln Gly Val Asp Gly Ala Pro Leu Asn Ser Cys Lys Thr Thr Ile Ala
            195                 200                 205
Gly Gly Tyr Thr Val Thr Lys Lys Ile Lys Ile Pro Asp Tyr Asn Ser
            210                 215                 220
Ala His Thr Leu Leu Arg Phe Arg Trp Asn Ser Phe Gln Thr Ala Gln
225                 230                 235                 240
Ala Tyr Leu His Cys Ala Asp Ile Ala Ile Gly Gly Ser Gly Gly Pro
                245                 250                 255
Gly Ser Thr Ser Thr Lys Thr Thr Ala Thr Thr Leu Thr Ala Thr Thr
            260                 265                 270
Ser Lys Thr Thr Thr Ser Thr Thr Thr Thr Thr Thr Thr Thr Thr Thr
            275                 280                 285
Thr Ala Cys Ala Thr Thr Ala Val Pro Val Ala Phe Asn Glu Leu Val
290                 295                 300
Thr Thr Ala Tyr Gly Gln Asn Ile Phe Leu Thr Gly Ser Ile Ser Gln
305                 310                 315                 320
Leu Ser Ser Trp Ser Thr Thr Ser Ala Ile Ala Leu Ser Ala Ser Ser
                325                 330                 335
Tyr Thr Ser Ser Asn Pro Leu Trp Thr Thr Ser Leu Thr Leu Pro Ala
            340                 345                 350
Gly Thr Thr Phe Glu Tyr Lys Phe Phe Arg Lys Asn Thr Asp Gly Ser
            355                 360                 365
Ile Thr Trp Glu Ser Asp Pro Asn Arg Ser Tyr Thr Val Pro Ser Gly
            370                 375                 380
Cys Ser Gly Thr Ala Ala Thr Ala Gly Gly Ser Trp Arg
385                 390                 395

<210> SEQ ID NO 148
<211> LENGTH: 393
<212> TYPE: PRT
<213> ORGANISM: Pestalotiopsis sp-71627

<400> SEQUENCE: 148

Met Phe Ala Leu Pro Ala Leu Leu Phe Ala Ala Ser Val Ser Gly His
1               5                   10                  15
Gly Tyr Leu Thr Ile Pro Ser Ser Arg Thr Arg Leu Gly Phe Glu Ala
            20                  25                  30
Gly Thr Asp Thr Cys Pro Glu Cys Thr Ile Leu Glu Pro Val Ser Ser
            35                  40                  45
Trp Pro Asp Leu Asp Val Ala Ala Val Gly Arg Ser Gly Val Cys Gly
        50                  55                  60
```

-continued

```
Tyr Asn Ala Arg Val Ser Val Asp Tyr Asn Phe Pro Ala Ser Thr Trp
 65                  70                  75                  80

Gly Ser Asn Thr Val Ala Thr Tyr Ser Pro Gly Gln Ile Val Asp Val
                 85                  90                  95

Gln Trp Cys Val Asp Asn Asn Gly Asp His Gly Gly Met Phe Ser Tyr
            100                 105                 110

Arg Ile Cys Gln Asp Gln Ser Val Val Asp Lys Phe Leu Thr Pro Gly
        115                 120                 125

Tyr Ile Pro Thr Asp Ala Glu Lys Gln Ala Gly Glu Asp Cys Phe Asp
    130                 135                 140

Ala Gly Leu Leu Pro Cys Thr Asp Val Ser Gly Gln Val Cys Asp Tyr
145                 150                 155                 160

Ser Pro Asp Cys Thr Ala Gly Gln Ala Cys Tyr Arg Asn Asp Trp Phe
                165                 170                 175

Thr Cys Asn Ala Phe Gly Ala Thr Asp Arg Arg Gly Cys Glu Gly Val
            180                 185                 190

Asp Asn Ala Pro Leu Asn Ser Cys Lys Thr Thr Ile Ala Gly Gly Tyr
        195                 200                 205

Thr Val Ser Lys Gln Ile Lys Ile Pro Asp Tyr Val Ser Asn His Thr
    210                 215                 220

Leu Leu Gln Phe Lys Trp Asn Ser Phe Gln Thr Gly Gln Ile Tyr Ile
225                 230                 235                 240

Ser Cys Ala Asp Ile Ala Ile Ser Gly Ser Gly Ser Ser Pro Ala Pro
                245                 250                 255

Ala Pro Gly Thr Thr Leu Thr Thr Ser Lys Thr Thr Ala Thr Thr Thr
            260                 265                 270

Ser Thr Lys Thr Thr Thr Ser Ala Ala Ser Thr Ser Thr Ala Thr Cys
        275                 280                 285

Val Ala Ala Asn Val Ala Val Thr Phe Asn Glu Val Val Thr Thr
    290                 295                 300

Ala Tyr Gly Glu Thr Ile Lys Ile Ala Gly Ser Ile Ala Ala Leu Gly
305                 310                 315                 320

Ser Trp Asp Pro Ser Ser Ala Pro Ala Leu Ser Ala Ser Ala Tyr Thr
                325                 330                 335

Thr Ala Asn Pro Leu Trp Ser Arg Thr Val Ser Leu Pro Ala Gly Thr
            340                 345                 350

Ala Phe Glu Tyr Lys Phe Val Arg Val Ser Ala Ser Gly Ala Ile Thr
        355                 360                 365

Trp Glu Ser Asp Pro Asn Arg Ser Tyr Thr Val Pro Thr Cys Gly Ser
    370                 375                 380

Thr Ala Thr Val Gly Thr Ser Trp Lys
385                 390
```

<210> SEQ ID NO 149
<211> LENGTH: 382
<212> TYPE: PRT
<213> ORGANISM: Setophaeosphaeria sp. NN051506

<400> SEQUENCE: 149

```
Met Arg Ser Ala Ile Gly Lys Val Ile Ala Phe Val Ala Ser Val Asn
  1               5                  10                  15

Ala His Gly Tyr Leu Thr Ser Pro Met Ser Arg Thr Gly Leu Asn Ala
             20                  25                  30

Gln Ser Gly Ala Asp Thr Cys Pro Glu Cys Thr Ile Leu Glu Pro Val
         35                  40                  45
```

Thr Ala Trp Pro Asp Leu Asp Ser Ala Gln Val Gly Arg Ser Gly Pro
    50                  55                  60

Cys Gly Tyr Asn Ala Arg Val Ser Val Asp Tyr Asn Gln Pro Gly Pro
65                  70                  75                  80

Arg Trp Gly Ser Ala Pro Val Ile Thr Tyr Thr Ala Gly Asp Val Val
                85                  90                  95

Asp Val Gln Trp Cys Val Asp Asn Gly Asp His Gly Gly Met Phe
                100                 105                 110

Thr Tyr Arg Ile Cys Gln Asp Gln Ala Leu Val Asp Lys Leu Ile Thr
            115                 120                 125

Pro Gly Tyr Leu Pro Thr Asp Ala Glu Lys Gln Ala Ala Glu Asp Cys
        130                 135                 140

Phe Glu Arg Gly Leu Leu Lys Cys Thr Asp Val Ser Gly Gln Thr Cys
145                 150                 155                 160

Gly Tyr Asn Pro Asp Cys Gln Ser Gly Gln Ala Cys Trp Arg Asn Asp
                165                 170                 175

Trp Phe Thr Cys Lys Gly Phe Asn Glu Gly Ser Lys Cys Lys Gly Val
            180                 185                 190

Asp Gly Ala Pro Leu Asn Ser Cys Tyr Thr Ser Ile Ala Gly Gly Tyr
        195                 200                 205

Thr Val Ser Ser Lys Ile Lys Ile Pro Asn Tyr Ser Ser Asn His Thr
    210                 215                 220

Leu Leu Ser Phe Lys Trp Asn Ser Phe Gln Thr Pro Gln Val Tyr Leu
225                 230                 235                 240

Thr Cys Ala Asp Ile Lys Ile Val Gly Ser Gly Thr Thr Pro Thr
                245                 250                 255

Ser Ser Ser Thr Thr Thr Val Ser Thr Ser Ala Thr Ala Ser Ala
                260                 265                 270

Thr Ser Cys Ala Thr Pro Val Ser Asn Val Ala Val Thr Phe Thr Ser
        275                 280                 285

Lys Thr Thr Thr Ile Phe Gly Gln Thr Ile Lys Ile Ala Gly Ser Ile
    290                 295                 300

Ala Gln Leu Gly Ser Trp Asn Thr Ala Asn Ala Pro Ala Leu Ser Ala
305                 310                 315                 320

Asp Gln Tyr Thr Ala Ala Asn Pro Ile Trp Arg Thr Thr Ile Ser Leu
                325                 330                 335

Pro Ala Gly Thr Ser Phe Glu Tyr Lys Phe Ile Lys Val Glu Ser Ser
            340                 345                 350

Gly Ala Val Thr Tyr Glu Ser Gly Ala Asn Arg Val Tyr Thr Val Pro
        355                 360                 365

Asn Gly Cys Ala Gly Thr Ala Ser Val Asp Thr Thr Trp Lys
    370                 375                 380

<210> SEQ ID NO 150
<211> LENGTH: 379
<212> TYPE: PRT
<213> ORGANISM: Talaromyces sayulitensis

<400> SEQUENCE: 150

Met Ile Val Ser Ile Ile Val Ala Ala Ala Cys Phe Ala Ser Ala Tyr
1               5                   10                  15

Gly His Gly Tyr Leu Thr Ile Pro Ala Ser Arg Thr Arg Leu Gly Phe
                20                  25                  30

Glu Ala Gly Ile Asp Ile Cys Pro Glu Cys Ser Ile Leu Glu Pro Val

```
                35                  40                  45
Thr Ala Trp Pro Asp Leu Glu Thr Ala Gln Val Gly Arg Ser Gly Pro
 50                  55                  60

Cys Gly Tyr Asn Ala Arg Val Ser Val Asp Tyr Asn Gln Pro Gly Glu
 65                  70                  75                  80

Tyr Trp Gly Val Glu Pro Val Val Thr Tyr Met Ser Gly Glu Val Val
                 85                  90                  95

Glu Val Gln Trp Cys Val Asp Ala Asn Gly Asp His Gly Gly Met Phe
            100                 105                 110

Thr Tyr Gly Val Cys Gln Asn Gln Thr Leu Val Asp Lys Phe Leu Thr
        115                 120                 125

Arg Gly Tyr Leu Pro Thr Asn Asp Glu Lys Gln Ala Ala Glu Asn Cys
130                 135                 140

Phe Leu Glu Gly Glu Leu Lys Cys Thr Asp Val Ser Gly Gln Thr Cys
145                 150                 155                 160

Gly Tyr Asn Pro Asp Cys Thr Ala Gly Glu Ala Cys Trp Arg Asn Asp
                165                 170                 175

Trp Phe Thr Cys Asn Ala Phe Gln Ala Asn Thr Ala Arg Ala Cys Glu
            180                 185                 190

Gly Val Asp Gly Ala Pro Leu Asn Ser Cys Lys Thr Thr Ile Ala Gly
        195                 200                 205

Gly Tyr Thr Val Thr Lys Lys Ile Lys Ile Pro Asp Tyr Ser Ser Asn
210                 215                 220

His Thr Leu Leu Arg Phe Arg Trp Asn Ser Phe Gln Thr Ala Gln Val
225                 230                 235                 240

Tyr Leu His Cys Ala Asp Ile Ala Ile Ser Gly Ser Gly Asn Thr Thr
                245                 250                 255

Thr Ser Thr Ser Thr Ser Ala Thr Ser Thr Ala Val Ser Ser Cys Thr
            260                 265                 270

Ala Thr Ala Asn Leu Ile Pro Val Thr Phe Arg Glu Leu Val Thr Thr
        275                 280                 285

Thr Trp Gly Glu Asn Ile Phe Ile Thr Gly Ser Ile Ser Gln Leu Gly
290                 295                 300

Ser Trp Ser Thr Gly Asn Ala Val Ala Leu Ser Ala Ser Gln Tyr Thr
305                 310                 315                 320

Ala Ser Asn Pro Leu Trp Ile Thr Thr Ile Asp Leu Pro Ala Gly Thr
                325                 330                 335

Thr Phe Glu Tyr Lys Phe Ile Lys Lys Glu Ser Asp Gly Ser Val Ile
            340                 345                 350

Trp Glu Ser Asp Pro Asn Arg Ser Tyr Thr Val Pro Thr Gly Cys Ser
        355                 360                 365

Ser Thr Ile Ala Thr Ala Ala Ser Trp Arg
370                 375

<210> SEQ ID NO 151
<211> LENGTH: 383
<212> TYPE: PRT
<213> ORGANISM: Trichocladium asperum

<400> SEQUENCE: 151

Met Lys Gln Val Thr Ala Leu Ser Leu Ile Ala Leu Ala Thr Ser Val
  1               5                  10                  15

Gln Gly His Gly Tyr Met Ile Gly Pro Ala Ser Arg Thr Arg Gln Gly
             20                  25                  30
```

-continued

```
Phe Glu Ala Gly Thr Asp Thr Cys Pro Glu Cys Thr Ile Leu Glu Pro
         35                  40                  45

Val Ala Ser Trp Pro Asp Leu Asp Ala Ala Ile Gly Arg Ser Gly
 50                  55                  60

Pro Cys Gly Tyr Asn Ala Arg Val Ser Val Asp Tyr Asn Gln Pro Gly
 65                  70                  75                  80

Lys Ala Trp Gly Asn Glu Ile Val Glu Thr Tyr Ala Ala Gly Asp Val
                 85                  90                  95

Ile Thr Val Gln Trp Cys Val Asp Asn Asn Gly Asp His Gly Gly Met
             100                 105                 110

Phe Thr Tyr Arg Ile Cys Gln Asp Gln Ala Leu Val Asp Lys Phe Thr
             115                 120                 125

Asp Pro Ser Tyr Leu Pro Thr Asp Ala Glu Lys Gln Ala Ala Glu Asp
     130                 135                 140

Cys Phe Asn Glu Gly Ile Leu Ser Cys Gly Asp Val Asp Gly Gln Asp
145                 150                 155                 160

Cys Ser Tyr Ser Pro Asp Cys Ser Glu Gly Ala Ala Cys Trp Arg Asn
                 165                 170                 175

Asp Trp Phe Thr Cys Glu Lys Phe Gly Glu Gly Ser Cys Lys Gly Val
             180                 185                 190

Asp Gly Ala Ala Leu Asn Ser Cys Val Thr Thr Ile Ala Gly Gly Tyr
     195                 200                 205

Thr Val Thr Lys Lys Val Lys Leu Pro Asp Tyr Ser Ser Glu His Thr
     210                 215                 220

Leu Leu Ser Phe Lys Trp Asn Ser Phe Gln Thr Gly Gln Ile Tyr Leu
225                 230                 235                 240

Ser Cys Ala Asp Ile Ala Ile Thr Gly Gly Ser Gly Gly Gly Thr Ser
                 245                 250                 255

Pro Asn Thr Thr Ser Ser Leu Ala Pro Val Ser Ser Thr Ser Ala Pro
             260                 265                 270

Pro Ser Ser Ser Thr Ser Ser Ser Pro Gln Glu Thr Cys Asp Ala Gly
             275                 280                 285

Thr Ser Val Pro Val Thr Phe Glu Glu Val Ala Val Pro Glu Ala Gly
     290                 295                 300

Gln Val Ile Lys Leu Val Gly Ser Ile Ser Glu Leu Gly Ser Trp Ser
305                 310                 315                 320

Pro Ser Ala Ala Ile Ala Leu Ala Arg Ser Ala Asn Thr Trp Ser Ala
                 325                 330                 335

Thr Val Asn Ile Thr Ala Gly Glu Ser Phe Glu Tyr Lys Phe Ile Asn
             340                 345                 350

Val Glu Gly Ser Gln Val Trp Trp Glu Ser Asp Pro Asn Arg Ser Phe
     355                 360                 365

Thr Val Pro Cys Gly Ala Ser Ala Asn Val Thr Gly Thr Trp Arg
     370                 375                 380
```